US008002891B2

(12) United States Patent
Xie et al.

(10) Patent No.: US 8,002,891 B2
(45) Date of Patent: *Aug. 23, 2011

(54) CRYSTALLIZATION OF C-JUN N-TERMINAL KINASE 3 (JNK3)

(75) Inventors: Xiaoling Xie, Cambridge, MA (US); Yong Gu, Brookline, MA (US); William Markland, Milford, MA (US); Michael S. Su, Newton, MA (US); Paul R. Caron, Malden, MA (US); Edward Fox, Maynard, MA (US); Keith P. Wilson, Hopkinton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 12/150,328

(22) Filed: Apr. 25, 2008

(65) Prior Publication Data

US 2009/0186394 A1  Jul. 23, 2009

Related U.S. Application Data

(60) Division of application No. 09/706,128, filed on Nov. 3, 2000, now Pat. No. 7,383,135, which is a continuation of application No. PCT/US99/09824, filed on May 4, 1999.

(60) Provisional application No. 60/084,056, filed on May 4, 1998.

(51) Int. Cl.
*C30B 11/00* (2006.01)
*C30B 7/00* (2006.01)
*C12N 9/12* (2006.01)

(52) U.S. Cl. .............................. 117/11; 117/68; 435/194

(58) Field of Classification Search .................. None
See application file for complete search history.

(56) References Cited

U.S. PATENT DOCUMENTS

| | | | |
|---|---|---|---|
| 4,833,233 A | 5/1989 | Carter | |
| 5,353,236 A | 10/1994 | Subbiah | |
| 5,557,535 A | 9/1996 | Srinivasan et al. | |
| 6,162,613 A | 12/2000 | Su et al. | |
| 6,849,716 B1 * | 2/2005 | Su et al. | 530/350 |
| 6,943,000 B2 | 9/2005 | Davis et al. | |
| 7,383,135 B1 * | 6/2008 | Xie et al. | 702/27 |
| 2008/0201123 A1 * | 8/2008 | Cosgrove | 703/11 |

FOREIGN PATENT DOCUMENTS

| | | |
|---|---|---|
| WO | WO 92/14211 | 8/1992 |
| WO | WO 93/02209 | 2/1993 |
| WO | WO 94/25860 | 11/1994 |
| WO | WO 97/06246 | 2/1997 |
| WO | WO 97/15588 | 5/1997 |
| WO | WO 98/35048 | 8/1998 |
| WO | WO 99/57253 | * 11/1999 |

OTHER PUBLICATIONS

Balbes et al., "A Perspective of Modern Methods in Computer-Aided Drug Design," in *Reviews in Computational Chemistry*, K.B. Lipkowitz and D.B. Boyd, Eds., VCH Publishers, New York, 5:337-379 (1994).

Bartlett et al., "CAVEAT: A Program to Facilitate the Structure-Derived Design of Biologically Active Molecules," in *Molecular Recognition in Chemical and Biological Problems*, S.M. Roberts, Ed., Royal Society of Chemistry, Special Publication No. 78:182-196 (1989).

Böhm, "The Computer Program LUDI: A New Method for the De Novo Design of Enzyme Inhibitors", *Journal of Computer-Aided Molecular Design*, 6:61-78 (1992).

Bossemeyer et al., "Phosphotransferase and Substrate Binding Mechanishm of the cAMP-Dependent Protein Kinase Catalytic Subunit from Porcine Heart as Deduced from the 2.0Å Structure of the Complex with $Mn^{2+}$ Adenylyl Imidodiphosphate and Inhibitor Peptide PKI(5-24)," *The EMBO Journal*, 12:849-859 (1993).

Boulton et al., "ERKs: A Family of Protein-Serine/Threonine Kinases that are Activated and Tyrosine Phosphorylated in Response to Insulin and NGF," *Cell*, 65:663-675 (1991).

Brown et al., "Crystallography in the Study of Protein-DNA Interactions," *Methods in Molecular Biology*, 56:293-318 (1996).

Bryan, "Protein Engineering," *Biotech Adv.*, 5:221-234 (1987).

Campbell et al., "Diffraction, in Biological Spectroscopy," *The Benjamin/Cummings Publishing Company, Inc.*, Menlo Park, CA, 299-326 (1984).

Canagarajah et al., "Activation Mechanism of the MAP Kinase ERK2 by Dual Phosphorylation," *Cell*, 90:859-869 (1997).

Cohen et al., "Molecular Modeling Software and Methods for Medicinal Chemistry", *Journal of Medicinal Chemistry*, 33(3):883-894 (1990).

Drenth, "Principles of Protein X-Ray Crystallography," *Springer-Verlag*, 16-17 (1995).

Eisen et al., "HOOK: A Program for Finding Novel Molecular Architectures that Satisfy the Chemical and Steric Requirements of a Macromolecule Binding Site," *Proteins Struct. Funct. Genet.*, 19:199-221 (1994).

Gillet et al., "SPROUT: A Program for Structure Generation," *J. Comp. Aid. Molec. Design*, 7:127-153 (1993).

Goldsmith et al., "Protein Kinases," *Current Opinion in Structural Biology*, 4:833-840 (1994).

Goodford, "A Computational Procedure for Determining Energetically Favorable Binding Sites on Biologically Important Macromolecules," *J. Med. Chem.*, 28:849-857 (1985).

Goodsell et al., "Automated Docking of Substrates to Proteins by Simulated Annealing," *Proteins Struct. Funct. Genet.*, 8:195-202 (1990).

Gregory et al., "Treatment With Rapamycin and Mycophenolic Acid Reduces Arterial Intimal Thickening Produced by Mechanical Injury and Allows Endothelial Replacement," *Transplantation*, 59(5):655-661 (Mar. 1995).

(Continued)

*Primary Examiner* — David J Steadman
(74) *Attorney, Agent, or Firm* — Ropes & Gray LLP; James F. Haley, Jr.; Raymond M. Doss

(57) ABSTRACT

The present invention relates to molecules and molecular complexes which comprise the active site binding pockets of JNK3 or close structural homologues of the active site binding pockets.

5 Claims, 69 Drawing Sheets

OTHER PUBLICATIONS

Guida, "Software for Structure-Based Drug Design," *Curr. Opin. Struct. Biology*, 4:777-781 (1994).

Gupta et al., "Selective Interaction of JNK Protein Kinase Isoforms with Transcription Factors," *The EMBO Journal*, 15:2760-2770 (1996).

Jancarik et al., "Sparse Matrix Sampling: A Screening Method for Crystallization of Proteins," *J. Appl. Cryst.*, 24:409-411 (1991).

Johnson et al., "Active and Inactive Protein Kinases: Structural Basis for Regulation," *Cell*, 85:149-158 (1996).

Kajihara et al., "Protein Modeling Using a Chimera Reference Protein Derived From Exons," *Protein Eng'g*, 6: 615-620 (1993).

Knighton et al., "Crystal Structure of the Catalytic Subunit of Cyclic Adenosine Monophosphate-Dependent Protein Kinase," *Science*, 253:407-413 (1991).

Knighton et al., "Structure of Peptide Inhibitor Bound to the Catalytic Subunit of Cyclic Adenosine Monophosphate-Dependent Protein Kinase," *Science*, 253:414-420 (1991).

Kuntz et al., "A Geometric Approach to Macromolecule-Ligand Interactions," *J. Mol. Biol.*, 161:269-288 (1982).

Lauri et al., "CAVEAT: A Program to Facilitate the Design of Organic Molecules," *J. Comp. Aid. Molec. Design*, 8:51-66 (1994).

Lee et al., "A Protein Kinase Involved in the Regulation of Inflammatory Cytokine Biosynthesis," *Nature*, 372:739-746 (1994).

Martin, "3D Database Searching in Drug Design," *Journal of Medicinal Chemistry*, 35(12):2145-54, (1992).

Meng, et al., "Automated Docking with Grid-Based Energy Evaluation," *Journal of Computational Chemistry*, 13:505-524 (1992).

Miranker et al., "Functionality Maps of Binding Sites: A Multiple Copy Simultaneous Search Method," *Proteins Struct. Funct. Genet.*, 11:29-34 (1991).

Morris, "New Small Molecule Immunosuppressants for Transplantation: Review of Essential Concepts," *The Journal of Heart and Lung Transplantation*, 12:S275-S286 (1993).

Navia et al., "Use of Structural Information in Drug Design," *Current Opinion in Structural Biology*, 2:202-210 (1992).

Nishibata et al., "Automatic Creation of Drug Candidate Structures Based on Receptor Structure. Starting Point for Artificial Lead Generation," *Tetrahedron*, 47:8985-8990 (1991).

Russell et al., "Rational Modification of Enzyme Catalysis by Engineering Surface Charge," *Nature*, 328:496-500 (1987).

Scapin et al., "The Structure of JNK3 in Complex with Small Molecule Inhibitors: Structural Basis for Potency and Selectivity," *Chemistry & Biology*, 10:705-712 (2003).

Service, "Tapping DNA for Structures Produces a Trickle," *Science*, 298:948-950 (2002).

Singh et al., "Structure-Based Design of a Potent, Selective, and Irreversible Inhibitor of the Catalytic Domain of the erbB Receptor Subfamily of Protein Tyrosine Kinases", *J. Med. Chem.*, 40:1130-1135 (1997).

Taylor et al., "Three Protein Kinase Structures Define a Common Motif," *Structure*, 2:345-355 (1994).

Uhlin et al., "Crystallization and Crystallographic Investigations of Ribonucleotide Reductase Protein R1 From *Escherichia Coli*," *FEBS*, 336:148-152 (1993).

Wilson et al., "Crystal Structure of p38 Mitogen-activated Protein Kinase," *J. Biol. Chem.*, 271:27696-27700 (1996).

Wilson et al., "The Structural Basis for the Specificity of Pyridinylimidazole Inhibitors of p38 MAP Kinase," *Chem. & Biol.*, 4:423-431 (1997).

Xie et al., "Crystal Structure of JNK3: A Kinase Implicated in Neuronal Apoptosis," *Structure*, 6:983-991 (1998).

Zhang et al., "Activity of the MAP Kinase ERK2 is Controlled by a Flexible Surface Loop," *Structure*, 3:299-307 (1995).

Zhang et al., "Atomic Structure of the MAP Kinase ERK2 at 2.3 Å Resolution," *Nature*, 367:704-711 (1994).

Zheng et al., "2.2 Å Refined Crystal Structure of the Catalytic Subunit of cAMP-Dependent Protein Kinase Complexed with MnATP and a Peptide Inhibitor," *Acta Cryst.*, D49:362-365 (1993).

* cited by examiner

FIGURE 1A-1

JNK3 COMPLEX COORDINATES

| | | Atom Type | Resid | # | X | Y | Z | Occ | B |
|---|---|---|---|---|---|---|---|---|---|
| ATOM | 1 | CB | ASP | 45 | 19.855 | 9.724 | 63.725 | 1.00 | 59.68 |
| ATOM | 2 | CG | ASP | 45 | 18.571 | 8.907 | 63.752 | 1.00 | 61.53 |
| ATOM | 3 | OD1 | ASP | 45 | 18.663 | 7.663 | 63.664 | 1.00 | 61.74 |
| ATOM | 4 | OD2 | ASP | 45 | 17.474 | 9.503 | 63.865 | 1.00 | 62.02 |
| ATOM | 5 | C | ASP | 45 | 20.366 | 10.309 | 61.336 | 1.00 | 54.84 |
| ATOM | 6 | O | ASP | 45 | 19.187 | 10.519 | 61.046 | 1.00 | 56.31 |
| ATOM | 7 | N | ASP | 45 | 22.176 | 9.526 | 62.871 | 1.00 | 58.74 |
| ATOM | 8 | CA | ASP | 45 | 20.734 | 9.398 | 62.511 | 1.00 | 57.25 |
| ATOM | 9 | N | ASN | 46 | 21.384 | 10.834 | 60.657 | 1.00 | 49.39 |
| ATOM | 10 | CA | ASN | 46 | 21.183 | 11.715 | 59.508 | 1.00 | 43.84 |
| ATOM | 11 | CB | ASN | 46 | 22.526 | 12.303 | 59.078 | 1.00 | 43.66 |
| ATOM | 12 | CG | ASN | 46 | 22.376 | 13.518 | 58.173 | 1.00 | 43.79 |
| ATOM | 13 | OD1 | ASN | 46 | 21.327 | 13.742 | 57.563 | 1.00 | 41.55 |
| ATOM | 14 | ND2 | ASN | 46 | 23.429 | 14.318 | 58.098 | 1.00 | 43.95 |
| ATOM | 15 | C | ASN | 46 | 20.578 | 10.932 | 58.340 | 1.00 | 39.71 |
| ATOM | 16 | O | ASN | 46 | 20.974 | 9.795 | 58.083 | 1.00 | 44.80 |
| ATOM | 17 | N | GLN | 47 | 19.618 | 11.532 | 57.638 | 1.00 | 32.92 |
| ATOM | 18 | CA | GLN | 47 | 18.983 | 10.871 | 56.491 | 1.00 | 27.87 |
| ATOM | 19 | CB | GLN | 47 | 17.702 | 11.598 | 56.079 | 1.00 | 24.65 |
| ATOM | 20 | CG | GLN | 47 | 16.592 | 11.570 | 57.103 | 1.00 | 31.78 |
| ATOM | 21 | CD | GLN | 47 | 15.324 | 12.233 | 56.601 | 1.00 | 35.86 |
| ATOM | 22 | OE1 | GLN | 47 | 14.234 | 11.667 | 56.700 | 1.00 | 42.77 |
| ATOM | 23 | NE2 | GLN | 47 | 15.458 | 13.439 | 56.055 | 1.00 | 41.45 |
| ATOM | 24 | C | GLN | 47 | 19.887 | 10.794 | 55.263 | 1.00 | 23.85 |
| ATOM | 25 | O | GLN | 47 | 19.618 | 10.019 | 54.351 | 1.00 | 26.05 |
| ATOM | 26 | N | PHE | 48 | 20.962 | 11.576 | 55.248 | 1.00 | 16.65 |
| ATOM | 27 | CA | PHE | 48 | 21.856 | 11.617 | 54.098 | 1.00 | 14.45 |
| ATOM | 28 | CB | PHE | 48 | 21.966 | 13.055 | 53.561 | 1.00 | 12.62 |
| ATOM | 29 | CG | PHE | 48 | 20.635 | 13.677 | 53.220 | 1.00 | 10.62 |
| ATOM | 30 | CD1 | PHE | 48 | 19.868 | 14.284 | 54.210 | 1.00 | 10.89 |
| ATOM | 31 | CD2 | PHE | 48 | 20.131 | 13.615 | 51.926 | 1.00 | 5.14 |
| ATOM | 32 | CE1 | PHE | 48 | 18.609 | 14.813 | 53.927 | 1.00 | 10.54 |
| ATOM | 33 | CE2 | PHE | 48 | 18.869 | 14.138 | 51.617 | 1.00 | 3.36 |
| ATOM | 34 | CZ | PHE | 48 | 18.102 | 14.737 | 52.622 | 1.00 | 9.23 |
| ATOM | 35 | C | PHE | 48 | 23.239 | 11.121 | 54.417 | 1.00 | 16.43 |
| ATOM | 36 | O | PHE | 48 | 23.562 | 10.879 | 55.577 | 1.00 | 18.81 |
| ATOM | 37 | N | TYR | 49 | 24.036 | 10.929 | 53.367 | 1.00 | 17.90 |
| ATOM | 38 | CA | TYR | 49 | 25.428 | 10.511 | 53.496 | 1.00 | 18.71 |
| ATOM | 39 | CB | TYR | 49 | 25.567 | 8.988 | 53.656 | 1.00 | 20.34 |
| ATOM | 40 | CG | TYR | 49 | 25.513 | 8.147 | 52.407 | 1.00 | 16.91 |
| ATOM | 41 | CD1 | TYR | 49 | 26.678 | 7.769 | 51.758 | 1.00 | 15.47 |
| ATOM | 42 | CE1 | TYR | 49 | 26.640 | 6.941 | 50.654 | 1.00 | 16.30 |
| ATOM | 43 | CD2 | TYR | 49 | 24.305 | 7.678 | 51.912 | 1.00 | 18.79 |
| ATOM | 44 | CE2 | TYR | 49 | 24.261 | 6.853 | 50.804 | 1.00 | 19.84 |
| ATOM | 45 | CZ | TYR | 49 | 25.433 | 6.495 | 50.183 | 1.00 | 18.33 |
| ATOM | 46 | OH | TYR | 49 | 25.404 | 5.695 | 49.083 | 1.00 | 25.93 |
| ATOM | 47 | C | TYR | 49 | 26.216 | 11.060 | 52.310 | 1.00 | 20.43 |
| ATOM | 48 | O | TYR | 49 | 25.629 | 11.493 | 51.325 | 1.00 | 22.19 |

FIGURE 1A-2

| ATOM | 49 | N | SER | 50 | 27.537 | 11.090 | 52.420 | 1.00 | 23.90 |
| --- | --- | --- | --- | --- | --- | --- | --- | --- | --- |
| ATOM | 50 | CA | SER | 50 | 28.367 | 11.639 | 51.362 | 1.00 | 26.18 |
| ATOM | 51 | CB | SER | 50 | 28.947 | 12.982 | 51.801 | 1.00 | 28.95 |
| ATOM | 52 | OG | SER | 50 | 27.919 | 13.900 | 52.087 | 1.00 | 32.44 |
| ATOM | 53 | C | SER | 50 | 29.504 | 10.768 | 50.878 | 1.00 | 32.00 |
| ATOM | 54 | O | SER | 50 | 30.376 | 10.360 | 51.648 | 1.00 | 37.97 |
| ATOM | 55 | N | VAL | 51 | 29.510 | 10.540 | 49.571 | 1.00 | 33.98 |
| ATOM | 56 | CA | VAL | 51 | 30.545 | 9.752 | 48.911 | 1.00 | 34.16 |
| ATOM | 57 | CB | VAL | 51 | 29.987 | 8.434 | 48.301 | 1.00 | 32.24 |
| ATOM | 58 | CG1 | VAL | 51 | 29.974 | 7.342 | 49.356 | 1.00 | 35.18 |
| ATOM | 59 | CG2 | VAL | 51 | 28.587 | 8.642 | 47.749 | 1.00 | 30.52 |
| ATOM | 60 | C | VAL | 51 | 31.199 | 10.589 | 47.822 | 1.00 | 34.80 |
| ATOM | 61 | O | VAL | 51 | 30.571 | 11.476 | 47.245 | 1.00 | 32.49 |
| ATOM | 62 | N | GLU | 52 | 32.484 | 10.361 | 47.593 | 1.00 | 37.36 |
| ATOM | 63 | CA | GLU | 52 | 33.193 | 11.105 | 46.565 | 1.00 | 44.38 |
| ATOM | 64 | CB | GLU | 52 | 34.655 | 11.337 | 46.955 | 1.00 | 52.03 |
| ATOM | 65 | CG | GLU | 52 | 34.869 | 12.349 | 48.069 | 1.00 | 62.48 |
| ATOM | 66 | CD | GLU | 52 | 34.480 | 11.811 | 49.429 | 1.00 | 68.97 |
| ATOM | 67 | OE1 | GLU | 52 | 35.057 | 10.780 | 49.845 | 1.00 | 74.13 |
| ATOM | 68 | OE2 | GLU | 52 | 33.591 | 12.410 | 50.074 | 1.00 | 69.68 |
| ATOM | 69 | C | GLU | 52 | 33.119 | 10.361 | 45.240 | 1.00 | 47.86 |
| ATOM | 70 | O | GLU | 52 | 33.677 | 9.273 | 45.092 | 1.00 | 50.27 |
| ATOM | 71 | N | VAL | 53 | 32.405 | 10.949 | 44.286 | 1.00 | 49.87 |
| ATOM | 72 | CA | VAL | 53 | 32.247 | 10.372 | 42.955 | 1.00 | 47.53 |
| ATOM | 73 | CB | VAL | 53 | 30.753 | 10.268 | 42.552 | 1.00 | 44.14 |
| ATOM | 74 | CG1 | VAL | 53 | 30.624 | 9.624 | 41.191 | 1.00 | 45.06 |
| ATOM | 75 | CG2 | VAL | 53 | 29.975 | 9.465 | 43.583 | 1.00 | 43.80 |
| ATOM | 76 | C | VAL | 53 | 32.978 | 11.227 | 41.922 | 1.00 | 46.71 |
| ATOM | 77 | O | VAL | 53 | 32.661 | 12.403 | 41.740 | 1.00 | 43.42 |
| ATOM | 78 | N | GLY | 54 | 33.976 | 10.633 | 41.273 | 1.00 | 50.31 |
| ATOM | 79 | CA | GLY | 54 | 34.744 | 11.328 | 40.250 | 1.00 | 57.02 |
| ATOM | 80 | C | GLY | 54 | 35.661 | 12.434 | 40.742 | 1.00 | 60.53 |
| ATOM | 81 | O | GLY | 54 | 36.883 | 12.261 | 40.806 | 1.00 | 64.18 |
| ATOM | 82 | N | ASP | 55 | 35.072 | 13.589 | 41.041 | 1.00 | 58.56 |
| ATOM | 83 | CA | ASP | 55 | 35.810 | 14.750 | 41.526 | 1.00 | 55.60 |
| ATOM | 84 | CB | ASP | 55 | 36.186 | 15.667 | 40.356 | 1.00 | 59.27 |
| ATOM | 85 | CG | ASP | 55 | 37.681 | 15.919 | 40.258 | 1.00 | 61.84 |
| ATOM | 86 | OD1 | ASP | 55 | 38.333 | 16.134 | 41.303 | 1.00 | 63.50 |
| ATOM | 87 | OD2 | ASP | 55 | 38.202 | 15.908 | 39.123 | 1.00 | 63.95 |
| ATOM | 88 | C | ASP | 55 | 34.907 | 15.517 | 42.474 | 1.00 | 51.89 |
| ATOM | 89 | O | ASP | 55 | 35.362 | 16.362 | 43.238 | 1.00 | 51.55 |
| ATOM | 90 | N | SER | 56 | 33.615 | 15.223 | 42.394 | 1.00 | 47.71 |
| ATOM | 91 | CA | SER | 56 | 32.614 | 15.877 | 43.220 | 1.00 | 45.23 |
| ATOM | 92 | CB | SER | 56 | 31.376 | 16.200 | 42.376 | 1.00 | 44.53 |
| ATOM | 93 | OG | SER | 56 | 30.852 | 15.025 | 41.780 | 1.00 | 40.81 |
| ATOM | 94 | C | SER | 56 | 32.205 | 15.011 | 44.405 | 1.00 | 42.41 |
| ATOM | 95 | O | SER | 56 | 32.593 | 13.846 | 44.513 | 1.00 | 42.21 |
| ATOM | 96 | N | THR | 57 | 31.410 | 15.598 | 45.289 | 1.00 | 37.21 |
| ATOM | 97 | CA | THR | 57 | 30.915 | 14.902 | 46.460 | 1.00 | 32.81 |
| ATOM | 98 | CB | THR | 57 | 31.310 | 15.633 | 47.774 | 1.00 | 30.55 |
| ATOM | 99 | OG1 | THR | 57 | 32.732 | 15.563 | 47.953 | 1.00 | 29.57 |

FIGURE 1A-3

| | | | | | | | | |
|---|---|---|---|---|---|---|---|---|
| ATOM | 100 | CG2 | THR | 57 | 30.636 | 14.997 | 48.974 | 1.00 29.35 |
| ATOM | 101 | C | THR | 57 | 29.400 | 14.798 | 46.352 | 1.00 29.88 |
| ATOM | 102 | O | THR | 57 | 28.698 | 15.806 | 46.262 | 1.00 29.02 |
| ATOM | 103 | N | PHE | 58 | 28.918 | 13.563 | 46.302 | 1.00 25.51 |
| ATOM | 104 | CA | PHE | 58 | 27.495 | 13.287 | 46.221 | 1.00 21.72 |
| ATOM | 105 | CB | PHE | 58 | 27.248 | 12.031 | 45.391 | 1.00 17.66 |
| ATOM | 106 | CG | PHE | 58 | 26.769 | 12.310 | 43.996 | 1.00 9.82 |
| ATOM | 107 | CD1 | PHE | 58 | 27.637 | 12.820 | 43.038 | 1.00 3.78 |
| ATOM | 108 | CD2 | PHE | 58 | 25.451 | 12.055 | 43.648 | 1.00 8.40 |
| ATOM | 109 | CE1 | PHE | 58 | 27.206 | 13.065 | 41.747 | 1.00 7.61 |
| ATOM | 110 | CE2 | PHE | 58 | 24.996 | 12.294 | 42.362 | 1.00 5.47 |
| ATOM | 111 | CZ | PHE | 58 | 25.872 | 12.805 | 41.404 | 1.00 5.92 |
| ATOM | 112 | C | PHE | 58 | 26.942 | 13.060 | 47.618 | 1.00 22.96 |
| ATOM | 113 | O | PHE | 58 | 27.443 | 12.206 | 48.351 | 1.00 21.76 |
| ATOM | 114 | N | THR | 59 | 25.968 | 13.874 | 48.009 | 1.00 23.15 |
| ATOM | 115 | CA | THR | 59 | 25.327 | 13.719 | 49.305 | 1.00 19.82 |
| ATOM | 116 | CB | THR | 59 | 25.303 | 15.012 | 50.131 | 1.00 18.35 |
| ATOM | 117 | OG1 | THR | 59 | 26.643 | 15.432 | 50.403 | 1.00 18.16 |
| ATOM | 118 | CG2 | THR | 59 | 24.596 | 14.763 | 51.434 | 1.00 13.77 |
| ATOM | 119 | C | THR | 59 | 23.909 | 13.285 | 49.018 | 1.00 19.29 |
| ATOM | 120 | O | THR | 59 | 23.045 | 14.098 | 48.702 | 1.00 20.81 |
| ATOM | 121 | N | VAL | 60 | 23.687 | 11.979 | 49.082 | 1.00 20.45 |
| ATOM | 122 | CA | VAL | 60 | 22.375 | 11.409 | 48.810 | 1.00 13.63 |
| ATOM | 123 | CB | VAL | 60 | 22.464 | 10.393 | 47.654 | 1.00 8.69 |
| ATOM | 124 | CG1 | VAL | 60 | 22.999 | 11.069 | 46.416 | 1.00 11.26 |
| ATOM | 125 | CG2 | VAL | 60 | 23.369 | 9.232 | 48.022 | 1.00 7.60 |
| ATOM | 126 | C | VAL | 60 | 21.712 | 10.746 | 50.016 | 1.00 15.53 |
| ATOM | 127 | O | VAL | 60 | 22.346 | 10.497 | 51.048 | 1.00 13.21 |
| ATOM | 128 | N | LEU | 61 | 20.415 | 10.488 | 49.869 | 1.00 12.54 |
| ATOM | 129 | CA | LEU | 61 | 19.632 | 9.833 | 50.903 | 1.00 11.17 |
| ATOM | 130 | CB | LEU | 61 | 18.165 | 9.722 | 50.468 | 1.00 4.25 |
| ATOM | 131 | CG | LEU | 61 | 17.225 | 10.931 | 50.544 | 1.00 5.48 |
| ATOM | 132 | CD1 | LEU | 61 | 15.897 | 10.609 | 49.858 | 1.00 2.00 |
| ATOM | 133 | CD2 | LEU | 61 | 16.979 | 11.310 | 52.002 | 1.00 9.02 |
| ATOM | 134 | C | LEU | 61 | 20.216 | 8.434 | 51.104 | 1.00 18.95 |
| ATOM | 135 | O | LEU | 61 | 20.764 | 7.845 | 50.173 | 1.00 22.04 |
| ATOM | 136 | N | LYS | 62 | 20.090 | 7.913 | 52.322 | 1.00 22.69 |
| ATOM | 137 | CA | LYS | 62 | 20.605 | 6.595 | 52.693 | 1.00 23.07 |
| ATOM | 138 | CB | LYS | 62 | 20.334 | 6.338 | 54.181 | 1.00 24.86 |
| ATOM | 139 | CG | LYS | 62 | 21.017 | 7.287 | 55.142 | 1.00 17.47 |
| ATOM | 140 | CD | LYS | 62 | 22.507 | 7.034 | 55.229 | 1.00 20.53 |
| ATOM | 141 | CE | LYS | 62 | 23.118 | 7.776 | 56.412 | 1.00 28.67 |
| ATOM | 142 | NZ | LYS | 62 | 22.500 | 7.369 | 57.721 | 1.00 32.57 |
| ATOM | 143 | C | LYS | 62 | 20.060 | 5.423 | 51.863 | 1.00 22.06 |
| ATOM | 144 | O | LYS | 62 | 20.718 | 4.383 | 51.756 | 1.00 20.43 |
| ATOM | 145 | N | ARG | 63 | 18.861 | 5.584 | 51.298 | 1.00 18.56 |
| ATOM | 146 | CA | ARG | 63 | 18.244 | 4.538 | 50.480 | 1.00 14.06 |
| ATOM | 147 | CB | ARG | 63 | 16.792 | 4.899 | 50.141 | 1.00 8.17 |
| ATOM | 148 | CG | ARG | 63 | 16.627 | 6.191 | 49.361 | 1.00 2.60 |
| ATOM | 149 | CD | ARG | 63 | 15.168 | 6.597 | 49.201 | 1.00 5.10 |
| ATOM | 150 | NE | ARG | 63 | 14.416 | 5.718 | 48.307 | 1.00 2.00 |

FIGURE 1A-4

| ATOM | 151 | CZ | ARG | 63 | 13.127 | 5.871 | 48.014 | 1.00 | 7.33 |
| ATOM | 152 | NH1 | ARG | 63 | 12.429 | 6.861 | 48.546 | 1.00 | 5.57 |
| ATOM | 153 | NH2 | ARG | 63 | 12.537 | 5.058 | 47.150 | 1.00 | 7.75 |
| ATOM | 154 | C | ARG | 63 | 19.030 | 4.317 | 49.191 | 1.00 | 17.87 |
| ATOM | 155 | O | ARG | 63 | 18.973 | 3.235 | 48.610 | 1.00 | 22.92 |
| ATOM | 156 | N | TYR | 64 | 19.770 | 5.335 | 48.753 | 1.00 | 19.66 |
| ATOM | 157 | CA | TYR | 64 | 20.562 | 5.230 | 47.532 | 1.00 | 17.19 |
| ATOM | 158 | CB | TYR | 64 | 20.575 | 6.569 | 46.796 | 1.00 | 6.78 |
| ATOM | 159 | CG | TYR | 64 | 19.183 | 7.009 | 46.447 | 1.00 | 2.11 |
| ATOM | 160 | CD1 | TYR | 64 | 18.307 | 6.145 | 45.791 | 1.00 | 2.00 |
| ATOM | 161 | CE1 | TYR | 64 | 16.988 | 6.501 | 45.550 | 1.00 | 2.00 |
| ATOM | 162 | CD2 | TYR | 64 | 18.701 | 8.252 | 46.842 | 1.00 | 2.00 |
| ATOM | 163 | CE2 | TYR | 64 | 17.376 | 8.618 | 46.593 | 1.00 | 2.00 |
| ATOM | 164 | CZ | TYR | 64 | 16.524 | 7.731 | 45.952 | 1.00 | 2.00 |
| ATOM | 165 | OH | TYR | 64 | 15.202 | 8.076 | 45.737 | 1.00 | 8.54 |
| ATOM | 166 | C | TYR | 64 | 21.965 | 4.699 | 47.789 | 1.00 | 21.14 |
| ATOM | 167 | O | TYR | 64 | 22.834 | 5.406 | 48.299 | 1.00 | 21.24 |
| ATOM | 168 | N | GLN | 65 | 22.159 | 3.430 | 47.431 | 1.00 | 27.22 |
| ATOM | 169 | CA | GLN | 65 | 23.421 | 2.722 | 47.636 | 1.00 | 27.45 |
| ATOM | 170 | CB | GLN | 65 | 23.134 | 1.360 | 48.276 | 1.00 | 29.61 |
| ATOM | 171 | CG | GLN | 65 | 22.391 | 1.448 | 49.596 | 1.00 | 35.96 |
| ATOM | 172 | CD | GLN | 65 | 21.547 | 0.222 | 49.878 | 1.00 | 43.45 |
| ATOM | 173 | OE1 | GLN | 65 | 20.587 | 0.286 | 50.640 | 1.00 | 47.74 |
| ATOM | 174 | NE2 | GLN | 65 | 21.893 | -0.902 | 49.255 | 1.00 | 46.71 |
| ATOM | 175 | C | GLN | 65 | 24.278 | 2.495 | 46.395 | 1.00 | 26.46 |
| ATOM | 176 | O | GLN | 65 | 23.772 | 2.354 | 45.291 | 1.00 | 29.57 |
| ATOM | 177 | N | ASN | 66 | 25.585 | 2.414 | 46.619 | 1.00 | 25.84 |
| ATOM | 178 | CA | ASN | 66 | 26.573 | 2.171 | 45.584 | 1.00 | 28.21 |
| ATOM | 179 | CB | ASN | 66 | 26.535 | 0.701 | 45.170 | 1.00 | 30.35 |
| ATOM | 180 | CG | ASN | 66 | 27.845 | 0.225 | 44.552 | 1.00 | 37.13 |
| ATOM | 181 | OD1 | ASN | 66 | 27.908 | -0.864 | 43.983 | 1.00 | 39.88 |
| ATOM | 182 | ND2 | ASN | 66 | 28.895 | 1.025 | 44.674 | 1.00 | 36.89 |
| ATOM | 183 | C | ASN | 66 | 26.413 | 3.059 | 44.362 | 1.00 | 28.62 |
| ATOM | 184 | O | ASN | 66 | 25.693 | 2.714 | 43.431 | 1.00 | 29.80 |
| ATOM | 185 | N | LEU | 67 | 27.121 | 4.183 | 44.352 | 1.00 | 29.79 |
| ATOM | 186 | CA | LEU | 67 | 27.036 | 5.116 | 43.234 | 1.00 | 28.16 |
| ATOM | 187 | CB | LEU | 67 | 27.111 | 6.569 | 43.712 | 1.00 | 23.90 |
| ATOM | 188 | CG | LEU | 67 | 26.120 | 7.092 | 44.751 | 1.00 | 24.89 |
| ATOM | 189 | CD1 | LEU | 67 | 26.164 | 8.607 | 44.738 | 1.00 | 24.81 |
| ATOM | 190 | CD2 | LEU | 67 | 24.721 | 6.610 | 44.464 | 1.00 | 21.68 |
| ATOM | 191 | C | LEU | 67 | 28.126 | 4.872 | 42.204 | 1.00 | 27.71 |
| ATOM | 192 | O | LEU | 67 | 29.307 | 4.791 | 42.543 | 1.00 | 27.19 |
| ATOM | 193 | N | LYS | 68 | 27.722 | 4.737 | 40.949 | 1.00 | 26.71 |
| ATOM | 194 | CA | LYS | 68 | 28.675 | 4.531 | 39.871 | 1.00 | 24.93 |
| ATOM | 195 | CB | LYS | 68 | 28.454 | 3.160 | 39.210 | 1.00 | 26.13 |
| ATOM | 196 | CG | LYS | 68 | 29.375 | 2.894 | 38.023 | 1.00 | 39.51 |
| ATOM | 197 | CD | LYS | 68 | 29.032 | 1.587 | 37.314 | 1.00 | 44.51 |
| ATOM | 198 | CE | LYS | 68 | 30.089 | 1.240 | 36.274 | 1.00 | 49.00 |
| ATOM | 199 | NZ | LYS | 68 | 29.914 | -0.144 | 35.735 | 1.00 | 51.87 |
| ATOM | 200 | C | LYS | 68 | 28.451 | 5.645 | 38.865 | 1.00 | 21.36 |
| ATOM | 201 | O | LYS | 68 | 27.330 | 5.853 | 38.404 | 1.00 | 19.41 |

FIGURE 1A-5

| | | | | | | | | | |
|---|---|---|---|---|---|---|---|---|---|
| ATOM | 202 | N   | PRO | 69 | 29.496 | 6.428  | 38.570 | 1.00 | 19.98 |
| ATOM | 203 | CD  | PRO | 69 | 30.873 | 6.339  | 39.078 | 1.00 | 17.93 |
| ATOM | 204 | CA  | PRO | 69 | 29.356 | 7.521  | 37.603 | 1.00 | 22.42 |
| ATOM | 205 | CB  | PRO | 69 | 30.717 | 8.215  | 37.680 | 1.00 | 17.86 |
| ATOM | 206 | CG  | PRO | 69 | 31.650 | 7.092  | 38.032 | 1.00 | 19.98 |
| ATOM | 207 | C   | PRO | 69 | 29.063 | 6.972  | 36.199 | 1.00 | 26.23 |
| ATOM | 208 | O   | PRO | 69 | 29.854 | 6.199  | 35.639 | 1.00 | 28.01 |
| ATOM | 209 | N   | ILE | 70 | 27.888 | 7.310  | 35.667 | 1.00 | 22.90 |
| ATOM | 210 | CA  | ILE | 70 | 27.491 | 6.837  | 34.351 | 1.00 | 26.23 |
| ATOM | 211 | CB  | ILE | 70 | 26.114 | 6.156  | 34.390 | 1.00 | 22.92 |
| ATOM | 212 | CG2 | ILE | 70 | 26.198 | 4.885  | 35.210 | 1.00 | 28.36 |
| ATOM | 213 | CG1 | ILE | 70 | 25.060 | 7.112  | 34.935 | 1.00 | 18.94 |
| ATOM | 214 | CD1 | ILE | 70 | 23.646 | 6.586  | 34.850 | 1.00 | 18.68 |
| ATOM | 215 | C   | ILE | 70 | 27.456 | 7.922  | 33.284 | 1.00 | 30.56 |
| ATOM | 216 | O   | ILE | 70 | 27.708 | 7.654  | 32.108 | 1.00 | 33.33 |
| ATOM | 217 | N   | GLY | 71 | 27.145 | 9.146  | 33.696 | 1.00 | 33.40 |
| ATOM | 218 | CA  | GLY | 71 | 27.071 | 10.251 | 32.757 | 1.00 | 32.37 |
| ATOM | 219 | C   | GLY | 71 | 27.497 | 11.575 | 33.354 | 1.00 | 34.96 |
| ATOM | 220 | O   | GLY | 71 | 27.702 | 11.693 | 34.567 | 1.00 | 37.67 |
| ATOM | 221 | N   | SER | 72 | 27.667 | 12.564 | 32.485 | 1.00 | 35.42 |
| ATOM | 222 | CA  | SER | 72 | 28.073 | 13.905 | 32.889 | 1.00 | 36.39 |
| ATOM | 223 | CB  | SER | 72 | 29.601 | 14.008 | 32.987 | 1.00 | 35.92 |
| ATOM | 224 | OG  | SER | 72 | 30.003 | 15.287 | 33.445 | 1.00 | 40.15 |
| ATOM | 225 | C   | SER | 72 | 27.575 | 14.875 | 31.836 | 1.00 | 37.52 |
| ATOM | 226 | O   | SER | 72 | 27.582 | 14.569 | 30.645 | 1.00 | 41.66 |
| ATOM | 227 | N   | GLY | 73 | 27.156 | 16.054 | 32.271 | 1.00 | 38.17 |
| ATOM | 228 | CA  | GLY | 73 | 26.662 | 17.038 | 31.329 | 1.00 | 37.55 |
| ATOM | 229 | C   | GLY | 73 | 27.150 | 18.439 | 31.622 | 1.00 | 36.51 |
| ATOM | 230 | O   | GLY | 73 | 28.273 | 18.638 | 32.079 | 1.00 | 38.35 |
| ATOM | 231 | N   | ALA | 74 | 26.300 | 19.412 | 31.326 | 1.00 | 34.72 |
| ATOM | 232 | CA  | ALA | 74 | 26.622 | 20.806 | 31.551 | 1.00 | 32.45 |
| ATOM | 233 | CB  | ALA | 74 | 26.113 | 21.657 | 30.384 | 1.00 | 29.14 |
| ATOM | 234 | C   | ALA | 74 | 25.976 | 21.242 | 32.848 | 1.00 | 31.28 |
| ATOM | 235 | O   | ALA | 74 | 26.533 | 22.045 | 33.590 | 1.00 | 29.81 |
| ATOM | 236 | N   | GLN | 75 | 24.793 | 20.703 | 33.115 | 1.00 | 31.98 |
| ATOM | 237 | CA  | GLN | 75 | 24.082 | 21.058 | 34.329 | 1.00 | 37.42 |
| ATOM | 238 | CB  | GLN | 75 | 22.597 | 21.269 | 34.035 | 1.00 | 41.42 |
| ATOM | 239 | CG  | GLN | 75 | 21.848 | 20.038 | 33.584 | 1.00 | 47.83 |
| ATOM | 240 | CD  | GLN | 75 | 20.357 | 20.292 | 33.469 | 1.00 | 52.31 |
| ATOM | 241 | OE1 | GLN | 75 | 19.773 | 20.169 | 32.392 | 1.00 | 59.59 |
| ATOM | 242 | NE2 | GLN | 75 | 19.738 | 20.682 | 34.576 | 1.00 | 51.30 |
| ATOM | 243 | C   | GLN | 75 | 24.267 | 20.098 | 35.507 | 1.00 | 37.77 |
| ATOM | 244 | O   | GLN | 75 | 23.865 | 20.416 | 36.630 | 1.00 | 39.87 |
| ATOM | 245 | N   | GLY | 76 | 24.888 | 18.945 | 35.270 | 1.00 | 33.92 |
| ATOM | 246 | CA  | GLY | 76 | 25.078 | 18.009 | 36.361 | 1.00 | 31.74 |
| ATOM | 247 | C   | GLY | 76 | 25.698 | 16.667 | 36.036 | 1.00 | 27.60 |
| ATOM | 248 | O   | GLY | 76 | 25.777 | 16.257 | 34.880 | 1.00 | 26.55 |
| ATOM | 249 | N   | ILE | 77 | 26.159 | 15.992 | 37.086 | 1.00 | 25.52 |
| ATOM | 250 | CA  | ILE | 77 | 26.776 | 14.675 | 36.976 | 1.00 | 24.04 |
| ATOM | 251 | CB  | ILE | 77 | 27.985 | 14.555 | 37.913 | 1.00 | 22.44 |
| ATOM | 252 | CG2 | ILE | 77 | 28.656 | 13.199 | 37.733 | 1.00 | 20.17 |

FIGURE 1A-6

| | | | | | | | | | |
|---|---|---|---|---|---|---|---|---|---|
| ATOM | 253 | CG1 | ILE | 77 | 28.971 | 15.685 | 37.604 | 1.00 | 29.00 |
| ATOM | 254 | CD1 | ILE | 77 | 29.931 | 16.017 | 38.717 | 1.00 | 34.72 |
| ATOM | 255 | C | ILE | 77 | 25.744 | 13.606 | 37.297 | 1.00 | 21.59 |
| ATOM | 256 | O | ILE | 77 | 24.981 | 13.728 | 38.259 | 1.00 | 24.81 |
| ATOM | 257 | N | VAL | 78 | 25.685 | 12.577 | 36.457 | 1.00 | 18.79 |
| ATOM | 258 | CA | VAL | 78 | 24.713 | 11.502 | 36.641 | 1.00 | 16.12 |
| ATOM | 259 | CB | VAL | 78 | 23.923 | 11.218 | 35.333 | 1.00 | 11.25 |
| ATOM | 260 | CG1 | VAL | 78 | 22.695 | 10.376 | 35.628 | 1.00 | 6.59 |
| ATOM | 261 | CG2 | VAL | 78 | 23.514 | 12.521 | 34.652 | 1.00 | 8.30 |
| ATOM | 262 | C | VAL | 78 | 25.368 | 10.210 | 37.130 | 1.00 | 15.52 |
| ATOM | 263 | O | VAL | 78 | 26.348 | 9.733 | 36.548 | 1.00 | 14.58 |
| ATOM | 264 | N | CYS | 79 | 24.837 | 9.680 | 38.231 | 1.00 | 12.77 |
| ATOM | 265 | CA | CYS | 79 | 25.325 | 8.446 | 38.833 | 1.00 | 11.16 |
| ATOM | 266 | CB | CYS | 79 | 25.748 | 8.671 | 40.290 | 1.00 | 2.26 |
| ATOM | 267 | SG | CYS | 79 | 27.507 | 9.003 | 40.534 | 1.00 | 23.87 |
| ATOM | 268 | C | CYS | 79 | 24.225 | 7.403 | 38.814 | 1.00 | 6.57 |
| ATOM | 269 | O | CYS | 79 | 23.048 | 7.740 | 38.835 | 1.00 | 5.80 |
| ATOM | 270 | N | ALA | 80 | 24.613 | 6.141 | 38.687 | 1.00 | 9.09 |
| ATOM | 271 | CA | ALA | 80 | 23.661 | 5.032 | 38.726 | 1.00 | 11.89 |
| ATOM | 272 | CB | ALA | 80 | 24.111 | 3.919 | 37.811 | 1.00 | 11.41 |
| ATOM | 273 | C | ALA | 80 | 23.711 | 4.562 | 40.182 | 1.00 | 14.64 |
| ATOM | 274 | O | ALA | 80 | 24.778 | 4.620 | 40.812 | 1.00 | 12.69 |
| ATOM | 275 | N | ALA | 81 | 22.581 | 4.110 | 40.724 | 1.00 | 10.97 |
| ATOM | 276 | CA | ALA | 81 | 22.567 | 3.643 | 42.110 | 1.00 | 16.09 |
| ATOM | 277 | CB | ALA | 81 | 22.428 | 4.817 | 43.047 | 1.00 | 15.42 |
| ATOM | 278 | C | ALA | 81 | 21.462 | 2.641 | 42.393 | 1.00 | 17.84 |
| ATOM | 279 | O | ALA | 81 | 20.537 | 2.476 | 41.588 | 1.00 | 20.95 |
| ATOM | 280 | N | TYR | 82 | 21.575 | 1.972 | 43.543 | 1.00 | 18.54 |
| ATOM | 281 | CA | TYR | 82 | 20.585 | 0.998 | 43.999 | 1.00 | 16.92 |
| ATOM | 282 | CB | TYR | 82 | 21.273 | -0.212 | 44.667 | 1.00 | 19.00 |
| ATOM | 283 | CG | TYR | 82 | 20.303 | -1.209 | 45.271 | 1.00 | 17.27 |
| ATOM | 284 | CD1 | TYR | 82 | 19.296 | -1.782 | 44.504 | 1.00 | 15.48 |
| ATOM | 285 | CE1 | TYR | 82 | 18.362 | -2.639 | 45.064 | 1.00 | 17.07 |
| ATOM | 286 | CD2 | TYR | 82 | 20.355 | -1.534 | 46.624 | 1.00 | 19.01 |
| ATOM | 287 | CE2 | TYR | 82 | 19.422 | -2.396 | 47.194 | 1.00 | 12.98 |
| ATOM | 288 | CZ | TYR | 82 | 18.427 | -2.939 | 46.408 | 1.00 | 18.14 |
| ATOM | 289 | OH | TYR | 82 | 17.462 | -3.745 | 46.966 | 1.00 | 20.11 |
| ATOM | 290 | C | TYR | 82 | 19.673 | 1.696 | 45.000 | 1.00 | 14.40 |
| ATOM | 291 | O | TYR | 82 | 20.141 | 2.444 | 45.849 | 1.00 | 17.63 |
| ATOM | 292 | N | ASP | 83 | 18.373 | 1.478 | 44.875 | 1.00 | 10.34 |
| ATOM | 293 | CA | ASP | 83 | 17.416 | 2.079 | 45.782 | 1.00 | 12.26 |
| ATOM | 294 | CB | ASP | 83 | 16.301 | 2.779 | 44.990 | 1.00 | 14.10 |
| ATOM | 295 | CG | ASP | 83 | 15.215 | 3.392 | 45.880 | 1.00 | 19.22 |
| ATOM | 296 | OD1 | ASP | 83 | 15.332 | 3.357 | 47.118 | 1.00 | 20.02 |
| ATOM | 297 | OD2 | ASP | 83 | 14.223 | 3.921 | 45.326 | 1.00 | 26.80 |
| ATOM | 298 | C | ASP | 83 | 16.841 | 0.965 | 46.652 | 1.00 | 15.94 |
| ATOM | 299 | O | ASP | 83 | 15.918 | 0.244 | 46.237 | 1.00 | 15.40 |
| ATOM | 300 | N | ALA | 84 | 17.337 | 0.886 | 47.889 | 1.00 | 15.60 |
| ATOM | 301 | CA | ALA | 84 | 16.896 | -0.115 | 48.859 | 1.00 | 9.42 |
| ATOM | 302 | CB | ALA | 84 | 17.626 | 0.099 | 50.175 | 1.00 | 7.63 |
| ATOM | 303 | C | ALA | 84 | 15.383 | -0.135 | 49.081 | 1.00 | 5.20 |

FIGURE 1A-7

| | | | | | | | | | |
|---|---|---|---|---|---|---|---|---|---|
| ATOM | 304 | O | ALA | 84 | 14.766 | -1.184 | 49.020 | 1.00 | 14.84 |
| ATOM | 305 | N | VAL | 85 | 14.775 | 1.026 | 49.272 | 1.00 | 7.36 |
| ATOM | 306 | CA | VAL | 85 | 13.340 | 1.111 | 49.509 | 1.00 | 9.77 |
| ATOM | 307 | CB | VAL | 85 | 12.902 | 2.600 | 49.776 | 1.00 | 10.21 |
| ATOM | 308 | CG1 | VAL | 85 | 11.377 | 2.720 | 49.961 | 1.00 | 3.58 |
| ATOM | 309 | CG2 | VAL | 85 | 13.624 | 3.140 | 50.996 | 1.00 | 8.96 |
| ATOM | 310 | C | VAL | 85 | 12.507 | 0.529 | 48.372 | 1.00 | 14.78 |
| ATOM | 311 | O | VAL | 85 | 11.641 | -0.309 | 48.596 | 1.00 | 15.67 |
| ATOM | 312 | N | LEU | 86 | 12.783 | 0.962 | 47.146 | 1.00 | 19.36 |
| ATOM | 313 | CA | LEU | 86 | 12.020 | 0.496 | 45.996 | 1.00 | 21.40 |
| ATOM | 314 | CB | LEU | 86 | 12.074 | 1.545 | 44.894 | 1.00 | 23.52 |
| ATOM | 315 | CG | LEU | 86 | 10.735 | 2.206 | 44.576 | 1.00 | 27.04 |
| ATOM | 316 | CD1 | LEU | 86 | 10.115 | 2.801 | 45.823 | 1.00 | 23.18 |
| ATOM | 317 | CD2 | LEU | 86 | 10.939 | 3.260 | 43.516 | 1.00 | 27.53 |
| ATOM | 318 | C | LEU | 86 | 12.494 | -0.854 | 45.474 | 1.00 | 22.48 |
| ATOM | 319 | O | LEU | 86 | 11.791 | -1.516 | 44.705 | 1.00 | 25.35 |
| ATOM | 320 | N | ASP | 87 | 13.678 | -1.257 | 45.914 | 1.00 | 21.80 |
| ATOM | 321 | CA | ASP | 87 | 14.274 | -2.516 | 45.515 | 1.00 | 26.40 |
| ATOM | 322 | CB | ASP | 87 | 13.415 | -3.704 | 45.979 | 1.00 | 27.11 |
| ATOM | 323 | CG | ASP | 87 | 14.087 | -5.045 | 45.731 | 1.00 | 28.62 |
| ATOM | 324 | OD1 | ASP | 87 | 15.337 | -5.119 | 45.783 | 1.00 | 26.23 |
| ATOM | 325 | OD2 | ASP | 87 | 13.361 | -6.030 | 45.480 | 1.00 | 29.07 |
| ATOM | 326 | C | ASP | 87 | 14.469 | -2.556 | 44.011 | 1.00 | 26.83 |
| ATOM | 327 | O | ASP | 87 | 13.893 | -3.404 | 43.319 | 1.00 | 29.65 |
| ATOM | 328 | N | ARG | 88 | 15.257 | -1.605 | 43.516 | 1.00 | 27.20 |
| ATOM | 329 | CA | ARG | 88 | 15.584 | -1.486 | 42.094 | 1.00 | 26.19 |
| ATOM | 330 | CB | ARG | 88 | 14.348 | -1.119 | 41.267 | 1.00 | 24.80 |
| ATOM | 331 | CG | ARG | 88 | 13.721 | 0.205 | 41.628 | 1.00 | 23.72 |
| ATOM | 332 | CD | ARG | 88 | 12.338 | 0.327 | 41.035 | 1.00 | 22.66 |
| ATOM | 333 | NE | ARG | 88 | 12.340 | 1.060 | 39.779 | 1.00 | 24.38 |
| ATOM | 334 | CZ | ARG | 88 | 11.301 | 1.756 | 39.318 | 1.00 | 29.43 |
| ATOM | 335 | NH1 | ARG | 88 | 10.168 | 1.813 | 40.011 | 1.00 | 26.79 |
| ATOM | 336 | NH2 | ARG | 88 | 11.401 | 2.421 | 38.169 | 1.00 | 27.96 |
| ATOM | 337 | C | ARG | 88 | 16.651 | -0.425 | 41.903 | 1.00 | 25.29 |
| ATOM | 338 | O | ARG | 88 | 16.915 | 0.370 | 42.801 | 1.00 | 23.48 |
| ATOM | 339 | N | ASN | 89 | 17.267 | -0.418 | 40.728 | 1.00 | 25.06 |
| ATOM | 340 | CA | ASN | 89 | 18.286 | 0.567 | 40.429 | 1.00 | 18.99 |
| ATOM | 341 | CB | ASN | 89 | 19.336 | -0.012 | 39.499 | 1.00 | 25.01 |
| ATOM | 342 | CG | ASN | 89 | 20.377 | -0.809 | 40.241 | 1.00 | 28.48 |
| ATOM | 343 | OD1 | ASN | 89 | 21.419 | -0.275 | 40.622 | 1.00 | 32.62 |
| ATOM | 344 | ND2 | ASN | 89 | 20.103 | -2.090 | 40.467 | 1.00 | 29.90 |
| ATOM | 345 | C | ASN | 89 | 17.670 | 1.824 | 39.833 | 1.00 | 15.61 |
| ATOM | 346 | O | ASN | 89 | 16.615 | 1.785 | 39.189 | 1.00 | 7.33 |
| ATOM | 347 | N | VAL | 90 | 18.322 | 2.950 | 40.121 | 1.00 | 17.22 |
| ATOM | 348 | CA | VAL | 90 | 17.911 | 4.273 | 39.659 | 1.00 | 12.47 |
| ATOM | 349 | CB | VAL | 90 | 17.196 | 5.091 | 40.776 | 1.00 | 10.69 |
| ATOM | 350 | CG1 | VAL | 90 | 15.835 | 4.505 | 41.081 | 1.00 | 8.43 |
| ATOM | 351 | CG2 | VAL | 90 | 18.057 | 5.141 | 42.032 | 1.00 | 8.83 |
| ATOM | 352 | C | VAL | 90 | 19.114 | 5.086 | 39.199 | 1.00 | 8.85 |
| ATOM | 353 | O | VAL | 90 | 20.266 | 4.686 | 39.372 | 1.00 | 11.47 |
| ATOM | 354 | N | ALA | 91 | 18.820 | 6.217 | 38.571 | 1.00 | 5.44 |

FIGURE 1A-8

| ATOM | 355 | CA | ALA | 91 | 19.837 | 7.141 | 38.087 | 1.00 | 7.90 |
| --- | --- | --- | --- | --- | --- | --- | --- | --- | --- |
| ATOM | 356 | CB | ALA | 91 | 19.661 | 7.402 | 36.590 | 1.00 | 2.56 |
| ATOM | 357 | C | ALA | 91 | 19.610 | 8.428 | 38.888 | 1.00 | 6.95 |
| ATOM | 358 | O | ALA | 91 | 18.465 | 8.872 | 39.045 | 1.00 | 2.00 |
| ATOM | 359 | N | ILE | 92 | 20.685 | 8.932 | 39.492 | 1.00 | 6.14 |
| ATOM | 360 | CA | ILE | 92 | 20.665 | 10.162 | 40.288 | 1.00 | 9.92 |
| ATOM | 361 | CB | ILE | 92 | 21.292 | 9.961 | 41.705 | 1.00 | 8.33 |
| ATOM | 362 | CG2 | ILE | 92 | 21.191 | 11.252 | 42.506 | 1.00 | 2.00 |
| ATOM | 363 | CG1 | ILE | 92 | 20.580 | 8.855 | 42.471 | 1.00 | 9.79 |
| ATOM | 364 | CD1 | ILE | 92 | 21.344 | 8.415 | 43.698 | 1.00 | 15.47 |
| ATOM | 365 | C | ILE | 92 | 21.507 | 11.227 | 39.600 | 1.00 | 7.67 |
| ATOM | 366 | O | ILE | 92 | 22.714 | 11.054 | 39.427 | 1.00 | 5.86 |
| ATOM | 367 | N | LYS | 93 | 20.880 | 12.341 | 39.249 | 1.00 | 7.85 |
| ATOM | 368 | CA | LYS | 93 | 21.589 | 13.438 | 38.608 | 1.00 | 13.90 |
| ATOM | 369 | CB | LYS | 93 | 20.824 | 13.881 | 37.354 | 1.00 | 11.99 |
| ATOM | 370 | CG | LYS | 93 | 21.483 | 14.996 | 36.565 | 1.00 | 12.48 |
| ATOM | 371 | CD | LYS | 93 | 20.522 | 15.493 | 35.505 | 1.00 | 17.28 |
| ATOM | 372 | CE | LYS | 93 | 21.153 | 16.492 | 34.567 | 1.00 | 17.95 |
| ATOM | 373 | NZ | LYS | 93 | 20.095 | 17.017 | 33.649 | 1.00 | 17.45 |
| ATOM | 374 | C | LYS | 93 | 21.700 | 14.594 | 39.611 | 1.00 | 10.74 |
| ATOM | 375 | O | LYS | 93 | 20.707 | 14.998 | 40.223 | 1.00 | 11.60 |
| ATOM | 376 | N | LYS | 94 | 22.910 | 15.103 | 39.804 | 1.00 | 13.09 |
| ATOM | 377 | CA | LYS | 94 | 23.122 | 16.201 | 40.738 | 1.00 | 15.19 |
| ATOM | 378 | CB | LYS | 94 | 24.376 | 15.946 | 41.565 | 1.00 | 13.73 |
| ATOM | 379 | CG | LYS | 94 | 24.659 | 17.007 | 42.620 | 1.00 | 2.95 |
| ATOM | 380 | CD | LYS | 94 | 26.093 | 16.906 | 43.062 | 1.00 | 3.67 |
| ATOM | 381 | CE | LYS | 94 | 26.451 | 17.966 | 44.076 | 1.00 | 3.86 |
| ATOM | 382 | NZ | LYS | 94 | 27.925 | 17.937 | 44.262 | 1.00 | 3.92 |
| ATOM | 383 | C | LYS | 94 | 23.249 | 17.578 | 40.079 | 1.00 | 20.95 |
| ATOM | 384 | O | LYS | 94 | 24.202 | 17.844 | 39.338 | 1.00 | 16.41 |
| ATOM | 385 | N | LEU | 95 | 22.290 | 18.454 | 40.355 | 1.00 | 20.67 |
| ATOM | 386 | CA | LEU | 95 | 22.341 | 19.808 | 39.832 | 1.00 | 19.27 |
| ATOM | 387 | CB | LEU | 95 | 20.935 | 20.370 | 39.633 | 1.00 | 17.32 |
| ATOM | 388 | CG | LEU | 95 | 20.195 | 20.051 | 38.339 | 1.00 | 15.46 |
| ATOM | 389 | CD1 | LEU | 95 | 20.506 | 18.661 | 37.829 | 1.00 | 18.95 |
| ATOM | 390 | CD2 | LEU | 95 | 18.701 | 20.215 | 38.592 | 1.00 | 19.13 |
| ATOM | 391 | C | LEU | 95 | 23.102 | 20.655 | 40.847 | 1.00 | 20.29 |
| ATOM | 392 | O | LEU | 95 | 22.570 | 21.055 | 41.880 | 1.00 | 16.99 |
| ATOM | 393 | N | SER | 96 | 24.381 | 20.855 | 40.582 | 1.00 | 22.55 |
| ATOM | 394 | CA | SER | 96 | 25.208 | 21.650 | 41.462 | 1.00 | 27.78 |
| ATOM | 395 | CB | SER | 96 | 26.678 | 21.376 | 41.158 | 1.00 | 32.32 |
| ATOM | 396 | OG | SER | 96 | 27.525 | 22.091 | 42.035 | 1.00 | 44.45 |
| ATOM | 397 | C | SER | 96 | 24.892 | 23.134 | 41.291 | 1.00 | 28.53 |
| ATOM | 398 | O | SER | 96 | 25.143 | 23.702 | 40.231 | 1.00 | 29.08 |
| ATOM | 399 | N | ARG | 97 | 24.282 | 23.744 | 42.310 | 1.00 | 31.71 |
| ATOM | 400 | CA | ARG | 97 | 23.963 | 25.176 | 42.279 | 1.00 | 32.49 |
| ATOM | 401 | CB | ARG | 97 | 25.264 | 25.974 | 42.415 | 1.00 | 37.97 |
| ATOM | 402 | CG | ARG | 97 | 25.753 | 26.177 | 43.816 | 1.00 | 41.24 |
| ATOM | 403 | CD | ARG | 97 | 25.254 | 27.493 | 44.346 | 1.00 | 45.78 |
| ATOM | 404 | NE | ARG | 97 | 25.677 | 27.690 | 45.722 | 1.00 | 55.70 |
| ATOM | 405 | CZ | ARG | 97 | 25.500 | 28.806 | 46.419 | 1.00 | 57.73 |

FIGURE 1A-9

| ATOM | 406 | NH1 | ARG | 97 | 24.900 | 29.858 | 45.873 | 1.00 | 54.33 |
|------|-----|-----|-----|-----|--------|--------|--------|------|-------|
| ATOM | 407 | NH2 | ARG | 97 | 25.934 | 28.862 | 47.669 | 1.00 | 61.83 |
| ATOM | 408 | C | ARG | 97 | 23.247 | 25.597 | 40.994 | 1.00 | 30.21 |
| ATOM | 409 | O | ARG | 97 | 23.742 | 26.441 | 40.258 | 1.00 | 30.65 |
| ATOM | 410 | N | PRO | 98 | 22.053 | 25.042 | 40.737 | 1.00 | 31.21 |
| ATOM | 411 | CD | PRO | 98 | 21.306 | 24.196 | 41.684 | 1.00 | 31.34 |
| ATOM | 412 | CA | PRO | 98 | 21.236 | 25.325 | 39.545 | 1.00 | 31.16 |
| ATOM | 413 | CB | PRO | 98 | 19.990 | 24.461 | 39.774 | 1.00 | 32.17 |
| ATOM | 414 | CG | PRO | 98 | 19.868 | 24.423 | 41.266 | 1.00 | 30.31 |
| ATOM | 415 | C | PRO | 98 | 20.851 | 26.793 | 39.338 | 1.00 | 29.03 |
| ATOM | 416 | O | PRO | 98 | 20.734 | 27.263 | 38.196 | 1.00 | 25.00 |
| ATOM | 417 | N | PHE | 99 | 20.666 | 27.504 | 40.445 | 1.00 | 27.73 |
| ATOM | 418 | CA | PHE | 99 | 20.270 | 28.910 | 40.438 | 1.00 | 23.81 |
| ATOM | 419 | CB | PHE | 99 | 19.569 | 29.257 | 41.757 | 1.00 | 24.93 |
| ATOM | 420 | CG | PHE | 99 | 20.317 | 28.786 | 42.977 | 1.00 | 28.86 |
| ATOM | 421 | CD1 | PHE | 99 | 20.022 | 27.551 | 43.549 | 1.00 | 28.62 |
| ATOM | 422 | CD2 | PHE | 99 | 21.322 | 29.570 | 43.541 | 1.00 | 32.28 |
| ATOM | 423 | CE1 | PHE | 99 | 20.717 | 27.094 | 44.662 | 1.00 | 26.79 |
| ATOM | 424 | CE2 | PHE | 99 | 22.029 | 29.128 | 44.658 | 1.00 | 33.11 |
| ATOM | 425 | CZ | PHE | 99 | 21.725 | 27.881 | 45.221 | 1.00 | 29.32 |
| ATOM | 426 | C | PHE | 99 | 21.421 | 29.888 | 40.196 | 1.00 | 22.67 |
| ATOM | 427 | O | PHE | 99 | 21.197 | 31.100 | 40.157 | 1.00 | 19.68 |
| ATOM | 428 | N | GLN | 100 | 22.632 | 29.383 | 39.981 | 1.00 | 21.49 |
| ATOM | 429 | CA | GLN | 100 | 23.764 | 30.267 | 39.759 | 1.00 | 22.41 |
| ATOM | 430 | CB | GLN | 100 | 25.071 | 29.488 | 39.687 | 1.00 | 25.88 |
| ATOM | 431 | CG | GLN | 100 | 25.235 | 28.646 | 38.462 | 1.00 | 31.78 |
| ATOM | 432 | CD | GLN | 100 | 26.621 | 28.078 | 38.379 | 1.00 | 36.79 |
| ATOM | 433 | OE1 | GLN | 100 | 27.606 | 28.816 | 38.271 | 1.00 | 39.50 |
| ATOM | 434 | NE2 | GLN | 100 | 26.719 | 26.761 | 38.466 | 1.00 | 44.23 |
| ATOM | 435 | C | GLN | 100 | 23.610 | 31.204 | 38.557 | 1.00 | 25.62 |
| ATOM | 436 | O | GLN | 100 | 24.258 | 32.256 | 38.511 | 1.00 | 27.19 |
| ATOM | 437 | N | ASN | 101 | 22.802 | 30.817 | 37.572 | 1.00 | 23.78 |
| ATOM | 438 | CA | ASN | 101 | 22.549 | 31.681 | 36.427 | 1.00 | 22.70 |
| ATOM | 439 | CB | ASN | 101 | 23.675 | 31.650 | 35.374 | 1.00 | 19.75 |
| ATOM | 440 | CG | ASN | 101 | 23.936 | 30.275 | 34.795 | 1.00 | 22.36 |
| ATOM | 441 | OD1 | ASN | 101 | 23.072 | 29.683 | 34.139 | 1.00 | 28.52 |
| ATOM | 442 | ND2 | ASN | 101 | 25.165 | 29.788 | 34.968 | 1.00 | 26.20 |
| ATOM | 443 | C | ASN | 101 | 21.164 | 31.428 | 35.844 | 1.00 | 24.49 |
| ATOM | 444 | O | ASN | 101 | 20.608 | 30.345 | 36.001 | 1.00 | 27.14 |
| ATOM | 445 | N | GLN | 102 | 20.586 | 32.455 | 35.231 | 1.00 | 28.37 |
| ATOM | 446 | CA | GLN | 102 | 19.240 | 32.358 | 34.667 | 1.00 | 32.20 |
| ATOM | 447 | CB | GLN | 102 | 18.805 | 33.708 | 34.097 | 1.00 | 38.21 |
| ATOM | 448 | CG | GLN | 102 | 18.677 | 34.810 | 35.127 | 1.00 | 46.24 |
| ATOM | 449 | CD | GLN | 102 | 18.370 | 36.155 | 34.499 | 1.00 | 53.54 |
| ATOM | 450 | OE1 | GLN | 102 | 17.557 | 36.256 | 33.576 | 1.00 | 57.22 |
| ATOM | 451 | NE2 | GLN | 102 | 19.020 | 37.198 | 34.995 | 1.00 | 56.50 |
| ATOM | 452 | C | GLN | 102 | 18.988 | 31.262 | 33.632 | 1.00 | 29.06 |
| ATOM | 453 | O | GLN | 102 | 17.861 | 30.790 | 33.505 | 1.00 | 29.64 |
| ATOM | 454 | N | THR | 103 | 20.013 | 30.867 | 32.882 | 1.00 | 30.36 |
| ATOM | 455 | CA | THR | 103 | 19.837 | 29.822 | 31.872 | 1.00 | 25.82 |
| ATOM | 456 | CB | THR | 103 | 21.054 | 29.725 | 30.920 | 1.00 | 27.64 |

FIGURE 1A-10

| | | | | | | | | |
|---|---|---|---|---|---|---|---|---|
| ATOM | 457 | OG1 | THR | 103 | 21.422 | 31.033 | 30.460 | 1.00 27.46 |
| ATOM | 458 | CG2 | THR | 103 | 20.714 | 28.852 | 29.727 | 1.00 27.03 |
| ATOM | 459 | C | THR | 103 | 19.664 | 28.502 | 32.612 | 1.00 21.35 |
| ATOM | 460 | O | THR | 103 | 18.625 | 27.849 | 32.515 | 1.00 21.08 |
| ATOM | 461 | N | HIS | 104 | 20.667 | 28.158 | 33.409 | 1.00 18.46 |
| ATOM | 462 | CA | HIS | 104 | 20.649 | 26.939 | 34.204 | 1.00 20.81 |
| ATOM | 463 | CB | HIS | 104 | 21.962 | 26.803 | 34.964 | 1.00 19.92 |
| ATOM | 464 | CG | HIS | 104 | 23.006 | 26.042 | 34.216 | 1.00 20.28 |
| ATOM | 465 | CD2 | HIS | 104 | 22.920 | 25.237 | 33.137 | 1.00 22.34 |
| ATOM | 466 | ND1 | HIS | 104 | 24.330 | 26.013 | 34.612 | 1.00 26.15 |
| ATOM | 467 | CE1 | HIS | 104 | 25.008 | 25.216 | 33.804 | 1.00 31.72 |
| ATOM | 468 | NE2 | HIS | 104 | 24.174 | 24.731 | 32.901 | 1.00 28.63 |
| ATOM | 469 | C | HIS | 104 | 19.475 | 26.892 | 35.179 | 1.00 20.80 |
| ATOM | 470 | O | HIS | 104 | 18.954 | 25.819 | 35.475 | 1.00 24.70 |
| ATOM | 471 | N | ALA | 105 | 19.025 | 28.067 | 35.607 | 1.00 18.31 |
| ATOM | 472 | CA | ALA | 105 | 17.919 | 28.194 | 36.548 | 1.00 17.66 |
| ATOM | 473 | CB | ALA | 105 | 17.927 | 29.575 | 37.183 | 1.00 14.86 |
| ATOM | 474 | C | ALA | 105 | 16.591 | 27.939 | 35.870 | 1.00 14.51 |
| ATOM | 475 | O | ALA | 105 | 15.733 | 27.239 | 36.411 | 1.00 17.60 |
| ATOM | 476 | N | LYS | 106 | 16.430 | 28.499 | 34.677 | 1.00 16.85 |
| ATOM | 477 | CA | LYS | 106 | 15.213 | 28.339 | 33.898 | 1.00 18.12 |
| ATOM | 478 | CB | LYS | 106 | 15.279 | 29.232 | 32.658 | 1.00 24.32 |
| ATOM | 479 | CG | LYS | 106 | 14.080 | 29.115 | 31.737 | 1.00 34.17 |
| ATOM | 480 | CD | LYS | 106 | 12.798 | 29.489 | 32.450 | 1.00 40.94 |
| ATOM | 481 | CE | LYS | 106 | 11.571 | 28.936 | 31.735 | 1.00 50.20 |
| ATOM | 482 | NZ | LYS | 106 | 10.333 | 29.575 | 32.255 | 1.00 57.20 |
| ATOM | 483 | C | LYS | 106 | 15.089 | 26.873 | 33.495 | 1.00 17.85 |
| ATOM | 484 | O | LYS | 106 | 14.003 | 26.290 | 33.564 | 1.00 17.04 |
| ATOM | 485 | N | ARG | 107 | 16.227 | 26.284 | 33.128 | 1.00 17.13 |
| ATOM | 486 | CA | ARG | 107 | 16.321 | 24.886 | 32.716 | 1.00 22.93 |
| ATOM | 487 | CB | ARG | 107 | 17.763 | 24.548 | 32.315 | 1.00 26.21 |
| ATOM | 488 | CG | ARG | 107 | 17.945 | 23.136 | 31.769 | 1.00 35.27 |
| ATOM | 489 | CD | ARG | 107 | 18.494 | 23.158 | 30.352 | 1.00 44.47 |
| ATOM | 490 | NE | ARG | 107 | 18.104 | 21.972 | 29.589 | 1.00 48.78 |
| ATOM | 491 | CZ | ARG | 107 | 18.037 | 21.919 | 28.259 | 1.00 52.31 |
| ATOM | 492 | NH1 | ARG | 107 | 18.339 | 22.980 | 27.521 | 1.00 57.96 |
| ATOM | 493 | NH2 | ARG | 107 | 17.630 | 20.808 | 27.658 | 1.00 51.77 |
| ATOM | 494 | C | ARG | 107 | 15.892 | 23.950 | 33.834 | 1.00 23.51 |
| ATOM | 495 | O | ARG | 107 | 14.971 | 23.144 | 33.656 | 1.00 24.03 |
| ATOM | 496 | N | ALA | 108 | 16.562 | 24.068 | 34.982 | 1.00 21.43 |
| ATOM | 497 | CA | ALA | 108 | 16.291 | 23.241 | 36.155 | 1.00 17.28 |
| ATOM | 498 | CB | ALA | 108 | 17.198 | 23.651 | 37.295 | 1.00 14.49 |
| ATOM | 499 | C | ALA | 108 | 14.840 | 23.329 | 36.601 | 1.00 15.02 |
| ATOM | 500 | O | ALA | 108 | 14.176 | 22.315 | 36.782 | 1.00 17.29 |
| ATOM | 501 | N | TYR | 109 | 14.339 | 24.550 | 36.730 | 1.00 18.02 |
| ATOM | 502 | CA | TYR | 109 | 12.980 | 24.789 | 37.178 | 1.00 16.48 |
| ATOM | 503 | CB | TYR | 109 | 12.740 | 26.297 | 37.363 | 1.00 16.97 |
| ATOM | 504 | CG | TYR | 109 | 11.356 | 26.633 | 37.861 | 1.00 18.32 |
| ATOM | 505 | CD1 | TYR | 109 | 10.973 | 26.339 | 39.166 | 1.00 17.84 |
| ATOM | 506 | CE1 | TYR | 109 | 9.687 | 26.597 | 39.612 | 1.00 19.35 |
| ATOM | 507 | CD2 | TYR | 109 | 10.411 | 27.203 | 37.016 | 1.00 17.80 |

FIGURE 1A-11

| ATOM | 508 | CE2 | TYR | 109 | 9.124 | 27.463 | 37.464 | 1.00 | 20.38 |
|---|---|---|---|---|---|---|---|---|---|
| ATOM | 509 | CZ | TYR | 109 | 8.772 | 27.155 | 38.758 | 1.00 | 17.34 |
| ATOM | 510 | OH | TYR | 109 | 7.494 | 27.402 | 39.187 | 1.00 | 27.48 |
| ATOM | 511 | C | TYR | 109 | 11.947 | 24.185 | 36.242 | 1.00 | 16.14 |
| ATOM | 512 | O | TYR | 109 | 10.962 | 23.613 | 36.694 | 1.00 | 18.04 |
| ATOM | 513 | N | ARG | 110 | 12.176 | 24.317 | 34.939 | 1.00 | 23.44 |
| ATOM | 514 | CA | ARG | 110 | 11.267 | 23.795 | 33.919 | 1.00 | 24.04 |
| ATOM | 515 | CB | ARG | 110 | 11.612 | 24.402 | 32.558 | 1.00 | 23.89 |
| ATOM | 516 | CG | ARG | 110 | 10.638 | 24.054 | 31.452 | 1.00 | 28.47 |
| ATOM | 517 | CD | ARG | 110 | 10.740 | 25.035 | 30.285 | 1.00 | 36.55 |
| ATOM | 518 | NE | ARG | 110 | 10.185 | 24.464 | 29.063 | 1.00 | 33.27 |
| ATOM | 519 | CZ | ARG | 110 | 10.917 | 23.917 | 28.099 | 1.00 | 31.44 |
| ATOM | 520 | NH1 | ARG | 110 | 12.238 | 23.882 | 28.197 | 1.00 | 27.27 |
| ATOM | 521 | NH2 | ARG | 110 | 10.323 | 23.343 | 27.067 | 1.00 | 35.05 |
| ATOM | 522 | C | ARG | 110 | 11.234 | 22.266 | 33.837 | 1.00 | 21.17 |
| ATOM | 523 | O | ARG | 110 | 10.164 | 21.673 | 33.710 | 1.00 | 22.40 |
| ATOM | 524 | N | GLU | 111 | 12.400 | 21.629 | 33.875 | 1.00 | 21.81 |
| ATOM | 525 | CA | GLU | 111 | 12.478 | 20.167 | 33.832 | 1.00 | 31.14 |
| ATOM | 526 | CB | GLU | 111 | 13.931 | 19.703 | 33.839 | 1.00 | 35.59 |
| ATOM | 527 | CG | GLU | 111 | 14.708 | 20.021 | 32.584 | 1.00 | 44.96 |
| ATOM | 528 | CD | GLU | 111 | 16.070 | 19.347 | 32.571 | 1.00 | 52.92 |
| ATOM | 529 | OE1 | GLU | 111 | 16.779 | 19.386 | 33.609 | 1.00 | 54.09 |
| ATOM | 530 | OE2 | GLU | 111 | 16.430 | 18.765 | 31.527 | 1.00 | 52.37 |
| ATOM | 531 | C | GLU | 111 | 11.791 | 19.556 | 35.049 | 1.00 | 32.80 |
| ATOM | 532 | O | GLU | 111 | 11.070 | 18.562 | 34.946 | 1.00 | 33.10 |
| ATOM | 533 | N | LEU | 112 | 12.015 | 20.188 | 36.196 | 1.00 | 33.59 |
| ATOM | 534 | CA | LEU | 112 | 11.481 | 19.768 | 37.480 | 1.00 | 30.16 |
| ATOM | 535 | CB | LEU | 112 | 12.018 | 20.718 | 38.551 | 1.00 | 30.32 |
| ATOM | 536 | CG | LEU | 112 | 12.069 | 20.345 | 40.025 | 1.00 | 34.22 |
| ATOM | 537 | CD1 | LEU | 112 | 12.781 | 19.020 | 40.200 | 1.00 | 34.51 |
| ATOM | 538 | CD2 | LEU | 112 | 12.808 | 21.449 | 40.777 | 1.00 | 36.94 |
| ATOM | 539 | C | LEU | 112 | 9.958 | 19.786 | 37.473 | 1.00 | 29.61 |
| ATOM | 540 | O | LEU | 112 | 9.326 | 18.866 | 37.974 | 1.00 | 31.49 |
| ATOM | 541 | N | VAL | 113 | 9.375 | 20.827 | 36.886 | 1.00 | 30.73 |
| ATOM | 542 | CA | VAL | 113 | 7.925 | 20.978 | 36.814 | 1.00 | 30.87 |
| ATOM | 543 | CB | VAL | 113 | 7.531 | 22.439 | 36.420 | 1.00 | 30.41 |
| ATOM | 544 | CG1 | VAL | 113 | 6.017 | 22.581 | 36.315 | 1.00 | 26.67 |
| ATOM | 545 | CG2 | VAL | 113 | 8.085 | 23.427 | 37.442 | 1.00 | 28.70 |
| ATOM | 546 | C | VAL | 113 | 7.285 | 20.014 | 35.810 | 1.00 | 31.53 |
| ATOM | 547 | O | VAL | 113 | 6.202 | 19.470 | 36.048 | 1.00 | 35.01 |
| ATOM | 548 | N | LEU | 114 | 7.981 | 19.773 | 34.706 | 1.00 | 27.72 |
| ATOM | 549 | CA | LEU | 114 | 7.465 | 18.899 | 33.669 | 1.00 | 25.16 |
| ATOM | 550 | CB | LEU | 114 | 8.040 | 19.314 | 32.315 | 1.00 | 22.40 |
| ATOM | 551 | CG | LEU | 114 | 7.666 | 20.752 | 31.956 | 1.00 | 11.71 |
| ATOM | 552 | CD1 | LEU | 114 | 8.541 | 21.262 | 30.849 | 1.00 | 12.01 |
| ATOM | 553 | CD2 | LEU | 114 | 6.194 | 20.832 | 31.599 | 1.00 | 7.52 |
| ATOM | 554 | C | LEU | 114 | 7.681 | 17.417 | 33.935 | 1.00 | 24.42 |
| ATOM | 555 | O | LEU | 114 | 6.793 | 16.605 | 33.677 | 1.00 | 24.15 |
| ATOM | 556 | N | MET | 115 | 8.828 | 17.063 | 34.500 | 1.00 | 22.99 |
| ATOM | 557 | CA | MET | 115 | 9.099 | 15.664 | 34.783 | 1.00 | 24.82 |
| ATOM | 558 | CB | MET | 115 | 10.520 | 15.482 | 35.313 | 1.00 | 30.46 |

FIGURE 1A-12

| | | | | | | | | | |
|---|---|---|---|---|---|---|---|---|---|
| ATOM | 559 | CG | MET | 115 | 11.453 | 14.767 | 34.349 | 1.00 | 31.53 |
| ATOM | 560 | SD | MET | 115 | 13.083 | 14.457 | 35.064 | 1.00 | 36.11 |
| ATOM | 561 | CE | MET | 115 | 13.786 | 16.077 | 34.959 | 1.00 | 29.19 |
| ATOM | 562 | C | MET | 115 | 8.086 | 15.123 | 35.785 | 1.00 | 28.99 |
| ATOM | 563 | O | MET | 115 | 7.945 | 13.911 | 35.944 | 1.00 | 29.42 |
| ATOM | 564 | N | LYS | 116 | 7.367 | 16.038 | 36.435 | 1.00 | 32.30 |
| ATOM | 565 | CA | LYS | 116 | 6.355 | 15.685 | 37.418 | 1.00 | 33.86 |
| ATOM | 566 | CB | LYS | 116 | 6.342 | 16.696 | 38.571 | 1.00 | 35.45 |
| ATOM | 567 | CG | LYS | 116 | 7.574 | 16.676 | 39.462 | 1.00 | 32.83 |
| ATOM | 568 | CD | LYS | 116 | 7.517 | 17.807 | 40.462 | 1.00 | 33.93 |
| ATOM | 569 | CE | LYS | 116 | 8.729 | 17.797 | 41.375 | 1.00 | 38.19 |
| ATOM | 570 | NZ | LYS | 116 | 8.730 | 18.964 | 42.304 | 1.00 | 41.76 |
| ATOM | 571 | C | LYS | 116 | 4.972 | 15.613 | 36.788 | 1.00 | 35.82 |
| ATOM | 572 | O | LYS | 116 | 4.199 | 14.697 | 37.076 | 1.00 | 39.00 |
| ATOM | 573 | N | CYS | 117 | 4.661 | 16.570 | 35.919 | 1.00 | 34.29 |
| ATOM | 574 | CA | CYS | 117 | 3.356 | 16.588 | 35.278 | 1.00 | 37.16 |
| ATOM | 575 | CB | CYS | 117 | 2.965 | 18.013 | 34.883 | 1.00 | 34.35 |
| ATOM | 576 | SG | CYS | 117 | 4.121 | 18.807 | 33.773 | 1.00 | 47.57 |
| ATOM | 577 | C | CYS | 117 | 3.239 | 15.643 | 34.081 | 1.00 | 39.87 |
| ATOM | 578 | O | CYS | 117 | 2.290 | 14.864 | 34.014 | 1.00 | 45.72 |
| ATOM | 579 | N | VAL | 118 | 4.201 | 15.687 | 33.154 | 1.00 | 38.93 |
| ATOM | 580 | CA | VAL | 118 | 4.173 | 14.826 | 31.968 | 1.00 | 29.45 |
| ATOM | 581 | CB | VAL | 118 | 5.334 | 15.125 | 30.987 | 1.00 | 31.96 |
| ATOM | 582 | CG1 | VAL | 118 | 5.258 | 14.204 | 29.772 | 1.00 | 28.88 |
| ATOM | 583 | CG2 | VAL | 118 | 5.285 | 16.578 | 30.536 | 1.00 | 34.87 |
| ATOM | 584 | C | VAL | 118 | 4.258 | 13.378 | 32.398 | 1.00 | 30.47 |
| ATOM | 585 | O | VAL | 118 | 5.123 | 13.003 | 33.190 | 1.00 | 30.36 |
| ATOM | 586 | N | ASN | 119 | 3.388 | 12.553 | 31.828 | 1.00 | 31.17 |
| ATOM | 587 | CA | ASN | 119 | 3.322 | 11.138 | 32.170 | 1.00 | 33.20 |
| ATOM | 588 | CB | ASN | 119 | 2.094 | 10.928 | 33.066 | 1.00 | 38.32 |
| ATOM | 589 | CG | ASN | 119 | 1.944 | 9.501 | 33.527 | 1.00 | 44.29 |
| ATOM | 590 | OD1 | ASN | 119 | 2.933 | 8.822 | 33.823 | 1.00 | 44.25 |
| ATOM | 591 | ND2 | ASN | 119 | 0.692 | 9.033 | 33.604 | 1.00 | 49.51 |
| ATOM | 592 | C | ASN | 119 | 3.234 | 10.246 | 30.930 | 1.00 | 28.70 |
| ATOM | 593 | O | ASN | 119 | 2.137 | 9.888 | 30.503 | 1.00 | 28.33 |
| ATOM | 594 | N | HIS | 120 | 4.378 | 9.869 | 30.365 | 1.00 | 24.94 |
| ATOM | 595 | CA | HIS | 120 | 4.396 | 9.026 | 29.172 | 1.00 | 16.81 |
| ATOM | 596 | CB | HIS | 120 | 4.528 | 9.890 | 27.924 | 1.00 | 23.29 |
| ATOM | 597 | CG | HIS | 120 | 4.280 | 9.149 | 26.638 | 1.00 | 26.02 |
| ATOM | 598 | CD2 | HIS | 120 | 5.120 | 8.725 | 25.676 | 1.00 | 21.14 |
| ATOM | 599 | ND1 | HIS | 120 | 3.012 | 8.773 | 26.240 | 1.00 | 25.65 |
| ATOM | 600 | CE1 | HIS | 120 | 3.093 | 8.150 | 25.081 | 1.00 | 24.08 |
| ATOM | 601 | NE2 | HIS | 120 | 4.358 | 8.105 | 24.711 | 1.00 | 21.68 |
| ATOM | 602 | C | HIS | 120 | 5.558 | 8.044 | 29.235 | 1.00 | 21.15 |
| ATOM | 603 | O | HIS | 120 | 6.639 | 8.393 | 29.704 | 1.00 | 18.90 |
| ATOM | 604 | N | LYS | 121 | 5.356 | 6.846 | 28.680 | 1.00 | 19.16 |
| ATOM | 605 | CA | LYS | 121 | 6.377 | 5.803 | 28.696 | 1.00 | 17.60 |
| ATOM | 606 | CB | LYS | 121 | 5.788 | 4.462 | 28.244 | 1.00 | 22.87 |
| ATOM | 607 | CG | LYS | 121 | 5.266 | 4.469 | 26.819 | 1.00 | 30.39 |
| ATOM | 608 | CD | LYS | 121 | 4.419 | 3.255 | 26.501 | 1.00 | 36.20 |
| ATOM | 609 | CE | LYS | 121 | 5.249 | 1.989 | 26.330 | 1.00 | 38.19 |

FIGURE 1A-13

| ATOM | 610 | NZ | LYS | 121 | 4.365 | 0.825 | 26.027 | 1.00 | 37.63 |
| --- | --- | --- | --- | --- | --- | --- | --- | --- | --- |
| ATOM | 611 | C | LYS | 121 | 7.630 | 6.114 | 27.888 | 1.00 | 16.98 |
| ATOM | 612 | O | LYS | 121 | 8.655 | 5.464 | 28.073 | 1.00 | 19.26 |
| ATOM | 613 | N | ASN | 122 | 7.568 | 7.117 | 27.013 | 1.00 | 16.98 |
| ATOM | 614 | CA | ASN | 122 | 8.737 | 7.477 | 26.214 | 1.00 | 17.50 |
| ATOM | 615 | CB | ASN | 122 | 8.403 | 7.501 | 24.726 | 1.00 | 14.49 |
| ATOM | 616 | CG | ASN | 122 | 7.952 | 6.154 | 24.224 | 1.00 | 10.30 |
| ATOM | 617 | OD1 | ASN | 122 | 6.789 | 5.968 | 23.878 | 1.00 | 7.13 |
| ATOM | 618 | ND2 | ASN | 122 | 8.854 | 5.179 | 24.262 | 1.00 | 4.91 |
| ATOM | 619 | C | ASN | 122 | 9.409 | 8.766 | 26.646 | 1.00 | 18.71 |
| ATOM | 620 | O | ASN | 122 | 10.280 | 9.286 | 25.932 | 1.00 | 18.12 |
| ATOM | 621 | N | ILE | 123 | 8.997 | 9.279 | 27.808 | 1.00 | 15.69 |
| ATOM | 622 | CA | ILE | 123 | 9.570 | 10.487 | 28.399 | 1.00 | 13.54 |
| ATOM | 623 | CB | ILE | 123 | 8.554 | 11.662 | 28.520 | 1.00 | 14.27 |
| ATOM | 624 | CG2 | ILE | 123 | 9.226 | 12.830 | 29.268 | 1.00 | 11.05 |
| ATOM | 625 | CG1 | ILE | 123 | 8.021 | 12.105 | 27.149 | 1.00 | 3.83 |
| ATOM | 626 | CD1 | ILE | 123 | 9.072 | 12.723 | 26.270 | 1.00 | 6.90 |
| ATOM | 627 | C | ILE | 123 | 9.988 | 10.106 | 29.823 | 1.00 | 14.09 |
| ATOM | 628 | O | ILE | 123 | 9.149 | 9.735 | 30.650 | 1.00 | 16.47 |
| ATOM | 629 | N | ILE | 124 | 11.275 | 10.256 | 30.119 | 1.00 | 13.88 |
| ATOM | 630 | CA | ILE | 124 | 11.838 | 9.915 | 31.425 | 1.00 | 16.33 |
| ATOM | 631 | CB | ILE | 124 | 13.277 | 10.460 | 31.577 | 1.00 | 16.46 |
| ATOM | 632 | CG2 | ILE | 124 | 13.260 | 11.918 | 31.998 | 1.00 | 11.54 |
| ATOM | 633 | CG1 | ILE | 124 | 14.075 | 9.600 | 32.550 | 1.00 | 13.70 |
| ATOM | 634 | CD1 | ILE | 124 | 14.319 | 8.189 | 32.041 | 1.00 | 18.40 |
| ATOM | 635 | C | ILE | 124 | 10.981 | 10.408 | 32.579 | 1.00 | 19.52 |
| ATOM | 636 | O | ILE | 124 | 10.467 | 11.531 | 32.564 | 1.00 | 14.73 |
| ATOM | 637 | N | SER | 125 | 10.750 | 9.508 | 33.533 | 1.00 | 23.81 |
| ATOM | 638 | CA | SER | 125 | 9.956 | 9.813 | 34.721 | 1.00 | 25.13 |
| ATOM | 639 | CB | SER | 125 | 9.018 | 8.648 | 35.077 | 1.00 | 30.70 |
| ATOM | 640 | OG | SER | 125 | 7.846 | 8.644 | 34.282 | 1.00 | 35.87 |
| ATOM | 641 | C | SER | 125 | 10.836 | 10.124 | 35.918 | 1.00 | 19.31 |
| ATOM | 642 | O | SER | 125 | 11.935 | 9.590 | 36.067 | 1.00 | 22.94 |
| ATOM | 643 | N | LEU | 126 | 10.338 | 11.007 | 36.769 | 1.00 | 19.68 |
| ATOM | 644 | CA | LEU | 126 | 11.045 | 11.400 | 37.978 | 1.00 | 16.45 |
| ATOM | 645 | CB | LEU | 126 | 10.787 | 12.884 | 38.245 | 1.00 | 12.14 |
| ATOM | 646 | CG | LEU | 126 | 11.615 | 13.662 | 39.258 | 1.00 | 12.00 |
| ATOM | 647 | CD1 | LEU | 126 | 13.078 | 13.687 | 38.847 | 1.00 | 10.46 |
| ATOM | 648 | CD2 | LEU | 126 | 11.058 | 15.077 | 39.360 | 1.00 | 16.58 |
| ATOM | 649 | C | LEU | 126 | 10.477 | 10.535 | 39.109 | 1.00 | 15.49 |
| ATOM | 650 | O | LEU | 126 | 9.258 | 10.397 | 39.250 | 1.00 | 18.64 |
| ATOM | 651 | N | LEU | 127 | 11.354 | 9.894 | 39.870 | 1.00 | 12.91 |
| ATOM | 652 | CA | LEU | 127 | 10.904 | 9.055 | 40.972 | 1.00 | 15.12 |
| ATOM | 653 | CB | LEU | 127 | 11.754 | 7.788 | 41.067 | 1.00 | 11.61 |
| ATOM | 654 | CG | LEU | 127 | 11.969 | 6.916 | 39.835 | 1.00 | 18.63 |
| ATOM | 655 | CD1 | LEU | 127 | 12.785 | 5.691 | 40.251 | 1.00 | 15.81 |
| ATOM | 656 | CD2 | LEU | 127 | 10.633 | 6.515 | 39.227 | 1.00 | 14.19 |
| ATOM | 657 | C | LEU | 127 | 10.955 | 9.778 | 42.314 | 1.00 | 13.38 |
| ATOM | 658 | O | LEU | 127 | 10.044 | 9.635 | 43.128 | 1.00 | 11.61 |
| ATOM | 659 | N | ASN | 128 | 11.985 | 10.594 | 42.515 | 1.00 | 10.66 |
| ATOM | 660 | CA | ASN | 128 | 12.157 | 11.287 | 43.784 | 1.00 | 15.93 |

FIGURE 1A-14

| ATOM | 661 | CB  | ASN | 128 | 12.838 | 10.319 | 44.760 | 1.00 | 13.66 |
|------|-----|-----|-----|-----|--------|--------|--------|------|-------|
| ATOM | 662 | CG  | ASN | 128 | 12.819 | 10.801 | 46.192 | 1.00 |  6.15 |
| ATOM | 663 | OD1 | ASN | 128 | 11.866 | 11.430 | 46.638 | 1.00 | 10.96 |
| ATOM | 664 | ND2 | ASN | 128 | 13.866 | 10.483 | 46.929 | 1.00 | 10.24 |
| ATOM | 665 | C   | ASN | 128 | 13.012 | 12.538 | 43.615 | 1.00 | 15.39 |
| ATOM | 666 | O   | ASN | 128 | 13.917 | 12.559 | 42.787 | 1.00 | 20.43 |
| ATOM | 667 | N   | VAL | 129 | 12.707 | 13.587 | 44.377 | 1.00 | 14.58 |
| ATOM | 668 | CA  | VAL | 129 | 13.491 | 14.823 | 44.332 | 1.00 | 13.07 |
| ATOM | 669 | CB  | VAL | 129 | 12.698 | 16.048 | 43.863 | 1.00 | 13.20 |
| ATOM | 670 | CG1 | VAL | 129 | 13.683 | 17.150 | 43.491 | 1.00 | 12.16 |
| ATOM | 671 | CG2 | VAL | 129 | 11.784 | 15.705 | 42.703 | 1.00 | 20.18 |
| ATOM | 672 | C   | VAL | 129 | 13.943 | 15.149 | 45.742 | 1.00 | 11.95 |
| ATOM | 673 | O   | VAL | 129 | 13.208 | 14.933 | 46.705 | 1.00 | 16.13 |
| ATOM | 674 | N   | PHE | 130 | 15.143 | 15.684 | 45.875 | 1.00 | 13.56 |
| ATOM | 675 | CA  | PHE | 130 | 15.620 | 16.017 | 47.196 | 1.00 | 16.06 |
| ATOM | 676 | CB  | PHE | 130 | 15.876 | 14.738 | 48.007 | 1.00 |  4.31 |
| ATOM | 677 | CG  | PHE | 130 | 17.044 | 13.922 | 47.512 | 1.00 |  4.25 |
| ATOM | 678 | CD1 | PHE | 130 | 16.844 | 12.847 | 46.648 | 1.00 |  2.00 |
| ATOM | 679 | CD2 | PHE | 130 | 18.330 | 14.206 | 47.938 | 1.00 |  2.00 |
| ATOM | 680 | CE1 | PHE | 130 | 17.903 | 12.069 | 46.208 | 1.00 |  2.00 |
| ATOM | 681 | CE2 | PHE | 130 | 19.408 | 13.436 | 47.510 | 1.00 |  8.96 |
| ATOM | 682 | CZ  | PHE | 130 | 19.195 | 12.358 | 46.638 | 1.00 |  2.00 |
| ATOM | 683 | C   | PHE | 130 | 16.855 | 16.897 | 47.204 | 1.00 | 17.06 |
| ATOM | 684 | O   | PHE | 130 | 17.589 | 16.998 | 46.210 | 1.00 | 11.31 |
| ATOM | 685 | N   | THR | 131 | 17.041 | 17.543 | 48.356 | 1.00 | 16.62 |
| ATOM | 686 | CA  | THR | 131 | 18.164 | 18.416 | 48.634 | 1.00 |  9.93 |
| ATOM | 687 | CB  | THR | 131 | 17.769 | 19.926 | 48.586 | 1.00 | 13.86 |
| ATOM | 688 | OG1 | THR | 131 | 18.866 | 20.728 | 49.045 | 1.00 | 15.79 |
| ATOM | 689 | CG2 | THR | 131 | 16.546 | 20.217 | 49.455 | 1.00 |  8.11 |
| ATOM | 690 | C   | THR | 131 | 18.646 | 18.099 | 50.040 | 1.00 | 12.47 |
| ATOM | 691 | O   | THR | 131 | 17.846 | 17.906 | 50.951 | 1.00 | 11.03 |
| ATOM | 692 | N   | PRO | 132 | 19.956 | 17.922 | 50.205 | 1.00 | 10.61 |
| ATOM | 693 | CD  | PRO | 132 | 20.946 | 17.707 | 49.143 | 1.00 | 10.90 |
| ATOM | 694 | CA  | PRO | 132 | 20.531 | 17.630 | 51.517 | 1.00 | 11.58 |
| ATOM | 695 | CB  | PRO | 132 | 21.958 | 17.203 | 51.175 | 1.00 | 10.19 |
| ATOM | 696 | CG  | PRO | 132 | 22.238 | 17.895 | 49.881 | 1.00 | 11.71 |
| ATOM | 697 | C   | PRO | 132 | 20.516 | 18.846 | 52.460 | 1.00 | 14.09 |
| ATOM | 698 | O   | PRO | 132 | 20.712 | 18.700 | 53.661 | 1.00 | 16.09 |
| ATOM | 699 | N   | GLN | 133 | 20.289 | 20.043 | 51.926 | 1.00 | 18.69 |
| ATOM | 700 | CA  | GLN | 133 | 20.270 | 21.252 | 52.749 | 1.00 | 14.30 |
| ATOM | 701 | CB  | GLN | 133 | 20.729 | 22.466 | 51.951 | 1.00 | 12.30 |
| ATOM | 702 | CG  | GLN | 133 | 22.228 | 22.426 | 51.596 | 1.00 | 11.50 |
| ATOM | 703 | CD  | GLN | 133 | 22.538 | 21.651 | 50.318 | 1.00 | 20.05 |
| ATOM | 704 | OE1 | GLN | 133 | 23.599 | 21.037 | 50.193 | 1.00 | 23.45 |
| ATOM | 705 | NE2 | GLN | 133 | 21.622 | 21.698 | 49.352 | 1.00 | 17.39 |
| ATOM | 706 | C   | GLN | 133 | 18.906 | 21.467 | 53.377 | 1.00 | 16.11 |
| ATOM | 707 | O   | GLN | 133 | 17.886 | 21.259 | 52.734 | 1.00 |  8.26 |
| ATOM | 708 | N   | LYS | 134 | 18.908 | 21.866 | 54.652 | 1.00 | 25.02 |
| ATOM | 709 | CA  | LYS | 134 | 17.690 | 22.054 | 55.443 | 1.00 | 24.98 |
| ATOM | 710 | CB  | LYS | 134 | 17.995 | 21.862 | 56.937 | 1.00 | 29.58 |
| ATOM | 711 | CG  | LYS | 134 | 18.577 | 20.500 | 57.319 | 1.00 | 38.62 |

FIGURE 1A-15

| ATOM | 712 | CD  | LYS | 134 | 17.969 | 19.359 | 56.490 | 1.00 | 46.81 |
|------|-----|-----|-----|-----|--------|--------|--------|------|-------|
| ATOM | 713 | CE  | LYS | 134 | 18.078 | 18.013 | 57.185 | 1.00 | 50.25 |
| ATOM | 714 | NZ  | LYS | 134 | 16.874 | 17.749 | 58.040 | 1.00 | 53.63 |
| ATOM | 715 | C   | LYS | 134 | 16.907 | 23.339 | 55.267 | 1.00 | 26.18 |
| ATOM | 716 | O   | LYS | 134 | 15.693 | 23.357 | 55.476 | 1.00 | 30.14 |
| ATOM | 717 | N   | THR | 135 | 17.591 | 24.429 | 54.958 | 1.00 | 26.94 |
| ATOM | 718 | CA  | THR | 135 | 16.903 | 25.699 | 54.780 | 1.00 | 28.26 |
| ATOM | 719 | CB  | THR | 135 | 17.270 | 26.662 | 55.896 | 1.00 | 26.26 |
| ATOM | 720 | OG1 | THR | 135 | 18.697 | 26.729 | 56.014 | 1.00 | 25.42 |
| ATOM | 721 | CG2 | THR | 135 | 16.675 | 26.177 | 57.204 | 1.00 | 28.69 |
| ATOM | 722 | C   | THR | 135 | 17.167 | 26.359 | 53.437 | 1.00 | 29.44 |
| ATOM | 723 | O   | THR | 135 | 18.131 | 26.022 | 52.744 | 1.00 | 32.11 |
| ATOM | 724 | N   | LEU | 136 | 16.322 | 27.328 | 53.093 | 1.00 | 29.17 |
| ATOM | 725 | CA  | LEU | 136 | 16.449 | 28.065 | 51.843 | 1.00 | 28.84 |
| ATOM | 726 | CB  | LEU | 136 | 15.278 | 29.036 | 51.674 | 1.00 | 28.71 |
| ATOM | 727 | CG  | LEU | 136 | 15.302 | 30.012 | 50.490 | 1.00 | 28.07 |
| ATOM | 728 | CD1 | LEU | 136 | 15.475 | 29.269 | 49.182 | 1.00 | 22.20 |
| ATOM | 729 | CD2 | LEU | 136 | 14.011 | 30.810 | 50.471 | 1.00 | 33.32 |
| ATOM | 730 | C   | LEU | 136 | 17.773 | 28.811 | 51.793 | 1.00 | 28.87 |
| ATOM | 731 | O   | LEU | 136 | 18.339 | 28.995 | 50.722 | 1.00 | 31.87 |
| ATOM | 732 | N   | GLU | 137 | 18.278 | 29.209 | 52.957 | 1.00 | 30.59 |
| ATOM | 733 | CA  | GLU | 137 | 19.541 | 29.929 | 53.032 | 1.00 | 35.29 |
| ATOM | 734 | CB  | GLU | 137 | 19.694 | 30.638 | 54.389 | 1.00 | 38.82 |
| ATOM | 735 | CG  | GLU | 137 | 18.619 | 31.676 | 54.708 | 1.00 | 44.98 |
| ATOM | 736 | CD  | GLU | 137 | 17.420 | 31.078 | 55.413 | 1.00 | 49.68 |
| ATOM | 737 | OE1 | GLU | 137 | 17.388 | 31.103 | 56.665 | 1.00 | 53.88 |
| ATOM | 738 | OE2 | GLU | 137 | 16.512 | 30.579 | 54.718 | 1.00 | 48.95 |
| ATOM | 739 | C   | GLU | 137 | 20.739 | 29.017 | 52.790 | 1.00 | 34.30 |
| ATOM | 740 | O   | GLU | 137 | 21.739 | 29.427 | 52.193 | 1.00 | 33.76 |
| ATOM | 741 | N   | GLU | 138 | 20.641 | 27.781 | 53.260 | 1.00 | 34.25 |
| ATOM | 742 | CA  | GLU | 138 | 21.730 | 26.823 | 53.102 | 1.00 | 36.03 |
| ATOM | 743 | CB  | GLU | 138 | 21.656 | 25.786 | 54.212 | 1.00 | 43.43 |
| ATOM | 744 | CG  | GLU | 138 | 21.803 | 26.371 | 55.595 | 1.00 | 50.42 |
| ATOM | 745 | CD  | GLU | 138 | 21.624 | 25.319 | 56.662 | 1.00 | 53.11 |
| ATOM | 746 | OE1 | GLU | 138 | 22.645 | 24.728 | 57.082 | 1.00 | 53.73 |
| ATOM | 747 | OE2 | GLU | 138 | 20.464 | 25.076 | 57.067 | 1.00 | 50.34 |
| ATOM | 748 | C   | GLU | 138 | 21.717 | 26.119 | 51.751 | 1.00 | 31.96 |
| ATOM | 749 | O   | GLU | 138 | 22.746 | 25.597 | 51.302 | 1.00 | 28.48 |
| ATOM | 750 | N   | PHE | 139 | 20.534 | 26.113 | 51.136 | 1.00 | 32.06 |
| ATOM | 751 | CA  | PHE | 139 | 20.241 | 25.499 | 49.844 | 1.00 | 28.08 |
| ATOM | 752 | CB  | PHE | 139 | 18.893 | 26.016 | 49.352 | 1.00 | 22.92 |
| ATOM | 753 | CG  | PHE | 139 | 18.445 | 25.402 | 48.063 | 1.00 | 27.31 |
| ATOM | 754 | CD1 | PHE | 139 | 18.534 | 24.024 | 47.875 | 1.00 | 26.81 |
| ATOM | 755 | CD2 | PHE | 139 | 17.932 | 26.192 | 47.037 | 1.00 | 30.25 |
| ATOM | 756 | CE1 | PHE | 139 | 18.119 | 23.437 | 46.689 | 1.00 | 31.14 |
| ATOM | 757 | CE2 | PHE | 139 | 17.509 | 25.618 | 45.832 | 1.00 | 29.16 |
| ATOM | 758 | CZ  | PHE | 139 | 17.602 | 24.236 | 45.657 | 1.00 | 28.69 |
| ATOM | 759 | C   | PHE | 139 | 21.304 | 25.700 | 48.761 | 1.00 | 26.83 |
| ATOM | 760 | O   | PHE | 139 | 21.658 | 26.832 | 48.427 | 1.00 | 23.74 |
| ATOM | 761 | N   | GLN | 140 | 21.822 | 24.591 | 48.235 | 1.00 | 30.31 |
| ATOM | 762 | CA  | GLN | 140 | 22.851 | 24.620 | 47.197 | 1.00 | 30.50 |

FIGURE 1A-16

| ATOM | 763 | CB | GLN | 140 | 24.219 | 24.218 | 47.761 | 1.00 | 31.60 |
| ATOM | 764 | CG | GLN | 140 | 25.057 | 25.355 | 48.309 | 1.00 | 38.07 |
| ATOM | 765 | CD | GLN | 140 | 26.546 | 25.036 | 48.257 | 1.00 | 41.40 |
| ATOM | 766 | OE1 | GLN | 140 | 27.008 | 24.074 | 48.873 | 1.00 | 47.00 |
| ATOM | 767 | NE2 | GLN | 140 | 27.305 | 25.849 | 47.529 | 1.00 | 40.91 |
| ATOM | 768 | C | GLN | 140 | 22.547 | 23.690 | 46.037 | 1.00 | 29.73 |
| ATOM | 769 | O | GLN | 140 | 22.527 | 24.117 | 44.881 | 1.00 | 32.28 |
| ATOM | 770 | N | ASP | 141 | 22.311 | 22.418 | 46.360 | 1.00 | 28.02 |
| ATOM | 771 | CA | ASP | 141 | 22.078 | 21.392 | 45.349 | 1.00 | 18.82 |
| ATOM | 772 | CB | ASP | 141 | 23.071 | 20.257 | 45.558 | 1.00 | 14.74 |
| ATOM | 773 | CG | ASP | 141 | 24.469 | 20.740 | 45.874 | 1.00 | 13.03 |
| ATOM | 774 | OD1 | ASP | 141 | 25.048 | 20.227 | 46.847 | 1.00 | 19.94 |
| ATOM | 775 | OD2 | ASP | 141 | 25.011 | 21.619 | 45.170 | 1.00 | 12.40 |
| ATOM | 776 | C | ASP | 141 | 20.688 | 20.783 | 45.255 | 1.00 | 18.30 |
| ATOM | 777 | O | ASP | 141 | 19.875 | 20.888 | 46.177 | 1.00 | 22.17 |
| ATOM | 778 | N | VAL | 142 | 20.422 | 20.170 | 44.104 | 1.00 | 19.01 |
| ATOM | 779 | CA | VAL | 142 | 19.171 | 19.462 | 43.817 | 1.00 | 17.45 |
| ATOM | 780 | CB | VAL | 142 | 18.282 | 20.195 | 42.807 | 1.00 | 11.93 |
| ATOM | 781 | CG1 | VAL | 142 | 17.011 | 19.390 | 42.556 | 1.00 | 8.45 |
| ATOM | 782 | CG2 | VAL | 142 | 17.941 | 21.575 | 43.333 | 1.00 | 19.03 |
| ATOM | 783 | C | VAL | 142 | 19.546 | 18.110 | 43.234 | 1.00 | 13.89 |
| ATOM | 784 | O | VAL | 142 | 20.512 | 17.988 | 42.478 | 1.00 | 11.88 |
| ATOM | 785 | N | TYR | 143 | 18.806 | 17.085 | 43.640 | 1.00 | 16.32 |
| ATOM | 786 | CA | TYR | 143 | 19.065 | 15.724 | 43.183 | 1.00 | 13.43 |
| ATOM | 787 | CB | TYR | 143 | 19.455 | 14.830 | 44.351 | 1.00 | 10.06 |
| ATOM | 788 | CG | TYR | 143 | 20.845 | 15.093 | 44.851 | 1.00 | 6.33 |
| ATOM | 789 | CD1 | TYR | 143 | 21.110 | 16.167 | 45.698 | 1.00 | 6.88 |
| ATOM | 790 | CE1 | TYR | 143 | 22.398 | 16.438 | 46.127 | 1.00 | 2.00 |
| ATOM | 791 | CD2 | TYR | 143 | 21.909 | 14.296 | 44.458 | 1.00 | 2.00 |
| ATOM | 792 | CE2 | TYR | 143 | 23.197 | 14.573 | 44.890 | 1.00 | 7.27 |
| ATOM | 793 | CZ | TYR | 143 | 23.427 | 15.644 | 45.727 | 1.00 | 2.00 |
| ATOM | 794 | OH | TYR | 143 | 24.699 | 15.925 | 46.158 | 1.00 | 7.24 |
| ATOM | 795 | C | TYR | 143 | 17.861 | 15.150 | 42.498 | 1.00 | 12.75 |
| ATOM | 796 | O | TYR | 143 | 16.801 | 15.028 | 43.103 | 1.00 | 9.66 |
| ATOM | 797 | N | LEU | 144 | 18.010 | 14.858 | 41.211 | 1.00 | 16.62 |
| ATOM | 798 | CA | LEU | 144 | 16.923 | 14.286 | 40.438 | 1.00 | 14.20 |
| ATOM | 799 | CB | LEU | 144 | 16.918 | 14.863 | 39.018 | 1.00 | 18.91 |
| ATOM | 800 | CG | LEU | 144 | 16.790 | 16.375 | 38.862 | 1.00 | 19.87 |
| ATOM | 801 | CD1 | LEU | 144 | 16.909 | 16.736 | 37.391 | 1.00 | 24.50 |
| ATOM | 802 | CD2 | LEU | 144 | 15.463 | 16.863 | 39.422 | 1.00 | 20.28 |
| ATOM | 803 | C | LEU | 144 | 17.147 | 12.781 | 40.382 | 1.00 | 13.67 |
| ATOM | 804 | O | LEU | 144 | 18.237 | 12.319 | 40.023 | 1.00 | 8.53 |
| ATOM | 805 | N | VAL | 145 | 16.138 | 12.026 | 40.808 | 1.00 | 7.59 |
| ATOM | 806 | CA | VAL | 145 | 16.206 | 10.575 | 40.790 | 1.00 | 6.00 |
| ATOM | 807 | CB | VAL | 145 | 15.901 | 9.983 | 42.180 | 1.00 | 4.77 |
| ATOM | 808 | CG1 | VAL | 145 | 15.835 | 8.487 | 42.097 | 1.00 | 11.52 |
| ATOM | 809 | CG2 | VAL | 145 | 16.993 | 10.378 | 43.156 | 1.00 | 11.69 |
| ATOM | 810 | C | VAL | 145 | 15.237 | 10.042 | 39.746 | 1.00 | 6.88 |
| ATOM | 811 | O | VAL | 145 | 14.042 | 10.339 | 39.776 | 1.00 | 3.82 |
| ATOM | 812 | N | MET | 146 | 15.761 | 9.278 | 38.795 | 1.00 | 6.77 |
| ATOM | 813 | CA | MET | 146 | 14.935 | 8.729 | 37.716 | 1.00 | 12.80 |

FIGURE 1A-17

| | | | | | | | | |
|---|---|---|---|---|---|---|---|---|
| ATOM | 814 | CB | MET | 146 | 15.278 | 9.438 | 36.395 | 1.00 12.24 |
| ATOM | 815 | CG | MET | 146 | 15.576 | 10.923 | 36.513 | 1.00 13.09 |
| ATOM | 816 | SD | MET | 146 | 16.584 | 11.507 | 35.140 | 1.00 17.28 |
| ATOM | 817 | CE | MET | 146 | 18.229 | 11.220 | 35.764 | 1.00 6.80 |
| ATOM | 818 | C | MET | 146 | 15.208 | 7.240 | 37.522 | 1.00 9.74 |
| ATOM | 819 | O | MET | 146 | 16.184 | 6.698 | 38.029 | 1.00 8.35 |
| ATOM | 820 | N | GLU | 147 | 14.371 | 6.594 | 36.723 | 1.00 14.69 |
| ATOM | 821 | CA | GLU | 147 | 14.568 | 5.184 | 36.427 | 1.00 14.85 |
| ATOM | 822 | CB | GLU | 147 | 13.411 | 4.640 | 35.620 | 1.00 17.82 |
| ATOM | 823 | CG | GLU | 147 | 13.037 | 5.459 | 34.434 | 1.00 25.77 |
| ATOM | 824 | CD | GLU | 147 | 11.686 | 5.049 | 33.927 | 1.00 38.84 |
| ATOM | 825 | OE1 | GLU | 147 | 10.700 | 5.784 | 34.177 | 1.00 41.01 |
| ATOM | 826 | OE2 | GLU | 147 | 11.612 | 3.957 | 33.324 | 1.00 43.13 |
| ATOM | 827 | C | GLU | 147 | 15.853 | 5.057 | 35.647 | 1.00 10.32 |
| ATOM | 828 | O | GLU | 147 | 16.211 | 5.951 | 34.888 | 1.00 12.54 |
| ATOM | 829 | N | LEU | 148 | 16.570 | 3.965 | 35.874 | 1.00 11.99 |
| ATOM | 830 | CA | LEU | 148 | 17.842 | 3.734 | 35.211 | 1.00 14.42 |
| ATOM | 831 | CB | LEU | 148 | 18.784 | 2.964 | 36.138 | 1.00 9.01 |
| ATOM | 832 | CG | LEU | 148 | 20.212 | 2.730 | 35.650 | 1.00 6.85 |
| ATOM | 833 | CD1 | LEU | 148 | 20.966 | 4.050 | 35.580 | 1.00 6.22 |
| ATOM | 834 | CD2 | LEU | 148 | 20.916 | 1.773 | 36.595 | 1.00 8.02 |
| ATOM | 835 | C | LEU | 148 | 17.712 | 3.007 | 33.879 | 1.00 20.95 |
| ATOM | 836 | O | LEU | 148 | 17.060 | 1.963 | 33.766 | 1.00 24.70 |
| ATOM | 837 | N | MET | 149 | 18.323 | 3.610 | 32.865 | 1.00 21.81 |
| ATOM | 838 | CA | MET | 149 | 18.345 | 3.081 | 31.516 | 1.00 14.83 |
| ATOM | 839 | CB | MET | 149 | 18.040 | 4.187 | 30.515 | 1.00 17.66 |
| ATOM | 840 | CG | MET | 149 | 16.683 | 4.834 | 30.722 | 1.00 13.57 |
| ATOM | 841 | SD | MET | 149 | 15.314 | 3.699 | 30.520 | 1.00 19.54 |
| ATOM | 842 | CE | MET | 149 | 15.040 | 3.826 | 28.759 | 1.00 21.66 |
| ATOM | 843 | C | MET | 149 | 19.753 | 2.556 | 31.314 | 1.00 13.76 |
| ATOM | 844 | O | MET | 149 | 20.660 | 2.872 | 32.086 | 1.00 10.86 |
| ATOM | 845 | N | ASP | 150 | 19.964 | 1.796 | 30.248 | 1.00 10.35 |
| ATOM | 846 | CA | ASP | 150 | 21.277 | 1.223 | 30.048 | 1.00 9.93 |
| ATOM | 847 | CB | ASP | 150 | 21.135 | -0.188 | 29.516 | 1.00 14.68 |
| ATOM | 848 | CG | ASP | 150 | 20.135 | -0.990 | 30.303 | 1.00 21.37 |
| ATOM | 849 | OD1 | ASP | 150 | 19.145 | -1.459 | 29.713 | 1.00 24.03 |
| ATOM | 850 | OD2 | ASP | 150 | 20.320 | -1.128 | 31.531 | 1.00 30.81 |
| ATOM | 851 | C | ASP | 150 | 22.269 | 2.013 | 29.237 | 1.00 14.32 |
| ATOM | 852 | O | ASP | 150 | 23.473 | 1.810 | 29.407 | 1.00 13.42 |
| ATOM | 853 | N | ALA | 151 | 21.791 | 2.917 | 28.377 | 1.00 16.87 |
| ATOM | 854 | CA | ALA | 151 | 22.696 | 3.701 | 27.546 | 1.00 9.54 |
| ATOM | 855 | CB | ALA | 151 | 23.393 | 2.768 | 26.543 | 1.00 13.47 |
| ATOM | 856 | C | ALA | 151 | 22.087 | 4.872 | 26.793 | 1.00 10.16 |
| ATOM | 857 | O | ALA | 151 | 20.884 | 5.131 | 26.857 | 1.00 7.36 |
| ATOM | 858 | N | ASN | 152 | 22.970 | 5.529 | 26.043 | 1.00 14.20 |
| ATOM | 859 | CA | ASN | 152 | 22.690 | 6.682 | 25.179 | 1.00 18.79 |
| ATOM | 860 | CB | ASN | 152 | 23.979 | 7.471 | 24.991 | 1.00 16.64 |
| ATOM | 861 | CG | ASN | 152 | 23.922 | 8.824 | 25.590 | 1.00 20.82 |
| ATOM | 862 | OD1 | ASN | 152 | 24.963 | 9.399 | 25.907 | 1.00 25.78 |
| ATOM | 863 | ND2 | ASN | 152 | 22.716 | 9.363 | 25.759 | 1.00 19.24 |
| ATOM | 864 | C | ASN | 152 | 22.297 | 6.250 | 23.765 | 1.00 19.14 |

FIGURE 1A-18

| ATOM | 865 | O   | ASN | 152 | 22.513 | 5.108  | 23.364 | 1.00 | 16.29 |
|------|-----|-----|-----|-----|--------|--------|--------|------|-------|
| ATOM | 866 | N   | LEU | 153 | 21.786 | 7.198  | 22.986 | 1.00 | 19.51 |
| ATOM | 867 | CA  | LEU | 153 | 21.471 | 6.907  | 21.600 | 1.00 | 17.10 |
| ATOM | 868 | CB  | LEU | 153 | 20.446 | 7.885  | 21.039 | 1.00 | 19.12 |
| ATOM | 869 | CG  | LEU | 153 | 19.186 | 7.234  | 20.470 | 1.00 | 21.37 |
| ATOM | 870 | CD1 | LEU | 153 | 18.442 | 8.243  | 19.604 | 1.00 | 11.80 |
| ATOM | 871 | CD2 | LEU | 153 | 19.563 | 6.017  | 19.648 | 1.00 | 18.59 |
| ATOM | 872 | C   | LEU | 153 | 22.796 | 7.014  | 20.834 | 1.00 | 19.42 |
| ATOM | 873 | O   | LEU | 153 | 22.921 | 6.488  | 19.734 | 1.00 | 26.18 |
| ATOM | 874 | N   | CYS | 154 | 23.805 | 7.614  | 21.468 | 1.00 | 18.62 |
| ATOM | 875 | CA  | CYS | 154 | 25.132 | 7.773  | 20.878 | 1.00 | 19.92 |
| ATOM | 876 | CB  | CYS | 154 | 25.993 | 8.731  | 21.711 | 1.00 | 19.36 |
| ATOM | 877 | SG  | CYS | 154 | 25.469 | 10.472 | 21.823 | 1.00 | 24.19 |
| ATOM | 878 | C   | CYS | 154 | 25.837 | 6.421  | 20.823 | 1.00 | 23.80 |
| ATOM | 879 | O   | CYS | 154 | 26.665 | 6.172  | 19.942 | 1.00 | 27.37 |
| ATOM | 880 | N   | GLN | 155 | 25.526 | 5.572  | 21.799 | 1.00 | 25.88 |
| ATOM | 881 | CA  | GLN | 155 | 26.109 | 4.240  | 21.904 | 1.00 | 22.95 |
| ATOM | 882 | CB  | GLN | 155 | 25.972 | 3.733  | 23.337 | 1.00 | 29.14 |
| ATOM | 883 | CG  | GLN | 155 | 26.771 | 4.536  | 24.348 | 1.00 | 38.27 |
| ATOM | 884 | CD  | GLN | 155 | 26.356 | 4.244  | 25.778 | 1.00 | 42.71 |
| ATOM | 885 | OE1 | GLN | 155 | 25.778 | 5.097  | 26.453 | 1.00 | 42.62 |
| ATOM | 886 | NE2 | GLN | 155 | 26.649 | 3.034  | 26.248 | 1.00 | 43.79 |
| ATOM | 887 | C   | GLN | 155 | 25.399 | 3.290  | 20.959 | 1.00 | 21.22 |
| ATOM | 888 | O   | GLN | 155 | 25.978 | 2.313  | 20.494 | 1.00 | 21.08 |
| ATOM | 889 | N   | VAL | 156 | 24.137 | 3.594  | 20.682 | 1.00 | 17.67 |
| ATOM | 890 | CA  | VAL | 156 | 23.323 | 2.789  | 19.786 | 1.00 | 17.89 |
| ATOM | 891 | CB  | VAL | 156 | 21.807 | 3.032  | 20.057 | 1.00 | 15.35 |
| ATOM | 892 | CG1 | VAL | 156 | 20.951 | 2.295  | 19.054 | 1.00 | 12.62 |
| ATOM | 893 | CG2 | VAL | 156 | 21.447 | 2.608  | 21.486 | 1.00 | 11.91 |
| ATOM | 894 | C   | VAL | 156 | 23.676 | 3.156  | 18.332 | 1.00 | 21.00 |
| ATOM | 895 | O   | VAL | 156 | 23.574 | 2.326  | 17.437 | 1.00 | 26.45 |
| ATOM | 896 | N   | ILE | 157 | 24.155 | 4.380  | 18.123 | 1.00 | 21.26 |
| ATOM | 897 | CA  | ILE | 157 | 24.523 | 4.875  | 16.803 | 1.00 | 17.41 |
| ATOM | 898 | CB  | ILE | 157 | 24.708 | 6.430  | 16.820 | 1.00 | 15.18 |
| ATOM | 899 | CG2 | ILE | 157 | 25.734 | 6.885  | 15.788 | 1.00 | 14.77 |
| ATOM | 900 | CG1 | ILE | 157 | 23.362 | 7.112  | 16.545 | 1.00 | 12.44 |
| ATOM | 901 | CD1 | ILE | 157 | 23.268 | 8.544  | 17.031 | 1.00 | 2.00  |
| ATOM | 902 | C   | ILE | 157 | 25.789 | 4.178  | 16.337 | 1.00 | 22.21 |
| ATOM | 903 | O   | ILE | 157 | 25.954 | 3.904  | 15.140 | 1.00 | 24.52 |
| ATOM | 904 | N   | GLN | 158 | 26.648 | 3.834  | 17.293 | 1.00 | 22.13 |
| ATOM | 905 | CA  | GLN | 158 | 27.905 | 3.146  | 16.998 | 1.00 | 22.25 |
| ATOM | 906 | CB  | GLN | 158 | 28.848 | 3.240  | 18.197 | 1.00 | 27.33 |
| ATOM | 907 | CG  | GLN | 158 | 29.395 | 4.621  | 18.475 | 1.00 | 36.72 |
| ATOM | 908 | CD  | GLN | 158 | 30.279 | 4.641  | 19.705 | 1.00 | 40.66 |
| ATOM | 909 | OE1 | GLN | 158 | 31.244 | 3.879  | 19.805 | 1.00 | 40.25 |
| ATOM | 910 | NE2 | GLN | 158 | 29.955 | 5.517  | 20.651 | 1.00 | 45.49 |
| ATOM | 911 | C   | GLN | 158 | 27.733 | 1.672  | 16.609 | 1.00 | 20.29 |
| ATOM | 912 | O   | GLN | 158 | 28.723 | 0.957  | 16.445 | 1.00 | 23.68 |
| ATOM | 913 | N   | MET | 159 | 26.495 | 1.207  | 16.490 | 1.00 | 11.45 |
| ATOM | 914 | CA  | MET | 159 | 26.266 | -0.180 | 16.136 | 1.00 | 15.26 |
| ATOM | 915 | CB  | MET | 159 | 25.749 | -0.934 | 17.347 | 1.00 | 17.92 |

FIGURE 1A-19

| ATOM | 916 | CG  | MET | 159 | 24.424 | -0.437 | 17.855 | 1.00 | 15.71 |
| ATOM | 917 | SD  | MET | 159 | 24.108 | -1.018 | 19.506 | 1.00 | 28.81 |
| ATOM | 918 | CE  | MET | 159 | 22.751 | -2.047 | 19.181 | 1.00 | 21.54 |
| ATOM | 919 | C   | MET | 159 | 25.288 | -0.334 | 14.982 | 1.00 | 19.55 |
| ATOM | 920 | O   | MET | 159 | 24.513 |  0.574 | 14.684 | 1.00 | 23.40 |
| ATOM | 921 | N   | GLU | 160 | 25.365 | -1.468 | 14.296 | 1.00 | 18.11 |
| ATOM | 922 | CA  | GLU | 160 | 24.473 | -1.741 | 13.186 | 1.00 | 21.70 |
| ATOM | 923 | CB  | GLU | 160 | 25.063 | -2.803 | 12.260 | 1.00 | 23.55 |
| ATOM | 924 | CG  | GLU | 160 | 26.379 | -2.405 | 11.634 | 1.00 | 31.11 |
| ATOM | 925 | CD  | GLU | 160 | 26.735 | -3.216 | 10.402 | 1.00 | 36.84 |
| ATOM | 926 | OE1 | GLU | 160 | 26.400 | -4.420 | 10.352 | 1.00 | 37.17 |
| ATOM | 927 | OE2 | GLU | 160 | 27.356 | -2.640 |  9.484 | 1.00 | 40.60 |
| ATOM | 928 | C   | GLU | 160 | 23.158 | -2.232 | 13.735 | 1.00 | 21.51 |
| ATOM | 929 | O   | GLU | 160 | 23.107 | -3.254 | 14.398 | 1.00 | 31.06 |
| ATOM | 930 | N   | LEU | 161 | 22.104 | -1.466 | 13.501 | 1.00 | 25.53 |
| ATOM | 931 | CA  | LEU | 161 | 20.769 | -1.827 | 13.966 | 1.00 | 26.99 |
| ATOM | 932 | CB  | LEU | 161 | 20.013 | -0.570 | 14.410 | 1.00 | 28.33 |
| ATOM | 933 | CG  | LEU | 161 | 20.359 |  0.135 | 15.716 | 1.00 | 24.22 |
| ATOM | 934 | CD1 | LEU | 161 | 20.164 |  1.617 | 15.522 | 1.00 | 19.83 |
| ATOM | 935 | CD2 | LEU | 161 | 19.482 | -0.393 | 16.849 | 1.00 | 23.16 |
| ATOM | 936 | C   | LEU | 161 | 19.971 | -2.505 | 12.846 | 1.00 | 29.16 |
| ATOM | 937 | O   | LEU | 161 | 20.160 | -2.207 | 11.665 | 1.00 | 29.50 |
| ATOM | 938 | N   | ASP | 162 | 19.106 | -3.441 | 13.214 | 1.00 | 26.92 |
| ATOM | 939 | CA  | ASP | 162 | 18.274 | -4.099 | 12.226 | 1.00 | 25.75 |
| ATOM | 940 | CB  | ASP | 162 | 17.860 | -5.503 | 12.688 | 1.00 | 26.09 |
| ATOM | 941 | CG  | ASP | 162 | 17.355 | -5.530 | 14.113 | 1.00 | 21.29 |
| ATOM | 942 | OD1 | ASP | 162 | 16.120 | -5.563 | 14.312 | 1.00 | 18.43 |
| ATOM | 943 | OD2 | ASP | 162 | 18.199 | -5.536 | 15.032 | 1.00 | 25.29 |
| ATOM | 944 | C   | ASP | 162 | 17.057 | -3.211 | 12.016 | 1.00 | 24.69 |
| ATOM | 945 | O   | ASP | 162 | 16.790 | -2.345 | 12.834 | 1.00 | 28.26 |
| ATOM | 946 | N   | HIS | 163 | 16.308 | -3.439 | 10.943 | 1.00 | 22.18 |
| ATOM | 947 | CA  | HIS | 163 | 15.129 | -2.631 | 10.649 | 1.00 | 23.33 |
| ATOM | 948 | CB  | HIS | 163 | 14.538 | -3.017 |  9.290 | 1.00 | 27.89 |
| ATOM | 949 | CG  | HIS | 163 | 15.397 | -2.625 |  8.128 | 1.00 | 26.83 |
| ATOM | 950 | CD2 | HIS | 163 | 15.979 | -3.370 |  7.159 | 1.00 | 21.89 |
| ATOM | 951 | ND1 | HIS | 163 | 15.764 | -1.320 |  7.884 | 1.00 | 23.26 |
| ATOM | 952 | CE1 | HIS | 163 | 16.542 | -1.278 |  6.820 | 1.00 | 21.96 |
| ATOM | 953 | NE2 | HIS | 163 | 16.690 | -2.508 |  6.361 | 1.00 | 24.46 |
| ATOM | 954 | C   | HIS | 163 | 14.043 | -2.699 | 11.713 | 1.00 | 23.09 |
| ATOM | 955 | O   | HIS | 163 | 13.229 | -1.782 | 11.837 | 1.00 | 24.42 |
| ATOM | 956 | N   | GLU | 164 | 14.024 | -3.784 | 12.479 | 1.00 | 25.18 |
| ATOM | 957 | CA  | GLU | 164 | 13.013 | -3.960 | 13.518 | 1.00 | 23.63 |
| ATOM | 958 | CB  | GLU | 164 | 13.025 | -5.408 | 14.003 | 1.00 | 24.74 |
| ATOM | 959 | CG  | GLU | 164 | 12.026 | -5.699 | 15.092 | 1.00 | 35.63 |
| ATOM | 960 | CD  | GLU | 164 | 12.246 | -7.055 | 15.728 | 1.00 | 42.84 |
| ATOM | 961 | OE1 | GLU | 164 | 13.382 | -7.321 | 16.187 | 1.00 | 45.14 |
| ATOM | 962 | OE2 | GLU | 164 | 11.281 | -7.845 | 15.769 | 1.00 | 46.80 |
| ATOM | 963 | C   | GLU | 164 | 13.239 | -3.004 | 14.692 | 1.00 | 23.82 |
| ATOM | 964 | O   | GLU | 164 | 12.322 | -2.309 | 15.138 | 1.00 | 18.08 |
| ATOM | 965 | N   | ARG | 165 | 14.484 | -2.959 | 15.149 | 1.00 | 21.96 |
| ATOM | 966 | CA  | ARG | 165 | 14.885 | -2.127 | 16.271 | 1.00 | 26.22 |

FIGURE 1A-20

| ATOM | 967 | CB | ARG | 165 | 16.206 | -2.645 | 16.839 | 1.00 | 26.58 |
|---|---|---|---|---|---|---|---|---|---|
| ATOM | 968 | CG | ARG | 165 | 16.081 | -4.100 | 17.302 | 1.00 | 33.43 |
| ATOM | 969 | CD | ARG | 165 | 17.183 | -4.565 | 18.228 | 1.00 | 33.14 |
| ATOM | 970 | NE | ARG | 165 | 16.614 | -5.457 | 19.233 | 1.00 | 42.33 |
| ATOM | 971 | CZ | ARG | 165 | 17.044 | -6.687 | 19.490 | 1.00 | 45.95 |
| ATOM | 972 | NH1 | ARG | 165 | 18.072 | -7.193 | 18.822 | 1.00 | 47.36 |
| ATOM | 973 | NH2 | ARG | 165 | 16.412 | -7.426 | 20.393 | 1.00 | 47.96 |
| ATOM | 974 | C | ARG | 165 | 14.969 | -0.650 | 15.921 | 1.00 | 25.33 |
| ATOM | 975 | O | ARG | 165 | 14.518 | 0.204 | 16.684 | 1.00 | 24.23 |
| ATOM | 976 | N | MET | 166 | 15.469 | -0.361 | 14.726 | 1.00 | 24.23 |
| ATOM | 977 | CA | MET | 166 | 15.598 | 1.007 | 14.258 | 1.00 | 21.76 |
| ATOM | 978 | CB | MET | 166 | 16.297 | 1.029 | 12.912 | 1.00 | 26.70 |
| ATOM | 979 | CG | MET | 166 | 17.076 | 2.285 | 12.654 | 1.00 | 33.31 |
| ATOM | 980 | SD | MET | 166 | 17.692 | 2.313 | 10.993 | 1.00 | 41.74 |
| ATOM | 981 | CE | MET | 166 | 19.140 | 1.316 | 11.141 | 1.00 | 33.89 |
| ATOM | 982 | C | MET | 166 | 14.233 | 1.681 | 14.144 | 1.00 | 16.50 |
| ATOM | 983 | O | MET | 166 | 14.047 | 2.795 | 14.611 | 1.00 | 19.03 |
| ATOM | 984 | N | SER | 167 | 13.265 | 0.998 | 13.550 | 1.00 | 12.30 |
| ATOM | 985 | CA | SER | 167 | 11.932 | 1.560 | 13.411 | 1.00 | 12.88 |
| ATOM | 986 | CB | SER | 167 | 11.106 | 0.763 | 12.405 | 1.00 | 7.62 |
| ATOM | 987 | OG | SER | 167 | 11.077 | -0.605 | 12.760 | 1.00 | 11.73 |
| ATOM | 988 | C | SER | 167 | 11.182 | 1.620 | 14.734 | 1.00 | 12.01 |
| ATOM | 989 | O | SER | 167 | 10.225 | 2.385 | 14.856 | 1.00 | 19.38 |
| ATOM | 990 | N | TYR | 168 | 11.557 | 0.782 | 15.702 | 1.00 | 18.68 |
| ATOM | 991 | CA | TYR | 168 | 10.879 | 0.772 | 17.001 | 1.00 | 13.13 |
| ATOM | 992 | CB | TYR | 168 | 11.098 | -0.555 | 17.746 | 1.00 | 9.77 |
| ATOM | 993 | CG | TYR | 168 | 10.357 | -0.654 | 19.071 | 1.00 | 6.35 |
| ATOM | 994 | CD1 | TYR | 168 | 8.987 | -0.398 | 19.157 | 1.00 | 5.54 |
| ATOM | 995 | CE1 | TYR | 168 | 8.312 | -0.459 | 20.376 | 1.00 | 10.71 |
| ATOM | 996 | CD2 | TYR | 168 | 11.031 | -0.980 | 20.243 | 1.00 | 10.12 |
| ATOM | 997 | CE2 | TYR | 168 | 10.366 | -1.046 | 21.468 | 1.00 | 13.57 |
| ATOM | 998 | CZ | TYR | 168 | 9.010 | -0.782 | 21.528 | 1.00 | 16.27 |
| ATOM | 999 | OH | TYR | 168 | 8.374 | -0.828 | 22.749 | 1.00 | 23.08 |
| ATOM | 1000 | C | TYR | 168 | 11.396 | 1.934 | 17.826 | 1.00 | 13.36 |
| ATOM | 1001 | O | TYR | 168 | 10.624 | 2.620 | 18.504 | 1.00 | 17.51 |
| ATOM | 1002 | N | LEU | 169 | 12.707 | 2.142 | 17.779 | 1.00 | 10.03 |
| ATOM | 1003 | CA | LEU | 169 | 13.313 | 3.241 | 18.499 | 1.00 | 12.41 |
| ATOM | 1004 | CB | LEU | 169 | 14.833 | 3.232 | 18.312 | 1.00 | 11.55 |
| ATOM | 1005 | CG | LEU | 169 | 15.675 | 2.180 | 19.050 | 1.00 | 8.24 |
| ATOM | 1006 | CD1 | LEU | 169 | 17.157 | 2.409 | 18.762 | 1.00 | 4.82 |
| ATOM | 1007 | CD2 | LEU | 169 | 15.430 | 2.277 | 20.536 | 1.00 | 2.00 |
| ATOM | 1008 | C | LEU | 169 | 12.703 | 4.519 | 17.927 | 1.00 | 14.52 |
| ATOM | 1009 | O | LEU | 169 | 12.100 | 5.316 | 18.659 | 1.00 | 16.77 |
| ATOM | 1010 | N | LEU | 170 | 12.749 | 4.630 | 16.599 | 1.00 | 11.62 |
| ATOM | 1011 | CA | LEU | 170 | 12.207 | 5.774 | 15.883 | 1.00 | 6.21 |
| ATOM | 1012 | CB | LEU | 170 | 12.358 | 5.571 | 14.385 | 1.00 | 8.83 |
| ATOM | 1013 | CG | LEU | 170 | 13.568 | 6.203 | 13.714 | 1.00 | 7.61 |
| ATOM | 1014 | CD1 | LEU | 170 | 13.444 | 7.704 | 13.797 | 1.00 | 9.74 |
| ATOM | 1015 | CD2 | LEU | 170 | 14.835 | 5.731 | 14.368 | 1.00 | 14.52 |
| ATOM | 1016 | C | LEU | 170 | 10.743 | 5.985 | 16.216 | 1.00 | 4.88 |
| ATOM | 1017 | O | LEU | 170 | 10.301 | 7.114 | 16.386 | 1.00 | 6.39 |

FIGURE 1A-21

| ATOM | 1018 | N | TYR | 171 | 9.978 | 4.906 | 16.305 | 1.00 | 6.07 |
| ATOM | 1019 | CA | TYR | 171 | 8.559 | 5.012 | 16.637 | 1.00 | 7.40 |
| ATOM | 1020 | CB | TYR | 171 | 7.882 | 3.651 | 16.467 | 1.00 | 2.00 |
| ATOM | 1021 | CG | TYR | 171 | 6.514 | 3.539 | 17.100 | 1.00 | 2.00 |
| ATOM | 1022 | CD1 | TYR | 171 | 5.380 | 4.052 | 16.474 | 1.00 | 2.00 |
| ATOM | 1023 | CE1 | TYR | 171 | 4.131 | 3.960 | 17.070 | 1.00 | 2.32 |
| ATOM | 1024 | CD2 | TYR | 171 | 6.355 | 2.930 | 18.339 | 1.00 | 2.00 |
| ATOM | 1025 | CE2 | TYR | 171 | 5.109 | 2.836 | 18.942 | 1.00 | 2.00 |
| ATOM | 1026 | CZ | TYR | 171 | 4.010 | 3.355 | 18.308 | 1.00 | 5.59 |
| ATOM | 1027 | OH | TYR | 171 | 2.783 | 3.273 | 18.911 | 1.00 | 15.66 |
| ATOM | 1028 | C | TYR | 171 | 8.356 | 5.525 | 18.069 | 1.00 | 13.97 |
| ATOM | 1029 | O | TYR | 171 | 7.317 | 6.122 | 18.386 | 1.00 | 14.20 |
| ATOM | 1030 | N | GLN | 172 | 9.318 | 5.248 | 18.950 | 1.00 | 13.79 |
| ATOM | 1031 | CA | GLN | 172 | 9.208 | 5.692 | 20.334 | 1.00 | 13.72 |
| ATOM | 1032 | CB | GLN | 172 | 10.106 | 4.853 | 21.237 | 1.00 | 16.88 |
| ATOM | 1033 | CG | GLN | 172 | 9.565 | 3.444 | 21.486 | 1.00 | 8.23 |
| ATOM | 1034 | CD | GLN | 172 | 10.501 | 2.621 | 22.310 | 1.00 | 10.79 |
| ATOM | 1035 | OE1 | GLN | 172 | 10.258 | 2.381 | 23.489 | 1.00 | 13.96 |
| ATOM | 1036 | NE2 | GLN | 172 | 11.596 | 2.186 | 21.699 | 1.00 | 8.99 |
| ATOM | 1037 | C | GLN | 172 | 9.487 | 7.178 | 20.464 | 1.00 | 13.21 |
| ATOM | 1038 | O | GLN | 172 | 8.746 | 7.898 | 21.138 | 1.00 | 9.93 |
| ATOM | 1039 | N | MET | 173 | 10.508 | 7.646 | 19.753 | 1.00 | 14.88 |
| ATOM | 1040 | CA | MET | 173 | 10.862 | 9.057 | 19.752 | 1.00 | 10.49 |
| ATOM | 1041 | CB | MET | 173 | 11.983 | 9.321 | 18.766 | 1.00 | 4.87 |
| ATOM | 1042 | CG | MET | 173 | 13.267 | 8.712 | 19.153 | 1.00 | 2.00 |
| ATOM | 1043 | SD | MET | 173 | 14.520 | 9.140 | 18.000 | 1.00 | 19.69 |
| ATOM | 1044 | CE | MET | 173 | 15.484 | 7.674 | 18.067 | 1.00 | 16.38 |
| ATOM | 1045 | C | MET | 173 | 9.655 | 9.863 | 19.314 | 1.00 | 12.28 |
| ATOM | 1046 | O | MET | 173 | 9.263 | 10.812 | 19.972 | 1.00 | 21.25 |
| ATOM | 1047 | N | LEU | 174 | 9.055 | 9.461 | 18.201 | 1.00 | 14.54 |
| ATOM | 1048 | CA | LEU | 174 | 7.891 | 10.150 | 17.675 | 1.00 | 15.25 |
| ATOM | 1049 | CB | LEU | 174 | 7.532 | 9.600 | 16.296 | 1.00 | 12.52 |
| ATOM | 1050 | CG | LEU | 174 | 8.557 | 9.874 | 15.197 | 1.00 | 14.12 |
| ATOM | 1051 | CD1 | LEU | 174 | 8.373 | 8.874 | 14.067 | 1.00 | 21.17 |
| ATOM | 1052 | CD2 | LEU | 174 | 8.386 | 11.291 | 14.687 | 1.00 | 18.38 |
| ATOM | 1053 | C | LEU | 174 | 6.704 | 10.016 | 18.620 | 1.00 | 17.77 |
| ATOM | 1054 | O | LEU | 174 | 5.798 | 10.855 | 18.614 | 1.00 | 22.45 |
| ATOM | 1055 | N | CYS | 175 | 6.711 | 8.974 | 19.444 | 1.00 | 17.26 |
| ATOM | 1056 | CA | CYS | 175 | 5.617 | 8.760 | 20.374 | 1.00 | 14.93 |
| ATOM | 1057 | CB | CYS | 175 | 5.640 | 7.327 | 20.898 | 1.00 | 11.46 |
| ATOM | 1058 | SG | CYS | 175 | 4.522 | 6.216 | 20.022 | 1.00 | 20.44 |
| ATOM | 1059 | C | CYS | 175 | 5.685 | 9.764 | 21.511 | 1.00 | 14.80 |
| ATOM | 1060 | O | CYS | 175 | 4.680 | 10.381 | 21.861 | 1.00 | 16.85 |
| ATOM | 1061 | N | GLY | 176 | 6.890 | 9.957 | 22.039 | 1.00 | 12.26 |
| ATOM | 1062 | CA | GLY | 176 | 7.102 | 10.892 | 23.118 | 1.00 | 15.07 |
| ATOM | 1063 | C | GLY | 176 | 6.965 | 12.318 | 22.638 | 1.00 | 17.60 |
| ATOM | 1064 | O | GLY | 176 | 6.256 | 13.106 | 23.254 | 1.00 | 24.90 |
| ATOM | 1065 | N | ILE | 177 | 7.589 | 12.628 | 21.506 | 1.00 | 16.52 |
| ATOM | 1066 | CA | ILE | 177 | 7.562 | 13.959 | 20.906 | 1.00 | 15.82 |
| ATOM | 1067 | CB | ILE | 177 | 8.373 | 13.963 | 19.594 | 1.00 | 17.96 |
| ATOM | 1068 | CG2 | ILE | 177 | 8.045 | 15.170 | 18.734 | 1.00 | 19.67 |

FIGURE 1A-22

| ATOM | 1069 | CG1 | ILE | 177 | 9.859 | 13.922 | 19.917 | 1.00 | 14.38 |
|---|---|---|---|---|---|---|---|---|---|
| ATOM | 1070 | CD1 | ILE | 177 | 10.689 | 13.361 | 18.803 | 1.00 | 20.28 |
| ATOM | 1071 | C | ILE | 177 | 6.129 | 14.390 | 20.641 | 1.00 | 16.99 |
| ATOM | 1072 | O | ILE | 177 | 5.775 | 15.558 | 20.807 | 1.00 | 16.68 |
| ATOM | 1073 | N | LYS | 178 | 5.302 | 13.435 | 20.242 | 1.00 | 18.14 |
| ATOM | 1074 | CA | LYS | 178 | 3.893 | 13.684 | 19.974 | 1.00 | 20.23 |
| ATOM | 1075 | CB | LYS | 178 | 3.272 | 12.431 | 19.347 | 1.00 | 20.60 |
| ATOM | 1076 | CG | LYS | 178 | 1.763 | 12.310 | 19.444 | 1.00 | 23.53 |
| ATOM | 1077 | CD | LYS | 178 | 1.015 | 13.037 | 18.344 | 1.00 | 27.18 |
| ATOM | 1078 | CE | LYS | 178 | -0.448 | 12.613 | 18.376 | 1.00 | 32.33 |
| ATOM | 1079 | NZ | LYS | 178 | -1.295 | 13.401 | 17.453 | 1.00 | 43.56 |
| ATOM | 1080 | C | LYS | 178 | 3.193 | 14.039 | 21.285 | 1.00 | 19.40 |
| ATOM | 1081 | O | LYS | 178 | 2.385 | 14.968 | 21.336 | 1.00 | 21.61 |
| ATOM | 1082 | N | HIS | 179 | 3.534 | 13.318 | 22.350 | 1.00 | 19.14 |
| ATOM | 1083 | CA | HIS | 179 | 2.938 | 13.553 | 23.653 | 1.00 | 17.16 |
| ATOM | 1084 | CB | HIS | 179 | 3.387 | 12.490 | 24.657 | 1.00 | 19.83 |
| ATOM | 1085 | CG | HIS | 179 | 2.551 | 12.461 | 25.900 | 1.00 | 25.11 |
| ATOM | 1086 | CD2 | HIS | 179 | 2.743 | 13.031 | 27.114 | 1.00 | 16.83 |
| ATOM | 1087 | ND1 | HIS | 179 | 1.317 | 11.851 | 25.952 | 1.00 | 23.89 |
| ATOM | 1088 | CE1 | HIS | 179 | 0.775 | 12.055 | 27.139 | 1.00 | 22.25 |
| ATOM | 1089 | NE2 | HIS | 179 | 1.623 | 12.768 | 27.860 | 1.00 | 24.89 |
| ATOM | 1090 | C | HIS | 179 | 3.317 | 14.941 | 24.149 | 1.00 | 18.00 |
| ATOM | 1091 | O | HIS | 179 | 2.470 | 15.693 | 24.633 | 1.00 | 15.78 |
| ATOM | 1092 | N | LEU | 180 | 4.592 | 15.280 | 24.007 | 1.00 | 14.13 |
| ATOM | 1093 | CA | LEU | 180 | 5.110 | 16.579 | 24.398 | 1.00 | 13.97 |
| ATOM | 1094 | CB | LEU | 180 | 6.591 | 16.655 | 24.050 | 1.00 | 10.61 |
| ATOM | 1095 | CG | LEU | 180 | 7.593 | 16.782 | 25.188 | 1.00 | 18.96 |
| ATOM | 1096 | CD1 | LEU | 180 | 7.178 | 15.903 | 26.353 | 1.00 | 17.68 |
| ATOM | 1097 | CD2 | LEU | 180 | 8.988 | 16.442 | 24.687 | 1.00 | 15.14 |
| ATOM | 1098 | C | LEU | 180 | 4.376 | 17.686 | 23.645 | 1.00 | 18.94 |
| ATOM | 1099 | O | LEU | 180 | 3.983 | 18.685 | 24.235 | 1.00 | 25.95 |
| ATOM | 1100 | N | HIS | 181 | 4.150 | 17.474 | 22.350 | 1.00 | 21.66 |
| ATOM | 1101 | CA | HIS | 181 | 3.486 | 18.451 | 21.503 | 1.00 | 17.22 |
| ATOM | 1102 | CB | HIS | 181 | 3.505 | 18.001 | 20.053 | 1.00 | 16.68 |
| ATOM | 1103 | CG | HIS | 181 | 4.831 | 18.181 | 19.394 | 1.00 | 14.49 |
| ATOM | 1104 | CD2 | HIS | 181 | 6.021 | 18.596 | 19.878 | 1.00 | 19.94 |
| ATOM | 1105 | ND1 | HIS | 181 | 5.031 | 17.940 | 18.050 | 1.00 | 17.57 |
| ATOM | 1106 | CE1 | HIS | 181 | 6.285 | 18.201 | 17.742 | 1.00 | 24.23 |
| ATOM | 1107 | NE2 | HIS | 181 | 6.909 | 18.603 | 18.830 | 1.00 | 19.09 |
| ATOM | 1108 | C | HIS | 181 | 2.071 | 18.730 | 21.921 | 1.00 | 20.84 |
| ATOM | 1109 | O | HIS | 181 | 1.612 | 19.869 | 21.832 | 1.00 | 23.26 |
| ATOM | 1110 | N | SER | 182 | 1.391 | 17.699 | 22.406 | 1.00 | 24.60 |
| ATOM | 1111 | CA | SER | 182 | 0.011 | 17.827 | 22.850 | 1.00 | 27.68 |
| ATOM | 1112 | CB | SER | 182 | -0.642 | 16.445 | 22.974 | 1.00 | 32.30 |
| ATOM | 1113 | OG | SER | 182 | 0.077 | 15.591 | 23.849 | 1.00 | 34.95 |
| ATOM | 1114 | C | SER | 182 | -0.061 | 18.578 | 24.175 | 1.00 | 26.17 |
| ATOM | 1115 | O | SER | 182 | -1.089 | 19.155 | 24.511 | 1.00 | 28.02 |
| ATOM | 1116 | N | ALA | 183 | 1.049 | 18.572 | 24.910 | 1.00 | 26.53 |
| ATOM | 1117 | CA | ALA | 183 | 1.149 | 19.244 | 26.200 | 1.00 | 26.54 |
| ATOM | 1118 | CB | ALA | 183 | 2.091 | 18.476 | 27.122 | 1.00 | 26.67 |
| ATOM | 1119 | C | ALA | 183 | 1.619 | 20.686 | 26.057 | 1.00 | 24.83 |

FIGURE 1A-23

```
ATOM   1120  O    ALA  183      1.712   21.408   27.040  1.00  30.64
ATOM   1121  N    GLY  184      1.918   21.097   24.829  1.00  24.98
ATOM   1122  CA   GLY  184      2.371   22.451   24.572  1.00  17.11
ATOM   1123  C    GLY  184      3.880   22.565   24.550  1.00  14.96
ATOM   1124  O    GLY  184      4.434   23.658   24.448  1.00  23.31
ATOM   1125  N    ILE  185      4.557   21.433   24.618  1.00  13.02
ATOM   1126  CA   ILE  185      6.007   21.414   24.624  1.00  12.13
ATOM   1127  CB   ILE  185      6.523   20.409   25.691  1.00   6.39
ATOM   1128  CG2  ILE  185      8.042   20.366   25.713  1.00   2.61
ATOM   1129  CG1  ILE  185      6.002   20.804   27.066  1.00   7.63
ATOM   1130  CD1  ILE  185      5.998   19.675   28.089  1.00  16.86
ATOM   1131  C    ILE  185      6.584   21.066   23.255  1.00  18.60
ATOM   1132  O    ILE  185      6.296   20.003   22.701  1.00  23.06
ATOM   1133  N    ILE  186      7.322   22.008   22.672  1.00  21.27
ATOM   1134  CA   ILE  186      7.987   21.783   21.393  1.00  18.91
ATOM   1135  CB   ILE  186      7.574   22.791   20.309  1.00  19.73
ATOM   1136  CG2  ILE  186      8.494   22.664   19.112  1.00  17.68
ATOM   1137  CG1  ILE  186      6.127   22.523   19.878  1.00  11.83
ATOM   1138  CD1  ILE  186      5.575   23.544   18.919  1.00  11.72
ATOM   1139  C    ILE  186      9.463   21.885   21.726  1.00  21.30
ATOM   1140  O    ILE  186     10.007   22.962   21.969  1.00  23.79
ATOM   1141  N    HIS  187     10.057   20.707   21.829  1.00  21.98
ATOM   1142  CA   HIS  187     11.448   20.499   22.186  1.00  19.23
ATOM   1143  CB   HIS  187     11.781   19.032   21.966  1.00  12.51
ATOM   1144  CG   HIS  187     12.865   18.528   22.847  1.00   4.61
ATOM   1145  CD2  HIS  187     12.830   17.670   23.895  1.00   3.44
ATOM   1146  ND1  HIS  187     14.185   18.886   22.697  1.00   6.79
ATOM   1147  CE1  HIS  187     14.916   18.271   23.609  1.00   5.55
ATOM   1148  NE2  HIS  187     14.113   17.530   24.346  1.00   3.81
ATOM   1149  C    HIS  187     12.485   21.372   21.504  1.00  20.74
ATOM   1150  O    HIS  187     13.142   22.176   22.162  1.00  24.08
ATOM   1151  N    ARG  188     12.668   21.159   20.201  1.00  23.60
ATOM   1152  CA   ARG  188     13.625   21.911   19.391  1.00  19.02
ATOM   1153  CB   ARG  188     13.385   23.417   19.495  1.00  21.06
ATOM   1154  CG   ARG  188     12.132   23.907   18.814  1.00  19.41
ATOM   1155  CD   ARG  188     11.585   25.109   19.552  1.00  33.60
ATOM   1156  NE   ARG  188     12.604   26.113   19.856  1.00  41.94
ATOM   1157  CZ   ARG  188     12.507   26.995   20.849  1.00  46.24
ATOM   1158  NH1  ARG  188     11.439   26.991   21.639  1.00  44.65
ATOM   1159  NH2  ARG  188     13.471   27.890   21.046  1.00  49.68
ATOM   1160  C    ARG  188     15.087   21.633   19.683  1.00  19.40
ATOM   1161  O    ARG  188     15.953   22.248   19.063  1.00  23.08
ATOM   1162  N    ASP  189     15.382   20.723   20.610  1.00  16.00
ATOM   1163  CA   ASP  189     16.779   20.432   20.906  1.00  12.74
ATOM   1164  CB   ASP  189     17.274   21.290   22.075  1.00  15.31
ATOM   1165  CG   ASP  189     18.794   21.325   22.187  1.00  21.73
ATOM   1166  OD1  ASP  189     19.502   21.064   21.186  1.00  22.19
ATOM   1167  OD2  ASP  189     19.291   21.623   23.293  1.00  31.34
ATOM   1168  C    ASP  189     17.088   18.954   21.131  1.00  14.28
ATOM   1169  O    ASP  189     17.972   18.602   21.910  1.00  15.81
ATOM   1170  N    LEU  190     16.386   18.094   20.401  1.00  15.63
```

FIGURE 1A-24

| ATOM | 1171 | CA | LEU | 190 | 16.601 | 16.655 | 20.502 | 1.00 | 13.07 |
|---|---|---|---|---|---|---|---|---|---|
| ATOM | 1172 | CB | LEU | 190 | 15.547 | 15.894 | 19.717 | 1.00 | 8.18 |
| ATOM | 1173 | CG | LEU | 190 | 14.230 | 15.833 | 20.474 | 1.00 | 9.26 |
| ATOM | 1174 | CD1 | LEU | 190 | 13.076 | 15.704 | 19.519 | 1.00 | 18.14 |
| ATOM | 1175 | CD2 | LEU | 190 | 14.255 | 14.691 | 21.481 | 1.00 | 16.07 |
| ATOM | 1176 | C | LEU | 190 | 17.972 | 16.289 | 19.980 | 1.00 | 14.19 |
| ATOM | 1177 | O | LEU | 190 | 18.409 | 16.780 | 18.946 | 1.00 | 16.91 |
| ATOM | 1178 | N | LYS | 191 | 18.690 | 15.509 | 20.770 | 1.00 | 13.28 |
| ATOM | 1179 | CA | LYS | 191 | 20.005 | 15.037 | 20.396 | 1.00 | 12.45 |
| ATOM | 1180 | CB | LYS | 191 | 21.099 | 15.994 | 20.864 | 1.00 | 22.33 |
| ATOM | 1181 | CG | LYS | 191 | 20.825 | 16.724 | 22.159 | 1.00 | 25.88 |
| ATOM | 1182 | CD | LYS | 191 | 21.913 | 17.763 | 22.400 | 1.00 | 30.61 |
| ATOM | 1183 | CE | LYS | 191 | 21.645 | 18.583 | 23.643 | 1.00 | 34.73 |
| ATOM | 1184 | NZ | LYS | 191 | 22.809 | 19.432 | 23.999 | 1.00 | 40.68 |
| ATOM | 1185 | C | LYS | 191 | 20.176 | 13.637 | 20.964 | 1.00 | 13.19 |
| ATOM | 1186 | O | LYS | 191 | 19.467 | 13.246 | 21.882 | 1.00 | 10.10 |
| ATOM | 1187 | N | PRO | 192 | 21.063 | 12.831 | 20.378 | 1.00 | 15.27 |
| ATOM | 1188 | CD | PRO | 192 | 21.858 | 13.065 | 19.160 | 1.00 | 17.77 |
| ATOM | 1189 | CA | PRO | 192 | 21.266 | 11.470 | 20.876 | 1.00 | 17.88 |
| ATOM | 1190 | CB | PRO | 192 | 22.376 | 10.942 | 19.963 | 1.00 | 21.29 |
| ATOM | 1191 | CG | PRO | 192 | 22.095 | 11.670 | 18.648 | 1.00 | 16.64 |
| ATOM | 1192 | C | PRO | 192 | 21.645 | 11.379 | 22.354 | 1.00 | 16.86 |
| ATOM | 1193 | O | PRO | 192 | 21.176 | 10.502 | 23.070 | 1.00 | 15.98 |
| ATOM | 1194 | N | SER | 193 | 22.441 | 12.336 | 22.819 | 1.00 | 19.17 |
| ATOM | 1195 | CA | SER | 193 | 22.904 | 12.359 | 24.197 | 1.00 | 18.42 |
| ATOM | 1196 | CB | SER | 193 | 23.898 | 13.513 | 24.392 | 1.00 | 21.43 |
| ATOM | 1197 | OG | SER | 193 | 23.344 | 14.777 | 24.035 | 1.00 | 25.19 |
| ATOM | 1198 | C | SER | 193 | 21.758 | 12.448 | 25.202 | 1.00 | 17.71 |
| ATOM | 1199 | O | SER | 193 | 21.880 | 11.973 | 26.335 | 1.00 | 20.64 |
| ATOM | 1200 | N | ASN | 194 | 20.628 | 12.995 | 24.767 | 1.00 | 14.84 |
| ATOM | 1201 | CA | ASN | 194 | 19.474 | 13.152 | 25.641 | 1.00 | 16.25 |
| ATOM | 1202 | CB | ASN | 194 | 18.888 | 14.550 | 25.492 | 1.00 | 21.48 |
| ATOM | 1203 | CG | ASN | 194 | 19.879 | 15.637 | 25.829 | 1.00 | 28.01 |
| ATOM | 1204 | OD1 | ASN | 194 | 20.837 | 15.426 | 26.579 | 1.00 | 27.75 |
| ATOM | 1205 | ND2 | ASN | 194 | 19.657 | 16.815 | 25.268 | 1.00 | 34.86 |
| ATOM | 1206 | C | ASN | 194 | 18.372 | 12.132 | 25.417 | 1.00 | 13.03 |
| ATOM | 1207 | O | ASN | 194 | 17.229 | 12.331 | 25.829 | 1.00 | 10.27 |
| ATOM | 1208 | N | ILE | 195 | 18.678 | 11.086 | 24.675 | 1.00 | 14.95 |
| ATOM | 1209 | CA | ILE | 195 | 17.701 | 10.044 | 24.429 | 1.00 | 14.75 |
| ATOM | 1210 | CB | ILE | 195 | 17.361 | 9.915 | 22.923 | 1.00 | 15.15 |
| ATOM | 1211 | CG2 | ILE | 195 | 16.355 | 8.803 | 22.711 | 1.00 | 17.60 |
| ATOM | 1212 | CG1 | ILE | 195 | 16.759 | 11.230 | 22.411 | 1.00 | 10.53 |
| ATOM | 1213 | CD1 | ILE | 195 | 16.602 | 11.298 | 20.905 | 1.00 | 13.24 |
| ATOM | 1214 | C | ILE | 195 | 18.349 | 8.790 | 24.993 | 1.00 | 16.72 |
| ATOM | 1215 | O | ILE | 195 | 19.505 | 8.473 | 24.683 | 1.00 | 18.77 |
| ATOM | 1216 | N | VAL | 196 | 17.652 | 8.152 | 25.929 | 1.00 | 14.00 |
| ATOM | 1217 | CA | VAL | 196 | 18.174 | 6.951 | 26.574 | 1.00 | 9.04 |
| ATOM | 1218 | CB | VAL | 196 | 18.271 | 7.094 | 28.116 | 1.00 | 5.40 |
| ATOM | 1219 | CG1 | VAL | 196 | 19.478 | 7.940 | 28.487 | 1.00 | 4.57 |
| ATOM | 1220 | CG2 | VAL | 196 | 17.005 | 7.725 | 28.691 | 1.00 | 2.00 |
| ATOM | 1221 | C | VAL | 196 | 17.394 | 5.706 | 26.225 | 1.00 | 12.09 |

FIGURE 1A-25

| ATOM | 1222 | O   | VAL | 196 | 16.169 | 5.725  | 26.058 | 1.00 | 10.12 |
|------|------|-----|-----|-----|--------|--------|--------|------|-------|
| ATOM | 1223 | N   | VAL | 197 | 18.138 | 4.612  | 26.101 | 1.00 | 13.72 |
| ATOM | 1224 | CA  | VAL | 197 | 17.566 | 3.317  | 25.765 | 1.00 | 16.48 |
| ATOM | 1225 | CB  | VAL | 197 | 18.022 | 2.863  | 24.341 | 1.00 | 14.83 |
| ATOM | 1226 | CG1 | VAL | 197 | 17.734 | 3.957  | 23.307 | 1.00 | 9.08  |
| ATOM | 1227 | CG2 | VAL | 197 | 19.506 | 2.520  | 24.343 | 1.00 | 2.00  |
| ATOM | 1228 | C   | VAL | 197 | 17.926 | 2.224  | 26.788 | 1.00 | 14.19 |
| ATOM | 1229 | O   | VAL | 197 | 18.921 | 2.312  | 27.510 | 1.00 | 13.80 |
| ATOM | 1230 | N   | LYS | 198 | 17.090 | 1.196  | 26.824 | 1.00 | 15.84 |
| ATOM | 1231 | CA  | LYS | 198 | 17.274 | 0.041  | 27.692 | 1.00 | 22.32 |
| ATOM | 1232 | CB  | LYS | 198 | 15.954 | -0.307 | 28.391 | 1.00 | 20.80 |
| ATOM | 1233 | CG  | LYS | 198 | 16.068 | -0.524 | 29.903 | 1.00 | 23.97 |
| ATOM | 1234 | CD  | LYS | 198 | 14.701 | -0.766 | 30.529 | 1.00 | 22.67 |
| ATOM | 1235 | CE  | LYS | 198 | 13.797 | 0.447  | 30.362 | 1.00 | 25.82 |
| ATOM | 1236 | NZ  | LYS | 198 | 12.340 | 0.142  | 30.519 | 1.00 | 25.82 |
| ATOM | 1237 | C   | LYS | 198 | 17.715 | -1.119 | 26.783 | 1.00 | 24.42 |
| ATOM | 1238 | O   | LYS | 198 | 17.726 | -0.989 | 25.559 | 1.00 | 25.21 |
| ATOM | 1239 | N   | SER | 199 | 18.057 | -2.256 | 27.377 | 1.00 | 23.72 |
| ATOM | 1240 | CA  | SER | 199 | 18.489 | -3.407 | 26.602 | 1.00 | 20.97 |
| ATOM | 1241 | CB  | SER | 199 | 19.155 | -4.442 | 27.507 | 1.00 | 23.31 |
| ATOM | 1242 | OG  | SER | 199 | 20.444 | -3.998 | 27.911 | 1.00 | 25.37 |
| ATOM | 1243 | C   | SER | 199 | 17.388 | -4.057 | 25.759 | 1.00 | 21.31 |
| ATOM | 1244 | O   | SER | 199 | 17.673 | -4.605 | 24.699 | 1.00 | 23.38 |
| ATOM | 1245 | N   | ASP | 200 | 16.135 | -3.956 | 26.202 | 1.00 | 18.40 |
| ATOM | 1246 | CA  | ASP | 200 | 15.007 | -4.551 | 25.476 | 1.00 | 21.38 |
| ATOM | 1247 | CB  | ASP | 200 | 13.860 | -4.881 | 26.436 | 1.00 | 25.50 |
| ATOM | 1248 | CG  | ASP | 200 | 13.230 | -3.646 | 27.034 | 1.00 | 26.04 |
| ATOM | 1249 | OD1 | ASP | 200 | 13.977 | -2.688 | 27.298 | 1.00 | 29.77 |
| ATOM | 1250 | OD2 | ASP | 200 | 11.995 | -3.631 | 27.232 | 1.00 | 29.50 |
| ATOM | 1251 | C   | ASP | 200 | 14.485 | -3.631 | 24.378 | 1.00 | 25.24 |
| ATOM | 1252 | O   | ASP | 200 | 13.338 | -3.761 | 23.933 | 1.00 | 26.25 |
| ATOM | 1253 | N   | CYS | 201 | 15.323 | -2.671 | 23.994 | 1.00 | 25.88 |
| ATOM | 1254 | CA  | CYS | 201 | 15.018 | -1.691 | 22.957 | 1.00 | 23.40 |
| ATOM | 1255 | CB  | CYS | 201 | 14.672 | -2.393 | 21.642 | 1.00 | 25.53 |
| ATOM | 1256 | SG  | CYS | 201 | 15.247 | -1.506 | 20.186 | 1.00 | 26.53 |
| ATOM | 1257 | C   | CYS | 201 | 13.948 | -0.648 | 23.318 | 1.00 | 23.17 |
| ATOM | 1258 | O   | CYS | 201 | 13.335 | -0.050 | 22.439 | 1.00 | 26.58 |
| ATOM | 1259 | N   | THR | 202 | 13.682 | -0.471 | 24.608 | 1.00 | 20.78 |
| ATOM | 1260 | CA  | THR | 202 | 12.728 | 0.545  | 25.043 | 1.00 | 16.13 |
| ATOM | 1261 | CB  | THR | 202 | 12.110 | 0.225  | 26.414 | 1.00 | 19.54 |
| ATOM | 1262 | OG1 | THR | 202 | 13.099 | -0.365 | 27.259 | 1.00 | 21.26 |
| ATOM | 1263 | CG2 | THR | 202 | 10.936 | -0.731 | 26.256 | 1.00 | 15.32 |
| ATOM | 1264 | C   | THR | 202 | 13.468 | 1.879  | 25.072 | 1.00 | 10.63 |
| ATOM | 1265 | O   | THR | 202 | 14.668 | 1.937  | 25.383 | 1.00 | 2.00  |
| ATOM | 1266 | N   | LEU | 203 | 12.752 | 2.943  | 24.708 | 1.00 | 13.67 |
| ATOM | 1267 | CA  | LEU | 203 | 13.334 | 4.284  | 24.612 | 1.00 | 12.20 |
| ATOM | 1268 | CB  | LEU | 203 | 13.362 | 4.720  | 23.133 | 1.00 | 8.58  |
| ATOM | 1269 | CG  | LEU | 203 | 13.969 | 6.068  | 22.715 | 1.00 | 11.45 |
| ATOM | 1270 | CD1 | LEU | 203 | 14.650 | 5.942  | 21.363 | 1.00 | 10.52 |
| ATOM | 1271 | CD2 | LEU | 203 | 12.895 | 7.142  | 22.666 | 1.00 | 3.20  |
| ATOM | 1272 | C   | LEU | 203 | 12.632 | 5.349  | 25.426 | 1.00 | 8.50  |

FIGURE 1A-26

| ATOM | 1273 | O | LEU | 203 | 11.418 | 5.308 | 25.619 | 1.00 | 9.53 |
|---|---|---|---|---|---|---|---|---|---|
| ATOM | 1274 | N | LYS | 204 | 13.416 | 6.336 | 25.844 | 1.00 | 8.07 |
| ATOM | 1275 | CA | LYS | 204 | 12.912 | 7.469 | 26.601 | 1.00 | 9.43 |
| ATOM | 1276 | CB | LYS | 204 | 12.939 | 7.166 | 28.105 | 1.00 | 11.68 |
| ATOM | 1277 | CG | LYS | 204 | 11.685 | 6.484 | 28.615 | 1.00 | 13.40 |
| ATOM | 1278 | CD | LYS | 204 | 11.985 | 5.627 | 29.833 | 1.00 | 17.55 |
| ATOM | 1279 | CE | LYS | 204 | 10.719 | 4.992 | 30.384 | 1.00 | 10.73 |
| ATOM | 1280 | NZ | LYS | 204 | 9.904 | 5.962 | 31.176 | 1.00 | 15.81 |
| ATOM | 1281 | C | LYS | 204 | 13.728 | 8.729 | 26.299 | 1.00 | 7.72 |
| ATOM | 1282 | O | LYS | 204 | 14.931 | 8.652 | 26.012 | 1.00 | 4.99 |
| ATOM | 1283 | N | ILE | 205 | 13.050 | 9.874 | 26.299 | 1.00 | 6.14 |
| ATOM | 1284 | CA | ILE | 205 | 13.699 | 11.165 | 26.074 | 1.00 | 10.95 |
| ATOM | 1285 | CB | ILE | 205 | 12.804 | 12.101 | 25.212 | 1.00 | 11.78 |
| ATOM | 1286 | CG2 | ILE | 205 | 13.512 | 13.446 | 24.975 | 1.00 | 10.41 |
| ATOM | 1287 | CG1 | ILE | 205 | 12.522 | 11.446 | 23.855 | 1.00 | 12.13 |
| ATOM | 1288 | CD1 | ILE | 205 | 11.411 | 12.119 | 23.065 | 1.00 | 8.77 |
| ATOM | 1289 | C | ILE | 205 | 13.980 | 11.791 | 27.458 | 1.00 | 12.59 |
| ATOM | 1290 | O | ILE | 205 | 13.118 | 11.805 | 28.332 | 1.00 | 9.96 |
| ATOM | 1291 | N | LEU | 206 | 15.188 | 12.309 | 27.645 | 1.00 | 12.29 |
| ATOM | 1292 | CA | LEU | 206 | 15.612 | 12.895 | 28.919 | 1.00 | 14.53 |
| ATOM | 1293 | CB | LEU | 206 | 17.139 | 12.860 | 29.025 | 1.00 | 7.15 |
| ATOM | 1294 | CG | LEU | 206 | 17.863 | 11.538 | 29.216 | 1.00 | 6.46 |
| ATOM | 1295 | CD1 | LEU | 206 | 19.332 | 11.848 | 29.391 | 1.00 | 3.73 |
| ATOM | 1296 | CD2 | LEU | 206 | 17.317 | 10.796 | 30.435 | 1.00 | 7.09 |
| ATOM | 1297 | C | LEU | 206 | 15.146 | 14.308 | 29.292 | 1.00 | 20.70 |
| ATOM | 1298 | O | LEU | 206 | 14.564 | 14.516 | 30.370 | 1.00 | 18.15 |
| ATOM | 1299 | N | ASP | 207 | 15.458 | 15.275 | 28.427 | 1.00 | 20.32 |
| ATOM | 1300 | CA | ASP | 207 | 15.133 | 16.682 | 28.666 | 1.00 | 16.60 |
| ATOM | 1301 | CB | ASP | 207 | 16.337 | 17.543 | 28.272 | 1.00 | 19.38 |
| ATOM | 1302 | CG | ASP | 207 | 16.626 | 17.520 | 26.774 | 1.00 | 29.66 |
| ATOM | 1303 | OD1 | ASP | 207 | 17.303 | 18.455 | 26.303 | 1.00 | 35.89 |
| ATOM | 1304 | OD2 | ASP | 207 | 16.182 | 16.581 | 26.068 | 1.00 | 34.19 |
| ATOM | 1305 | C | ASP | 207 | 13.866 | 17.191 | 27.968 | 1.00 | 16.12 |
| ATOM | 1306 | O | ASP | 207 | 13.218 | 16.451 | 27.237 | 1.00 | 14.14 |
| ATOM | 1307 | N | PHE | 208 | 13.520 | 18.458 | 28.211 | 1.00 | 17.73 |
| ATOM | 1308 | CA | PHE | 208 | 12.335 | 19.062 | 27.604 | 1.00 | 19.23 |
| ATOM | 1309 | CB | PHE | 208 | 11.356 | 19.559 | 28.673 | 1.00 | 23.45 |
| ATOM | 1310 | CG | PHE | 208 | 10.762 | 18.443 | 29.500 | 1.00 | 30.96 |
| ATOM | 1311 | CD1 | PHE | 208 | 11.439 | 17.947 | 30.615 | 1.00 | 31.76 |
| ATOM | 1312 | CD2 | PHE | 208 | 9.561 | 17.852 | 29.127 | 1.00 | 32.20 |
| ATOM | 1313 | CE1 | PHE | 208 | 10.935 | 16.867 | 31.342 | 1.00 | 30.65 |
| ATOM | 1314 | CE2 | PHE | 208 | 9.041 | 16.770 | 29.845 | 1.00 | 34.21 |
| ATOM | 1315 | CZ | PHE | 208 | 9.730 | 16.275 | 30.954 | 1.00 | 32.18 |
| ATOM | 1316 | C | PHE | 208 | 12.634 | 20.125 | 26.551 | 1.00 | 13.96 |
| ATOM | 1317 | O | PHE | 208 | 11.736 | 20.797 | 26.067 | 1.00 | 11.83 |
| ATOM | 1318 | N | GLY | 209 | 13.909 | 20.273 | 26.218 | 1.00 | 15.53 |
| ATOM | 1319 | CA | GLY | 209 | 14.309 | 21.190 | 25.171 | 1.00 | 22.47 |
| ATOM | 1320 | C | GLY | 209 | 14.682 | 22.630 | 25.446 | 1.00 | 28.87 |
| ATOM | 1321 | O | GLY | 209 | 15.415 | 22.933 | 26.386 | 1.00 | 29.96 |
| ATOM | 1322 | N | LEU | 210 | 14.194 | 23.506 | 24.569 | 1.00 | 30.88 |
| ATOM | 1323 | CA | LEU | 210 | 14.452 | 24.945 | 24.616 | 1.00 | 32.32 |

FIGURE 1A-27

```
ATOM   1324  CB   LEU   210      14.871  25.414  23.219  1.00 24.06
ATOM   1325  CG   LEU   210      16.345  25.465  22.818  1.00 21.00
ATOM   1326  CD1  LEU   210      17.176  24.420  23.522  1.00 19.19
ATOM   1327  CD2  LEU   210      16.451  25.335  21.312  1.00 20.21
ATOM   1328  C    LEU   210      13.219  25.726  25.062  1.00 35.13
ATOM   1329  O    LEU   210      12.100  25.394  24.680  1.00 38.91
ATOM   1330  N    ALA   211      13.417  26.776  25.851  1.00 39.38
ATOM   1331  CA   ALA   211      12.284  27.581  26.299  1.00 43.50
ATOM   1332  CB   ALA   211      12.633  28.333  27.579  1.00 46.17
ATOM   1333  C    ALA   211      11.851  28.556  25.204  1.00 45.67
ATOM   1334  O    ALA   211      12.513  28.576  24.139  1.00 48.25
ATOM   1335  CB   SER   217      20.876  31.837  26.039  1.00 46.19
ATOM   1336  OG   SER   217      21.055  30.565  26.642  1.00 44.18
ATOM   1337  C    SER   217      22.981  32.766  27.045  1.00 46.05
ATOM   1338  O    SER   217      23.546  31.785  26.549  1.00 44.57
ATOM   1339  N    SER   217      21.162  34.287  26.306  1.00 49.72
ATOM   1340  CA   SER   217      21.470  32.955  26.905  1.00 46.64
ATOM   1341  N    PHE   218      23.626  33.701  27.741  1.00 44.34
ATOM   1342  CA   PHE   218      25.073  33.652  27.943  1.00 40.63
ATOM   1343  CB   PHE   218      25.617  35.032  28.316  1.00 34.04
ATOM   1344  CG   PHE   218      27.107  35.049  28.533  1.00 22.27
ATOM   1345  CD1  PHE   218      27.651  35.540  29.713  1.00 19.55
ATOM   1346  CD2  PHE   218      27.965  34.560  27.549  1.00 15.08
ATOM   1347  CE1  PHE   218      29.033  35.539  29.914  1.00 18.53
ATOM   1348  CE2  PHE   218      29.340  34.554  27.732  1.00  9.13
ATOM   1349  CZ   PHE   218      29.881  35.045  28.916  1.00 14.73
ATOM   1350  C    PHE   218      25.488  32.652  29.015  1.00 42.37
ATOM   1351  O    PHE   218      24.956  32.651  30.125  1.00 43.83
ATOM   1352  N    MET   219      26.448  31.807  28.672  1.00 42.99
ATOM   1353  CA   MET   219      26.952  30.813  29.599  1.00 40.46
ATOM   1354  CB   MET   219      26.391  29.426  29.277  1.00 46.00
ATOM   1355  CG   MET   219      25.017  29.168  29.896  1.00 53.48
ATOM   1356  SD   MET   219      25.066  28.034  31.298  1.00 53.31
ATOM   1357  CE   MET   219      25.111  26.504  30.403  1.00 58.49
ATOM   1358  C    MET   219      28.466  30.795  29.590  1.00 38.80
ATOM   1359  O    MET   219      29.098  30.543  28.563  1.00 35.67
ATOM   1360  N    MET   220      29.035  31.167  30.727  1.00 41.74
ATOM   1361  CA   MET   220      30.481  31.190  30.903  1.00 44.58
ATOM   1362  CB   MET   220      30.848  32.246  31.941  1.00 43.58
ATOM   1363  CG   MET   220      32.316  32.507  32.067  1.00 43.55
ATOM   1364  SD   MET   220      32.560  33.936  33.084  1.00 48.17
ATOM   1365  CE   MET   220      33.104  35.087  31.881  1.00 45.75
ATOM   1366  C    MET   220      30.849  29.803  31.399  1.00 46.36
ATOM   1367  O    MET   220      30.991  29.571  32.602  1.00 49.99
ATOM   1368  N    THR   221      30.995  28.871  30.466  1.00 47.69
ATOM   1369  CA   THR   221      31.283  27.495  30.823  1.00 49.03
ATOM   1370  CB   THR   221      30.094  26.591  30.454  1.00 50.18
ATOM   1371  OG1  THR   221      29.862  26.671  29.041  1.00 53.53
ATOM   1372  CG2  THR   221      28.834  27.015  31.202  1.00 55.05
ATOM   1373  C    THR   221      32.491  26.911  30.131  1.00 51.69
ATOM   1374  O    THR   221      32.995  27.454  29.153  1.00 49.11
```

FIGURE 1A-28

| ATOM | 1375 | N   | PRO | 222 | 33.006 | 25.803 | 30.680 | 1.00 | 56.46 |
|------|------|-----|-----|-----|--------|--------|--------|------|-------|
| ATOM | 1376 | CD  | PRO | 222 | 32.765 | 25.376 | 32.068 | 1.00 | 59.12 |
| ATOM | 1377 | CA  | PRO | 222 | 34.163 | 25.101 | 30.124 | 1.00 | 57.77 |
| ATOM | 1378 | CB  | PRO | 222 | 34.676 | 24.279 | 31.320 | 1.00 | 58.47 |
| ATOM | 1379 | CG  | PRO | 222 | 34.150 | 25.021 | 32.524 | 1.00 | 62.22 |
| ATOM | 1380 | C   | PRO | 222 | 33.701 | 24.165 | 29.003 | 1.00 | 56.24 |
| ATOM | 1381 | O   | PRO | 222 | 34.531 | 23.643 | 28.257 | 1.00 | 54.58 |
| ATOM | 1382 | N   | TYR | 223 | 32.388 | 23.947 | 28.879 | 1.00 | 54.69 |
| ATOM | 1383 | CA  | TYR | 223 | 31.898 | 23.040 | 27.841 | 1.00 | 56.89 |
| ATOM | 1384 | CB  | TYR | 223 | 31.600 | 21.660 | 28.435 | 1.00 | 55.72 |
| ATOM | 1385 | CG  | TYR | 223 | 32.879 | 20.890 | 28.678 | 1.00 | 56.59 |
| ATOM | 1386 | CD1 | TYR | 223 | 33.775 | 20.647 | 27.633 | 1.00 | 55.10 |
| ATOM | 1387 | CE1 | TYR | 223 | 34.978 | 19.996 | 27.857 | 1.00 | 56.43 |
| ATOM | 1388 | CD2 | TYR | 223 | 33.226 | 20.449 | 29.951 | 1.00 | 55.66 |
| ATOM | 1389 | CE2 | TYR | 223 | 34.429 | 19.792 | 30.177 | 1.00 | 56.40 |
| ATOM | 1390 | CZ  | TYR | 223 | 35.299 | 19.573 | 29.127 | 1.00 | 56.57 |
| ATOM | 1391 | OH  | TYR | 223 | 36.500 | 18.942 | 29.345 | 1.00 | 60.45 |
| ATOM | 1392 | C   | TYR | 223 | 30.882 | 23.434 | 26.752 | 1.00 | 59.52 |
| ATOM | 1393 | O   | TYR | 223 | 30.032 | 24.324 | 26.910 | 1.00 | 58.05 |
| ATOM | 1394 | N   | VAL | 224 | 31.012 | 22.700 | 25.644 | 1.00 | 61.35 |
| ATOM | 1395 | CA  | VAL | 224 | 30.262 | 22.860 | 24.393 | 1.00 | 58.81 |
| ATOM | 1396 | CB  | VAL | 224 | 30.880 | 21.998 | 23.248 | 1.00 | 61.26 |
| ATOM | 1397 | CG1 | VAL | 224 | 30.951 | 22.810 | 21.969 | 1.00 | 64.71 |
| ATOM | 1398 | CG2 | VAL | 224 | 32.258 | 21.424 | 23.623 | 1.00 | 59.84 |
| ATOM | 1399 | C   | VAL | 224 | 28.767 | 22.583 | 24.351 | 1.00 | 56.71 |
| ATOM | 1400 | O   | VAL | 224 | 28.212 | 21.872 | 25.196 | 1.00 | 60.65 |
| ATOM | 1401 | N   | VAL | 225 | 28.139 | 23.136 | 23.313 | 1.00 | 51.57 |
| ATOM | 1402 | CA  | VAL | 225 | 26.714 | 22.959 | 23.048 | 1.00 | 48.08 |
| ATOM | 1403 | CB  | VAL | 225 | 25.960 | 24.306 | 22.985 | 1.00 | 44.80 |
| ATOM | 1404 | CG1 | VAL | 225 | 24.464 | 24.060 | 22.956 | 1.00 | 37.42 |
| ATOM | 1405 | CG2 | VAL | 225 | 26.334 | 25.182 | 24.164 | 1.00 | 48.15 |
| ATOM | 1406 | C   | VAL | 225 | 26.600 | 22.267 | 21.679 | 1.00 | 45.63 |
| ATOM | 1407 | O   | VAL | 225 | 27.287 | 22.637 | 20.721 | 1.00 | 45.88 |
| ATOM | 1408 | N   | THR | 226 | 25.748 | 21.251 | 21.595 | 1.00 | 41.83 |
| ATOM | 1409 | CA  | THR | 226 | 25.569 | 20.518 | 20.350 | 1.00 | 35.50 |
| ATOM | 1410 | CB  | THR | 226 | 25.239 | 19.041 | 20.625 | 1.00 | 32.52 |
| ATOM | 1411 | OG1 | THR | 226 | 26.253 | 18.489 | 21.475 | 1.00 | 33.01 |
| ATOM | 1412 | CG2 | THR | 226 | 25.218 | 18.249 | 19.333 | 1.00 | 35.40 |
| ATOM | 1413 | C   | THR | 226 | 24.480 | 21.149 | 19.498 | 1.00 | 32.21 |
| ATOM | 1414 | O   | THR | 226 | 23.323 | 21.228 | 19.910 | 1.00 | 33.24 |
| ATOM | 1415 | N   | ARG | 227 | 24.860 | 21.604 | 18.308 | 1.00 | 26.80 |
| ATOM | 1416 | CA  | ARG | 227 | 23.909 | 22.240 | 17.398 | 1.00 | 26.96 |
| ATOM | 1417 | CB  | ARG | 227 | 24.522 | 23.516 | 16.817 | 1.00 | 30.52 |
| ATOM | 1418 | CG  | ARG | 227 | 25.230 | 24.389 | 17.843 | 1.00 | 43.25 |
| ATOM | 1419 | CD  | ARG | 227 | 26.112 | 25.429 | 17.162 | 1.00 | 50.45 |
| ATOM | 1420 | NE  | ARG | 227 | 27.414 | 25.546 | 17.814 | 1.00 | 61.71 |
| ATOM | 1421 | CZ  | ARG | 227 | 27.670 | 26.331 | 18.859 | 1.00 | 66.83 |
| ATOM | 1422 | NH1 | ARG | 227 | 26.713 | 27.090 | 19.383 | 1.00 | 71.58 |
| ATOM | 1423 | NH2 | ARG | 227 | 28.887 | 26.356 | 19.391 | 1.00 | 68.59 |
| ATOM | 1424 | C   | ARG | 227 | 23.476 | 21.341 | 16.240 | 1.00 | 21.53 |
| ATOM | 1425 | O   | ARG | 227 | 22.406 | 21.544 | 15.662 | 1.00 | 16.15 |

FIGURE 1A-29

| ATOM | 1426 | N   | TYR | 228 | 24.287 | 20.320 | 15.957 | 1.00 | 17.38 |
| ATOM | 1427 | CA  | TYR | 228 | 24.079 | 19.388 | 14.841 | 1.00 | 12.67 |
| ATOM | 1428 | CB  | TYR | 228 | 24.965 | 18.160 | 15.006 | 1.00 | 12.13 |
| ATOM | 1429 | CG  | TYR | 228 | 26.393 | 18.451 | 15.386 | 1.00 | 15.81 |
| ATOM | 1430 | CD1 | TYR | 228 | 27.108 | 17.568 | 16.197 | 1.00 | 12.36 |
| ATOM | 1431 | CE1 | TYR | 228 | 28.436 | 17.810 | 16.520 | 1.00 | 17.68 |
| ATOM | 1432 | CD2 | TYR | 228 | 27.046 | 19.585 | 14.913 | 1.00 | 12.94 |
| ATOM | 1433 | CE2 | TYR | 228 | 28.375 | 19.834 | 15.234 | 1.00 | 14.72 |
| ATOM | 1434 | CZ  | TYR | 228 | 29.065 | 18.946 | 16.036 | 1.00 | 17.75 |
| ATOM | 1435 | OH  | TYR | 228 | 30.387 | 19.181 | 16.348 | 1.00 | 23.97 |
| ATOM | 1436 | C   | TYR | 228 | 22.670 | 18.892 | 14.501 | 1.00 | 12.86 |
| ATOM | 1437 | O   | TYR | 228 | 22.407 | 18.531 | 13.352 | 1.00 | 8.19 |
| ATOM | 1438 | N   | TYR | 229 | 21.759 | 18.905 | 15.471 | 1.00 | 8.89 |
| ATOM | 1439 | CA  | TYR | 229 | 20.411 | 18.377 | 15.248 | 1.00 | 3.37 |
| ATOM | 1440 | CB  | TYR | 229 | 20.097 | 17.324 | 16.326 | 1.00 | 4.48 |
| ATOM | 1441 | CG  | TYR | 229 | 21.227 | 16.341 | 16.522 | 1.00 | 2.00 |
| ATOM | 1442 | CD1 | TYR | 229 | 22.319 | 16.654 | 17.328 | 1.00 | 4.23 |
| ATOM | 1443 | CE1 | TYR | 229 | 23.423 | 15.813 | 17.397 | 1.00 | 6.82 |
| ATOM | 1444 | CD2 | TYR | 229 | 21.269 | 15.150 | 15.804 | 1.00 | 3.40 |
| ATOM | 1445 | CE2 | TYR | 229 | 22.366 | 14.307 | 15.874 | 1.00 | 2.00 |
| ATOM | 1446 | CZ  | TYR | 229 | 23.439 | 14.646 | 16.659 | 1.00 | 5.23 |
| ATOM | 1447 | OH  | TYR | 229 | 24.545 | 13.833 | 16.696 | 1.00 | 6.46 |
| ATOM | 1448 | C   | TYR | 229 | 19.325 | 19.428 | 15.191 | 1.00 | 7.35 |
| ATOM | 1449 | O   | TYR | 229 | 18.140 | 19.107 | 15.089 | 1.00 | 7.36 |
| ATOM | 1450 | N   | ARG | 230 | 19.728 | 20.691 | 15.197 | 1.00 | 9.86 |
| ATOM | 1451 | CA  | ARG | 230 | 18.762 | 21.782 | 15.145 | 1.00 | 13.59 |
| ATOM | 1452 | CB  | ARG | 230 | 19.368 | 23.054 | 15.738 | 1.00 | 19.14 |
| ATOM | 1453 | CG  | ARG | 230 | 19.896 | 22.857 | 17.165 | 1.00 | 27.85 |
| ATOM | 1454 | CD  | ARG | 230 | 20.023 | 24.167 | 17.921 | 1.00 | 35.17 |
| ATOM | 1455 | NE  | ARG | 230 | 20.949 | 24.082 | 19.051 | 1.00 | 38.48 |
| ATOM | 1456 | CZ  | ARG | 230 | 20.595 | 24.164 | 20.331 | 1.00 | 40.43 |
| ATOM | 1457 | NH1 | ARG | 230 | 19.324 | 24.314 | 20.671 | 1.00 | 40.64 |
| ATOM | 1458 | NH2 | ARG | 230 | 21.529 | 24.190 | 21.275 | 1.00 | 45.32 |
| ATOM | 1459 | C   | ARG | 230 | 18.244 | 22.036 | 13.723 | 1.00 | 13.05 |
| ATOM | 1460 | O   | ARG | 230 | 18.988 | 21.933 | 12.741 | 1.00 | 11.91 |
| ATOM | 1461 | N   | ALA | 231 | 16.960 | 22.372 | 13.640 | 1.00 | 8.43 |
| ATOM | 1462 | CA  | ALA | 231 | 16.271 | 22.630 | 12.378 | 1.00 | 12.42 |
| ATOM | 1463 | CB  | ALA | 231 | 14.771 | 22.605 | 12.602 | 1.00 | 6.61 |
| ATOM | 1464 | C   | ALA | 231 | 16.687 | 23.973 | 11.782 | 1.00 | 19.56 |
| ATOM | 1465 | O   | ALA | 231 | 17.153 | 24.853 | 12.499 | 1.00 | 25.90 |
| ATOM | 1466 | N   | PRO | 232 | 16.495 | 24.170 | 10.463 | 1.00 | 19.58 |
| ATOM | 1467 | CD  | PRO | 232 | 15.955 | 23.207 | 9.492  | 1.00 | 22.66 |
| ATOM | 1468 | CA  | PRO | 232 | 16.851 | 25.418 | 9.782  | 1.00 | 19.60 |
| ATOM | 1469 | CB  | PRO | 232 | 16.345 | 25.179 | 8.357  | 1.00 | 19.68 |
| ATOM | 1470 | CG  | PRO | 232 | 16.501 | 23.727 | 8.189  | 1.00 | 21.68 |
| ATOM | 1471 | C   | PRO | 232 | 16.117 | 26.583 | 10.425 | 1.00 | 18.17 |
| ATOM | 1472 | O   | PRO | 232 | 16.645 | 27.680 | 10.572 | 1.00 | 20.54 |
| ATOM | 1473 | N   | GLU | 233 | 14.905 | 26.300 | 10.881 | 1.00 | 20.66 |
| ATOM | 1474 | CA  | GLU | 233 | 14.089 | 27.302 | 11.532 | 1.00 | 21.36 |
| ATOM | 1475 | CB  | GLU | 233 | 12.602 | 26.918 | 11.474 | 1.00 | 19.79 |
| ATOM | 1476 | CG  | GLU | 233 | 12.260 | 25.547 | 12.040 | 1.00 | 24.86 |

FIGURE 1A-30

| ATOM | 1477 | CD | GLU | 233 | 12.106 | 24.467 | 10.974 | 1.00 | 17.54 |
|---|---|---|---|---|---|---|---|---|---|
| ATOM | 1478 | OE1 | GLU | 233 | 13.079 | 24.194 | 10.250 | 1.00 | 16.74 |
| ATOM | 1479 | OE2 | GLU | 233 | 11.001 | 23.900 | 10.866 | 1.00 | 6.42 |
| ATOM | 1480 | C | GLU | 233 | 14.545 | 27.487 | 12.981 | 1.00 | 20.32 |
| ATOM | 1481 | O | GLU | 233 | 13.739 | 27.723 | 13.869 | 1.00 | 24.49 |
| ATOM | 1482 | N | VAL | 234 | 15.830 | 27.263 | 13.223 | 1.00 | 18.23 |
| ATOM | 1483 | CA | VAL | 234 | 16.430 | 27.448 | 14.531 | 1.00 | 20.54 |
| ATOM | 1484 | CB | VAL | 234 | 16.448 | 26.132 | 15.367 | 1.00 | 21.18 |
| ATOM | 1485 | CG1 | VAL | 234 | 17.228 | 26.332 | 16.666 | 1.00 | 19.88 |
| ATOM | 1486 | CG2 | VAL | 234 | 15.021 | 25.703 | 15.702 | 1.00 | 20.38 |
| ATOM | 1487 | C | VAL | 234 | 17.856 | 27.932 | 14.244 | 1.00 | 22.57 |
| ATOM | 1488 | O | VAL | 234 | 18.371 | 28.815 | 14.932 | 1.00 | 34.81 |
| ATOM | 1489 | N | ILE | 235 | 18.475 | 27.373 | 13.208 | 1.00 | 20.10 |
| ATOM | 1490 | CA | ILE | 235 | 19.815 | 27.771 | 12.787 | 1.00 | 20.52 |
| ATOM | 1491 | CB | ILE | 235 | 20.332 | 26.847 | 11.672 | 1.00 | 17.05 |
| ATOM | 1492 | CG2 | ILE | 235 | 21.596 | 27.423 | 11.016 | 1.00 | 9.23 |
| ATOM | 1493 | CG1 | ILE | 235 | 20.546 | 25.438 | 12.223 | 1.00 | 18.12 |
| ATOM | 1494 | CD1 | ILE | 235 | 20.878 | 24.404 | 11.146 | 1.00 | 20.24 |
| ATOM | 1495 | C | ILE | 235 | 19.720 | 29.179 | 12.212 | 1.00 | 25.31 |
| ATOM | 1496 | O | ILE | 235 | 20.550 | 30.039 | 12.491 | 1.00 | 30.76 |
| ATOM | 1497 | N | LEU | 236 | 18.675 | 29.407 | 11.424 | 1.00 | 27.44 |
| ATOM | 1498 | CA | LEU | 236 | 18.463 | 30.691 | 10.773 | 1.00 | 27.56 |
| ATOM | 1499 | CB | LEU | 236 | 18.042 | 30.455 | 9.314 | 1.00 | 22.74 |
| ATOM | 1500 | CG | LEU | 236 | 18.921 | 29.578 | 8.410 | 1.00 | 18.98 |
| ATOM | 1501 | CD1 | LEU | 236 | 18.260 | 29.448 | 7.056 | 1.00 | 16.72 |
| ATOM | 1502 | CD2 | LEU | 236 | 20.318 | 30.149 | 8.254 | 1.00 | 13.48 |
| ATOM | 1503 | C | LEU | 236 | 17.440 | 31.595 | 11.463 | 1.00 | 27.60 |
| ATOM | 1504 | O | LEU | 236 | 17.117 | 32.653 | 10.934 | 1.00 | 26.13 |
| ATOM | 1505 | N | GLY | 237 | 16.925 | 31.167 | 12.620 | 1.00 | 31.84 |
| ATOM | 1506 | CA | GLY | 237 | 15.929 | 31.937 | 13.358 | 1.00 | 32.79 |
| ATOM | 1507 | C | GLY | 237 | 14.787 | 32.247 | 12.420 | 1.00 | 34.71 |
| ATOM | 1508 | O | GLY | 237 | 14.896 | 33.163 | 11.613 | 1.00 | 41.49 |
| ATOM | 1509 | N | MET | 238 | 13.674 | 31.526 | 12.526 | 1.00 | 34.54 |
| ATOM | 1510 | CA | MET | 238 | 12.588 | 31.744 | 11.577 | 1.00 | 32.74 |
| ATOM | 1511 | CB | MET | 238 | 12.690 | 30.676 | 10.495 | 1.00 | 28.26 |
| ATOM | 1512 | CG | MET | 238 | 12.729 | 31.177 | 9.092 | 1.00 | 30.49 |
| ATOM | 1513 | SD | MET | 238 | 12.960 | 29.769 | 8.043 | 1.00 | 31.88 |
| ATOM | 1514 | CE | MET | 238 | 14.658 | 29.411 | 8.399 | 1.00 | 31.60 |
| ATOM | 1515 | C | MET | 238 | 11.178 | 31.701 | 12.106 | 1.00 | 33.97 |
| ATOM | 1516 | O | MET | 238 | 10.254 | 32.236 | 11.486 | 1.00 | 39.97 |
| ATOM | 1517 | N | GLY | 239 | 10.998 | 31.016 | 13.222 | 1.00 | 33.62 |
| ATOM | 1518 | CA | GLY | 239 | 9.666 | 30.858 | 13.755 | 1.00 | 34.10 |
| ATOM | 1519 | C | GLY | 239 | 9.379 | 29.426 | 13.373 | 1.00 | 34.14 |
| ATOM | 1520 | O | GLY | 239 | 9.551 | 29.013 | 12.222 | 1.00 | 38.16 |
| ATOM | 1521 | N | TYR | 240 | 8.962 | 28.640 | 14.347 | 1.00 | 31.76 |
| ATOM | 1522 | CA | TYR | 240 | 8.722 | 27.241 | 14.098 | 1.00 | 25.22 |
| ATOM | 1523 | CB | TYR | 240 | 9.636 | 26.450 | 15.031 | 1.00 | 30.31 |
| ATOM | 1524 | CG | TYR | 240 | 9.465 | 26.817 | 16.487 | 1.00 | 28.07 |
| ATOM | 1525 | CD1 | TYR | 240 | 8.485 | 26.210 | 17.272 | 1.00 | 27.58 |
| ATOM | 1526 | CE1 | TYR | 240 | 8.306 | 26.568 | 18.608 | 1.00 | 32.98 |
| ATOM | 1527 | CD2 | TYR | 240 | 10.264 | 27.788 | 17.074 | 1.00 | 30.08 |

FIGURE 1A-31

| ATOM | 1528 | CE2 | TYR | 240 | 10.089 | 28.153 | 18.408 | 1.00 | 35.93 |
| ATOM | 1529 | CZ | TYR | 240 | 9.107 | 27.540 | 19.165 | 1.00 | 34.05 |
| ATOM | 1530 | OH | TYR | 240 | 8.917 | 27.924 | 20.468 | 1.00 | 35.42 |
| ATOM | 1531 | C | TYR | 240 | 7.283 | 26.790 | 14.285 | 1.00 | 26.12 |
| ATOM | 1532 | O | TYR | 240 | 6.355 | 27.594 | 14.367 | 1.00 | 29.40 |
| ATOM | 1533 | N | LYS | 241 | 7.116 | 25.475 | 14.263 | 1.00 | 28.03 |
| ATOM | 1534 | CA | LYS | 241 | 5.846 | 24.815 | 14.502 | 1.00 | 26.91 |
| ATOM | 1535 | CB | LYS | 241 | 4.929 | 24.834 | 13.270 | 1.00 | 27.67 |
| ATOM | 1536 | CG | LYS | 241 | 5.431 | 24.072 | 12.060 | 1.00 | 33.07 |
| ATOM | 1537 | CD | LYS | 241 | 4.291 | 23.869 | 11.085 | 1.00 | 35.07 |
| ATOM | 1538 | CE | LYS | 241 | 4.768 | 23.331 | 9.753 | 1.00 | 39.12 |
| ATOM | 1539 | NZ | LYS | 241 | 3.619 | 22.945 | 8.873 | 1.00 | 45.66 |
| ATOM | 1540 | C | LYS | 241 | 6.207 | 23.394 | 14.943 | 1.00 | 22.23 |
| ATOM | 1541 | O | LYS | 241 | 7.389 | 23.058 | 15.085 | 1.00 | 18.84 |
| ATOM | 1542 | N | GLU | 242 | 5.196 | 22.575 | 15.186 | 1.00 | 24.12 |
| ATOM | 1543 | CA | GLU | 242 | 5.393 | 21.203 | 15.644 | 1.00 | 27.08 |
| ATOM | 1544 | CB | GLU | 242 | 4.087 | 20.407 | 15.508 | 1.00 | 31.19 |
| ATOM | 1545 | CG | GLU | 242 | 2.797 | 21.220 | 15.619 | 1.00 | 42.32 |
| ATOM | 1546 | CD | GLU | 242 | 2.474 | 21.666 | 17.029 | 1.00 | 45.14 |
| ATOM | 1547 | OE1 | GLU | 242 | 2.135 | 20.806 | 17.869 | 1.00 | 49.49 |
| ATOM | 1548 | OE2 | GLU | 242 | 2.522 | 22.884 | 17.288 | 1.00 | 50.83 |
| ATOM | 1549 | C | GLU | 242 | 6.518 | 20.424 | 14.939 | 1.00 | 28.87 |
| ATOM | 1550 | O | GLU | 242 | 7.445 | 19.931 | 15.597 | 1.00 | 29.46 |
| ATOM | 1551 | N | ASN | 243 | 6.459 | 20.348 | 13.609 | 1.00 | 26.64 |
| ATOM | 1552 | CA | ASN | 243 | 7.438 | 19.572 | 12.843 | 1.00 | 23.45 |
| ATOM | 1553 | CB | ASN | 243 | 6.962 | 19.370 | 11.395 | 1.00 | 30.05 |
| ATOM | 1554 | CG | ASN | 243 | 7.266 | 20.549 | 10.494 | 1.00 | 28.12 |
| ATOM | 1555 | OD1 | ASN | 243 | 7.363 | 21.681 | 10.951 | 1.00 | 30.53 |
| ATOM | 1556 | ND2 | ASN | 243 | 7.426 | 20.280 | 9.200 | 1.00 | 27.57 |
| ATOM | 1557 | C | ASN | 243 | 8.911 | 19.977 | 12.880 | 1.00 | 19.71 |
| ATOM | 1558 | O | ASN | 243 | 9.714 | 19.443 | 12.113 | 1.00 | 16.73 |
| ATOM | 1559 | N | VAL | 244 | 9.278 | 20.901 | 13.766 | 1.00 | 18.00 |
| ATOM | 1560 | CA | VAL | 244 | 10.678 | 21.311 | 13.889 | 1.00 | 13.13 |
| ATOM | 1561 | CB | VAL | 244 | 10.836 | 22.615 | 14.761 | 1.00 | 10.31 |
| ATOM | 1562 | CG1 | VAL | 244 | 10.220 | 22.432 | 16.138 | 1.00 | 8.51 |
| ATOM | 1563 | CG2 | VAL | 244 | 12.298 | 23.029 | 14.884 | 1.00 | 8.10 |
| ATOM | 1564 | C | VAL | 244 | 11.478 | 20.141 | 14.484 | 1.00 | 15.29 |
| ATOM | 1565 | O | VAL | 244 | 12.674 | 19.974 | 14.208 | 1.00 | 12.90 |
| ATOM | 1566 | N | ASP | 245 | 10.784 | 19.294 | 15.247 | 1.00 | 18.32 |
| ATOM | 1567 | CA | ASP | 245 | 11.394 | 18.128 | 15.892 | 1.00 | 19.89 |
| ATOM | 1568 | CB | ASP | 245 | 10.541 | 17.681 | 17.081 | 1.00 | 15.63 |
| ATOM | 1569 | CG | ASP | 245 | 10.706 | 18.588 | 18.284 | 1.00 | 17.09 |
| ATOM | 1570 | OD1 | ASP | 245 | 11.862 | 18.956 | 18.574 | 1.00 | 11.80 |
| ATOM | 1571 | OD2 | ASP | 245 | 9.697 | 18.937 | 18.931 | 1.00 | 6.44 |
| ATOM | 1572 | C | ASP | 245 | 11.586 | 16.968 | 14.933 | 1.00 | 19.67 |
| ATOM | 1573 | O | ASP | 245 | 12.340 | 16.029 | 15.212 | 1.00 | 19.03 |
| ATOM | 1574 | N | ILE | 246 | 10.881 | 17.032 | 13.812 | 1.00 | 17.61 |
| ATOM | 1575 | CA | ILE | 246 | 10.979 | 16.008 | 12.792 | 1.00 | 15.11 |
| ATOM | 1576 | CB | ILE | 246 | 9.848 | 16.165 | 11.741 | 1.00 | 17.78 |
| ATOM | 1577 | CG2 | ILE | 246 | 10.158 | 15.392 | 10.476 | 1.00 | 22.45 |
| ATOM | 1578 | CG1 | ILE | 246 | 8.528 | 15.676 | 12.337 | 1.00 | 16.97 |

FIGURE 1A-32

| | | | | | | | | |
|---|---|---|---|---|---|---|---|---|
| ATOM | 1579 | CD1 | ILE | 246 | 8.578 | 14.222 | 12.795 | 1.00 11.74 |
| ATOM | 1580 | C | ILE | 246 | 12.355 | 16.099 | 12.149 | 1.00 14.58 |
| ATOM | 1581 | O | ILE | 246 | 12.957 | 15.088 | 11.806 | 1.00 18.30 |
| ATOM | 1582 | N | TRP | 247 | 12.901 | 17.307 | 12.088 | 1.00 12.73 |
| ATOM | 1583 | CA | TRP | 247 | 14.206 | 17.488 | 11.491 | 1.00 7.70 |
| ATOM | 1584 | CB | TRP | 247 | 14.522 | 18.967 | 11.294 | 1.00 7.64 |
| ATOM | 1585 | CG | TRP | 247 | 15.901 | 19.209 | 10.783 | 1.00 2.00 |
| ATOM | 1586 | CD2 | TRP | 247 | 16.296 | 19.409 | 9.426 | 1.00 2.00 |
| ATOM | 1587 | CE2 | TRP | 247 | 17.702 | 19.580 | 9.422 | 1.00 2.00 |
| ATOM | 1588 | CE3 | TRP | 247 | 15.603 | 19.471 | 8.217 | 1.00 3.59 |
| ATOM | 1589 | CD1 | TRP | 247 | 17.051 | 19.269 | 11.525 | 1.00 4.54 |
| ATOM | 1590 | NE1 | TRP | 247 | 18.132 | 19.486 | 10.721 | 1.00 6.64 |
| ATOM | 1591 | CZ2 | TRP | 247 | 18.432 | 19.795 | 8.242 | 1.00 2.44 |
| ATOM | 1592 | CZ3 | TRP | 247 | 16.322 | 19.689 | 7.051 | 1.00 2.48 |
| ATOM | 1593 | CH2 | TRP | 247 | 17.725 | 19.850 | 7.071 | 1.00 7.66 |
| ATOM | 1594 | C | TRP | 247 | 15.266 | 16.838 | 12.346 | 1.00 12.44 |
| ATOM | 1595 | O | TRP | 247 | 16.209 | 16.243 | 11.820 | 1.00 22.20 |
| ATOM | 1596 | N | SER | 248 | 15.139 | 16.979 | 13.662 | 1.00 10.03 |
| ATOM | 1597 | CA | SER | 248 | 16.104 | 16.393 | 14.592 | 1.00 10.93 |
| ATOM | 1598 | CB | SER | 248 | 15.834 | 16.860 | 16.030 | 1.00 13.84 |
| ATOM | 1599 | OG | SER | 248 | 15.965 | 18.269 | 16.153 | 1.00 6.70 |
| ATOM | 1600 | C | SER | 248 | 16.025 | 14.873 | 14.512 | 1.00 7.94 |
| ATOM | 1601 | O | SER | 248 | 17.050 | 14.209 | 14.559 | 1.00 7.84 |
| ATOM | 1602 | N | VAL | 249 | 14.807 | 14.338 | 14.389 | 1.00 9.55 |
| ATOM | 1603 | CA | VAL | 249 | 14.562 | 12.896 | 14.275 | 1.00 9.07 |
| ATOM | 1604 | CB | VAL | 249 | 13.041 | 12.581 | 14.187 | 1.00 11.85 |
| ATOM | 1605 | CG1 | VAL | 249 | 12.811 | 11.104 | 13.810 | 1.00 5.79 |
| ATOM | 1606 | CG2 | VAL | 249 | 12.335 | 12.951 | 15.511 | 1.00 2.00 |
| ATOM | 1607 | C | VAL | 249 | 15.223 | 12.344 | 13.008 | 1.00 11.82 |
| ATOM | 1608 | O | VAL | 249 | 15.741 | 11.222 | 12.999 | 1.00 10.02 |
| ATOM | 1609 | N | GLY | 250 | 15.200 | 13.158 | 11.952 | 1.00 14.54 |
| ATOM | 1610 | CA | GLY | 250 | 15.775 | 12.782 | 10.677 | 1.00 2.72 |
| ATOM | 1611 | C | GLY | 250 | 17.276 | 12.821 | 10.737 | 1.00 4.85 |
| ATOM | 1612 | O | GLY | 250 | 17.936 | 12.007 | 10.099 | 1.00 7.91 |
| ATOM | 1613 | N | CYS | 251 | 17.823 | 13.767 | 11.495 | 1.00 7.77 |
| ATOM | 1614 | CA | CYS | 251 | 19.273 | 13.892 | 11.651 | 1.00 6.91 |
| ATOM | 1615 | CB | CYS | 251 | 19.648 | 15.182 | 12.393 | 1.00 9.42 |
| ATOM | 1616 | SG | CYS | 251 | 19.397 | 16.736 | 11.524 | 1.00 11.33 |
| ATOM | 1617 | C | CYS | 251 | 19.775 | 12.714 | 12.473 | 1.00 11.75 |
| ATOM | 1618 | O | CYS | 251 | 20.931 | 12.309 | 12.347 | 1.00 12.55 |
| ATOM | 1619 | N | ILE | 252 | 18.914 | 12.204 | 13.352 | 1.00 7.77 |
| ATOM | 1620 | CA | ILE | 252 | 19.273 | 11.077 | 14.197 | 1.00 11.16 |
| ATOM | 1621 | CB | ILE | 252 | 18.380 | 11.014 | 15.464 | 1.00 11.43 |
| ATOM | 1622 | CG2 | ILE | 252 | 18.474 | 9.651 | 16.117 | 1.00 2.95 |
| ATOM | 1623 | CG1 | ILE | 252 | 18.803 | 12.109 | 16.453 | 1.00 7.93 |
| ATOM | 1624 | CD1 | ILE | 252 | 17.813 | 12.329 | 17.587 | 1.00 8.60 |
| ATOM | 1625 | C | ILE | 252 | 19.189 | 9.779 | 13.399 | 1.00 10.11 |
| ATOM | 1626 | O | ILE | 252 | 20.136 | 9.003 | 13.387 | 1.00 9.91 |
| ATOM | 1627 | N | MET | 253 | 18.070 | 9.563 | 12.717 | 1.00 8.65 |
| ATOM | 1628 | CA | MET | 253 | 17.883 | 8.367 | 11.891 | 1.00 11.03 |
| ATOM | 1629 | CB | MET | 253 | 16.558 | 8.463 | 11.130 | 1.00 11.61 |

FIGURE 1A-33

| | | | | | | | | |
|---|---|---|---|---|---|---|---|---|
| ATOM | 1630 | CG | MET | 253 | 16.281 | 7.354 | 10.131 | 1.00 9.73 |
| ATOM | 1631 | SD | MET | 253 | 14.574 | 7.467 | 9.532 | 1.00 18.84 |
| ATOM | 1632 | CE | MET | 253 | 14.297 | 5.724 | 9.074 | 1.00 20.28 |
| ATOM | 1633 | C | MET | 253 | 19.036 | 8.269 | 10.899 | 1.00 10.95 |
| ATOM | 1634 | O | MET | 253 | 19.701 | 7.240 | 10.801 | 1.00 14.90 |
| ATOM | 1635 | N | GLY | 254 | 19.319 | 9.388 | 10.241 | 1.00 8.37 |
| ATOM | 1636 | CA | GLY | 254 | 20.376 | 9.453 | 9.255 | 1.00 11.09 |
| ATOM | 1637 | C | GLY | 254 | 21.727 | 9.091 | 9.819 | 1.00 10.62 |
| ATOM | 1638 | O | GLY | 254 | 22.593 | 8.588 | 9.108 | 1.00 14.66 |
| ATOM | 1639 | N | GLU | 255 | 21.910 | 9.346 | 11.103 | 1.00 13.26 |
| ATOM | 1640 | CA | GLU | 255 | 23.157 | 9.025 | 11.773 | 1.00 13.23 |
| ATOM | 1641 | CB | GLU | 255 | 23.371 | 9.956 | 12.954 | 1.00 12.81 |
| ATOM | 1642 | CG | GLU | 255 | 24.721 | 9.797 | 13.626 | 1.00 12.38 |
| ATOM | 1643 | CD | GLU | 255 | 24.981 | 10.884 | 14.629 | 1.00 16.63 |
| ATOM | 1644 | OE1 | GLU | 255 | 24.097 | 11.752 | 14.792 | 1.00 15.83 |
| ATOM | 1645 | OE2 | GLU | 255 | 26.066 | 10.876 | 15.241 | 1.00 13.69 |
| ATOM | 1646 | C | GLU | 255 | 23.128 | 7.573 | 12.232 | 1.00 12.50 |
| ATOM | 1647 | O | GLU | 255 | 24.167 | 6.914 | 12.274 | 1.00 15.69 |
| ATOM | 1648 | N | MET | 256 | 21.934 | 7.073 | 12.544 | 1.00 11.34 |
| ATOM | 1649 | CA | MET | 256 | 21.761 | 5.684 | 12.968 | 1.00 18.29 |
| ATOM | 1650 | CB | MET | 256 | 20.306 | 5.418 | 13.400 | 1.00 15.85 |
| ATOM | 1651 | CG | MET | 256 | 19.923 | 5.864 | 14.819 | 1.00 13.73 |
| ATOM | 1652 | SD | MET | 256 | 18.129 | 5.771 | 15.110 | 1.00 21.93 |
| ATOM | 1653 | CE | MET | 256 | 18.045 | 4.508 | 16.280 | 1.00 22.20 |
| ATOM | 1654 | C | MET | 256 | 22.104 | 4.784 | 11.771 | 1.00 21.35 |
| ATOM | 1655 | O | MET | 256 | 22.528 | 3.636 | 11.938 | 1.00 24.25 |
| ATOM | 1656 | N | VAL | 257 | 21.918 | 5.327 | 10.568 | 1.00 20.26 |
| ATOM | 1657 | CA | VAL | 257 | 22.179 | 4.628 | 9.319 | 1.00 17.94 |
| ATOM | 1658 | CB | VAL | 257 | 21.196 | 5.102 | 8.217 | 1.00 16.26 |
| ATOM | 1659 | CG1 | VAL | 257 | 21.532 | 4.460 | 6.873 | 1.00 20.24 |
| ATOM | 1660 | CG2 | VAL | 257 | 19.769 | 4.780 | 8.617 | 1.00 8.70 |
| ATOM | 1661 | C | VAL | 257 | 23.614 | 4.838 | 8.823 | 1.00 24.46 |
| ATOM | 1662 | O | VAL | 257 | 24.340 | 3.877 | 8.550 | 1.00 28.18 |
| ATOM | 1663 | N | ARG | 258 | 24.030 | 6.100 | 8.738 | 1.00 26.10 |
| ATOM | 1664 | CA | ARG | 258 | 25.355 | 6.452 | 8.246 | 1.00 25.83 |
| ATOM | 1665 | CB | ARG | 258 | 25.350 | 7.916 | 7.777 | 1.00 25.22 |
| ATOM | 1666 | CG | ARG | 258 | 26.446 | 8.265 | 6.778 | 1.00 29.73 |
| ATOM | 1667 | CD | ARG | 258 | 26.442 | 9.741 | 6.371 | 1.00 23.25 |
| ATOM | 1668 | NE | ARG | 258 | 25.447 | 10.070 | 5.347 | 1.00 26.29 |
| ATOM | 1669 | CZ | ARG | 258 | 25.292 | 11.286 | 4.824 | 1.00 27.73 |
| ATOM | 1670 | NH1 | ARG | 258 | 26.065 | 12.285 | 5.228 | 1.00 31.86 |
| ATOM | 1671 | NH2 | ARG | 258 | 24.358 | 11.514 | 3.907 | 1.00 25.21 |
| ATOM | 1672 | C | ARG | 258 | 26.493 | 6.190 | 9.247 | 1.00 29.04 |
| ATOM | 1673 | O | ARG | 258 | 27.632 | 5.967 | 8.839 | 1.00 30.93 |
| ATOM | 1674 | N | HIS | 259 | 26.167 | 6.165 | 10.541 | 1.00 31.54 |
| ATOM | 1675 | CA | HIS | 259 | 27.133 | 5.937 | 11.634 | 1.00 30.75 |
| ATOM | 1676 | CB | HIS | 259 | 27.950 | 4.654 | 11.416 | 1.00 29.60 |
| ATOM | 1677 | CG | HIS | 259 | 27.121 | 3.419 | 11.315 | 1.00 29.37 |
| ATOM | 1678 | CD2 | HIS | 259 | 26.895 | 2.578 | 10.277 | 1.00 24.51 |
| ATOM | 1679 | ND1 | HIS | 259 | 26.344 | 2.958 | 12.357 | 1.00 28.59 |
| ATOM | 1680 | CE1 | HIS | 259 | 25.672 | 1.894 | 11.960 | 1.00 30.73 |

FIGURE 1A-34

| ATOM | 1681 | NE2 | HIS | 259 | 25.986 | 1.643 | 10.706 | 1.00 | 24.74 |
|------|------|-----|-----|-----|--------|-------|--------|------|-------|
| ATOM | 1682 | C | HIS | 259 | 28.096 | 7.089 | 11.845 | 1.00 | 33.58 |
| ATOM | 1683 | O | HIS | 259 | 29.182 | 6.906 | 12.395 | 1.00 | 36.69 |
| ATOM | 1684 | N | LYS | 260 | 27.714 | 8.268 | 11.380 | 1.00 | 36.75 |
| ATOM | 1685 | CA | LYS | 260 | 28.550 | 9.446 | 11.536 | 1.00 | 37.29 |
| ATOM | 1686 | CB | LYS | 260 | 29.639 | 9.467 | 10.457 | 1.00 | 40.91 |
| ATOM | 1687 | CG | LYS | 260 | 30.874 | 10.270 | 10.846 | 1.00 | 51.71 |
| ATOM | 1688 | CD | LYS | 260 | 31.590 | 9.666 | 12.051 | 1.00 | 51.82 |
| ATOM | 1689 | CE | LYS | 260 | 32.701 | 10.582 | 12.546 | 1.00 | 54.23 |
| ATOM | 1690 | NZ | LYS | 260 | 33.590 | 9.914 | 13.543 | 1.00 | 58.59 |
| ATOM | 1691 | C | LYS | 260 | 27.647 | 10.673 | 11.447 | 1.00 | 35.83 |
| ATOM | 1692 | O | LYS | 260 | 26.604 | 10.636 | 10.790 | 1.00 | 33.85 |
| ATOM | 1693 | N | ILE | 261 | 28.026 | 11.753 | 12.122 | 1.00 | 33.84 |
| ATOM | 1694 | CA | ILE | 261 | 27.219 | 12.971 | 12.129 | 1.00 | 32.21 |
| ATOM | 1695 | CB | ILE | 261 | 27.855 | 14.052 | 13.030 | 1.00 | 32.27 |
| ATOM | 1696 | CG2 | ILE | 261 | 27.010 | 15.316 | 13.021 | 1.00 | 40.17 |
| ATOM | 1697 | CG1 | ILE | 261 | 27.926 | 13.544 | 14.478 | 1.00 | 34.02 |
| ATOM | 1698 | CD1 | ILE | 261 | 28.780 | 14.401 | 15.408 | 1.00 | 31.36 |
| ATOM | 1699 | C | ILE | 261 | 26.932 | 13.526 | 10.732 | 1.00 | 33.34 |
| ATOM | 1700 | O | ILE | 261 | 27.837 | 13.733 | 9.923 | 1.00 | 36.27 |
| ATOM | 1701 | N | LEU | 262 | 25.651 | 13.776 | 10.473 | 1.00 | 28.88 |
| ATOM | 1702 | CA | LEU | 262 | 25.186 | 14.291 | 9.186 | 1.00 | 22.44 |
| ATOM | 1703 | CB | LEU | 262 | 23.659 | 14.204 | 9.131 | 1.00 | 16.88 |
| ATOM | 1704 | CG | LEU | 262 | 23.030 | 13.115 | 8.256 | 1.00 | 10.03 |
| ATOM | 1705 | CD1 | LEU | 262 | 23.656 | 11.768 | 8.553 | 1.00 | 7.90 |
| ATOM | 1706 | CD2 | LEU | 262 | 21.525 | 13.082 | 8.471 | 1.00 | 5.23 |
| ATOM | 1707 | C | LEU | 262 | 25.637 | 15.710 | 8.811 | 1.00 | 23.91 |
| ATOM | 1708 | O | LEU | 262 | 26.308 | 15.894 | 7.791 | 1.00 | 27.63 |
| ATOM | 1709 | N | PHE | 263 | 25.256 | 16.701 | 9.617 | 1.00 | 24.26 |
| ATOM | 1710 | CA | PHE | 263 | 25.590 | 18.104 | 9.357 | 1.00 | 19.48 |
| ATOM | 1711 | CB | PHE | 263 | 24.309 | 18.947 | 9.253 | 1.00 | 18.64 |
| ATOM | 1712 | CG | PHE | 263 | 23.230 | 18.350 | 8.376 | 1.00 | 20.06 |
| ATOM | 1713 | CD1 | PHE | 263 | 23.499 | 17.946 | 7.072 | 1.00 | 20.42 |
| ATOM | 1714 | CD2 | PHE | 263 | 21.930 | 18.231 | 8.854 | 1.00 | 14.93 |
| ATOM | 1715 | CE1 | PHE | 263 | 22.487 | 17.428 | 6.257 | 1.00 | 18.22 |
| ATOM | 1716 | CE2 | PHE | 263 | 20.910 | 17.719 | 8.053 | 1.00 | 14.75 |
| ATOM | 1717 | CZ | PHE | 263 | 21.189 | 17.313 | 6.747 | 1.00 | 15.66 |
| ATOM | 1718 | C | PHE | 263 | 26.466 | 18.734 | 10.448 | 1.00 | 24.83 |
| ATOM | 1719 | O | PHE | 263 | 26.009 | 19.609 | 11.190 | 1.00 | 23.18 |
| ATOM | 1720 | N | PRO | 264 | 27.751 | 18.346 | 10.530 | 1.00 | 28.64 |
| ATOM | 1721 | CD | PRO | 264 | 28.486 | 17.451 | 9.620 | 1.00 | 29.89 |
| ATOM | 1722 | CA | PRO | 264 | 28.645 | 18.905 | 11.554 | 1.00 | 33.34 |
| ATOM | 1723 | CB | PRO | 264 | 29.870 | 17.994 | 11.460 | 1.00 | 32.47 |
| ATOM | 1724 | CG | PRO | 264 | 29.948 | 17.722 | 9.982 | 1.00 | 30.19 |
| ATOM | 1725 | C | PRO | 264 | 29.021 | 20.374 | 11.281 | 1.00 | 36.01 |
| ATOM | 1726 | O | PRO | 264 | 28.604 | 20.951 | 10.277 | 1.00 | 40.32 |
| ATOM | 1727 | N | GLY | 265 | 29.832 | 20.961 | 12.161 | 1.00 | 35.76 |
| ATOM | 1728 | CA | GLY | 265 | 30.248 | 22.338 | 11.970 | 1.00 | 35.31 |
| ATOM | 1729 | C | GLY | 265 | 30.673 | 23.045 | 13.239 | 1.00 | 37.91 |
| ATOM | 1730 | O | GLY | 265 | 30.198 | 22.719 | 14.325 | 1.00 | 38.81 |
| ATOM | 1731 | N | ARG | 266 | 31.586 | 24.005 | 13.094 | 1.00 | 39.09 |

FIGURE 1A-35

| ATOM | 1732 | CA | ARG | 266 | 32.098 | 24.801 | 14.207 | 1.00 | 37.34 |
|---|---|---|---|---|---|---|---|---|---|
| ATOM | 1733 | CB | ARG | 266 | 33.331 | 25.589 | 13.761 | 1.00 | 39.08 |
| ATOM | 1734 | CG | ARG | 266 | 34.358 | 24.788 | 12.972 | 1.00 | 41.45 |
| ATOM | 1735 | CD | ARG | 266 | 35.382 | 25.711 | 12.324 | 1.00 | 44.00 |
| ATOM | 1736 | NE | ARG | 266 | 34.750 | 26.735 | 11.489 | 1.00 | 44.04 |
| ATOM | 1737 | CZ | ARG | 266 | 35.406 | 27.564 | 10.679 | 1.00 | 43.78 |
| ATOM | 1738 | NH1 | ARG | 266 | 36.725 | 27.500 | 10.576 | 1.00 | 43.33 |
| ATOM | 1739 | NH2 | ARG | 266 | 34.739 | 28.481 | 9.986 | 1.00 | 43.71 |
| ATOM | 1740 | C | ARG | 266 | 31.037 | 25.807 | 14.636 | 1.00 | 33.96 |
| ATOM | 1741 | O | ARG | 266 | 30.805 | 26.030 | 15.825 | 1.00 | 33.73 |
| ATOM | 1742 | N | ASP | 267 | 30.399 | 26.413 | 13.645 | 1.00 | 30.72 |
| ATOM | 1743 | CA | ASP | 267 | 29.383 | 27.423 | 13.878 | 1.00 | 32.69 |
| ATOM | 1744 | CB | ASP | 267 | 29.936 | 28.791 | 13.449 | 1.00 | 43.33 |
| ATOM | 1745 | CG | ASP | 267 | 29.136 | 29.954 | 14.021 | 1.00 | 54.26 |
| ATOM | 1746 | OD1 | ASP | 267 | 28.466 | 30.658 | 13.228 | 1.00 | 55.75 |
| ATOM | 1747 | OD2 | ASP | 267 | 29.172 | 30.160 | 15.260 | 1.00 | 59.87 |
| ATOM | 1748 | C | ASP | 267 | 28.156 | 27.075 | 13.045 | 1.00 | 28.36 |
| ATOM | 1749 | O | ASP | 267 | 28.132 | 26.051 | 12.371 | 1.00 | 28.17 |
| ATOM | 1750 | N | TYR | 268 | 27.139 | 27.929 | 13.093 | 1.00 | 25.56 |
| ATOM | 1751 | CA | TYR | 268 | 25.938 | 27.718 | 12.303 | 1.00 | 22.27 |
| ATOM | 1752 | CB | TYR | 268 | 24.826 | 28.660 | 12.751 | 1.00 | 22.38 |
| ATOM | 1753 | CG | TYR | 268 | 23.987 | 28.168 | 13.897 | 1.00 | 29.62 |
| ATOM | 1754 | CD1 | TYR | 268 | 23.725 | 26.812 | 14.078 | 1.00 | 28.93 |
| ATOM | 1755 | CE1 | TYR | 268 | 22.893 | 26.372 | 15.116 | 1.00 | 31.11 |
| ATOM | 1756 | CD2 | TYR | 268 | 23.401 | 29.070 | 14.781 | 1.00 | 34.24 |
| ATOM | 1757 | CE2 | TYR | 268 | 22.573 | 28.640 | 15.812 | 1.00 | 33.57 |
| ATOM | 1758 | CZ | TYR | 268 | 22.320 | 27.294 | 15.977 | 1.00 | 32.49 |
| ATOM | 1759 | OH | TYR | 268 | 21.487 | 26.890 | 16.996 | 1.00 | 31.19 |
| ATOM | 1760 | C | TYR | 268 | 26.277 | 28.014 | 10.838 | 1.00 | 21.54 |
| ATOM | 1761 | O | TYR | 268 | 25.491 | 27.710 | 9.944 | 1.00 | 18.16 |
| ATOM | 1762 | N | ILE | 269 | 27.434 | 28.632 | 10.600 | 1.00 | 20.49 |
| ATOM | 1763 | CA | ILE | 269 | 27.866 | 28.961 | 9.239 | 1.00 | 21.51 |
| ATOM | 1764 | CB | ILE | 269 | 28.988 | 30.046 | 9.216 | 1.00 | 21.86 |
| ATOM | 1765 | CG2 | ILE | 269 | 29.423 | 30.316 | 7.778 | 1.00 | 17.40 |
| ATOM | 1766 | CG1 | ILE | 269 | 28.525 | 31.336 | 9.910 | 1.00 | 16.45 |
| ATOM | 1767 | CD1 | ILE | 269 | 27.282 | 31.977 | 9.334 | 1.00 | 16.88 |
| ATOM | 1768 | C | ILE | 269 | 28.377 | 27.691 | 8.558 | 1.00 | 22.26 |
| ATOM | 1769 | O | ILE | 269 | 28.009 | 27.404 | 7.417 | 1.00 | 15.96 |
| ATOM | 1770 | N | ASP | 270 | 29.220 | 26.939 | 9.269 | 1.00 | 22.67 |
| ATOM | 1771 | CA | ASP | 270 | 29.758 | 25.683 | 8.750 | 1.00 | 26.51 |
| ATOM | 1772 | CB | ASP | 270 | 30.912 | 25.185 | 9.616 | 1.00 | 29.81 |
| ATOM | 1773 | CG | ASP | 270 | 32.075 | 26.141 | 9.635 | 1.00 | 44.29 |
| ATOM | 1774 | OD1 | ASP | 270 | 32.029 | 27.119 | 10.416 | 1.00 | 51.03 |
| ATOM | 1775 | OD2 | ASP | 270 | 33.037 | 25.910 | 8.870 | 1.00 | 49.24 |
| ATOM | 1776 | C | ASP | 270 | 28.681 | 24.613 | 8.725 | 1.00 | 26.07 |
| ATOM | 1777 | O | ASP | 270 | 28.724 | 23.693 | 7.912 | 1.00 | 31.95 |
| ATOM | 1778 | N | GLN | 271 | 27.695 | 24.745 | 9.598 | 1.00 | 23.97 |
| ATOM | 1779 | CA | GLN | 271 | 26.645 | 23.759 | 9.651 | 1.00 | 22.27 |
| ATOM | 1780 | CB | GLN | 271 | 25.924 | 23.804 | 10.981 | 1.00 | 23.07 |
| ATOM | 1781 | CG | GLN | 271 | 25.510 | 22.437 | 11.433 | 1.00 | 24.75 |
| ATOM | 1782 | CD | GLN | 271 | 24.265 | 22.457 | 12.260 | 1.00 | 26.45 |

FIGURE 1A-36

```
ATOM   1783  OE1 GLN   271      24.169  23.183  13.248  1.00 22.23
ATOM   1784  NE2 GLN   271      23.302  21.634  11.879  1.00 29.79
ATOM   1785  C   GLN   271      25.646  23.911   8.527  1.00 24.44
ATOM   1786  O   GLN   271      25.189  22.921   7.963  1.00 27.22
ATOM   1787  N   TRP   272      25.283  25.147   8.211  1.00 24.10
ATOM   1788  CA  TRP   272      24.331  25.397   7.137  1.00 23.58
ATOM   1789  CB  TRP   272      23.902  26.864   7.141  1.00 20.11
ATOM   1790  CG  TRP   272      22.949  27.242   6.067  1.00 14.93
ATOM   1791  CD2 TRP   272      21.580  26.837   5.942  1.00  9.51
ATOM   1792  CE2 TRP   272      21.066  27.458   4.778  1.00 12.22
ATOM   1793  CE3 TRP   272      20.738  26.014   6.689  1.00 11.91
ATOM   1794  CD1 TRP   272      23.204  28.069   5.009  1.00 13.36
ATOM   1795  NE1 TRP   272      22.081  28.204   4.234  1.00 10.83
ATOM   1796  CZ2 TRP   272      19.746  27.272   4.351  1.00 10.25
ATOM   1797  CZ3 TRP   272      19.425  25.832   6.266  1.00  8.87
ATOM   1798  CH2 TRP   272      18.942  26.456   5.104  1.00  9.75
ATOM   1799  C   TRP   272      24.993  25.014   5.809  1.00 26.50
ATOM   1800  O   TRP   272      24.313  24.584   4.870  1.00 23.62
ATOM   1801  N   ASN   273      26.323  25.136   5.764  1.00 25.25
ATOM   1802  CA  ASN   273      27.119  24.787   4.591  1.00 24.62
ATOM   1803  CB  ASN   273      28.618  25.029   4.852  1.00 21.82
ATOM   1804  CG  ASN   273      29.053  26.474   4.575  1.00 19.16
ATOM   1805  OD1 ASN   273      28.257  27.301   4.148  1.00 15.66
ATOM   1806  ND2 ASN   273      30.333  26.766   4.799  1.00 17.18
ATOM   1807  C   ASN   273      26.905  23.311   4.307  1.00 27.52
ATOM   1808  O   ASN   273      26.687  22.900   3.162  1.00 29.06
ATOM   1809  N   LYS   274      26.927  22.520   5.376  1.00 29.19
ATOM   1810  CA  LYS   274      26.742  21.078   5.275  1.00 25.90
ATOM   1811  CB  LYS   274      27.255  20.384   6.539  1.00 21.96
ATOM   1812  CG  LYS   274      28.754  20.485   6.719  1.00 22.71
ATOM   1813  CD  LYS   274      29.484  19.906   5.511  1.00 28.75
ATOM   1814  CE  LYS   274      30.985  20.140   5.605  1.00 33.15
ATOM   1815  NZ  LYS   274      31.744  19.530   4.475  1.00 28.90
ATOM   1816  C   LYS   274      25.298  20.671   4.980  1.00 23.86
ATOM   1817  O   LYS   274      25.050  19.575   4.489  1.00 30.51
ATOM   1818  N   VAL   275      24.345  21.555   5.239  1.00 19.76
ATOM   1819  CA  VAL   275      22.947  21.242   4.973  1.00 18.58
ATOM   1820  CB  VAL   275      21.994  22.156   5.792  1.00 12.48
ATOM   1821  CG1 VAL   275      20.550  21.875   5.448  1.00  7.62
ATOM   1822  CG2 VAL   275      22.221  21.943   7.284  1.00 18.60
ATOM   1823  C   VAL   275      22.641  21.396   3.479  1.00 25.22
ATOM   1824  O   VAL   275      21.986  20.543   2.875  1.00 25.57
ATOM   1825  N   ILE   276      23.147  22.473   2.883  1.00 28.32
ATOM   1826  CA  ILE   276      22.919  22.741   1.471  1.00 25.82
ATOM   1827  CB  ILE   276      23.075  24.248   1.155  1.00 22.27
ATOM   1828  CG2 ILE   276      21.969  25.041   1.842  1.00 21.47
ATOM   1829  CG1 ILE   276      24.457  24.736   1.588  1.00 20.17
ATOM   1830  CD1 ILE   276      24.788  26.153   1.171  1.00 19.35
ATOM   1831  C   ILE   276      23.839  21.919   0.570  1.00 27.51
ATOM   1832  O   ILE   276      23.486  21.611  -0.564  1.00 27.33
ATOM   1833  N   GLU   277      25.006  21.544   1.083  1.00 30.87
```

FIGURE 1A-37

| | | | | | | | | | |
|---|---|---|---|---|---|---|---|---|---|
| ATOM | 1834 | CA | GLU | 277 | 25.961 | 20.745 | 0.319 | 1.00 | 32.93 |
| ATOM | 1835 | CB | GLU | 277 | 27.250 | 20.582 | 1.110 | 1.00 | 31.36 |
| ATOM | 1836 | CG | GLU | 277 | 28.279 | 21.620 | 0.815 | 1.00 | 33.16 |
| ATOM | 1837 | CD | GLU | 277 | 29.378 | 21.627 | 1.835 | 1.00 | 37.35 |
| ATOM | 1838 | OE1 | GLU | 277 | 29.962 | 20.553 | 2.097 | 1.00 | 39.55 |
| ATOM | 1839 | OE2 | GLU | 277 | 29.651 | 22.709 | 2.385 | 1.00 | 43.57 |
| ATOM | 1840 | C | GLU | 277 | 25.427 | 19.357 | -0.001 | 1.00 | 36.55 |
| ATOM | 1841 | O | GLU | 277 | 25.865 | 18.718 | -0.958 | 1.00 | 41.81 |
| ATOM | 1842 | N | GLN | 278 | 24.480 | 18.892 | 0.806 | 1.00 | 35.65 |
| ATOM | 1843 | CA | GLN | 278 | 23.926 | 17.565 | 0.632 | 1.00 | 28.59 |
| ATOM | 1844 | CB | GLN | 278 | 23.991 | 16.816 | 1.954 | 1.00 | 26.36 |
| ATOM | 1845 | CG | GLN | 278 | 25.385 | 16.655 | 2.503 | 1.00 | 26.53 |
| ATOM | 1846 | CD | GLN | 278 | 25.394 | 15.837 | 3.764 | 1.00 | 26.26 |
| ATOM | 1847 | OE1 | GLN | 278 | 24.718 | 14.812 | 3.854 | 1.00 | 23.86 |
| ATOM | 1848 | NE2 | GLN | 278 | 26.152 | 16.285 | 4.752 | 1.00 | 27.07 |
| ATOM | 1849 | C | GLN | 278 | 22.509 | 17.536 | 0.121 | 1.00 | 26.73 |
| ATOM | 1850 | O | GLN | 278 | 22.178 | 16.725 | -0.736 | 1.00 | 27.81 |
| ATOM | 1851 | N | LEU | 279 | 21.671 | 18.401 | 0.677 | 1.00 | 27.04 |
| ATOM | 1852 | CA | LEU | 279 | 20.268 | 18.466 | 0.309 | 1.00 | 29.79 |
| ATOM | 1853 | CB | LEU | 279 | 19.412 | 18.767 | 1.547 | 1.00 | 29.29 |
| ATOM | 1854 | CG | LEU | 279 | 19.659 | 18.049 | 2.888 | 1.00 | 32.21 |
| ATOM | 1855 | CD1 | LEU | 279 | 18.541 | 18.448 | 3.869 | 1.00 | 22.95 |
| ATOM | 1856 | CD2 | LEU | 279 | 19.720 | 16.520 | 2.731 | 1.00 | 22.23 |
| ATOM | 1857 | C | LEU | 279 | 20.013 | 19.520 | -0.767 | 1.00 | 31.21 |
| ATOM | 1858 | O | LEU | 279 | 18.950 | 19.535 | -1.398 | 1.00 | 33.37 |
| ATOM | 1859 | N | GLY | 280 | 20.987 | 20.405 | -0.959 | 1.00 | 33.43 |
| ATOM | 1860 | CA | GLY | 280 | 20.870 | 21.460 | -1.955 | 1.00 | 33.15 |
| ATOM | 1861 | C | GLY | 280 | 20.193 | 22.733 | -1.473 | 1.00 | 34.41 |
| ATOM | 1862 | O | GLY | 280 | 19.466 | 22.731 | -0.466 | 1.00 | 38.44 |
| ATOM | 1863 | N | THR | 281 | 20.419 | 23.825 | -2.201 | 1.00 | 31.13 |
| ATOM | 1864 | CA | THR | 281 | 19.840 | 25.132 | -1.885 | 1.00 | 23.59 |
| ATOM | 1865 | CB | THR | 281 | 20.358 | 26.237 | -2.882 | 1.00 | 19.38 |
| ATOM | 1866 | OG1 | THR | 281 | 21.769 | 26.442 | -2.697 | 1.00 | 17.50 |
| ATOM | 1867 | CG2 | THR | 281 | 19.625 | 27.561 | -2.685 | 1.00 | 15.70 |
| ATOM | 1868 | C | THR | 281 | 18.316 | 25.047 | -1.949 | 1.00 | 22.14 |
| ATOM | 1869 | O | THR | 281 | 17.761 | 24.662 | -2.968 | 1.00 | 30.81 |
| ATOM | 1870 | N | PRO | 282 | 17.628 | 25.404 | -0.857 | 1.00 | 23.37 |
| ATOM | 1871 | CD | PRO | 282 | 18.208 | 25.939 | 0.384 | 1.00 | 17.01 |
| ATOM | 1872 | CA | PRO | 282 | 16.162 | 25.371 | -0.771 | 1.00 | 28.74 |
| ATOM | 1873 | CB | PRO | 282 | 15.894 | 25.896 | 0.637 | 1.00 | 20.53 |
| ATOM | 1874 | CG | PRO | 282 | 17.081 | 26.768 | 0.916 | 1.00 | 21.80 |
| ATOM | 1875 | C | PRO | 282 | 15.441 | 26.210 | -1.828 | 1.00 | 34.15 |
| ATOM | 1876 | O | PRO | 282 | 15.996 | 27.163 | -2.374 | 1.00 | 37.77 |
| ATOM | 1877 | N | CYS | 283 | 14.183 | 25.863 | -2.086 | 1.00 | 38.65 |
| ATOM | 1878 | CA | CYS | 283 | 13.387 | 26.558 | -3.083 | 1.00 | 44.96 |
| ATOM | 1879 | CB | CYS | 283 | 12.048 | 25.841 | -3.286 | 1.00 | 45.92 |
| ATOM | 1880 | SG | CYS | 283 | 10.814 | 26.163 | -2.013 | 1.00 | 57.54 |
| ATOM | 1881 | C | CYS | 283 | 13.158 | 28.029 | -2.725 | 1.00 | 50.64 |
| ATOM | 1882 | O | CYS | 283 | 13.181 | 28.403 | -1.555 | 1.00 | 50.43 |
| ATOM | 1883 | N | PRO | 284 | 12.985 | 28.887 | -3.750 | 1.00 | 55.81 |
| ATOM | 1884 | CD | PRO | 284 | 13.283 | 28.516 | -5.142 | 1.00 | 59.07 |

FIGURE 1A-38

| ATOM | 1885 | CA | PRO | 284 | 12.748 | 30.336 | -3.658 | 1.00 | 55.08 |
|---|---|---|---|---|---|---|---|---|---|
| ATOM | 1886 | CB | PRO | 284 | 12.807 | 30.775 | -5.122 | 1.00 | 56.31 |
| ATOM | 1887 | CG | PRO | 284 | 13.761 | 29.818 | -5.726 | 1.00 | 56.46 |
| ATOM | 1888 | C | PRO | 284 | 11.413 | 30.742 | -3.018 | 1.00 | 55.00 |
| ATOM | 1889 | O | PRO | 284 | 10.908 | 31.841 | -3.271 | 1.00 | 57.93 |
| ATOM | 1890 | N | ALA | 285 | 10.807 | 29.836 | -2.260 | 1.00 | 52.87 |
| ATOM | 1891 | CA | ALA | 285 | 9.552 | 30.129 | -1.569 | 1.00 | 50.92 |
| ATOM | 1892 | CB | ALA | 285 | 8.481 | 29.100 | -1.928 | 1.00 | 51.24 |
| ATOM | 1893 | C | ALA | 285 | 9.871 | 30.079 | -0.077 | 1.00 | 48.68 |
| ATOM | 1894 | O | ALA | 285 | 9.190 | 30.688 | 0.753 | 1.00 | 47.40 |
| ATOM | 1895 | N | PHE | 286 | 10.939 | 29.352 | 0.234 | 1.00 | 42.92 |
| ATOM | 1896 | CA | PHE | 286 | 11.421 | 29.193 | 1.589 | 1.00 | 40.44 |
| ATOM | 1897 | CB | PHE | 286 | 12.330 | 27.962 | 1.651 | 1.00 | 32.71 |
| ATOM | 1898 | CG | PHE | 286 | 13.126 | 27.862 | 2.920 | 1.00 | 22.35 |
| ATOM | 1899 | CD1 | PHE | 286 | 12.530 | 27.428 | 4.100 | 1.00 | 22.02 |
| ATOM | 1900 | CD2 | PHE | 286 | 14.475 | 28.191 | 2.933 | 1.00 | 16.44 |
| ATOM | 1901 | CE1 | PHE | 286 | 13.266 | 27.347 | 5.273 | 1.00 | 18.13 |
| ATOM | 1902 | CE2 | PHE | 286 | 15.219 | 28.115 | 4.095 | 1.00 | 14.47 |
| ATOM | 1903 | CZ | PHE | 286 | 14.618 | 27.687 | 5.268 | 1.00 | 16.25 |
| ATOM | 1904 | C | PHE | 286 | 12.184 | 30.458 | 1.990 | 1.00 | 44.51 |
| ATOM | 1905 | O | PHE | 286 | 11.978 | 30.997 | 3.083 | 1.00 | 46.42 |
| ATOM | 1906 | N | MET | 287 | 13.010 | 30.962 | 1.072 | 1.00 | 45.85 |
| ATOM | 1907 | CA | MET | 287 | 13.810 | 32.159 | 1.307 | 1.00 | 44.99 |
| ATOM | 1908 | CB | MET | 287 | 14.811 | 32.351 | 0.171 | 1.00 | 42.64 |
| ATOM | 1909 | CG | MET | 287 | 15.939 | 31.333 | 0.187 | 1.00 | 47.68 |
| ATOM | 1910 | SD | MET | 287 | 17.113 | 31.525 | -1.172 | 1.00 | 58.03 |
| ATOM | 1911 | CE | MET | 287 | 18.241 | 30.187 | -0.856 | 1.00 | 49.46 |
| ATOM | 1912 | C | MET | 287 | 12.995 | 33.433 | 1.549 | 1.00 | 46.28 |
| ATOM | 1913 | O | MET | 287 | 13.425 | 34.311 | 2.300 | 1.00 | 47.34 |
| ATOM | 1914 | N | LYS | 288 | 11.807 | 33.517 | 0.958 | 1.00 | 47.32 |
| ATOM | 1915 | CA | LYS | 288 | 10.960 | 34.688 | 1.161 | 1.00 | 49.83 |
| ATOM | 1916 | CB | LYS | 288 | 9.892 | 34.774 | 0.068 | 1.00 | 51.05 |
| ATOM | 1917 | CG | LYS | 288 | 10.409 | 35.442 | -1.200 | 1.00 | 57.27 |
| ATOM | 1918 | CD | LYS | 288 | 11.645 | 34.733 | -1.763 | 1.00 | 56.72 |
| ATOM | 1919 | CE | LYS | 288 | 12.336 | 35.544 | -2.859 | 1.00 | 57.40 |
| ATOM | 1920 | NZ | LYS | 288 | 13.156 | 36.680 | -2.327 | 1.00 | 54.52 |
| ATOM | 1921 | C | LYS | 288 | 10.326 | 34.709 | 2.554 | 1.00 | 48.56 |
| ATOM | 1922 | O | LYS | 288 | 9.566 | 35.618 | 2.889 | 1.00 | 53.45 |
| ATOM | 1923 | N | LYS | 289 | 10.669 | 33.711 | 3.366 | 1.00 | 46.77 |
| ATOM | 1924 | CA | LYS | 289 | 10.160 | 33.593 | 4.724 | 1.00 | 42.81 |
| ATOM | 1925 | CB | LYS | 289 | 9.644 | 32.171 | 4.965 | 1.00 | 44.21 |
| ATOM | 1926 | CG | LYS | 289 | 8.448 | 31.796 | 4.105 | 1.00 | 47.39 |
| ATOM | 1927 | CD | LYS | 289 | 7.218 | 32.601 | 4.497 | 1.00 | 51.50 |
| ATOM | 1928 | CE | LYS | 289 | 6.166 | 32.578 | 3.397 | 1.00 | 54.43 |
| ATOM | 1929 | NZ | LYS | 289 | 5.796 | 33.970 | 3.002 | 1.00 | 58.57 |
| ATOM | 1930 | C | LYS | 289 | 11.248 | 33.937 | 5.743 | 1.00 | 40.41 |
| ATOM | 1931 | O | LYS | 289 | 10.986 | 34.025 | 6.942 | 1.00 | 38.63 |
| ATOM | 1932 | N | LEU | 290 | 12.467 | 34.126 | 5.255 | 1.00 | 38.54 |
| ATOM | 1933 | CA | LEU | 290 | 13.600 | 34.461 | 6.112 | 1.00 | 38.47 |
| ATOM | 1934 | CB | LEU | 290 | 14.904 | 34.064 | 5.424 | 1.00 | 37.63 |
| ATOM | 1935 | CG | LEU | 290 | 15.241 | 32.590 | 5.186 | 1.00 | 34.43 |

FIGURE 1A-39

| ATOM | 1936 | CD1 | LEU | 290 | 16.313 | 32.473 | 4.099 | 1.00 | 28.00 |
| --- | --- | --- | --- | --- | --- | --- | --- | --- | --- |
| ATOM | 1937 | CD2 | LEU | 290 | 15.709 | 31.960 | 6.486 | 1.00 | 32.07 |
| ATOM | 1938 | C | LEU | 290 | 13.653 | 35.958 | 6.423 | 1.00 | 42.89 |
| ATOM | 1939 | O | LEU | 290 | 13.133 | 36.771 | 5.662 | 1.00 | 42.67 |
| ATOM | 1940 | N | GLN | 291 | 14.302 | 36.319 | 7.530 | 1.00 | 42.91 |
| ATOM | 1941 | CA | GLN | 291 | 14.454 | 37.724 | 7.923 | 1.00 | 42.75 |
| ATOM | 1942 | CB | GLN | 291 | 15.156 | 37.812 | 9.284 | 1.00 | 46.62 |
| ATOM | 1943 | CG | GLN | 291 | 15.040 | 39.157 | 9.990 | 1.00 | 51.74 |
| ATOM | 1944 | CD | GLN | 291 | 13.720 | 39.312 | 10.720 | 1.00 | 55.31 |
| ATOM | 1945 | OE1 | GLN | 291 | 12.891 | 38.401 | 10.715 | 1.00 | 52.77 |
| ATOM | 1946 | NE2 | GLN | 291 | 13.522 | 40.463 | 11.365 | 1.00 | 57.27 |
| ATOM | 1947 | C | GLN | 291 | 15.358 | 38.342 | 6.860 | 1.00 | 43.55 |
| ATOM | 1948 | O | GLN | 291 | 16.306 | 37.708 | 6.423 | 1.00 | 46.06 |
| ATOM | 1949 | N | PRO | 292 | 15.099 | 39.591 | 6.458 | 1.00 | 42.29 |
| ATOM | 1950 | CD | PRO | 292 | 14.057 | 40.465 | 7.013 | 1.00 | 42.93 |
| ATOM | 1951 | CA | PRO | 292 | 15.883 | 40.309 | 5.442 | 1.00 | 39.74 |
| ATOM | 1952 | CB | PRO | 292 | 15.283 | 41.713 | 5.485 | 1.00 | 43.81 |
| ATOM | 1953 | CG | PRO | 292 | 14.690 | 41.800 | 6.870 | 1.00 | 42.70 |
| ATOM | 1954 | C | PRO | 292 | 17.413 | 40.327 | 5.608 | 1.00 | 37.90 |
| ATOM | 1955 | O | PRO | 292 | 18.139 | 40.435 | 4.623 | 1.00 | 36.33 |
| ATOM | 1956 | N | THR | 293 | 17.912 | 40.229 | 6.834 | 1.00 | 37.58 |
| ATOM | 1957 | CA | THR | 293 | 19.361 | 40.227 | 7.037 | 1.00 | 35.47 |
| ATOM | 1958 | CB | THR | 293 | 19.752 | 40.740 | 8.421 | 1.00 | 37.40 |
| ATOM | 1959 | OG1 | THR | 293 | 18.718 | 41.592 | 8.926 | 1.00 | 45.86 |
| ATOM | 1960 | CG2 | THR | 293 | 21.057 | 41.524 | 8.333 | 1.00 | 37.33 |
| ATOM | 1961 | C | THR | 293 | 19.910 | 38.810 | 6.902 | 1.00 | 32.74 |
| ATOM | 1962 | O | THR | 293 | 21.100 | 38.613 | 6.668 | 1.00 | 31.56 |
| ATOM | 1963 | N | VAL | 294 | 19.042 | 37.828 | 7.116 | 1.00 | 29.50 |
| ATOM | 1964 | CA | VAL | 294 | 19.401 | 36.416 | 7.012 | 1.00 | 30.18 |
| ATOM | 1965 | CB | VAL | 294 | 18.507 | 35.557 | 7.945 | 1.00 | 30.65 |
| ATOM | 1966 | CG1 | VAL | 294 | 18.879 | 34.083 | 7.834 | 1.00 | 34.32 |
| ATOM | 1967 | CG2 | VAL | 294 | 18.633 | 36.046 | 9.381 | 1.00 | 38.53 |
| ATOM | 1968 | C | VAL | 294 | 19.201 | 35.946 | 5.571 | 1.00 | 24.14 |
| ATOM | 1969 | O | VAL | 294 | 20.026 | 35.223 | 5.020 | 1.00 | 22.93 |
| ATOM | 1970 | N | ARG | 295 | 18.117 | 36.431 | 4.972 | 1.00 | 23.36 |
| ATOM | 1971 | CA | ARG | 295 | 17.693 | 36.139 | 3.604 | 1.00 | 26.76 |
| ATOM | 1972 | CB | ARG | 295 | 16.480 | 37.015 | 3.292 | 1.00 | 29.86 |
| ATOM | 1973 | CG | ARG | 295 | 15.549 | 36.513 | 2.220 | 1.00 | 34.67 |
| ATOM | 1974 | CD | ARG | 295 | 14.431 | 37.525 | 1.958 | 1.00 | 38.04 |
| ATOM | 1975 | NE | ARG | 295 | 13.756 | 37.962 | 3.182 | 1.00 | 42.32 |
| ATOM | 1976 | CZ | ARG | 295 | 12.674 | 38.736 | 3.211 | 1.00 | 46.77 |
| ATOM | 1977 | NH1 | ARG | 295 | 12.136 | 39.176 | 2.085 | 1.00 | 51.28 |
| ATOM | 1978 | NH2 | ARG | 295 | 12.117 | 39.063 | 4.373 | 1.00 | 48.09 |
| ATOM | 1979 | C | ARG | 295 | 18.828 | 36.497 | 2.656 | 1.00 | 27.84 |
| ATOM | 1980 | O | ARG | 295 | 19.154 | 35.751 | 1.735 | 1.00 | 28.40 |
| ATOM | 1981 | N | ASN | 296 | 19.443 | 37.644 | 2.917 | 1.00 | 30.47 |
| ATOM | 1982 | CA | ASN | 296 | 20.556 | 38.156 | 2.140 | 1.00 | 28.52 |
| ATOM | 1983 | CB | ASN | 296 | 21.057 | 39.454 | 2.767 | 1.00 | 30.79 |
| ATOM | 1984 | CG | ASN | 296 | 22.191 | 40.071 | 1.998 | 1.00 | 34.00 |
| ATOM | 1985 | OD1 | ASN | 296 | 21.973 | 40.972 | 1.204 | 1.00 | 46.91 |
| ATOM | 1986 | ND2 | ASN | 296 | 23.412 | 39.590 | 2.217 | 1.00 | 32.59 |

FIGURE 1A-40

| ATOM | 1987 | C   | ASN | 296 | 21.675 | 37.136 | 2.168  | 1.00 | 31.04 |
|------|------|-----|-----|-----|--------|--------|--------|------|-------|
| ATOM | 1988 | O   | ASN | 296 | 22.165 | 36.722 | 1.123  | 1.00 | 33.08 |
| ATOM | 1989 | N   | TYR | 297 | 22.059 | 36.724 | 3.376  | 1.00 | 33.18 |
| ATOM | 1990 | CA  | TYR | 297 | 23.134 | 35.756 | 3.597  | 1.00 | 32.48 |
| ATOM | 1991 | CB  | TYR | 297 | 23.335 | 35.512 | 5.103  | 1.00 | 30.14 |
| ATOM | 1992 | CG  | TYR | 297 | 24.321 | 34.405 | 5.401  | 1.00 | 26.64 |
| ATOM | 1993 | CD1 | TYR | 297 | 25.685 | 34.606 | 5.240  | 1.00 | 30.19 |
| ATOM | 1994 | CE1 | TYR | 297 | 26.600 | 33.586 | 5.478  | 1.00 | 30.44 |
| ATOM | 1995 | CD2 | TYR | 297 | 23.889 | 33.146 | 5.811  | 1.00 | 28.14 |
| ATOM | 1996 | CE2 | TYR | 297 | 24.802 | 32.115 | 6.049  | 1.00 | 32.60 |
| ATOM | 1997 | CZ  | TYR | 297 | 26.156 | 32.348 | 5.877  | 1.00 | 33.80 |
| ATOM | 1998 | OH  | TYR | 297 | 27.080 | 31.352 | 6.096  | 1.00 | 41.71 |
| ATOM | 1999 | C   | TYR | 297 | 22.954 | 34.417 | 2.896  | 1.00 | 29.02 |
| ATOM | 2000 | O   | TYR | 297 | 23.915 | 33.877 | 2.348  | 1.00 | 29.14 |
| ATOM | 2001 | N   | VAL | 298 | 21.745 | 33.860 | 2.984  | 1.00 | 30.89 |
| ATOM | 2002 | CA  | VAL | 298 | 21.420 | 32.567 | 2.379  | 1.00 | 32.86 |
| ATOM | 2003 | CB  | VAL | 298 | 20.090 | 31.971 | 2.953  | 1.00 | 32.01 |
| ATOM | 2004 | CG1 | VAL | 298 | 19.758 | 30.643 | 2.279  | 1.00 | 32.05 |
| ATOM | 2005 | CG2 | VAL | 298 | 20.205 | 31.763 | 4.458  | 1.00 | 33.57 |
| ATOM | 2006 | C   | VAL | 298 | 21.315 | 32.670 | 0.860  | 1.00 | 33.02 |
| ATOM | 2007 | O   | VAL | 298 | 21.912 | 31.871 | 0.142  | 1.00 | 30.89 |
| ATOM | 2008 | N   | GLU | 299 | 20.623 | 33.693 | 0.368  | 1.00 | 32.16 |
| ATOM | 2009 | CA  | GLU | 299 | 20.469 | 33.865 | -1.066 | 1.00 | 32.45 |
| ATOM | 2010 | CB  | GLU | 299 | 19.509 | 35.004 | -1.375 | 1.00 | 35.96 |
| ATOM | 2011 | CG  | GLU | 299 | 18.069 | 34.737 | -0.949 | 1.00 | 42.36 |
| ATOM | 2012 | CD  | GLU | 299 | 17.174 | 35.972 | -1.030 | 1.00 | 46.82 |
| ATOM | 2013 | OE1 | GLU | 299 | 15.938 | 35.810 | -1.001 | 1.00 | 48.87 |
| ATOM | 2014 | OE2 | GLU | 299 | 17.699 | 37.104 | -1.111 | 1.00 | 52.13 |
| ATOM | 2015 | C   | GLU | 299 | 21.801 | 34.116 | -1.756 | 1.00 | 33.07 |
| ATOM | 2016 | O   | GLU | 299 | 22.059 | 33.567 | -2.822 | 1.00 | 41.91 |
| ATOM | 2017 | N   | ASN | 300 | 22.687 | 34.870 | -1.118 | 1.00 | 30.13 |
| ATOM | 2018 | CA  | ASN | 300 | 23.965 | 35.175 | -1.747 | 1.00 | 31.29 |
| ATOM | 2019 | CB  | ASN | 300 | 24.457 | 36.565 | -1.328 | 1.00 | 30.74 |
| ATOM | 2020 | CG  | ASN | 300 | 23.371 | 37.644 | -1.450 | 1.00 | 29.69 |
| ATOM | 2021 | OD1 | ASN | 300 | 22.306 | 37.425 | -2.026 | 1.00 | 27.97 |
| ATOM | 2022 | ND2 | ASN | 300 | 23.640 | 38.812 | -0.885 | 1.00 | 36.41 |
| ATOM | 2023 | C   | ASN | 300 | 25.027 | 34.116 | -1.466 | 1.00 | 32.46 |
| ATOM | 2024 | O   | ASN | 300 | 26.210 | 34.319 | -1.741 | 1.00 | 33.53 |
| ATOM | 2025 | N   | ARG | 301 | 24.595 | 32.975 | -0.937 | 1.00 | 37.42 |
| ATOM | 2026 | CA  | ARG | 301 | 25.506 | 31.875 | -0.629 | 1.00 | 39.04 |
| ATOM | 2027 | CB  | ARG | 301 | 24.973 | 31.083 | 0.579  | 1.00 | 44.36 |
| ATOM | 2028 | CG  | ARG | 301 | 26.034 | 30.505 | 1.496  | 1.00 | 47.14 |
| ATOM | 2029 | CD  | ARG | 301 | 26.530 | 31.565 | 2.434  | 1.00 | 45.85 |
| ATOM | 2030 | NE  | ARG | 301 | 27.866 | 31.272 | 2.933  | 1.00 | 51.06 |
| ATOM | 2031 | CZ  | ARG | 301 | 28.931 | 32.033 | 2.694  | 1.00 | 56.15 |
| ATOM | 2032 | NH1 | ARG | 301 | 28.819 | 33.135 | 1.958  | 1.00 | 56.06 |
| ATOM | 2033 | NH2 | ARG | 301 | 30.112 | 31.698 | 3.203  | 1.00 | 57.37 |
| ATOM | 2034 | C   | ARG | 301 | 25.599 | 30.938 | -1.843 | 1.00 | 38.09 |
| ATOM | 2035 | O   | ARG | 301 | 24.587 | 30.685 | -2.512 | 1.00 | 33.98 |
| ATOM | 2036 | N   | PRO | 302 | 26.808 | 30.426 | -2.152 | 1.00 | 36.81 |
| ATOM | 2037 | CD  | PRO | 302 | 28.074 | 30.691 | -1.460 | 1.00 | 33.58 |

FIGURE 1A-41

| ATOM | 2038 | CA | PRO | 302 | 27.033 | 29.515 | -3.283 | 1.00 | 38.26 |
| --- | --- | --- | --- | --- | --- | --- | --- | --- | --- |
| ATOM | 2039 | CB | PRO | 302 | 28.408 | 28.894 | -2.972 | 1.00 | 35.86 |
| ATOM | 2040 | CG | PRO | 302 | 28.730 | 29.347 | -1.549 | 1.00 | 36.92 |
| ATOM | 2041 | C | PRO | 302 | 25.934 | 28.461 | -3.409 | 1.00 | 40.54 |
| ATOM | 2042 | O | PRO | 302 | 25.590 | 27.771 | -2.445 | 1.00 | 43.03 |
| ATOM | 2043 | N | LYS | 303 | 25.347 | 28.394 | -4.602 | 1.00 | 41.15 |
| ATOM | 2044 | CA | LYS | 303 | 24.267 | 27.462 | -4.887 | 1.00 | 37.54 |
| ATOM | 2045 | CB | LYS | 303 | 23.429 | 27.972 | -6.056 | 1.00 | 36.45 |
| ATOM | 2046 | CG | LYS | 303 | 22.771 | 29.298 | -5.745 | 1.00 | 38.55 |
| ATOM | 2047 | CD | LYS | 303 | 21.683 | 29.658 | -6.749 | 1.00 | 45.90 |
| ATOM | 2048 | CE | LYS | 303 | 21.067 | 31.022 | -6.376 | 1.00 | 55.36 |
| ATOM | 2049 | NZ | LYS | 303 | 20.188 | 31.598 | -7.454 | 1.00 | 60.50 |
| ATOM | 2050 | C | LYS | 303 | 24.670 | 26.017 | -5.113 | 1.00 | 36.20 |
| ATOM | 2051 | O | LYS | 303 | 25.789 | 25.712 | -5.546 | 1.00 | 30.44 |
| ATOM | 2052 | N | TYR | 304 | 23.740 | 25.133 | -4.752 | 1.00 | 37.48 |
| ATOM | 2053 | CA | TYR | 304 | 23.889 | 23.690 | -4.876 | 1.00 | 37.30 |
| ATOM | 2054 | CB | TYR | 304 | 24.217 | 23.072 | -3.512 | 1.00 | 35.87 |
| ATOM | 2055 | CG | TYR | 304 | 25.665 | 23.169 | -3.120 | 1.00 | 38.63 |
| ATOM | 2056 | CD1 | TYR | 304 | 26.087 | 24.084 | -2.162 | 1.00 | 38.82 |
| ATOM | 2057 | CE1 | TYR | 304 | 27.425 | 24.185 | -1.808 | 1.00 | 40.97 |
| ATOM | 2058 | CD2 | TYR | 304 | 26.620 | 22.349 | -3.714 | 1.00 | 42.20 |
| ATOM | 2059 | CE2 | TYR | 304 | 27.959 | 22.444 | -3.368 | 1.00 | 45.59 |
| ATOM | 2060 | CZ | TYR | 304 | 28.354 | 23.365 | -2.416 | 1.00 | 46.47 |
| ATOM | 2061 | OH | TYR | 304 | 29.686 | 23.487 | -2.095 | 1.00 | 51.02 |
| ATOM | 2062 | C | TYR | 304 | 22.572 | 23.098 | -5.372 | 1.00 | 40.69 |
| ATOM | 2063 | O | TYR | 304 | 21.496 | 23.536 | -4.960 | 1.00 | 39.35 |
| ATOM | 2064 | N | ALA | 305 | 22.647 | 22.132 | -6.282 | 1.00 | 42.95 |
| ATOM | 2065 | CA | ALA | 305 | 21.432 | 21.489 | -6.783 | 1.00 | 47.73 |
| ATOM | 2066 | CB | ALA | 305 | 21.689 | 20.846 | -8.130 | 1.00 | 52.09 |
| ATOM | 2067 | C | ALA | 305 | 21.006 | 20.436 | -5.760 | 1.00 | 48.79 |
| ATOM | 2068 | O | ALA | 305 | 19.812 | 20.233 | -5.514 | 1.00 | 48.68 |
| ATOM | 2069 | N | GLY | 306 | 22.003 | 19.772 | -5.170 | 1.00 | 48.79 |
| ATOM | 2070 | CA | GLY | 306 | 21.766 | 18.760 | -4.149 | 1.00 | 48.30 |
| ATOM | 2071 | C | GLY | 306 | 21.818 | 17.304 | -4.573 | 1.00 | 50.50 |
| ATOM | 2072 | O | GLY | 306 | 21.502 | 16.954 | -5.717 | 1.00 | 53.05 |
| ATOM | 2073 | N | LEU | 307 | 22.230 | 16.455 | -3.635 | 1.00 | 46.43 |
| ATOM | 2074 | CA | LEU | 307 | 22.312 | 15.016 | -3.858 | 1.00 | 37.71 |
| ATOM | 2075 | CB | LEU | 307 | 23.300 | 14.372 | -2.888 | 1.00 | 29.08 |
| ATOM | 2076 | CG | LEU | 307 | 24.651 | 15.049 | -2.686 | 1.00 | 28.08 |
| ATOM | 2077 | CD1 | LEU | 307 | 25.579 | 14.106 | -1.951 | 1.00 | 21.91 |
| ATOM | 2078 | CD2 | LEU | 307 | 25.246 | 15.444 | -4.027 | 1.00 | 32.08 |
| ATOM | 2079 | C | LEU | 307 | 20.939 | 14.415 | -3.600 | 1.00 | 37.09 |
| ATOM | 2080 | O | LEU | 307 | 20.087 | 15.038 | -2.959 | 1.00 | 36.14 |
| ATOM | 2081 | N | THR | 308 | 20.709 | 13.226 | -4.148 | 1.00 | 35.95 |
| ATOM | 2082 | CA | THR | 308 | 19.449 | 12.529 | -3.943 | 1.00 | 31.61 |
| ATOM | 2083 | CB | THR | 308 | 19.003 | 11.763 | -5.187 | 1.00 | 36.28 |
| ATOM | 2084 | OG1 | THR | 308 | 20.141 | 11.141 | -5.804 | 1.00 | 39.91 |
| ATOM | 2085 | CG2 | THR | 308 | 18.300 | 12.695 | -6.153 | 1.00 | 38.12 |
| ATOM | 2086 | C | THR | 308 | 19.651 | 11.557 | -2.796 | 1.00 | 26.26 |
| ATOM | 2087 | O | THR | 308 | 20.779 | 11.151 | -2.515 | 1.00 | 22.14 |
| ATOM | 2088 | N | PHE | 309 | 18.552 | 11.146 | -2.173 | 1.00 | 23.63 |

FIGURE 1A-42

| ATOM | 2089 | CA | PHE | 309 | 18.622 | 10.243 | -1.040 | 1.00 | 26.54 |
| ATOM | 2090 | CB | PHE | 309 | 17.289 | 10.179 | -0.315 | 1.00 | 30.07 |
| ATOM | 2091 | CG | PHE | 309 | 17.024 | 11.413 | 0.492 | 1.00 | 34.38 |
| ATOM | 2092 | CD1 | PHE | 309 | 16.483 | 12.544 | -0.113 | 1.00 | 33.64 |
| ATOM | 2093 | CD2 | PHE | 309 | 17.429 | 11.487 | 1.824 | 1.00 | 37.30 |
| ATOM | 2094 | CE1 | PHE | 309 | 16.352 | 13.748 | 0.587 | 1.00 | 37.54 |
| ATOM | 2095 | CE2 | PHE | 309 | 17.306 | 12.682 | 2.544 | 1.00 | 41.11 |
| ATOM | 2096 | CZ | PHE | 309 | 16.765 | 13.822 | 1.920 | 1.00 | 40.70 |
| ATOM | 2097 | C | PHE | 309 | 19.272 | 8.897 | -1.262 | 1.00 | 25.79 |
| ATOM | 2098 | O | PHE | 309 | 19.935 | 8.392 | -0.365 | 1.00 | 28.49 |
| ATOM | 2099 | N | PRO | 310 | 19.098 | 8.290 | -2.448 | 1.00 | 25.78 |
| ATOM | 2100 | CD | PRO | 310 | 18.186 | 8.538 | -3.578 | 1.00 | 28.04 |
| ATOM | 2101 | CA | PRO | 310 | 19.771 | 6.999 | -2.610 | 1.00 | 25.44 |
| ATOM | 2102 | CB | PRO | 310 | 19.239 | 6.499 | -3.957 | 1.00 | 23.23 |
| ATOM | 2103 | CG | PRO | 310 | 18.855 | 7.754 | -4.678 | 1.00 | 24.04 |
| ATOM | 2104 | C | PRO | 310 | 21.299 | 7.207 | -2.618 | 1.00 | 25.05 |
| ATOM | 2105 | O | PRO | 310 | 22.056 | 6.295 | -2.302 | 1.00 | 28.14 |
| ATOM | 2106 | N | LYS | 311 | 21.729 | 8.425 | -2.938 | 1.00 | 27.99 |
| ATOM | 2107 | CA | LYS | 311 | 23.142 | 8.791 | -2.971 | 1.00 | 31.04 |
| ATOM | 2108 | CB | LYS | 311 | 23.353 | 9.999 | -3.890 | 1.00 | 37.20 |
| ATOM | 2109 | CG | LYS | 311 | 23.512 | 9.683 | -5.373 | 1.00 | 44.52 |
| ATOM | 2110 | CD | LYS | 311 | 24.975 | 9.410 | -5.731 | 1.00 | 50.37 |
| ATOM | 2111 | CE | LYS | 311 | 25.179 | 9.269 | -7.245 | 1.00 | 52.61 |
| ATOM | 2112 | NZ | LYS | 311 | 26.636 | 9.273 | -7.609 | 1.00 | 55.78 |
| ATOM | 2113 | C | LYS | 311 | 23.641 | 9.140 | -1.564 | 1.00 | 32.78 |
| ATOM | 2114 | O | LYS | 311 | 24.769 | 8.805 | -1.195 | 1.00 | 35.06 |
| ATOM | 2115 | N | LEU | 312 | 22.815 | 9.868 | -0.811 | 1.00 | 30.20 |
| ATOM | 2116 | CA | LEU | 312 | 23.140 | 10.288 | 0.563 | 1.00 | 27.38 |
| ATOM | 2117 | CB | LEU | 312 | 22.075 | 11.247 | 1.090 | 1.00 | 28.91 |
| ATOM | 2118 | CG | LEU | 312 | 21.976 | 12.646 | 0.486 | 1.00 | 29.43 |
| ATOM | 2119 | CD1 | LEU | 312 | 20.675 | 13.301 | 0.897 | 1.00 | 30.24 |
| ATOM | 2120 | CD2 | LEU | 312 | 23.159 | 13.468 | 0.932 | 1.00 | 31.77 |
| ATOM | 2121 | C | LEU | 312 | 23.158 | 9.072 | 1.471 | 1.00 | 26.39 |
| ATOM | 2122 | O | LEU | 312 | 24.049 | 8.914 | 2.309 | 1.00 | 25.82 |
| ATOM | 2123 | N | PHE | 313 | 22.152 | 8.228 | 1.294 | 1.00 | 25.78 |
| ATOM | 2124 | CA | PHE | 313 | 22.000 | 7.011 | 2.064 | 1.00 | 24.22 |
| ATOM | 2125 | CB | PHE | 313 | 20.786 | 7.127 | 2.992 | 1.00 | 24.30 |
| ATOM | 2126 | CG | PHE | 313 | 20.847 | 8.316 | 3.920 | 1.00 | 26.79 |
| ATOM | 2127 | CD1 | PHE | 313 | 19.978 | 9.387 | 3.743 | 1.00 | 25.49 |
| ATOM | 2128 | CD2 | PHE | 313 | 21.806 | 8.383 | 4.935 | 1.00 | 24.85 |
| ATOM | 2129 | CE1 | PHE | 313 | 20.060 | 10.523 | 4.563 | 1.00 | 26.72 |
| ATOM | 2130 | CE2 | PHE | 313 | 21.904 | 9.505 | 5.765 | 1.00 | 20.11 |
| ATOM | 2131 | CZ | PHE | 313 | 21.033 | 10.584 | 5.576 | 1.00 | 23.65 |
| ATOM | 2132 | C | PHE | 313 | 21.839 | 5.810 | 1.128 | 1.00 | 25.30 |
| ATOM | 2133 | O | PHE | 313 | 20.727 | 5.353 | 0.878 | 1.00 | 20.38 |
| ATOM | 2134 | N | PRO | 314 | 22.959 | 5.311 | 0.573 | 1.00 | 29.03 |
| ATOM | 2135 | CD | PRO | 314 | 24.319 | 5.842 | 0.750 | 1.00 | 25.41 |
| ATOM | 2136 | CA | PRO | 314 | 22.973 | 4.166 | -0.341 | 1.00 | 33.12 |
| ATOM | 2137 | CB | PRO | 314 | 24.435 | 4.104 | -0.787 | 1.00 | 28.32 |
| ATOM | 2138 | CG | PRO | 314 | 25.173 | 4.653 | 0.386 | 1.00 | 29.23 |
| ATOM | 2139 | C | PRO | 314 | 22.534 | 2.860 | 0.322 | 1.00 | 39.77 |

FIGURE 1A-43

| | | | | | | | | | |
|---|---|---|---|---|---|---|---|---|---|
| ATOM | 2140 | O | PRO | 314 | 22.378 | 2.789 | 1.539 | 1.00 | 43.28 |
| ATOM | 2141 | N | ASP | 315 | 22.362 | 1.822 | -0.492 | 1.00 | 44.54 |
| ATOM | 2142 | CA | ASP | 315 | 21.943 | 0.513 | -0.009 | 1.00 | 47.30 |
| ATOM | 2143 | CB | ASP | 315 | 21.522 | -0.358 | -1.193 | 1.00 | 54.34 |
| ATOM | 2144 | CG | ASP | 315 | 20.492 | 0.323 | -2.083 | 1.00 | 59.60 |
| ATOM | 2145 | OD1 | ASP | 315 | 19.279 | 0.110 | -1.856 | 1.00 | 61.43 |
| ATOM | 2146 | OD2 | ASP | 315 | 20.893 | 1.076 | -3.003 | 1.00 | 61.16 |
| ATOM | 2147 | C | ASP | 315 | 23.050 | -0.181 | 0.785 | 1.00 | 49.20 |
| ATOM | 2148 | O | ASP | 315 | 22.805 | -1.174 | 1.470 | 1.00 | 53.25 |
| ATOM | 2149 | N | SER | 316 | 24.262 | 0.352 | 0.703 | 1.00 | 48.08 |
| ATOM | 2150 | CA | SER | 316 | 25.403 | -0.215 | 1.410 | 1.00 | 47.42 |
| ATOM | 2151 | CB | SER | 316 | 26.697 | 0.437 | 0.912 | 1.00 | 50.82 |
| ATOM | 2152 | OG | SER | 316 | 26.707 | 0.552 | -0.507 | 1.00 | 52.25 |
| ATOM | 2153 | C | SER | 316 | 25.280 | -0.032 | 2.923 | 1.00 | 45.18 |
| ATOM | 2154 | O | SER | 316 | 25.803 | -0.831 | 3.696 | 1.00 | 46.79 |
| ATOM | 2155 | N | LEU | 317 | 24.574 | 1.021 | 3.330 | 1.00 | 43.13 |
| ATOM | 2156 | CA | LEU | 317 | 24.377 | 1.349 | 4.744 | 1.00 | 39.57 |
| ATOM | 2157 | CB | LEU | 317 | 24.166 | 2.850 | 4.925 | 1.00 | 33.89 |
| ATOM | 2158 | CG | LEU | 317 | 25.140 | 3.828 | 4.279 | 1.00 | 29.31 |
| ATOM | 2159 | CD1 | LEU | 317 | 24.617 | 5.231 | 4.490 | 1.00 | 32.92 |
| ATOM | 2160 | CD2 | LEU | 317 | 26.535 | 3.669 | 4.860 | 1.00 | 31.23 |
| ATOM | 2161 | C | LEU | 317 | 23.177 | 0.641 | 5.345 | 1.00 | 39.61 |
| ATOM | 2162 | O | LEU | 317 | 23.019 | 0.622 | 6.563 | 1.00 | 39.14 |
| ATOM | 2163 | N | PHE | 318 | 22.308 | 0.120 | 4.489 | 1.00 | 43.76 |
| ATOM | 2164 | CA | PHE | 318 | 21.107 | -0.575 | 4.933 | 1.00 | 47.84 |
| ATOM | 2165 | CB | PHE | 318 | 19.888 | -0.113 | 4.132 | 1.00 | 49.10 |
| ATOM | 2166 | CG | PHE | 318 | 19.504 | 1.318 | 4.365 | 1.00 | 49.24 |
| ATOM | 2167 | CD1 | PHE | 318 | 19.910 | 2.309 | 3.475 | 1.00 | 48.02 |
| ATOM | 2168 | CD2 | PHE | 318 | 18.683 | 1.664 | 5.435 | 1.00 | 47.21 |
| ATOM | 2169 | CE1 | PHE | 318 | 19.501 | 3.635 | 3.642 | 1.00 | 46.27 |
| ATOM | 2170 | CE2 | PHE | 318 | 18.265 | 2.977 | 5.619 | 1.00 | 44.63 |
| ATOM | 2171 | CZ | PHE | 318 | 18.673 | 3.972 | 4.716 | 1.00 | 46.12 |
| ATOM | 2172 | C | PHE | 318 | 21.245 | -2.070 | 4.720 | 1.00 | 51.34 |
| ATOM | 2173 | O | PHE | 318 | 21.876 | -2.514 | 3.764 | 1.00 | 53.56 |
| ATOM | 2174 | N | PRO | 319 | 20.680 | -2.873 | 5.634 | 1.00 | 54.48 |
| ATOM | 2175 | CD | PRO | 319 | 20.052 | -2.534 | 6.923 | 1.00 | 53.52 |
| ATOM | 2176 | CA | PRO | 319 | 20.780 | -4.321 | 5.451 | 1.00 | 55.37 |
| ATOM | 2177 | CB | PRO | 319 | 20.336 | -4.867 | 6.812 | 1.00 | 55.43 |
| ATOM | 2178 | CG | PRO | 319 | 19.375 | -3.829 | 7.305 | 1.00 | 52.54 |
| ATOM | 2179 | C | PRO | 319 | 19.797 | -4.687 | 4.342 | 1.00 | 58.15 |
| ATOM | 2180 | O | PRO | 319 | 18.581 | -4.619 | 4.541 | 1.00 | 58.06 |
| ATOM | 2181 | N | ALA | 320 | 20.320 | -4.982 | 3.153 | 1.00 | 57.21 |
| ATOM | 2182 | CA | ALA | 320 | 19.476 | -5.330 | 2.019 | 1.00 | 56.19 |
| ATOM | 2183 | CB | ALA | 320 | 19.561 | -4.248 | 0.936 | 1.00 | 55.29 |
| ATOM | 2184 | C | ALA | 320 | 19.851 | -6.703 | 1.458 | 1.00 | 54.78 |
| ATOM | 2185 | O | ALA | 320 | 20.195 | -6.845 | 0.285 | 1.00 | 57.38 |
| ATOM | 2186 | N | ASP | 321 | 19.824 | -7.704 | 2.329 | 1.00 | 50.32 |
| ATOM | 2187 | CA | ASP | 321 | 20.144 | -9.067 | 1.937 | 1.00 | 45.64 |
| ATOM | 2188 | CB | ASP | 321 | 20.989 | -9.787 | 3.019 | 1.00 | 49.32 |
| ATOM | 2189 | CG | ASP | 321 | 20.381 | -9.728 | 4.442 | 1.00 | 50.68 |
| ATOM | 2190 | OD1 | ASP | 321 | 19.445 | -8.946 | 4.715 | 1.00 | 49.45 |

FIGURE 1A-44

| ATOM | 2191 | OD2 | ASP | 321 | 20.877 | -10.475 | 5.312 | 1.00 | 52.95 |
| --- | --- | --- | --- | --- | --- | --- | --- | --- | --- |
| ATOM | 2192 | C | ASP | 321 | 18.856 | -9.812 | 1.617 | 1.00 | 40.97 |
| ATOM | 2193 | O | ASP | 321 | 18.685 | -10.336 | 0.518 | 1.00 | 46.62 |
| ATOM | 2194 | N | SER | 322 | 17.929 | -9.794 | 2.564 | 1.00 | 33.74 |
| ATOM | 2195 | CA | SER | 322 | 16.642 | -10.447 | 2.418 | 1.00 | 25.86 |
| ATOM | 2196 | CB | SER | 322 | 16.027 | -10.626 | 3.804 | 1.00 | 22.91 |
| ATOM | 2197 | OG | SER | 322 | 14.616 | -10.751 | 3.751 | 1.00 | 25.57 |
| ATOM | 2198 | C | SER | 322 | 15.728 | -9.589 | 1.553 | 1.00 | 26.13 |
| ATOM | 2199 | O | SER | 322 | 16.040 | -8.436 | 1.246 | 1.00 | 28.50 |
| ATOM | 2200 | N | GLU | 323 | 14.586 | -10.144 | 1.179 | 1.00 | 23.65 |
| ATOM | 2201 | CA | GLU | 323 | 13.633 | -9.402 | 0.385 | 1.00 | 23.60 |
| ATOM | 2202 | CB | GLU | 323 | 12.661 | -10.351 | -0.309 | 1.00 | 26.51 |
| ATOM | 2203 | CG | GLU | 323 | 11.962 | -9.742 | -1.519 | 1.00 | 30.86 |
| ATOM | 2204 | CD | GLU | 323 | 12.908 | -9.419 | -2.668 | 1.00 | 30.15 |
| ATOM | 2205 | OE1 | GLU | 323 | 13.270 | -10.332 | -3.443 | 1.00 | 21.73 |
| ATOM | 2206 | OE2 | GLU | 323 | 13.278 | -8.234 | -2.803 | 1.00 | 34.50 |
| ATOM | 2207 | C | GLU | 323 | 12.900 | -8.449 | 1.324 | 1.00 | 23.17 |
| ATOM | 2208 | O | GLU | 323 | 12.491 | -7.358 | 0.923 | 1.00 | 22.51 |
| ATOM | 2209 | N | HIS | 324 | 12.768 | -8.860 | 2.585 | 1.00 | 21.20 |
| ATOM | 2210 | CA | HIS | 324 | 12.113 | -8.058 | 3.621 | 1.00 | 15.99 |
| ATOM | 2211 | CB | HIS | 324 | 11.994 | -8.873 | 4.913 | 1.00 | 20.85 |
| ATOM | 2212 | CG | HIS | 324 | 11.384 | -8.113 | 6.055 | 1.00 | 18.10 |
| ATOM | 2213 | CD2 | HIS | 324 | 10.096 | -7.928 | 6.418 | 1.00 | 15.13 |
| ATOM | 2214 | ND1 | HIS | 324 | 12.149 | -7.457 | 7.003 | 1.00 | 10.86 |
| ATOM | 2215 | CE1 | HIS | 324 | 11.352 | -6.902 | 7.896 | 1.00 | 13.28 |
| ATOM | 2216 | NE2 | HIS | 324 | 10.100 | -7.172 | 7.570 | 1.00 | 12.29 |
| ATOM | 2217 | C | HIS | 324 | 12.948 | -6.814 | 3.888 | 1.00 | 11.78 |
| ATOM | 2218 | O | HIS | 324 | 12.423 | -5.711 | 4.045 | 1.00 | 8.94 |
| ATOM | 2219 | N | ASN | 325 | 14.257 | -7.009 | 3.928 | 1.00 | 11.30 |
| ATOM | 2220 | CA | ASN | 325 | 15.209 | -5.939 | 4.161 | 1.00 | 17.60 |
| ATOM | 2221 | CB | ASN | 325 | 16.544 | -6.539 | 4.604 | 1.00 | 12.16 |
| ATOM | 2222 | CG | ASN | 325 | 16.468 | -7.128 | 6.002 | 1.00 | 15.67 |
| ATOM | 2223 | OD1 | ASN | 325 | 15.405 | -7.107 | 6.635 | 1.00 | 8.60 |
| ATOM | 2224 | ND2 | ASN | 325 | 17.591 | -7.638 | 6.501 | 1.00 | 10.27 |
| ATOM | 2225 | C | ASN | 325 | 15.390 | -4.979 | 2.981 | 1.00 | 21.99 |
| ATOM | 2226 | O | ASN | 325 | 15.794 | -3.820 | 3.163 | 1.00 | 22.91 |
| ATOM | 2227 | N | LYS | 326 | 15.065 | -5.457 | 1.782 | 1.00 | 24.22 |
| ATOM | 2228 | CA | LYS | 326 | 15.161 | -4.653 | 0.566 | 1.00 | 17.35 |
| ATOM | 2229 | CB | LYS | 326 | 15.106 | -5.547 | -0.673 | 1.00 | 19.98 |
| ATOM | 2230 | CG | LYS | 326 | 16.404 | -6.278 | -0.953 | 1.00 | 18.76 |
| ATOM | 2231 | CD | LYS | 326 | 16.258 | -7.200 | -2.145 | 1.00 | 22.04 |
| ATOM | 2232 | CE | LYS | 326 | 17.587 | -7.384 | -2.845 | 1.00 | 22.95 |
| ATOM | 2233 | NZ | LYS | 326 | 18.646 | -7.919 | -1.948 | 1.00 | 27.98 |
| ATOM | 2234 | C | LYS | 326 | 14.007 | -3.653 | 0.552 | 1.00 | 13.55 |
| ATOM | 2235 | O | LYS | 326 | 14.197 | -2.472 | 0.274 | 1.00 | 16.27 |
| ATOM | 2236 | N | LEU | 327 | 12.814 | -4.123 | 0.886 | 1.00 | 9.22 |
| ATOM | 2237 | CA | LEU | 327 | 11.652 | -3.264 | 0.929 | 1.00 | 9.91 |
| ATOM | 2238 | CB | LEU | 327 | 10.388 | -4.095 | 1.081 | 1.00 | 6.08 |
| ATOM | 2239 | CG | LEU | 327 | 9.078 | -3.313 | 1.102 | 1.00 | 7.00 |
| ATOM | 2240 | CD1 | LEU | 327 | 8.926 | -2.523 | -0.197 | 1.00 | 11.70 |
| ATOM | 2241 | CD2 | LEU | 327 | 7.912 | -4.257 | 1.283 | 1.00 | 3.79 |

FIGURE 1A-45

| | | | | | | | | | |
|---|---|---|---|---|---|---|---|---|---|
| ATOM | 2242 | C | LEU | 327 | 11.778 | -2.268 | 2.087 | 1.00 | 20.87 |
| ATOM | 2243 | O | LEU | 327 | 11.535 | -1.074 | 1.903 | 1.00 | 30.80 |
| ATOM | 2244 | N | LYS | 328 | 12.184 | -2.748 | 3.264 | 1.00 | 21.08 |
| ATOM | 2245 | CA | LYS | 328 | 12.355 | -1.892 | 4.442 | 1.00 | 16.85 |
| ATOM | 2246 | CB | LYS | 328 | 12.696 | -2.735 | 5.684 | 1.00 | 17.14 |
| ATOM | 2247 | CG | LYS | 328 | 11.504 | -3.484 | 6.280 | 1.00 | 14.93 |
| ATOM | 2248 | CD | LYS | 328 | 10.400 | -2.512 | 6.655 | 1.00 | 19.27 |
| ATOM | 2249 | CE | LYS | 328 | 9.107 | -3.215 | 7.000 | 1.00 | 24.20 |
| ATOM | 2250 | NZ | LYS | 328 | 7.980 | -2.256 | 7.201 | 1.00 | 25.97 |
| ATOM | 2251 | C | LYS | 328 | 13.430 | -0.822 | 4.221 | 1.00 | 15.14 |
| ATOM | 2252 | O | LYS | 328 | 13.301 | 0.301 | 4.708 | 1.00 | 8.24 |
| ATOM | 2253 | N | ALA | 329 | 14.466 | -1.169 | 3.458 | 1.00 | 16.08 |
| ATOM | 2254 | CA | ALA | 329 | 15.559 | -0.247 | 3.154 | 1.00 | 16.65 |
| ATOM | 2255 | CB | ALA | 329 | 16.728 | -0.983 | 2.536 | 1.00 | 11.60 |
| ATOM | 2256 | C | ALA | 329 | 15.107 | 0.890 | 2.240 | 1.00 | 18.51 |
| ATOM | 2257 | O | ALA | 329 | 15.727 | 1.955 | 2.224 | 1.00 | 19.92 |
| ATOM | 2258 | N | SER | 330 | 14.032 | 0.665 | 1.483 | 1.00 | 17.05 |
| ATOM | 2259 | CA | SER | 330 | 13.492 | 1.682 | 0.593 | 1.00 | 20.72 |
| ATOM | 2260 | CB | SER | 330 | 12.709 | 1.041 | -0.564 | 1.00 | 16.62 |
| ATOM | 2261 | OG | SER | 330 | 11.330 | 0.865 | -0.254 | 1.00 | 14.39 |
| ATOM | 2262 | C | SER | 330 | 12.582 | 2.571 | 1.438 | 1.00 | 25.16 |
| ATOM | 2263 | O | SER | 330 | 12.632 | 3.806 | 1.359 | 1.00 | 26.12 |
| ATOM | 2264 | N | GLN | 331 | 11.783 | 1.921 | 2.281 | 1.00 | 24.88 |
| ATOM | 2265 | CA | GLN | 331 | 10.859 | 2.601 | 3.181 | 1.00 | 22.50 |
| ATOM | 2266 | CB | GLN | 331 | 10.076 | 1.578 | 3.998 | 1.00 | 21.35 |
| ATOM | 2267 | CG | GLN | 331 | 9.168 | 0.704 | 3.176 | 1.00 | 16.71 |
| ATOM | 2268 | CD | GLN | 331 | 8.243 | -0.125 | 4.030 | 1.00 | 18.69 |
| ATOM | 2269 | OE1 | GLN | 331 | 8.565 | -0.462 | 5.162 | 1.00 | 19.08 |
| ATOM | 2270 | NE2 | GLN | 331 | 7.083 | -0.463 | 3.487 | 1.00 | 16.21 |
| ATOM | 2271 | C | GLN | 331 | 11.593 | 3.539 | 4.135 | 1.00 | 20.27 |
| ATOM | 2272 | O | GLN | 331 | 11.173 | 4.679 | 4.335 | 1.00 | 20.21 |
| ATOM | 2273 | N | ALA | 332 | 12.695 | 3.052 | 4.702 | 1.00 | 19.16 |
| ATOM | 2274 | CA | ALA | 332 | 13.504 | 3.819 | 5.638 | 1.00 | 18.51 |
| ATOM | 2275 | CB | ALA | 332 | 14.683 | 2.989 | 6.106 | 1.00 | 12.00 |
| ATOM | 2276 | C | ALA | 332 | 14.003 | 5.079 | 4.952 | 1.00 | 22.58 |
| ATOM | 2277 | O | ALA | 332 | 13.822 | 6.189 | 5.458 | 1.00 | 22.84 |
| ATOM | 2278 | N | ARG | 333 | 14.551 | 4.887 | 3.754 | 1.00 | 25.28 |
| ATOM | 2279 | CA | ARG | 333 | 15.099 | 5.954 | 2.932 | 1.00 | 20.25 |
| ATOM | 2280 | CB | ARG | 333 | 15.771 | 5.355 | 1.694 | 1.00 | 18.39 |
| ATOM | 2281 | CG | ARG | 333 | 16.568 | 6.342 | 0.859 | 1.00 | 21.60 |
| ATOM | 2282 | CD | ARG | 333 | 17.138 | 5.685 | -0.393 | 1.00 | 28.44 |
| ATOM | 2283 | NE | ARG | 333 | 18.198 | 4.725 | -0.094 | 1.00 | 31.11 |
| ATOM | 2284 | CZ | ARG | 333 | 18.233 | 3.470 | -0.536 | 1.00 | 27.42 |
| ATOM | 2285 | NH1 | ARG | 333 | 17.263 | 2.991 | -1.302 | 1.00 | 28.88 |
| ATOM | 2286 | NH2 | ARG | 333 | 19.250 | 2.689 | -0.210 | 1.00 | 26.70 |
| ATOM | 2287 | C | ARG | 333 | 14.001 | 6.935 | 2.535 | 1.00 | 20.63 |
| ATOM | 2288 | O | ARG | 333 | 14.237 | 8.141 | 2.470 | 1.00 | 25.50 |
| ATOM | 2289 | N | ASP | 334 | 12.784 | 6.434 | 2.351 | 1.00 | 13.59 |
| ATOM | 2290 | CA | ASP | 334 | 11.664 | 7.285 | 1.979 | 1.00 | 11.95 |
| ATOM | 2291 | CB | ASP | 334 | 10.468 | 6.445 | 1.550 | 1.00 | 7.85 |
| ATOM | 2292 | CG | ASP | 334 | 9.282 | 7.290 | 1.142 | 1.00 | 8.99 |

FIGURE 1A-46

| | | | | | | | | |
|---|---|---|---|---|---|---|---|---|
| ATOM | 2293 | OD1 | ASP | 334 | 9.441 | 8.183 | 0.281 | 1.00 27.05 |
| ATOM | 2294 | OD2 | ASP | 334 | 8.170 | 7.059 | 1.659 | 1.00 15.33 |
| ATOM | 2295 | C | ASP | 334 | 11.252 | 8.206 | 3.128 | 1.00 16.82 |
| ATOM | 2296 | O | ASP | 334 | 10.777 | 9.321 | 2.888 | 1.00 18.85 |
| ATOM | 2297 | N | LEU | 335 | 11.384 | 7.716 | 4.365 | 1.00 16.05 |
| ATOM | 2298 | CA | LEU | 335 | 11.040 | 8.487 | 5.561 | 1.00 11.34 |
| ATOM | 2299 | CB | LEU | 335 | 11.021 | 7.591 | 6.793 | 1.00 15.56 |
| ATOM | 2300 | CG | LEU | 335 | 10.636 | 8.208 | 8.144 | 1.00 13.24 |
| ATOM | 2301 | CD1 | LEU | 335 | 9.222 | 8.793 | 8.093 | 1.00 12.51 |
| ATOM | 2302 | CD2 | LEU | 335 | 10.728 | 7.127 | 9.216 | 1.00 15.03 |
| ATOM | 2303 | C | LEU | 335 | 12.091 | 9.561 | 5.731 | 1.00 12.11 |
| ATOM | 2304 | O | LEU | 335 | 11.764 | 10.724 | 5.939 | 1.00 13.48 |
| ATOM | 2305 | N | LEU | 336 | 13.357 | 9.167 | 5.648 | 1.00 6.60 |
| ATOM | 2306 | CA | LEU | 336 | 14.441 | 10.120 | 5.743 | 1.00 12.18 |
| ATOM | 2307 | CB | LEU | 336 | 15.772 | 9.457 | 5.400 | 1.00 9.65 |
| ATOM | 2308 | CG | LEU | 336 | 16.546 | 8.769 | 6.515 | 1.00 10.77 |
| ATOM | 2309 | CD1 | LEU | 336 | 17.709 | 7.958 | 5.952 | 1.00 3.08 |
| ATOM | 2310 | CD2 | LEU | 336 | 17.041 | 9.828 | 7.476 | 1.00 13.07 |
| ATOM | 2311 | C | LEU | 336 | 14.191 | 11.264 | 4.753 | 1.00 17.47 |
| ATOM | 2312 | O | LEU | 336 | 14.187 | 12.426 | 5.152 | 1.00 22.07 |
| ATOM | 2313 | N | SER | 337 | 13.852 | 10.928 | 3.504 | 1.00 20.48 |
| ATOM | 2314 | CA | SER | 337 | 13.634 | 11.931 | 2.467 | 1.00 19.10 |
| ATOM | 2315 | CB | SER | 337 | 13.355 | 11.268 | 1.101 | 1.00 14.57 |
| ATOM | 2316 | OG | SER | 337 | 12.003 | 10.864 | 0.951 | 1.00 10.68 |
| ATOM | 2317 | C | SER | 337 | 12.526 | 12.898 | 2.832 | 1.00 17.71 |
| ATOM | 2318 | O | SER | 337 | 12.492 | 14.026 | 2.346 | 1.00 19.99 |
| ATOM | 2319 | N | LYS | 338 | 11.622 | 12.458 | 3.697 | 1.00 19.06 |
| ATOM | 2320 | CA | LYS | 338 | 10.510 | 13.295 | 4.113 | 1.00 18.41 |
| ATOM | 2321 | CB | LYS | 338 | 9.226 | 12.474 | 4.158 | 1.00 20.76 |
| ATOM | 2322 | CG | LYS | 338 | 8.753 | 12.035 | 2.779 | 1.00 27.42 |
| ATOM | 2323 | CD | LYS | 338 | 7.577 | 11.089 | 2.859 | 1.00 29.81 |
| ATOM | 2324 | CE | LYS | 338 | 7.151 | 10.667 | 1.468 | 1.00 31.71 |
| ATOM | 2325 | NZ | LYS | 338 | 6.203 | 9.523 | 1.532 | 1.00 40.40 |
| ATOM | 2326 | C | LYS | 338 | 10.745 | 14.025 | 5.432 | 1.00 16.78 |
| ATOM | 2327 | O | LYS | 338 | 9.962 | 14.894 | 5.810 | 1.00 16.88 |
| ATOM | 2328 | N | MET | 339 | 11.827 | 13.682 | 6.125 | 1.00 15.75 |
| ATOM | 2329 | CA | MET | 339 | 12.147 | 14.332 | 7.392 | 1.00 15.82 |
| ATOM | 2330 | CB | MET | 339 | 12.557 | 13.311 | 8.454 | 1.00 15.62 |
| ATOM | 2331 | CG | MET | 339 | 11.415 | 12.471 | 8.967 | 1.00 12.99 |
| ATOM | 2332 | SD | MET | 339 | 11.978 | 11.311 | 10.204 | 1.00 15.91 |
| ATOM | 2333 | CE | MET | 339 | 10.503 | 11.137 | 11.137 | 1.00 25.09 |
| ATOM | 2334 | C | MET | 339 | 13.246 | 15.361 | 7.206 | 1.00 14.58 |
| ATOM | 2335 | O | MET | 339 | 13.191 | 16.439 | 7.780 | 1.00 14.57 |
| ATOM | 2336 | N | LEU | 340 | 14.232 | 15.021 | 6.386 | 1.00 16.07 |
| ATOM | 2337 | CA | LEU | 340 | 15.337 | 15.908 | 6.102 | 1.00 13.43 |
| ATOM | 2338 | CB | LEU | 340 | 16.607 | 15.108 | 5.833 | 1.00 14.55 |
| ATOM | 2339 | CG | LEU | 340 | 17.166 | 14.396 | 7.062 | 1.00 9.85 |
| ATOM | 2340 | CD1 | LEU | 340 | 18.269 | 13.443 | 6.662 | 1.00 15.43 |
| ATOM | 2341 | CD2 | LEU | 340 | 17.693 | 15.410 | 8.054 | 1.00 10.65 |
| ATOM | 2342 | C | LEU | 340 | 14.991 | 16.804 | 4.913 | 1.00 20.03 |
| ATOM | 2343 | O | LEU | 340 | 15.582 | 16.697 | 3.832 | 1.00 18.62 |

FIGURE 1A-47

| ATOM | 2344 | N   | VAL | 341 | 13.975 | 17.639 | 5.121  | 1.00 | 17.24 |
| ---- | ---- | --- | --- | --- | ------ | ------ | ------ | ---- | ----- |
| ATOM | 2345 | CA  | VAL | 341 | 13.504 | 18.612 | 4.147  | 1.00 | 21.90 |
| ATOM | 2346 | CB  | VAL | 341 | 12.000 | 18.443 | 3.875  | 1.00 | 21.91 |
| ATOM | 2347 | CG1 | VAL | 341 | 11.549 | 19.452 | 2.838  | 1.00 | 25.22 |
| ATOM | 2348 | CG2 | VAL | 341 | 11.703 | 17.024 | 3.410  | 1.00 | 17.15 |
| ATOM | 2349 | C   | VAL | 341 | 13.746 | 19.965 | 4.818  | 1.00 | 24.44 |
| ATOM | 2350 | O   | VAL | 341 | 13.358 | 20.166 | 5.973  | 1.00 | 21.02 |
| ATOM | 2351 | N   | ILE | 342 | 14.377 | 20.897 | 4.109  | 1.00 | 24.60 |
| ATOM | 2352 | CA  | ILE | 342 | 14.681 | 22.204 | 4.699  | 1.00 | 21.04 |
| ATOM | 2353 | CB  | ILE | 342 | 15.715 | 22.983 | 3.865  | 1.00 | 18.19 |
| ATOM | 2354 | CG2 | ILE | 342 | 16.087 | 24.279 | 4.572  | 1.00 | 13.29 |
| ATOM | 2355 | CG1 | ILE | 342 | 16.970 | 22.124 | 3.664  | 1.00 | 13.17 |
| ATOM | 2356 | CD1 | ILE | 342 | 18.053 | 22.821 | 2.866  | 1.00 | 13.24 |
| ATOM | 2357 | C   | ILE | 342 | 13.475 | 23.089 | 4.965  | 1.00 | 21.31 |
| ATOM | 2358 | O   | ILE | 342 | 13.421 | 23.766 | 5.984  | 1.00 | 25.27 |
| ATOM | 2359 | N   | ASP | 343 | 12.494 | 23.049 | 4.072  | 1.00 | 22.52 |
| ATOM | 2360 | CA  | ASP | 343 | 11.303 | 23.867 | 4.213  | 1.00 | 21.50 |
| ATOM | 2361 | CB  | ASP | 343 | 10.704 | 24.154 | 2.825  | 1.00 | 26.19 |
| ATOM | 2362 | CG  | ASP | 343 | 9.620  | 25.225 | 2.854  | 1.00 | 30.96 |
| ATOM | 2363 | OD1 | ASP | 343 | 9.707  | 26.160 | 3.684  | 1.00 | 34.87 |
| ATOM | 2364 | OD2 | ASP | 343 | 8.677  | 25.136 | 2.039  | 1.00 | 35.06 |
| ATOM | 2365 | C   | ASP | 343 | 10.285 | 23.180 | 5.111  | 1.00 | 20.47 |
| ATOM | 2366 | O   | ASP | 343 | 9.784  | 22.113 | 4.785  | 1.00 | 22.68 |
| ATOM | 2367 | N   | PRO | 344 | 9.970  | 23.788 | 6.264  | 1.00 | 27.06 |
| ATOM | 2368 | CD  | PRO | 344 | 10.560 | 25.054 | 6.739  | 1.00 | 28.43 |
| ATOM | 2369 | CA  | PRO | 344 | 9.001  | 23.266 | 7.239  | 1.00 | 23.29 |
| ATOM | 2370 | CB  | PRO | 344 | 8.929  | 24.386 | 8.283  | 1.00 | 23.65 |
| ATOM | 2371 | CG  | PRO | 344 | 10.288 | 25.016 | 8.210  | 1.00 | 21.20 |
| ATOM | 2372 | C   | PRO | 344 | 7.631  | 23.018 | 6.619  | 1.00 | 22.09 |
| ATOM | 2373 | O   | PRO | 344 | 6.877  | 22.165 | 7.092  | 1.00 | 22.95 |
| ATOM | 2374 | N   | ALA | 345 | 7.302  | 23.794 | 5.586  | 1.00 | 19.10 |
| ATOM | 2375 | CA  | ALA | 345 | 6.022  | 23.670 | 4.892  | 1.00 | 18.85 |
| ATOM | 2376 | CB  | ALA | 345 | 5.750  | 24.907 | 4.053  | 1.00 | 20.59 |
| ATOM | 2377 | C   | ALA | 345 | 5.984  | 22.425 | 4.024  | 1.00 | 17.38 |
| ATOM | 2378 | O   | ALA | 345 | 4.918  | 21.934 | 3.670  | 1.00 | 15.74 |
| ATOM | 2379 | N   | LYS | 346 | 7.161  | 21.940 | 3.657  | 1.00 | 20.18 |
| ATOM | 2380 | CA  | LYS | 346 | 7.272  | 20.735 | 2.856  | 1.00 | 29.96 |
| ATOM | 2381 | CB  | LYS | 346 | 8.236  | 20.965 | 1.684  | 1.00 | 31.70 |
| ATOM | 2382 | CG  | LYS | 346 | 7.757  | 22.017 | 0.691  | 1.00 | 35.24 |
| ATOM | 2383 | CD  | LYS | 346 | 8.772  | 22.213 | -0.434 | 1.00 | 39.13 |
| ATOM | 2384 | CE  | LYS | 346 | 8.289  | 23.244 | -1.465 | 1.00 | 41.80 |
| ATOM | 2385 | NZ  | LYS | 346 | 7.056  | 22.829 | -2.200 | 1.00 | 37.54 |
| ATOM | 2386 | C   | LYS | 346 | 7.747  | 19.553 | 3.723  | 1.00 | 32.59 |
| ATOM | 2387 | O   | LYS | 346 | 7.825  | 18.420 | 3.247  | 1.00 | 35.40 |
| ATOM | 2388 | N   | ARG | 347 | 8.032  | 19.815 | 4.998  | 1.00 | 28.61 |
| ATOM | 2389 | CA  | ARG | 347 | 8.498  | 18.765 | 5.894  | 1.00 | 26.41 |
| ATOM | 2390 | CB  | ARG | 347 | 9.412  | 19.347 | 6.969  | 1.00 | 27.10 |
| ATOM | 2391 | CG  | ARG | 347 | 10.236 | 18.306 | 7.693  | 1.00 | 23.71 |
| ATOM | 2392 | CD  | ARG | 347 | 11.039 | 18.915 | 8.814  | 1.00 | 20.63 |
| ATOM | 2393 | NE  | ARG | 347 | 11.984 | 19.919 | 8.334  | 1.00 | 20.30 |
| ATOM | 2394 | CZ  | ARG | 347 | 12.309 | 21.023 | 9.002  | 1.00 | 17.79 |

FIGURE 1A-48

```
ATOM   2395  NH1  ARG   347      11.765   21.271   10.185  1.00 15.67
ATOM   2396  NH2  ARG   347      13.180   21.878    8.492  1.00 16.36
ATOM   2397  C    ARG   347       7.342   18.007    6.540  1.00 24.61
ATOM   2398  O    ARG   347       6.358   18.609    6.979  1.00 23.18
ATOM   2399  N    ILE   348       7.494   16.684    6.629  1.00 22.60
ATOM   2400  CA   ILE   348       6.481   15.793    7.197  1.00 20.56
ATOM   2401  CB   ILE   348       6.854   14.284    6.974  1.00 20.94
ATOM   2402  CG2  ILE   348       8.049   13.874    7.842  1.00 18.48
ATOM   2403  CG1  ILE   348       5.645   13.399    7.291  1.00 16.25
ATOM   2404  CD1  ILE   348       5.871   11.921    7.004  1.00 23.35
ATOM   2405  C    ILE   348       6.162   16.016    8.671  1.00 19.79
ATOM   2406  O    ILE   348       7.040   16.337    9.478  1.00 17.53
ATOM   2407  N    SER   349       4.892   15.830    9.015  1.00 19.08
ATOM   2408  CA   SER   349       4.439   15.999   10.385  1.00 20.41
ATOM   2409  CB   SER   349       2.952   16.354   10.394  1.00 17.83
ATOM   2410  OG   SER   349       2.175   15.334    9.804  1.00 14.20
ATOM   2411  C    SER   349       4.698   14.733   11.219  1.00 26.67
ATOM   2412  O    SER   349       5.082   13.686   10.683  1.00 27.72
ATOM   2413  N    VAL   350       4.497   14.839   12.532  1.00 23.89
ATOM   2414  CA   VAL   350       4.699   13.730   13.459  1.00 20.94
ATOM   2415  CB   VAL   350       4.582   14.212   14.942  1.00 25.67
ATOM   2416  CG1  VAL   350       4.715   13.035   15.902  1.00 24.94
ATOM   2417  CG2  VAL   350       5.634   15.277   15.258  1.00 24.00
ATOM   2418  C    VAL   350       3.629   12.672   13.220  1.00 22.78
ATOM   2419  O    VAL   350       3.907   11.470   13.214  1.00 21.73
ATOM   2420  N    ASP   351       2.398   13.128   13.018  1.00 22.26
ATOM   2421  CA   ASP   351       1.279   12.225   12.796  1.00 27.24
ATOM   2422  CB   ASP   351      -0.047   12.992   12.816  1.00 30.98
ATOM   2423  CG   ASP   351      -0.374   13.583   14.194  1.00 36.22
ATOM   2424  OD1  ASP   351      -1.545   13.956   14.414  1.00 41.42
ATOM   2425  OD2  ASP   351       0.523   13.683   15.061  1.00 36.81
ATOM   2426  C    ASP   351       1.438   11.447   11.502  1.00 28.00
ATOM   2427  O    ASP   351       1.166   10.250   11.464  1.00 31.60
ATOM   2428  N    ASP   352       1.918   12.107   10.452  1.00 25.54
ATOM   2429  CA   ASP   352       2.107   11.431    9.169  1.00 23.63
ATOM   2430  CB   ASP   352       2.191   12.430    8.014  1.00 22.25
ATOM   2431  CG   ASP   352       0.841   13.022    7.640  1.00 20.43
ATOM   2432  OD1  ASP   352      -0.209   12.367    7.863  1.00 19.34
ATOM   2433  OD2  ASP   352       0.837   14.151    7.112  1.00 28.93
ATOM   2434  C    ASP   352       3.330   10.532    9.173  1.00 22.30
ATOM   2435  O    ASP   352       3.361    9.515    8.478  1.00 21.84
ATOM   2436  N    ALA   353       4.336   10.907    9.954  1.00 24.89
ATOM   2437  CA   ALA   353       5.555   10.109   10.062  1.00 24.70
ATOM   2438  CB   ALA   353       6.668   10.903   10.747  1.00 20.35
ATOM   2439  C    ALA   353       5.230    8.843   10.846  1.00 23.31
ATOM   2440  O    ALA   353       5.890    7.826   10.685  1.00 24.29
ATOM   2441  N    LEU   354       4.188    8.910   11.673  1.00 24.74
ATOM   2442  CA   LEU   354       3.760    7.769   12.467  1.00 22.74
ATOM   2443  CB   LEU   354       3.056    8.233   13.750  1.00 20.01
ATOM   2444  CG   LEU   354       3.986    8.598   14.917  1.00 19.51
ATOM   2445  CD1  LEU   354       3.278    9.398   16.003  1.00 12.95
```

FIGURE 1A-49

| | | | | | | | | |
|---|---|---|---|---|---|---|---|---|
| ATOM | 2446 | CD2 | LEU | 354 | 4.572 | 7.324 | 15.485 | 1.00 20.89 |
| ATOM | 2447 | C | LEU | 354 | 2.862 | 6.854 | 11.647 | 1.00 25.62 |
| ATOM | 2448 | O | LEU | 354 | 2.690 | 5.687 | 11.991 | 1.00 29.93 |
| ATOM | 2449 | N | GLN | 355 | 2.298 | 7.384 | 10.562 | 1.00 25.56 |
| ATOM | 2450 | CA | GLN | 355 | 1.439 | 6.601 | 9.682 | 1.00 26.42 |
| ATOM | 2451 | CB | GLN | 355 | 0.260 | 7.441 | 9.187 | 1.00 25.03 |
| ATOM | 2452 | CG | GLN | 355 | -0.756 | 7.782 | 10.262 | 1.00 29.12 |
| ATOM | 2453 | CD | GLN | 355 | -1.322 | 6.544 | 10.930 | 1.00 36.21 |
| ATOM | 2454 | OE1 | GLN | 355 | -0.918 | 6.179 | 12.037 | 1.00 37.70 |
| ATOM | 2455 | NE2 | GLN | 355 | -2.252 | 5.875 | 10.248 | 1.00 41.17 |
| ATOM | 2456 | C | GLN | 355 | 2.234 | 6.033 | 8.505 | 1.00 27.27 |
| ATOM | 2457 | O | GLN | 355 | 1.695 | 5.324 | 7.660 | 1.00 32.78 |
| ATOM | 2458 | N | HIS | 356 | 3.523 | 6.332 | 8.478 | 1.00 23.42 |
| ATOM | 2459 | CA | HIS | 356 | 4.420 | 5.863 | 7.432 | 1.00 22.71 |
| ATOM | 2460 | CB | HIS | 356 | 5.758 | 6.602 | 7.585 | 1.00 21.99 |
| ATOM | 2461 | CG | HIS | 356 | 6.730 | 6.356 | 6.476 | 1.00 19.91 |
| ATOM | 2462 | CD2 | HIS | 356 | 7.715 | 5.437 | 6.337 | 1.00 23.11 |
| ATOM | 2463 | ND1 | HIS | 356 | 6.802 | 7.163 | 5.362 | 1.00 26.91 |
| ATOM | 2464 | CE1 | HIS | 356 | 7.792 | 6.756 | 4.590 | 1.00 23.32 |
| ATOM | 2465 | NE2 | HIS | 356 | 8.363 | 5.710 | 5.159 | 1.00 19.25 |
| ATOM | 2466 | C | HIS | 356 | 4.614 | 4.349 | 7.624 | 1.00 28.03 |
| ATOM | 2467 | O | HIS | 356 | 4.728 | 3.883 | 8.753 | 1.00 27.09 |
| ATOM | 2468 | N | PRO | 357 | 4.669 | 3.573 | 6.523 | 1.00 29.77 |
| ATOM | 2469 | CD | PRO | 357 | 4.578 | 4.072 | 5.141 | 1.00 30.71 |
| ATOM | 2470 | CA | PRO | 357 | 4.849 | 2.114 | 6.509 | 1.00 25.46 |
| ATOM | 2471 | CB | PRO | 357 | 4.978 | 1.801 | 5.013 | 1.00 26.09 |
| ATOM | 2472 | CG | PRO | 357 | 5.450 | 3.097 | 4.413 | 1.00 22.98 |
| ATOM | 2473 | C | PRO | 357 | 6.053 | 1.568 | 7.290 | 1.00 25.37 |
| ATOM | 2474 | O | PRO | 357 | 6.027 | 0.415 | 7.728 | 1.00 28.62 |
| ATOM | 2475 | N | TYR | 358 | 7.117 | 2.358 | 7.425 | 1.00 24.82 |
| ATOM | 2476 | CA | TYR | 358 | 8.306 | 1.919 | 8.163 | 1.00 21.55 |
| ATOM | 2477 | CB | TYR | 358 | 9.546 | 2.693 | 7.707 | 1.00 13.35 |
| ATOM | 2478 | CG | TYR | 358 | 10.856 | 2.173 | 8.271 | 1.00 15.29 |
| ATOM | 2479 | CD1 | TYR | 358 | 11.389 | 0.962 | 7.838 | 1.00 9.37 |
| ATOM | 2480 | CE1 | TYR | 358 | 12.634 | 0.514 | 8.295 | 1.00 12.90 |
| ATOM | 2481 | CD2 | TYR | 358 | 11.599 | 2.923 | 9.186 | 1.00 6.75 |
| ATOM | 2482 | CE2 | TYR | 358 | 12.841 | 2.474 | 9.641 | 1.00 4.92 |
| ATOM | 2483 | CZ | TYR | 358 | 13.351 | 1.270 | 9.187 | 1.00 3.41 |
| ATOM | 2484 | OH | TYR | 358 | 14.585 | 0.827 | 9.601 | 1.00 9.40 |
| ATOM | 2485 | C | TYR | 358 | 8.136 | 2.088 | 9.678 | 1.00 21.47 |
| ATOM | 2486 | O | TYR | 358 | 8.842 | 1.450 | 10.453 | 1.00 15.64 |
| ATOM | 2487 | N | ILE | 359 | 7.210 | 2.961 | 10.081 | 1.00 22.57 |
| ATOM | 2488 | CA | ILE | 359 | 6.948 | 3.241 | 11.492 | 1.00 23.66 |
| ATOM | 2489 | CB | ILE | 359 | 6.913 | 4.785 | 11.763 | 1.00 23.54 |
| ATOM | 2490 | CG2 | ILE | 359 | 6.691 | 5.066 | 13.242 | 1.00 23.38 |
| ATOM | 2491 | CG1 | ILE | 359 | 8.200 | 5.469 | 11.291 | 1.00 18.97 |
| ATOM | 2492 | CD1 | ILE | 359 | 9.422 | 5.031 | 12.024 | 1.00 19.53 |
| ATOM | 2493 | C | ILE | 359 | 5.640 | 2.649 | 12.025 | 1.00 25.03 |
| ATOM | 2494 | O | ILE | 359 | 5.627 | 2.011 | 13.083 | 1.00 27.94 |
| ATOM | 2495 | N | ASN | 360 | 4.559 | 2.807 | 11.265 | 1.00 25.83 |
| ATOM | 2496 | CA | ASN | 360 | 3.235 | 2.341 | 11.669 | 1.00 28.97 |

FIGURE 1A-50

| ATOM | 2497 | CB | ASN | 360 | 2.172 | 2.751 | 10.637 | 1.00 | 32.13 |
| ATOM | 2498 | CG | ASN | 360 | 1.789 | 1.616 | 9.707 | 1.00 | 36.82 |
| ATOM | 2499 | OD1 | ASN | 360 | 2.623 | 1.092 | 8.968 | 1.00 | 35.54 |
| ATOM | 2500 | ND2 | ASN | 360 | 0.524 | 1.206 | 9.765 | 1.00 | 40.04 |
| ATOM | 2501 | C | ASN | 360 | 3.096 | 0.852 | 12.011 | 1.00 | 28.07 |
| ATOM | 2502 | O | ASN | 360 | 2.079 | 0.447 | 12.572 | 1.00 | 29.24 |
| ATOM | 2503 | N | VAL | 361 | 4.108 | 0.041 | 11.713 | 1.00 | 26.20 |
| ATOM | 2504 | CA | VAL | 361 | 4.019 | -1.374 | 12.040 | 1.00 | 25.00 |
| ATOM | 2505 | CB | VAL | 361 | 5.157 | -2.216 | 11.395 | 1.00 | 25.07 |
| ATOM | 2506 | CG1 | VAL | 361 | 5.162 | -2.026 | 9.880 | 1.00 | 26.82 |
| ATOM | 2507 | CG2 | VAL | 361 | 6.500 | -1.856 | 11.985 | 1.00 | 26.34 |
| ATOM | 2508 | C | VAL | 361 | 4.011 | -1.592 | 13.558 | 1.00 | 25.35 |
| ATOM | 2509 | O | VAL | 361 | 3.965 | -2.730 | 14.021 | 1.00 | 29.09 |
| ATOM | 2510 | N | TRP | 362 | 4.073 | -0.504 | 14.327 | 1.00 | 25.81 |
| ATOM | 2511 | CA | TRP | 362 | 4.054 | -0.579 | 15.794 | 1.00 | 22.28 |
| ATOM | 2512 | CB | TRP | 362 | 5.389 | -0.125 | 16.396 | 1.00 | 14.30 |
| ATOM | 2513 | CG | TRP | 362 | 6.611 | -0.762 | 15.854 | 1.00 | 12.11 |
| ATOM | 2514 | CD2 | TRP | 362 | 7.202 | -1.992 | 16.297 | 1.00 | 15.12 |
| ATOM | 2515 | CE2 | TRP | 362 | 8.437 | -2.125 | 15.625 | 1.00 | 11.85 |
| ATOM | 2516 | CE3 | TRP | 362 | 6.824 | -2.982 | 17.212 | 1.00 | 14.92 |
| ATOM | 2517 | CD1 | TRP | 362 | 7.463 | -0.232 | 14.940 | 1.00 | 10.39 |
| ATOM | 2518 | NE1 | TRP | 362 | 8.563 | -1.041 | 14.799 | 1.00 | 11.84 |
| ATOM | 2519 | CZ2 | TRP | 362 | 9.290 | -3.213 | 15.838 | 1.00 | 14.66 |
| ATOM | 2520 | CZ3 | TRP | 362 | 7.667 | -4.055 | 17.424 | 1.00 | 14.28 |
| ATOM | 2521 | CH2 | TRP | 362 | 8.890 | -4.163 | 16.743 | 1.00 | 12.90 |
| ATOM | 2522 | C | TRP | 362 | 2.978 | 0.322 | 16.389 | 1.00 | 23.10 |
| ATOM | 2523 | O | TRP | 362 | 2.878 | 0.427 | 17.603 | 1.00 | 25.93 |
| ATOM | 2524 | N | TYR | 363 | 2.187 | 0.977 | 15.545 | 1.00 | 29.10 |
| ATOM | 2525 | CA | TYR | 363 | 1.151 | 1.892 | 16.007 | 1.00 | 32.54 |
| ATOM | 2526 | CB | TYR | 363 | 0.286 | 2.356 | 14.836 | 1.00 | 33.45 |
| ATOM | 2527 | CG | TYR | 363 | -0.533 | 3.590 | 15.136 | 1.00 | 37.46 |
| ATOM | 2528 | CD1 | TYR | 363 | -1.861 | 3.491 | 15.551 | 1.00 | 36.31 |
| ATOM | 2529 | CE1 | TYR | 363 | -2.623 | 4.631 | 15.805 | 1.00 | 34.69 |
| ATOM | 2530 | CD2 | TYR | 363 | 0.014 | 4.864 | 14.986 | 1.00 | 38.36 |
| ATOM | 2531 | CE2 | TYR | 363 | -0.741 | 6.007 | 15.239 | 1.00 | 35.95 |
| ATOM | 2532 | CZ | TYR | 363 | -2.059 | 5.881 | 15.646 | 1.00 | 36.93 |
| ATOM | 2533 | OH | TYR | 363 | -2.828 | 6.995 | 15.884 | 1.00 | 35.93 |
| ATOM | 2534 | C | TYR | 363 | 0.277 | 1.293 | 17.096 | 1.00 | 34.54 |
| ATOM | 2535 | O | TYR | 363 | -0.146 | 0.137 | 17.005 | 1.00 | 36.71 |
| ATOM | 2536 | N | ASP | 364 | 0.024 | 2.088 | 18.133 | 1.00 | 38.80 |
| ATOM | 2537 | CA | ASP | 364 | -0.794 | 1.674 | 19.271 | 1.00 | 42.92 |
| ATOM | 2538 | CB | ASP | 364 | 0.099 | 1.029 | 20.344 | 1.00 | 46.81 |
| ATOM | 2539 | CG | ASP | 364 | -0.690 | 0.380 | 21.489 | 1.00 | 50.95 |
| ATOM | 2540 | OD1 | ASP | 364 | -1.890 | 0.685 | 21.682 | 1.00 | 49.91 |
| ATOM | 2541 | OD2 | ASP | 364 | -0.093 | -0.440 | 22.217 | 1.00 | 53.25 |
| ATOM | 2542 | C | ASP | 364 | -1.470 | 2.927 | 19.811 | 1.00 | 44.13 |
| ATOM | 2543 | O | ASP | 364 | -0.797 | 3.861 | 20.236 | 1.00 | 42.80 |
| ATOM | 2544 | N | PRO | 365 | -2.811 | 2.960 | 19.791 | 1.00 | 45.60 |
| ATOM | 2545 | CD | PRO | 365 | -3.657 | 1.891 | 19.233 | 1.00 | 47.93 |
| ATOM | 2546 | CA | PRO | 365 | -3.646 | 4.067 | 20.265 | 1.00 | 47.86 |
| ATOM | 2547 | CB | PRO | 365 | -5.041 | 3.450 | 20.256 | 1.00 | 48.88 |

FIGURE 1A-51

| ATOM | 2548 | CG  | PRO | 365 | -4.985 | 2.591  | 19.047 | 1.00 | 50.20 |
| ---- | ---- | --- | --- | --- | ------ | ------ | ------ | ---- | ----- |
| ATOM | 2549 | C   | PRO | 365 | -3.292 | 4.625  | 21.642 | 1.00 | 48.20 |
| ATOM | 2550 | O   | PRO | 365 | -3.327 | 5.838  | 21.853 | 1.00 | 47.66 |
| ATOM | 2551 | N   | ALA | 366 | -2.950 | 3.745  | 22.575 | 1.00 | 47.25 |
| ATOM | 2552 | CA  | ALA | 366 | -2.599 | 4.186  | 23.917 | 1.00 | 49.62 |
| ATOM | 2553 | CB  | ALA | 366 | -2.631 | 3.009  | 24.890 | 1.00 | 51.23 |
| ATOM | 2554 | C   | ALA | 366 | -1.233 | 4.872  | 23.950 | 1.00 | 49.58 |
| ATOM | 2555 | O   | ALA | 366 | -1.025 | 5.831  | 24.697 | 1.00 | 52.40 |
| ATOM | 2556 | N   | GLU | 367 | -0.307 | 4.409  | 23.120 | 1.00 | 45.46 |
| ATOM | 2557 | CA  | GLU | 367 | 1.025  | 5.006  | 23.087 | 1.00 | 42.07 |
| ATOM | 2558 | CB  | GLU | 367 | 2.040  | 4.003  | 22.553 | 1.00 | 40.00 |
| ATOM | 2559 | CG  | GLU | 367 | 2.030  | 2.688  | 23.304 | 1.00 | 40.37 |
| ATOM | 2560 | CD  | GLU | 367 | 2.899  | 1.627  | 22.664 | 1.00 | 41.41 |
| ATOM | 2561 | OE1 | GLU | 367 | 3.304  | 1.790  | 21.495 | 1.00 | 42.28 |
| ATOM | 2562 | OE2 | GLU | 367 | 3.175  | 0.614  | 23.329 | 1.00 | 43.45 |
| ATOM | 2563 | C   | GLU | 367 | 1.072  | 6.293  | 22.271 | 1.00 | 43.40 |
| ATOM | 2564 | O   | GLU | 367 | 1.676  | 7.271  | 22.702 | 1.00 | 43.28 |
| ATOM | 2565 | N   | VAL | 368 | 0.410  | 6.310  | 21.115 | 1.00 | 43.11 |
| ATOM | 2566 | CA  | VAL | 368 | 0.417  | 7.500  | 20.268 | 1.00 | 42.75 |
| ATOM | 2567 | CB  | VAL | 368 | 0.109  | 7.178  | 18.791 | 1.00 | 42.81 |
| ATOM | 2568 | CG1 | VAL | 368 | 0.051  | 8.464  | 17.974 | 1.00 | 38.41 |
| ATOM | 2569 | CG2 | VAL | 368 | 1.176  | 6.255  | 18.221 | 1.00 | 46.10 |
| ATOM | 2570 | C   | VAL | 368 | -0.531 | 8.585  | 20.756 | 1.00 | 42.69 |
| ATOM | 2571 | O   | VAL | 368 | -0.116 | 9.721  | 20.967 | 1.00 | 45.42 |
| ATOM | 2572 | N   | GLU | 369 | -1.809 | 8.258  | 20.901 | 1.00 | 42.51 |
| ATOM | 2573 | CA  | GLU | 369 | -2.760 | 9.244  | 21.385 | 1.00 | 46.23 |
| ATOM | 2574 | CB  | GLU | 369 | -4.037 | 9.265  | 20.546 | 1.00 | 49.84 |
| ATOM | 2575 | CG  | GLU | 369 | -4.372 | 7.963  | 19.856 | 1.00 | 57.22 |
| ATOM | 2576 | CD  | GLU | 369 | -4.610 | 8.149  | 18.371 | 1.00 | 60.57 |
| ATOM | 2577 | OE1 | GLU | 369 | -3.992 | 9.065  | 17.781 | 1.00 | 63.85 |
| ATOM | 2578 | OE2 | GLU | 369 | -5.411 | 7.385  | 17.792 | 1.00 | 63.00 |
| ATOM | 2579 | C   | GLU | 369 | -3.069 | 9.103  | 22.872 | 1.00 | 46.71 |
| ATOM | 2580 | O   | GLU | 369 | -4.190 | 8.774  | 23.272 | 1.00 | 47.55 |
| ATOM | 2581 | N   | ALA | 370 | -2.049 | 9.342  | 23.684 | 1.00 | 46.43 |
| ATOM | 2582 | CA  | ALA | 370 | -2.191 | 9.287  | 25.129 | 1.00 | 48.84 |
| ATOM | 2583 | CB  | ALA | 370 | -0.858 | 8.924  | 25.774 | 1.00 | 45.98 |
| ATOM | 2584 | C   | ALA | 370 | -2.650 | 10.685 | 25.562 | 1.00 | 51.43 |
| ATOM | 2585 | O   | ALA | 370 | -2.362 | 11.677 | 24.883 | 1.00 | 53.98 |
| ATOM | 2586 | N   | PRO | 371 | -3.402 | 10.773 | 26.674 | 1.00 | 52.66 |
| ATOM | 2587 | CD  | PRO | 371 | -3.938 | 9.667  | 27.482 | 1.00 | 50.83 |
| ATOM | 2588 | CA  | PRO | 371 | -3.881 | 12.075 | 27.156 | 1.00 | 52.48 |
| ATOM | 2589 | CB  | PRO | 371 | -5.007 | 11.677 | 28.115 | 1.00 | 52.32 |
| ATOM | 2590 | CG  | PRO | 371 | -4.514 | 10.377 | 28.690 | 1.00 | 51.42 |
| ATOM | 2591 | C   | PRO | 371 | -2.828 | 12.953 | 27.834 | 1.00 | 53.52 |
| ATOM | 2592 | O   | PRO | 371 | -2.028 | 12.477 | 28.642 | 1.00 | 54.16 |
| ATOM | 2593 | N   | PRO | 372 | -2.757 | 14.232 | 27.437 | 1.00 | 56.35 |
| ATOM | 2594 | CD  | PRO | 372 | -3.446 | 14.694 | 26.207 | 1.00 | 56.74 |
| ATOM | 2595 | CA  | PRO | 372 | -1.846 | 15.269 | 27.932 | 1.00 | 57.49 |
| ATOM | 2596 | CB  | PRO | 372 | -1.720 | 16.199 | 26.736 | 1.00 | 58.23 |
| ATOM | 2597 | CG  | PRO | 372 | -3.122 | 16.173 | 26.177 | 1.00 | 57.24 |
| ATOM | 2598 | C   | PRO | 372 | -2.494 | 16.002 | 29.119 | 1.00 | 59.84 |

FIGURE 1A-52

| ATOM | 2599 | O   | PRO | 372 | -3.712  | 15.973 | 29.279 | 1.00 | 60.75 |
| ---- | ---- | --- | --- | --- | ------- | ------ | ------ | ---- | ----- |
| ATOM | 2600 | N   | PRO | 373 | -1.687  | 16.662 | 29.959 | 1.00 | 61.31 |
| ATOM | 2601 | CD  | PRO | 373 | -0.219  | 16.749 | 29.838 | 1.00 | 61.00 |
| ATOM | 2602 | CA  | PRO | 373 | -2.146  | 17.415 | 31.133 | 1.00 | 63.03 |
| ATOM | 2603 | CB  | PRO | 373 | -0.839  | 17.843 | 31.794 | 1.00 | 64.43 |
| ATOM | 2604 | CG  | PRO | 373 | 0.085   | 17.999 | 30.623 | 1.00 | 61.85 |
| ATOM | 2605 | C   | PRO | 373 | -2.999  | 18.632 | 30.772 | 1.00 | 65.29 |
| ATOM | 2606 | O   | PRO | 373 | -4.226  | 18.558 | 30.997 | 1.00 | 68.11 |
| ATOM | 2607 | CB  | ALA | 379 | 1.444   | 28.783 | 36.579 | 1.00 | 64.68 |
| ATOM | 2608 | C   | ALA | 379 | 2.527   | 28.447 | 34.366 | 1.00 | 62.47 |
| ATOM | 2609 | O   | ALA | 379 | 3.747   | 28.435 | 34.518 | 1.00 | 63.20 |
| ATOM | 2610 | N   | ALA | 379 | 2.296   | 26.575 | 35.879 | 1.00 | 62.81 |
| ATOM | 2611 | CA  | ALA | 379 | 1.633   | 27.826 | 35.420 | 1.00 | 62.73 |
| ATOM | 2612 | N   | LEU | 380 | 1.907   | 28.993 | 33.318 | 1.00 | 60.69 |
| ATOM | 2613 | CA  | LEU | 380 | 2.605   | 29.623 | 32.186 | 1.00 | 59.18 |
| ATOM | 2614 | CB  | LEU | 380 | 1.801   | 30.812 | 31.670 | 1.00 | 58.64 |
| ATOM | 2615 | CG  | LEU | 380 | 0.405   | 30.387 | 31.178 | 1.00 | 58.85 |
| ATOM | 2616 | CD1 | LEU | 380 | -0.211  | 31.473 | 30.307 | 1.00 | 60.49 |
| ATOM | 2617 | CD2 | LEU | 380 | 0.487   | 29.080 | 30.392 | 1.00 | 56.19 |
| ATOM | 2618 | C   | LEU | 380 | 4.068   | 29.986 | 32.445 | 1.00 | 59.37 |
| ATOM | 2619 | O   | LEU | 380 | 4.401   | 31.076 | 32.909 | 1.00 | 59.74 |
| ATOM | 2620 | N   | ASP | 381 | 4.932   | 29.038 | 32.093 | 1.00 | 58.95 |
| ATOM | 2621 | CA  | ASP | 381 | 6.362   | 29.147 | 32.334 | 1.00 | 57.68 |
| ATOM | 2622 | CB  | ASP | 381 | 6.821   | 27.948 | 33.186 | 1.00 | 60.14 |
| ATOM | 2623 | CG  | ASP | 381 | 6.428   | 26.587 | 32.585 | 1.00 | 63.04 |
| ATOM | 2624 | OD1 | ASP | 381 | 7.023   | 25.566 | 33.009 | 1.00 | 63.06 |
| ATOM | 2625 | OD2 | ASP | 381 | 5.536   | 26.517 | 31.712 | 1.00 | 65.55 |
| ATOM | 2626 | C   | ASP | 381 | 7.379   | 29.397 | 31.218 | 1.00 | 56.94 |
| ATOM | 2627 | O   | ASP | 381 | 8.030   | 28.475 | 30.728 | 1.00 | 56.62 |
| ATOM | 2628 | N   | GLU | 382 | 7.527   | 30.665 | 30.849 | 1.00 | 58.23 |
| ATOM | 2629 | CA  | GLU | 382 | 8.515   | 31.126 | 29.857 | 1.00 | 59.98 |
| ATOM | 2630 | CB  | GLU | 382 | 7.948   | 31.059 | 28.432 | 1.00 | 62.05 |
| ATOM | 2631 | CG  | GLU | 382 | 7.158   | 29.767 | 28.099 | 1.00 | 62.71 |
| ATOM | 2632 | CD  | GLU | 382 | 8.020   | 28.610 | 27.545 | 1.00 | 60.12 |
| ATOM | 2633 | OE1 | GLU | 382 | 7.845   | 27.440 | 27.984 | 1.00 | 55.34 |
| ATOM | 2634 | OE2 | GLU | 382 | 8.840   | 28.862 | 26.629 | 1.00 | 60.13 |
| ATOM | 2635 | C   | GLU | 382 | 8.642   | 32.584 | 30.353 | 1.00 | 61.77 |
| ATOM | 2636 | O   | GLU | 382 | 8.022   | 33.502 | 29.807 | 1.00 | 60.69 |
| ATOM | 2637 | N   | ARG | 383 | 9.359   | 32.755 | 31.467 | 1.00 | 62.13 |
| ATOM | 2638 | CA  | ARG | 383 | 9.501   | 34.061 | 32.118 | 1.00 | 59.96 |
| ATOM | 2639 | CB  | ARG | 383 | 8.658   | 34.057 | 33.405 | 1.00 | 58.72 |
| ATOM | 2640 | CG  | ARG | 383 | 8.159   | 32.669 | 33.816 | 1.00 | 60.06 |
| ATOM | 2641 | CD  | ARG | 383 | 8.784   | 32.194 | 35.108 | 1.00 | 62.25 |
| ATOM | 2642 | NE  | ARG | 383 | 7.856   | 32.365 | 36.223 | 1.00 | 67.90 |
| ATOM | 2643 | CZ  | ARG | 383 | 7.211   | 31.364 | 36.813 | 1.00 | 68.22 |
| ATOM | 2644 | NH1 | ARG | 383 | 7.396   | 30.119 | 36.399 | 1.00 | 68.93 |
| ATOM | 2645 | NH2 | ARG | 383 | 6.340   | 31.612 | 37.787 | 1.00 | 69.41 |
| ATOM | 2646 | C   | ARG | 383 | 10.900  | 34.629 | 32.390 | 1.00 | 58.01 |
| ATOM | 2647 | O   | ARG | 383 | 11.864  | 34.257 | 31.726 | 1.00 | 57.29 |
| ATOM | 2648 | N   | GLU | 384 | 10.996  | 35.528 | 33.377 | 1.00 | 53.08 |
| ATOM | 2649 | CA  | GLU | 384 | 12.257  | 36.200 | 33.723 | 1.00 | 50.92 |

FIGURE 1A-53

| ATOM | 2650 | CB | GLU | 384 | 12.307 | 37.507 | 32.929 | 1.00 | 55.89 |
|---|---|---|---|---|---|---|---|---|---|
| ATOM | 2651 | CG | GLU | 384 | 13.668 | 38.175 | 32.807 | 1.00 | 66.70 |
| ATOM | 2652 | CD | GLU | 384 | 13.622 | 39.453 | 31.958 | 1.00 | 73.38 |
| ATOM | 2653 | OE1 | GLU | 384 | 14.667 | 40.122 | 31.828 | 1.00 | 75.65 |
| ATOM | 2654 | OE2 | GLU | 384 | 12.543 | 39.794 | 31.421 | 1.00 | 76.92 |
| ATOM | 2655 | C | GLU | 384 | 12.387 | 36.497 | 35.236 | 1.00 | 46.83 |
| ATOM | 2656 | O | GLU | 384 | 11.475 | 37.070 | 35.832 | 1.00 | 47.56 |
| ATOM | 2657 | N | HIS | 385 | 13.528 | 36.132 | 35.841 | 1.00 | 39.08 |
| ATOM | 2658 | CA | HIS | 385 | 13.792 | 36.349 | 37.281 | 1.00 | 23.37 |
| ATOM | 2659 | CB | HIS | 385 | 13.290 | 35.174 | 38.109 | 1.00 | 16.45 |
| ATOM | 2660 | CG | HIS | 385 | 11.819 | 34.944 | 38.038 | 1.00 | 8.98 |
| ATOM | 2661 | CD2 | HIS | 385 | 11.100 | 33.926 | 37.514 | 1.00 | 15.10 |
| ATOM | 2662 | ND1 | HIS | 385 | 10.906 | 35.824 | 38.570 | 1.00 | 14.59 |
| ATOM | 2663 | CE1 | HIS | 385 | 9.681 | 35.356 | 38.383 | 1.00 | 23.67 |
| ATOM | 2664 | NE2 | HIS | 385 | 9.776 | 34.199 | 37.743 | 1.00 | 20.58 |
| ATOM | 2665 | C | HIS | 385 | 15.275 | 36.499 | 37.601 | 1.00 | 21.41 |
| ATOM | 2666 | O | HIS | 385 | 16.126 | 36.211 | 36.763 | 1.00 | 22.10 |
| ATOM | 2667 | N | THR | 386 | 15.580 | 36.921 | 38.829 | 1.00 | 22.26 |
| ATOM | 2668 | CA | THR | 386 | 16.971 | 37.079 | 39.276 | 1.00 | 24.85 |
| ATOM | 2669 | CB | THR | 386 | 17.159 | 38.230 | 40.297 | 1.00 | 30.48 |
| ATOM | 2670 | OG1 | THR | 386 | 16.377 | 37.978 | 41.475 | 1.00 | 34.97 |
| ATOM | 2671 | CG2 | THR | 386 | 16.749 | 39.562 | 39.674 | 1.00 | 35.80 |
| ATOM | 2672 | C | THR | 386 | 17.433 | 35.775 | 39.902 | 1.00 | 24.02 |
| ATOM | 2673 | O | THR | 386 | 16.604 | 34.932 | 40.258 | 1.00 | 25.00 |
| ATOM | 2674 | N | ILE | 387 | 18.741 | 35.640 | 40.112 | 1.00 | 23.57 |
| ATOM | 2675 | CA | ILE | 387 | 19.305 | 34.404 | 40.657 | 1.00 | 25.53 |
| ATOM | 2676 | CB | ILE | 387 | 20.852 | 34.321 | 40.501 | 1.00 | 24.01 |
| ATOM | 2677 | CG2 | ILE | 387 | 21.216 | 34.089 | 39.031 | 1.00 | 26.74 |
| ATOM | 2678 | CG1 | ILE | 387 | 21.530 | 35.542 | 41.133 | 1.00 | 21.26 |
| ATOM | 2679 | CD1 | ILE | 387 | 23.042 | 35.543 | 41.031 | 1.00 | 14.17 |
| ATOM | 2680 | C | ILE | 387 | 18.918 | 33.990 | 42.064 | 1.00 | 26.81 |
| ATOM | 2681 | O | ILE | 387 | 19.179 | 32.858 | 42.454 | 1.00 | 30.18 |
| ATOM | 2682 | N | GLU | 388 | 18.328 | 34.891 | 42.839 | 1.00 | 25.04 |
| ATOM | 2683 | CA | GLU | 388 | 17.917 | 34.509 | 44.173 | 1.00 | 23.04 |
| ATOM | 2684 | CB | GLU | 388 | 18.376 | 35.538 | 45.200 | 1.00 | 26.13 |
| ATOM | 2685 | CG | GLU | 388 | 19.918 | 35.647 | 45.291 | 1.00 | 37.60 |
| ATOM | 2686 | CD | GLU | 388 | 20.631 | 34.293 | 45.458 | 1.00 | 40.42 |
| ATOM | 2687 | OE1 | GLU | 388 | 20.658 | 33.755 | 46.590 | 1.00 | 41.88 |
| ATOM | 2688 | OE2 | GLU | 388 | 21.175 | 33.766 | 44.458 | 1.00 | 39.83 |
| ATOM | 2689 | C | GLU | 388 | 16.413 | 34.263 | 44.178 | 1.00 | 22.67 |
| ATOM | 2690 | O | GLU | 388 | 15.887 | 33.569 | 45.048 | 1.00 | 26.93 |
| ATOM | 2691 | N | GLU | 389 | 15.734 | 34.805 | 43.171 | 1.00 | 23.95 |
| ATOM | 2692 | CA | GLU | 389 | 14.294 | 34.609 | 42.992 | 1.00 | 22.61 |
| ATOM | 2693 | CB | GLU | 389 | 13.732 | 35.584 | 41.967 | 1.00 | 25.77 |
| ATOM | 2694 | CG | GLU | 389 | 13.558 | 37.012 | 42.425 | 1.00 | 35.01 |
| ATOM | 2695 | CD | GLU | 389 | 12.845 | 37.842 | 41.368 | 1.00 | 38.49 |
| ATOM | 2696 | OE1 | GLU | 389 | 13.515 | 38.311 | 40.421 | 1.00 | 41.09 |
| ATOM | 2697 | OE2 | GLU | 389 | 11.607 | 38.004 | 41.465 | 1.00 | 41.88 |
| ATOM | 2698 | C | GLU | 389 | 14.110 | 33.207 | 42.425 | 1.00 | 22.40 |
| ATOM | 2699 | O | GLU | 389 | 13.082 | 32.577 | 42.650 | 1.00 | 24.62 |
| ATOM | 2700 | N | TRP | 390 | 15.085 | 32.774 | 41.620 | 1.00 | 22.87 |

FIGURE 1A-54

| ATOM | 2701 | CA | TRP | 390 | 15.083 | 31.452 | 41.002 | 1.00 | 20.40 |
|---|---|---|---|---|---|---|---|---|---|
| ATOM | 2702 | CB | TRP | 390 | 16.171 | 31.355 | 39.932 | 1.00 | 15.47 |
| ATOM | 2703 | CG | TRP | 390 | 15.798 | 31.858 | 38.570 | 1.00 | 19.44 |
| ATOM | 2704 | CD2 | TRP | 390 | 14.658 | 31.471 | 37.784 | 1.00 | 16.90 |
| ATOM | 2705 | CE2 | TRP | 390 | 14.754 | 32.158 | 36.548 | 1.00 | 14.52 |
| ATOM | 2706 | CE3 | TRP | 390 | 13.574 | 30.611 | 37.988 | 1.00 | 20.06 |
| ATOM | 2707 | CD1 | TRP | 390 | 16.510 | 32.741 | 37.807 | 1.00 | 15.66 |
| ATOM | 2708 | NE1 | TRP | 390 | 15.891 | 32.921 | 36.597 | 1.00 | 17.38 |
| ATOM | 2709 | CZ2 | TRP | 390 | 13.800 | 32.010 | 35.538 | 1.00 | 11.75 |
| ATOM | 2710 | CZ3 | TRP | 390 | 12.628 | 30.464 | 36.987 | 1.00 | 12.81 |
| ATOM | 2711 | CH2 | TRP | 390 | 12.747 | 31.160 | 35.773 | 1.00 | 12.71 |
| ATOM | 2712 | C | TRP | 390 | 15.367 | 30.389 | 42.064 | 1.00 | 23.99 |
| ATOM | 2713 | O | TRP | 390 | 14.818 | 29.293 | 42.011 | 1.00 | 26.51 |
| ATOM | 2714 | N | LYS | 391 | 16.247 | 30.718 | 43.005 | 1.00 | 24.18 |
| ATOM | 2715 | CA | LYS | 391 | 16.618 | 29.821 | 44.089 | 1.00 | 22.51 |
| ATOM | 2716 | CB | LYS | 391 | 17.621 | 30.528 | 44.997 | 1.00 | 22.81 |
| ATOM | 2717 | CG | LYS | 391 | 18.229 | 29.682 | 46.102 | 1.00 | 32.74 |
| ATOM | 2718 | CD | LYS | 391 | 19.176 | 30.520 | 46.960 | 1.00 | 34.93 |
| ATOM | 2719 | CE | LYS | 391 | 19.857 | 29.667 | 48.017 | 1.00 | 39.04 |
| ATOM | 2720 | NZ | LYS | 391 | 20.813 | 30.450 | 48.854 | 1.00 | 44.95 |
| ATOM | 2721 | C | LYS | 391 | 15.348 | 29.498 | 44.867 | 1.00 | 22.29 |
| ATOM | 2722 | O | LYS | 391 | 15.030 | 28.333 | 45.116 | 1.00 | 22.80 |
| ATOM | 2723 | N | GLU | 392 | 14.595 | 30.541 | 45.187 | 1.00 | 19.10 |
| ATOM | 2724 | CA | GLU | 392 | 13.356 | 30.421 | 45.930 | 1.00 | 21.08 |
| ATOM | 2725 | CB | GLU | 392 | 12.789 | 31.824 | 46.184 | 1.00 | 24.34 |
| ATOM | 2726 | CG | GLU | 392 | 11.321 | 31.885 | 46.581 | 1.00 | 35.14 |
| ATOM | 2727 | CD | GLU | 392 | 11.102 | 31.760 | 48.067 | 1.00 | 38.04 |
| ATOM | 2728 | OE1 | GLU | 392 | 10.930 | 32.799 | 48.732 | 1.00 | 43.47 |
| ATOM | 2729 | OE2 | GLU | 392 | 11.094 | 30.622 | 48.570 | 1.00 | 48.37 |
| ATOM | 2730 | C | GLU | 392 | 12.349 | 29.560 | 45.183 | 1.00 | 20.69 |
| ATOM | 2731 | O | GLU | 392 | 11.701 | 28.700 | 45.775 | 1.00 | 24.35 |
| ATOM | 2732 | N | LEU | 393 | 12.217 | 29.793 | 43.882 | 1.00 | 25.19 |
| ATOM | 2733 | CA | LEU | 393 | 11.273 | 29.044 | 43.058 | 1.00 | 22.23 |
| ATOM | 2734 | CB | LEU | 393 | 11.164 | 29.676 | 41.670 | 1.00 | 26.80 |
| ATOM | 2735 | CG | LEU | 393 | 10.307 | 30.935 | 41.536 | 1.00 | 25.48 |
| ATOM | 2736 | CD1 | LEU | 393 | 10.367 | 31.430 | 40.105 | 1.00 | 22.35 |
| ATOM | 2737 | CD2 | LEU | 393 | 8.875 | 30.597 | 41.924 | 1.00 | 29.12 |
| ATOM | 2738 | C | LEU | 393 | 11.652 | 27.573 | 42.924 | 1.00 | 21.74 |
| ATOM | 2739 | O | LEU | 393 | 10.785 | 26.698 | 42.900 | 1.00 | 20.13 |
| ATOM | 2740 | N | ILE | 394 | 12.950 | 27.304 | 42.855 | 1.00 | 20.32 |
| ATOM | 2741 | CA | ILE | 394 | 13.453 | 25.947 | 42.718 | 1.00 | 19.96 |
| ATOM | 2742 | CB | ILE | 394 | 14.934 | 25.957 | 42.264 | 1.00 | 17.19 |
| ATOM | 2743 | CG2 | ILE | 394 | 15.585 | 24.573 | 42.431 | 1.00 | 13.12 |
| ATOM | 2744 | CG1 | ILE | 394 | 15.004 | 26.448 | 40.815 | 1.00 | 13.64 |
| ATOM | 2745 | CD1 | ILE | 394 | 16.409 | 26.548 | 40.246 | 1.00 | 17.23 |
| ATOM | 2746 | C | ILE | 394 | 13.294 | 25.192 | 44.028 | 1.00 | 22.48 |
| ATOM | 2747 | O | ILE | 394 | 12.883 | 24.040 | 44.035 | 1.00 | 21.90 |
| ATOM | 2748 | N | TYR | 395 | 13.567 | 25.867 | 45.142 | 1.00 | 25.79 |
| ATOM | 2749 | CA | TYR | 395 | 13.444 | 25.264 | 46.460 | 1.00 | 24.44 |
| ATOM | 2750 | CB | TYR | 395 | 13.945 | 26.231 | 47.528 | 1.00 | 28.31 |
| ATOM | 2751 | CG | TYR | 395 | 14.078 | 25.629 | 48.903 | 1.00 | 27.27 |

FIGURE 1A-55

| | | | | | | | | |
|---|---|---|---|---|---|---|---|---|
| ATOM | 2752 | CD1 | TYR | 395 | 15.203 | 24.887 | 49.251 | 1.00 27.25 |
| ATOM | 2753 | CE1 | TYR | 395 | 15.363 | 24.379 | 50.538 | 1.00 27.52 |
| ATOM | 2754 | CD2 | TYR | 395 | 13.107 | 25.847 | 49.880 | 1.00 29.16 |
| ATOM | 2755 | CE2 | TYR | 395 | 13.262 | 25.341 | 51.176 | 1.00 25.05 |
| ATOM | 2756 | CZ | TYR | 395 | 14.391 | 24.613 | 51.493 | 1.00 25.64 |
| ATOM | 2757 | OH | TYR | 395 | 14.550 | 24.144 | 52.771 | 1.00 31.95 |
| ATOM | 2758 | C | TYR | 395 | 12.000 | 24.884 | 46.743 | 1.00 24.99 |
| ATOM | 2759 | O | TYR | 395 | 11.718 | 23.735 | 47.069 | 1.00 23.51 |
| ATOM | 2760 | N | LYS | 396 | 11.078 | 25.832 | 46.583 | 1.00 28.30 |
| ATOM | 2761 | CA | LYS | 396 | 9.673 | 25.551 | 46.847 | 1.00 32.87 |
| ATOM | 2762 | CB | LYS | 396 | 8.842 | 26.842 | 46.924 | 1.00 36.62 |
| ATOM | 2763 | CG | LYS | 396 | 8.883 | 27.723 | 45.688 | 1.00 42.55 |
| ATOM | 2764 | CD | LYS | 396 | 7.955 | 28.937 | 45.803 | 1.00 48.54 |
| ATOM | 2765 | CE | LYS | 396 | 8.292 | 29.830 | 46.999 | 1.00 52.32 |
| ATOM | 2766 | NZ | LYS | 396 | 7.822 | 31.238 | 46.803 | 1.00 53.39 |
| ATOM | 2767 | C | LYS | 396 | 9.053 | 24.530 | 45.894 | 1.00 32.33 |
| ATOM | 2768 | O | LYS | 396 | 7.908 | 24.115 | 46.090 | 1.00 37.35 |
| ATOM | 2769 | N | GLU | 397 | 9.808 | 24.122 | 44.873 | 1.00 34.21 |
| ATOM | 2770 | CA | GLU | 397 | 9.350 | 23.110 | 43.919 | 1.00 31.93 |
| ATOM | 2771 | CB | GLU | 397 | 9.867 | 23.389 | 42.509 | 1.00 33.43 |
| ATOM | 2772 | CG | GLU | 397 | 9.273 | 22.461 | 41.463 | 1.00 38.39 |
| ATOM | 2773 | CD | GLU | 397 | 7.808 | 22.736 | 41.216 | 1.00 44.36 |
| ATOM | 2774 | OE1 | GLU | 397 | 7.008 | 21.774 | 41.187 | 1.00 49.32 |
| ATOM | 2775 | OE2 | GLU | 397 | 7.458 | 23.924 | 41.047 | 1.00 48.39 |
| ATOM | 2776 | C | GLU | 397 | 9.912 | 21.777 | 44.389 | 1.00 29.02 |
| ATOM | 2777 | O | GLU | 397 | 9.218 | 20.763 | 44.384 | 1.00 28.55 |
| ATOM | 2778 | N | VAL | 398 | 11.176 | 21.806 | 44.803 | 1.00 25.39 |
| ATOM | 2779 | CA | VAL | 398 | 11.881 | 20.636 | 45.300 | 1.00 24.45 |
| ATOM | 2780 | CB | VAL | 398 | 13.351 | 20.971 | 45.655 | 1.00 20.32 |
| ATOM | 2781 | CG1 | VAL | 398 | 14.040 | 19.762 | 46.296 | 1.00 20.48 |
| ATOM | 2782 | CG2 | VAL | 398 | 14.100 | 21.428 | 44.418 | 1.00 11.66 |
| ATOM | 2783 | C | VAL | 398 | 11.197 | 20.163 | 46.569 | 1.00 33.54 |
| ATOM | 2784 | O | VAL | 398 | 11.107 | 18.965 | 46.838 | 1.00 36.92 |
| ATOM | 2785 | N | MET | 399 | 10.718 | 21.126 | 47.350 | 1.00 38.72 |
| ATOM | 2786 | CA | MET | 399 | 10.036 | 20.853 | 48.605 | 1.00 41.08 |
| ATOM | 2787 | CB | MET | 399 | 10.582 | 21.782 | 49.695 | 1.00 37.75 |
| ATOM | 2788 | CG | MET | 399 | 12.106 | 21.801 | 49.786 | 1.00 36.12 |
| ATOM | 2789 | SD | MET | 399 | 12.799 | 20.970 | 51.224 | 1.00 38.83 |
| ATOM | 2790 | CE | MET | 399 | 12.989 | 19.333 | 50.597 | 1.00 41.98 |
| ATOM | 2791 | C | MET | 399 | 8.569 | 21.142 | 48.351 | 1.00 43.23 |
| ATOM | 2792 | O | MET | 399 | 8.095 | 22.231 | 48.649 | 1.00 49.06 |
| ATOM | 2793 | N | ASN | 400 | 7.862 | 20.184 | 47.760 | 1.00 45.95 |
| ATOM | 2794 | CA | ASN | 400 | 6.445 | 20.367 | 47.456 | 1.00 50.08 |
| ATOM | 2795 | CB | ASN | 400 | 5.849 | 19.109 | 46.819 | 1.00 54.71 |
| ATOM | 2796 | CG | ASN | 400 | 6.055 | 19.064 | 45.315 | 1.00 59.81 |
| ATOM | 2797 | OD1 | ASN | 400 | 7.169 | 18.846 | 44.832 | 1.00 62.77 |
| ATOM | 2798 | ND2 | ASN | 400 | 4.974 | 19.266 | 44.564 | 1.00 62.37 |
| ATOM | 2799 | C | ASN | 400 | 5.652 | 20.743 | 48.698 | 1.00 52.31 |
| ATOM | 2800 | O | ASN | 400 | 5.453 | 21.963 | 48.877 | 1.00 54.69 |
| TER | | | ASN | 400 | | | | |
| HETATM | 2801 | PG | AMP | 1001 | 23.808 | 17.953 | 28.350 | 1.00 52.23 |

FIGURE 1A-56

```
HETATM 2802  O1G AMP  1001    25.321  17.822  27.960  1.00  48.89
HETATM 2803  O2G AMP  1001    22.835  17.587  27.198  1.00  52.11
HETATM 2804  O3G AMP  1001    23.638  19.469  28.750  1.00  52.21
HETATM 2805  PB  AMP  1001    23.032  17.172  31.015  1.00  39.76
HETATM 2806  O1B AMP  1001    23.984  18.046  31.864  1.00  33.22
HETATM 2807  O2B AMP  1001    21.558  17.654  31.095  1.00  39.03
HETATM 2808  N3B AMP  1001    23.510  16.996  29.534  1.00  46.06
HETATM 2809  PA  AMP  1001    22.296  14.584  31.143  1.00  17.54
HETATM 2810  O1A AMP  1001    20.969  14.466  31.823  1.00  21.14
HETATM 2811  O2A AMP  1001    21.754  14.739  29.743  1.00  33.84
HETATM 2812  O3A AMP  1001    23.208  15.751  31.649  1.00  31.78
HETATM 2813  O5* AMP  1001    23.117  13.303  31.321  1.00  21.24
HETATM 2814  C5* AMP  1001    24.321  13.045  30.557  1.00  14.83
HETATM 2815  C4* AMP  1001    24.418  11.539  30.279  1.00  21.05
HETATM 2816  O4* AMP  1001    24.090  10.783  31.464  1.00  17.30
HETATM 2817  C3* AMP  1001    23.399  11.109  29.180  1.00  20.17
HETATM 2818  O3* AMP  1001    23.998  11.137  27.874  1.00  25.52
HETATM 2819  C2* AMP  1001    23.135   9.632  29.537  1.00  17.59
HETATM 2820  O2* AMP  1001    24.224   8.802  29.063  1.00  18.00
HETATM 2821  C1* AMP  1001    23.206   9.747  31.079  1.00   9.52
HETATM 2822  N9  AMP  1001    22.007   9.611  31.844  1.00   9.28
HETATM 2823  C8  AMP  1001    21.217  10.687  32.155  1.00   2.78
HETATM 2824  N7  AMP  1001    20.024  10.235  32.613  1.00   8.52
HETATM 2825  C5  AMP  1001    20.047   8.848  32.606  1.00   7.00
HETATM 2826  C6  AMP  1001    19.189   7.795  32.949  1.00  11.21
HETATM 2827  N6  AMP  1001    17.932   8.033  33.518  1.00  12.86
HETATM 2828  N1  AMP  1001    19.588   6.517  32.777  1.00   8.84
HETATM 2829  C2  AMP  1001    20.786   6.187  32.301  1.00   8.60
HETATM 2830  N3  AMP  1001    21.713   7.062  31.949  1.00   6.38
HETATM 2831  C4  AMP  1001    21.347   8.407  32.100  1.00   9.95
TER              AMP  1001
HETATM 2832  MMG MG   1002    20.501  16.972  29.196  1.00  39.54
HETATM 2833  MMG MG   1003    22.860  15.695  27.727  1.00  25.19
TER              MG   1003
HETATM 2834  O   HOH  2001    18.747  13.277  33.393  1.00  28.24
HETATM 2835  O   HOH  2002    18.264  -0.452  33.390  1.00  19.73
HETATM 2836  O   HOH  2003    15.737  -0.307  35.388  1.00  65.63
HETATM 2837  O   HOH  2004     9.882   6.294  47.388  1.00  23.86
HETATM 2838  O   HOH  2005    30.785   7.788  32.936  1.00  33.87
HETATM 2839  O   HOH  2006    13.654   6.518  44.257  1.00  11.74
HETATM 2840  O   HOH  2007    14.303   2.135  37.646  1.00  44.40
HETATM 2841  O   HOH  2008    25.045  17.888  48.290  1.00  16.65
HETATM 2842  O   HOH  2009     8.018  12.540  32.848  1.00  19.47
HETATM 2843  O   HOH  2010     6.712  10.004  32.061  1.00  24.77
HETATM 2844  O   HOH  2011    23.266   3.294  32.566  1.00  20.33
HETATM 2845  O   HOH  2012    17.669  -3.177  31.269  1.00  37.10
HETATM 2846  O   HOH  2013    26.205   1.689  28.868  1.00  66.73
HETATM 2847  O   HOH  2014    23.774   5.926  29.839  1.00  21.04
HETATM 2848  O   HOH  2015    25.505   4.223  31.135  1.00  23.98
HETATM 2849  O   HOH  2016    28.292   8.351  18.973  1.00  23.14
HETATM 2850  O   HOH  2017    14.837  -8.139  13.818  1.00  35.36
```

FIGURE 1A-57

| | | | | | | | | |
|---|---|---|---|---|---|---|---|---|
| HETATM | 2851 | O | HOH | 2018 | 20.695 | -5.043 | 16.496 | 1.00 40.58 |
| HETATM | 2852 | O | HOH | 2019 | 20.736 | 20.241 | 11.594 | 1.00 5.30 |
| HETATM | 2853 | O | HOH | 2020 | 14.291 | 18.861 | 18.337 | 1.00 13.76 |
| HETATM | 2854 | O | HOH | 2021 | 32.442 | 24.489 | 2.563 | 1.00 56.54 |
| HETATM | 2855 | O | HOH | 2022 | 14.822 | 2.914 | -2.612 | 1.00 40.79 |
| HETATM | 2856 | O | HOH | 2023 | 0.887 | 3.204 | 5.554 | 1.00 22.49 |
| HETATM | 2857 | O | HOH | 2024 | 5.875 | 25.338 | 43.220 | 1.00 57.24 |
| HETATM | 2858 | O | HOH | 2025 | 35.759 | 13.833 | 52.013 | 1.00 33.89 |
| HETATM | 2859 | O | HOH | 2026 | 26.944 | 3.167 | 49.219 | 1.00 36.21 |
| HETATM | 2860 | O | HOH | 2027 | 30.069 | 10.917 | 35.731 | 1.00 52.95 |
| HETATM | 2861 | O | HOH | 2028 | 26.837 | 27.092 | 35.071 | 1.00 44.77 |
| HETATM | 2862 | O | HOH | 2029 | 21.194 | 21.466 | 25.605 | 1.00 38.88 |
| HETATM | 2863 | O | HOH | 2030 | 9.266 | 16.942 | 44.933 | 1.00 47.00 |
| HETATM | 2864 | O | HOH | 2031 | 3.951 | 19.345 | 37.998 | 1.00 21.80 |
| HETATM | 2865 | O | HOH | 2032 | 2.774 | 5.972 | 28.206 | 1.00 28.48 |
| HETATM | 2866 | O | HOH | 2033 | 7.344 | 6.390 | 32.118 | 1.00 47.08 |
| HETATM | 2867 | O | HOH | 2034 | 8.634 | -3.766 | 26.240 | 1.00 84.90 |
| HETATM | 2868 | O | HOH | 2035 | 8.098 | 2.170 | 25.119 | 1.00 36.87 |
| HETATM | 2869 | O | HOH | 2036 | 10.012 | 14.496 | 46.667 | 1.00 68.63 |
| HETATM | 2870 | O | HOH | 2037 | 15.571 | 21.318 | 52.875 | 1.00 4.35 |
| HETATM | 2871 | O | HOH | 2038 | 23.056 | -0.587 | 32.848 | 1.00 35.85 |
| HETATM | 2872 | O | HOH | 2039 | 8.299 | -8.916 | 16.671 | 1.00 34.31 |
| HETATM | 2873 | O | HOH | 2040 | 21.764 | -6.470 | 12.169 | 1.00 39.44 |
| HETATM | 2874 | O | HOH | 2041 | 24.033 | -5.711 | 10.610 | 1.00 15.37 |
| HETATM | 2875 | O | HOH | 2042 | 24.716 | 14.388 | 21.285 | 1.00 9.87 |
| HETATM | 2876 | O | HOH | 2043 | 26.019 | 13.236 | 18.849 | 1.00 37.43 |
| HETATM | 2877 | O | HOH | 2044 | 18.834 | 18.260 | 30.345 | 1.00 45.67 |
| HETATM | 2878 | O | HOH | 2045 | 23.164 | -3.820 | 29.147 | 1.00 47.32 |
| HETATM | 2879 | O | HOH | 2046 | 25.265 | 29.182 | 18.550 | 1.00 49.79 |
| HETATM | 2880 | O | HOH | 2047 | 23.456 | 27.648 | 19.913 | 1.00 26.97 |
| HETATM | 2881 | O | HOH | 2048 | 26.971 | 23.530 | 14.519 | 1.00 32.15 |
| HETATM | 2882 | O | HOH | 2049 | 28.858 | 10.345 | 15.329 | 1.00 49.60 |
| HETATM | 2883 | O | HOH | 2050 | 26.340 | 28.659 | 5.707 | 1.00 37.86 |
| HETATM | 2884 | O | HOH | 2051 | 33.141 | 20.939 | 2.723 | 1.00 52.80 |
| HETATM | 2885 | O | HOH | 2052 | 16.673 | 39.935 | 0.470 | 1.00 28.59 |
| HETATM | 2886 | O | HOH | 2053 | 31.631 | 30.025 | 4.850 | 1.00 28.56 |
| HETATM | 2887 | O | HOH | 2054 | 28.590 | 26.777 | -5.826 | 1.00 17.06 |
| HETATM | 2888 | O | HOH | 2055 | 12.229 | 8.400 | -1.370 | 1.00 65.82 |
| HETATM | 2889 | O | HOH | 2056 | -1.838 | 16.713 | 15.107 | 1.00 65.22 |
| HETATM | 2890 | O | HOH | 2057 | 10.924 | 39.338 | 38.771 | 1.00 47.54 |
| HETATM | 2891 | O | HOH | 2058 | 32.437 | 8.512 | 52.419 | 1.00 63.35 |
| HETATM | 2892 | O | HOH | 2059 | 35.315 | 15.364 | 47.499 | 1.00 32.09 |
| HETATM | 2893 | O | HOH | 2060 | 17.241 | 15.701 | 23.582 | 1.00 56.24 |
| HETATM | 2894 | O | HOH | 2061 | 26.910 | 18.252 | 39.740 | 1.00 33.90 |
| HETATM | 2895 | O | HOH | 2062 | 28.050 | 11.651 | 29.532 | 1.00 23.10 |
| HETATM | 2896 | O | HOH | 2063 | 27.818 | 12.666 | 24.882 | 1.00 53.74 |
| HETATM | 2897 | O | HOH | 2064 | 26.639 | 17.188 | 24.705 | 1.00 39.11 |
| HETATM | 2898 | O | HOH | 2065 | 22.069 | 21.395 | 22.233 | 1.00 47.05 |
| HETATM | 2899 | O | HOH | 2066 | 14.189 | 6.291 | 52.236 | 1.00 9.55 |
| HETATM | 2900 | O | HOH | 2067 | 16.439 | 7.231 | 52.610 | 1.00 8.64 |
| HETATM | 2901 | O | HOH | 2068 | 9.390 | 9.447 | 47.458 | 1.00 36.22 |

FIGURE 1A-58

| | | | | | | | | |
|---|---|---|---|---|---|---|---|---|
| HETATM | 2902 | O | HOH | 2069 | 10.691 | 7.108 | 44.467 | 1.00 26.35 |
| HETATM | 2903 | O | HOH | 2070 | 19.765 | 23.013 | 35.751 | 1.00 26.64 |
| HETATM | 2904 | O | HOH | 2071 | 22.111 | 23.029 | 37.211 | 1.00 16.20 |
| HETATM | 2905 | O | HOH | 2072 | 24.765 | 24.315 | 37.641 | 1.00 33.02 |
| HETATM | 2906 | O | HOH | 2073 | 7.015 | 11.353 | 35.546 | 1.00 66.93 |
| HETATM | 2907 | O | HOH | 2074 | 5.250 | 8.736 | 35.020 | 1.00 52.34 |
| HETATM | 2908 | O | HOH | 2075 | 18.502 | 14.677 | 57.699 | 1.00 40.88 |
| HETATM | 2909 | O | HOH | 2076 | 12.651 | 22.025 | 56.697 | 1.00 61.23 |
| HETATM | 2910 | O | HOH | 2077 | 26.412 | 10.553 | 18.145 | 1.00 32.08 |
| HETATM | 2911 | O | HOH | 2078 | 29.254 | 11.398 | 18.287 | 1.00 47.30 |
| HETATM | 2912 | O | HOH | 2079 | 22.211 | -0.178 | 10.255 | 1.00 32.50 |
| HETATM | 2913 | O | HOH | 2080 | 25.463 | 19.984 | 24.462 | 1.00 34.66 |
| HETATM | 2914 | O | HOH | 2081 | 6.733 | 11.675 | 38.332 | 1.00 44.81 |
| HETATM | 2915 | O | HOH | 2082 | 9.056 | 0.237 | 42.059 | 1.00 45.51 |
| HETATM | 2916 | O | HOH | 2083 | 16.973 | -8.269 | 16.506 | 1.00 58.35 |
| HETATM | 2917 | O | HOH | 2084 | 19.487 | 28.537 | 18.538 | 1.00 48.37 |
| HETATM | 2918 | O | HOH | 2085 | 12.669 | 4.647 | -1.484 | 1.00 16.84 |
| HETATM | 2919 | O | HOH | 2086 | 3.915 | 18.984 | 8.007 | 1.00 33.88 |
| HETATM | 2920 | O | HOH | 2087 | -1.909 | 2.861 | 10.360 | 1.00 56.48 |
| HETATM | 2921 | O | HOH | 2088 | 8.518 | 23.993 | 11.692 | 1.00 12.75 |
| HETATM | 2922 | O | HOH | 2089 | 15.049 | 21.884 | 16.071 | 1.00 32.74 |
| HETATM | 2923 | O | HOH | 2090 | 19.168 | 41.239 | 0.741 | 1.00 54.93 |
| HETATM | 2924 | O | HOH | 2091 | -3.461 | 4.101 | 12.469 | 1.00 84.37 |
| HETATM | 2925 | O | HOH | 2092 | -0.797 | 9.344 | 13.963 | 1.00 28.10 |
| HETATM | 2926 | O | HOH | 2093 | 8.500 | 1.281 | -0.263 | 1.00 22.71 |
| HETATM | 2927 | O | HOH | 2094 | 20.210 | 19.395 | 27.403 | 1.00 44.95 |
| HETATM | 2928 | O | HOH | 2095 | 18.619 | 15.475 | 60.580 | 1.00 61.93 |
| HETATM | 2929 | O | HOH | 2096 | 24.352 | 4.004 | 54.267 | 1.00 38.06 |
| HETATM | 2930 | O | HOH | 2097 | 23.541 | 3.715 | 51.478 | 1.00 56.45 |
| HETATM | 2931 | O | HOH | 2098 | 20.028 | 1.846 | 53.055 | 1.00 64.05 |
| HETATM | 2932 | O | HOH | 2099 | 29.742 | -2.509 | 45.585 | 1.00 62.38 |
| HETATM | 2933 | O | HOH | 2100 | 32.582 | 14.913 | 35.283 | 1.00 77.52 |
| HETATM | 2934 | O | HOH | 2101 | 17.896 | 15.591 | 31.078 | 1.00 74.30 |
| HETATM | 2935 | O | HOH | 2102 | 16.062 | -3.594 | 50.333 | 1.00 37.48 |
| HETATM | 2936 | O | HOH | 2103 | 16.672 | -6.300 | 49.672 | 1.00 67.85 |
| HETATM | 2937 | O | HOH | 2104 | 13.388 | -3.757 | 49.372 | 1.00 40.86 |
| HETATM | 2938 | O | HOH | 2105 | 12.197 | -7.497 | 48.374 | 1.00 57.18 |
| HETATM | 2939 | O | HOH | 2106 | 11.466 | -5.229 | 43.422 | 1.00 39.74 |
| HETATM | 2940 | O | HOH | 2107 | 10.506 | -6.482 | 45.828 | 1.00 63.14 |
| HETATM | 2941 | O | HOH | 2108 | 12.632 | -7.819 | 41.612 | 1.00 36.25 |
| HETATM | 2942 | O | HOH | 2109 | 10.540 | -8.437 | 43.411 | 1.00 85.88 |
| HETATM | 2943 | O | HOH | 2110 | 10.592 | -2.878 | 41.916 | 1.00 41.48 |
| HETATM | 2944 | O | HOH | 2111 | 10.441 | 0.037 | 36.465 | 1.00 43.37 |
| HETATM | 2945 | O | HOH | 2112 | 9.160 | 3.893 | 37.237 | 1.00 52.92 |
| HETATM | 2946 | O | HOH | 2113 | 13.798 | 1.506 | 33.649 | 1.00 29.44 |
| HETATM | 2947 | O | HOH | 2114 | 16.587 | -3.023 | 33.975 | 1.00 75.36 |
| HETATM | 2948 | O | HOH | 2115 | 20.071 | -4.335 | 31.620 | 1.00 40.05 |
| HETATM | 2949 | O | HOH | 2116 | 28.462 | 6.171 | 27.528 | 1.00 41.20 |
| HETATM | 2950 | O | HOH | 2117 | 30.100 | 19.272 | 41.462 | 1.00 33.52 |
| HETATM | 2951 | O | HOH | 2118 | 31.759 | 22.692 | 42.035 | 1.00 47.57 |
| HETATM | 2952 | O | HOH | 2119 | 4.153 | 12.032 | 36.133 | 1.00 25.04 |

FIGURE 1A-59

| | | | | | | | | |
|---|---|---|---|---|---|---|---|---|
| HETATM | 2953 | O | HOH | 2120 | 3.692 | 5.872 | 32.049 | 1.00 38.67 |
| HETATM | 2954 | O | HOH | 2121 | 12.601 | 13.393 | 49.259 | 1.00 27.21 |
| HETATM | 2955 | O | HOH | 2122 | 25.245 | 19.450 | 51.726 | 1.00 38.07 |
| HETATM | 2956 | O | HOH | 2123 | 12.405 | -4.792 | 18.743 | 1.00  9.92 |
| HETATM | 2957 | O | HOH | 2124 | 20.587 | 19.136 | 19.130 | 1.00 45.45 |
| HETATM | 2958 | O | HOH | 2125 | 3.006 | 17.110 | 16.387 | 1.00 19.84 |
| HETATM | 2959 | O | HOH | 2126 | 2.570 | 19.703 | 11.260 | 1.00 40.74 |
| HETATM | 2960 | O | HOH | 2127 | 0.054 | 16.583 | 12.457 | 1.00 33.18 |
| HETATM | 2961 | O | HOH | 2128 | -0.331 | 16.761 | 9.694 | 1.00 40.87 |
| HETATM | 2962 | O | HOH | 2129 | -2.165 | 14.991 | 10.967 | 1.00 61.04 |
| HETATM | 2963 | O | HOH | 2130 | 0.053 | 18.978 | 15.746 | 1.00 54.03 |
| HETATM | 2964 | O | HOH | 2131 | -0.498 | 24.488 | 19.585 | 1.00 40.80 |
| HETATM | 2965 | O | HOH | 2132 | 7.620 | 26.799 | 10.420 | 1.00 23.48 |
| HETATM | 2966 | O | HOH | 2133 | 4.133 | 30.284 | 13.683 | 1.00 25.12 |
| HETATM | 2967 | O | HOH | 2134 | 10.633 | 23.073 | 24.506 | 1.00 29.88 |
| HETATM | 2968 | O | HOH | 2135 | 7.758 | 25.781 | 22.008 | 1.00 38.38 |
| HETATM | 2969 | O | HOH | 2136 | 16.260 | 29.138 | 19.841 | 1.00 64.48 |
| HETATM | 2970 | O | HOH | 2137 | 29.587 | 17.805 | 24.381 | 1.00 33.41 |
| HETATM | 2971 | O | HOH | 2138 | 10.057 | 1.293 | 30.134 | 1.00 60.36 |
| HETATM | 2972 | O | HOH | 2139 | 10.403 | 1.510 | 34.049 | 1.00 82.87 |
| HETATM | 2973 | O | HOH | 2140 | 11.081 | -3.555 | 29.940 | 1.00 47.02 |
| HETATM | 2974 | O | HOH | 2141 | 32.932 | 18.745 | 18.471 | 1.00 50.62 |
| HETATM | 2975 | O | HOH | 2142 | 31.995 | 22.356 | 16.887 | 1.00 32.01 |
| HETATM | 2976 | O | HOH | 2143 | 23.373 | 13.394 | 12.543 | 1.00 17.46 |
| HETATM | 2977 | O | HOH | 2144 | 23.402 | 16.314 | 11.967 | 1.00 11.78 |
| HETATM | 2978 | O | HOH | 2145 | 25.340 | 1.368 | 7.914 | 1.00 31.33 |
| HETATM | 2979 | O | HOH | 2146 | 32.616 | 6.592 | 12.214 | 1.00 32.33 |
| HETATM | 2980 | O | HOH | 2147 | 10.709 | 38.383 | 0.246 | 1.00 31.98 |
| HETATM | 2981 | O | HOH | 2148 | 29.721 | 26.845 | 0.905 | 1.00 48.91 |
| HETATM | 2982 | O | HOH | 2149 | 32.239 | 27.487 | 2.052 | 1.00 31.20 |
| HETATM | 2983 | O | HOH | 2150 | 20.411 | -7.538 | -4.663 | 1.00 65.70 |
| HETATM | 2984 | O | HOH | 2151 | 25.185 | 14.956 | 27.473 | 1.00 15.58 |
| HETATM | 2985 | O | HOH | 2152 | 28.956 | 19.435 | 35.263 | 1.00 57.70 |
| HETATM | 2986 | O | HOH | 2153 | 6.411 | 1.106 | 22.507 | 1.00 41.33 |
| HETATM | 2987 | O | HOH | 2154 | 2.171 | 10.104 | 22.491 | 1.00 41.20 |
| HETATM | 2988 | O | HOH | 2155 | 4.026 | -0.731 | 19.899 | 1.00 42.49 |
| HETATM | 2989 | O | HOH | 2156 | 13.664 | 22.319 | 29.500 | 1.00 62.04 |
| HETATM | 2990 | O | HOH | 2157 | 15.643 | 20.418 | 29.554 | 1.00 20.18 |
| HETATM | 2991 | O | HOH | 2158 | 16.825 | 15.690 | 33.649 | 1.00 46.30 |
| HETATM | 2992 | O | HOH | 2159 | 22.633 | 28.768 | -1.709 | 1.00 23.91 |
| HETATM | 2993 | O | HOH | 2160 | 22.161 | 29.002 | 1.543 | 1.00 22.99 |
| HETATM | 2994 | O | HOH | 2161 | 26.403 | 34.743 | 1.709 | 1.00 30.07 |
| HETATM | 2995 | O | HOH | 2162 | 27.753 | 20.678 | 46.378 | 1.00 46.54 |
| HETATM | 2996 | O | HOH | 2163 | 18.477 | -1.753 | 35.893 | 1.00 51.04 |
| HETATM | 2997 | O | HOH | 2164 | 22.397 | 34.882 | 35.185 | 1.00 30.00 |
| HETATM | 2998 | O | HOH | 2165 | 24.362 | -2.206 | 6.074 | 1.00 68.24 |
| HETATM | 2999 | O | HOH | 2166 | 23.314 | -4.162 | 7.740 | 1.00 33.73 |
| HETATM | 3000 | O | HOH | 2167 | 13.071 | 22.119 | 0.822 | 1.00 15.04 |
| HETATM | 3001 | O | HOH | 2168 | 15.724 | 1.527 | 63.689 | 1.00 16.53 |
| HETATM | 3002 | O | HOH | 2169 | 9.810 | -5.073 | 11.575 | 1.00 45.23 |
| HETATM | 3003 | O | HOH | 2170 | 17.695 | 7.787 | 57.781 | 1.00 22.93 |

FIGURE 1A-60

```
HETATM 3004  O   HOH  2171      0.662  13.485  30.812  1.00 24.31
HETATM 3005  O   HOH  2172     22.690   2.837  14.573  1.00 52.20
HETATM 3006  O   HOH  2173      9.737   1.432  52.507  1.00 22.75
HETATM 3007  O   HOH  2174     30.492  25.789  -4.091  1.00 33.13
HETATM 3008  O   HOH  2175     15.254  17.642   1.034  1.00 22.56
HETATM 3009  O   HOH  2176     19.989  -0.881  54.265  1.00 25.86
HETATM 3010  O   HOH  2177     31.782  14.347   4.970  1.00 36.99
HETATM 3011  O   HOH  2178      8.157  27.077  42.512  1.00 46.08
HETATM 3012  O   HOH  2179      6.963  31.349  51.360  1.00 29.21
HETATM 3013  O   HOH  2180     -4.951  19.652  28.128  1.00 39.22
HETATM 3014  O   HOH  2181     32.807  18.030  35.571  1.00 46.10
HETATM 3015  O   HOH  2182     16.113  -3.989  29.212  1.00 33.19
HETATM 3016  O   HOH  2183      6.801   3.089  51.258  1.00 23.22
TER              HOH  2183
END
```

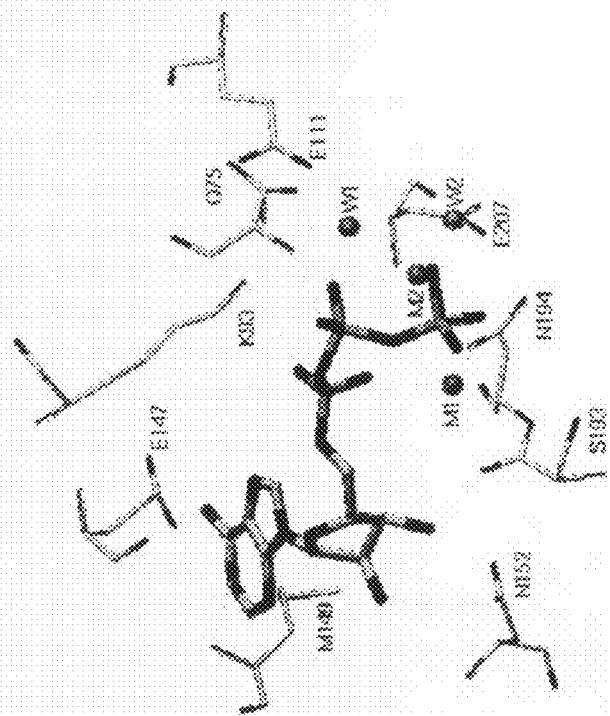
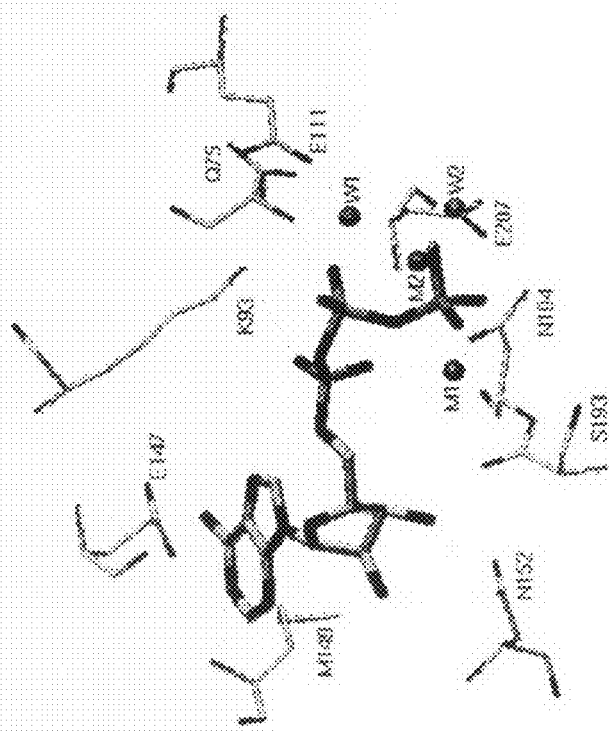
FIGURE 4A

FIGURE 4B
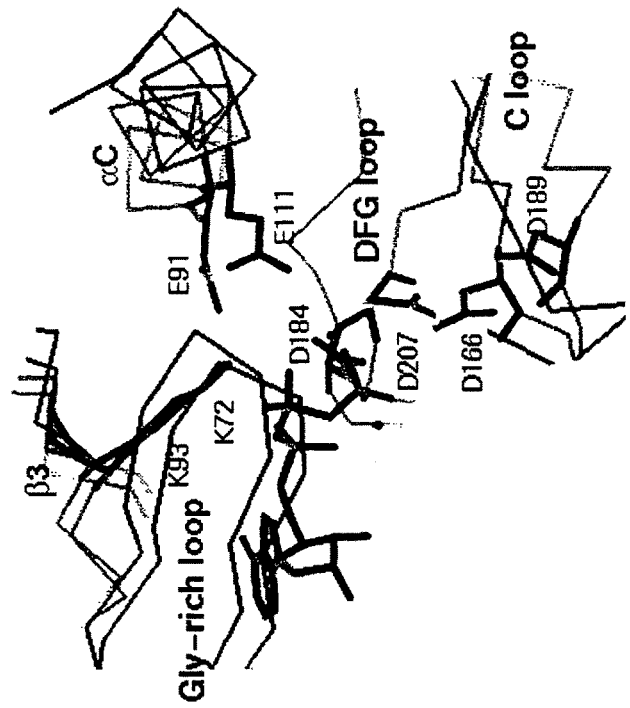
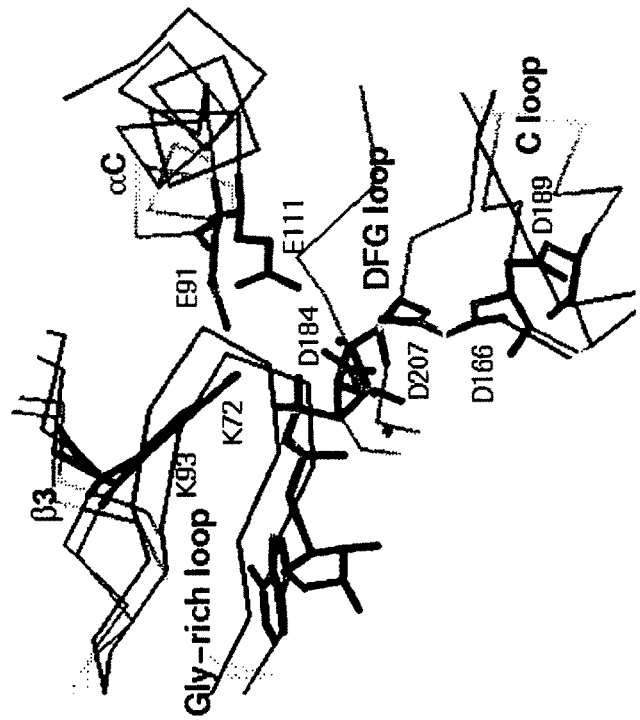

SEQUENCE LISTING

<160> NUMBER OF SEQ ID NOS: 9

<210> SEQ ID NO 1
<211> LENGTH: 422
<212> TYPE: PRT
<213> ORGANISM: Homo sapiens
<220> FEATURE:

<223> OTHER INFORMATION: JNK3

<400> SEQUENCE: 1

```
Met Ser Leu His Phe Leu Tyr Tyr Cys Ser Glu Pro Thr Leu Asp Val
  1               5                  10                  15

Lys Ile Ala Phe Cys Gln Gly Phe Asp Lys Gln Val Asp Val Ser Tyr
             20                  25                  30

Ile Ala Lys His Tyr Asn Met Ser Lys Ser Lys Val Asp Asn Gln Phe
         35                  40                  45

Tyr Ser Val Glu Val Gly Asp Ser Thr Phe Thr Val Leu Lys Arg Tyr
     50                  55                  60

Gln Asn Leu Lys Pro Ile Gly Ser Gly Ala Gln Gly Ile Val Cys Ala
 65                  70                  75                  80

Ala Tyr Asp Ala Val Leu Asp Arg Asn Val Ala Ile Lys Lys Leu Ser
                 85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
    370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
```

Ser Ala Gln Val Gln Gln
        420

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 2
gctctagagc tccatgggca gcaaaagcaa agttgacaa                    39

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 3
tagcggatcc tcattctgaa ttcattactt ccttgta                      37

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:
      glycine-rich phosphate anchor loop
<220> FEATURE:
<221> NAME/KEY: MOD_RES
<222> LOCATION: (2)
<223> OTHER INFORMATION: any amino acid
<220> FEATURE:
<221> NAME/KEY: MOD_RES
<222> LOCATION: (4)..(5)
<223> OTHER INFORMATION: any amino acid
<220> FEATURE:
<221> NAME/KEY: MOD_RES
<222> LOCATION: (7)..(8)
<223> OTHER INFORMATION: any amino acid

<400> SEQUENCE: 4

Gly Xaa Gly Xaa Xaa Gly Xaa Xaa
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:
      glycine-rich peptide

<400> SEQUENCE: 5

Gly Ser Gly Ala Gln Gly Ile Val
 1               5

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: EGF
      receptor peptide

<400> SEQUENCE: 6

Lys Arg Glu Leu Val Glu Pro Leu Thr Pro Ser Gly Glu Ala Pro Asn
1               5                   10                  15

Gln Ala Leu Leu Arg
            20

<210> SEQ ID NO 7
<211> LENGTH: 340
<212> TYPE: PRT
<213> ORGANISM: Homo sapiens
<220> FEATURE:
<223> OTHER INFORMATION: p38

<400> SEQUENCE: 7

Phe Tyr Arg Gln Glu Leu Asn Lys Thr Ile Trp Glu Val Pro Glu Arg
1               5                   10                  15

Tyr Gln Asn Leu Ser Pro Val Gly Ser Gly Ala Tyr Gly Ser Val Cys
            20                  25                  30

Ala Ala Phe Asp Thr Lys Thr Gly Leu Arg Val Ala Val Lys Lys Leu
        35                  40                  45

Ser Arg Pro Phe Gln Ser Ile Ile His Ala Lys Arg Thr Tyr Arg Glu
    50                  55                  60

Leu Arg Leu Leu Lys His Met Lys His Glu Asn Val Ile Gly Leu Leu
65                  70                  75                  80

Asp Val Phe Thr Pro Ala Arg Ser Leu Glu Glu Phe Asn Asp Val Tyr
                85                  90                  95

Leu Val Thr His Leu Met Gly Ala Asp Leu Asn Asn Ile Val Lys Cys
            100                 105                 110

Gln Lys Leu Thr Asp Asp His Val Gln Phe Leu Ile Tyr Gln Ile Leu
        115                 120                 125

Arg Gly Leu Lys Tyr Ile His Ser Ala Asp Ile Ile His Arg Asp Leu
    130                 135                 140

Lys Pro Ser Asn Leu Ala Val Asn Glu Asp Cys Glu Leu Lys Ile Leu
145                 150                 155                 160

Asp Phe Gly Leu Ala Arg His Thr Asp Asp Glu Met Thr Gly Tyr Val
                165                 170                 175

Ala Thr Arg Trp Tyr Arg Ala Pro Glu Ile Met Leu Asn Trp Met His
            180                 185                 190

Tyr Asn Gln Thr Val Asp Ile Trp Ser Val Gly Cys Ile Met Ala Glu
        195                 200                 205

Leu Leu Thr Gly Arg Thr Leu Phe Pro Gly Thr Asp His Ile Asp Gln
    210                 215                 220

Leu Lys Leu Ile Leu Arg Leu Val Gly Thr Pro Gly Ala Glu Leu Leu
225                 230                 235                 240

Lys Lys Ile Ser Ser Glu Ser Ala Arg Asn Tyr Ile Gln Ser Leu Thr
                245                 250                 255

Gln Met Pro Lys Met Asn Phe Ala Asn Val Phe Ile Gly Ala Asn Pro
            260                 265                 270

Leu Ala Val Asp Leu Leu Glu Lys Met Leu Val Leu Asp Ser Asp Lys
        275                 280                 285

Arg Ile Thr Ala Ala Gln Ala Leu Ala His Ala Tyr Phe Ala Gln Tyr
    290                 295                 300

His Asp Pro Asp Asp Glu Pro Val Ala Asp Pro Tyr Asp Gln Ser Phe
305                 310                 315                 320

Glu Ser Arg Asp Leu Leu Ile Asp Glu Trp Lys Ser Leu Thr Tyr Asp
                325                 330                 335

Glu Val Ile Ser

-continued

<210> SEQ ID NO 8
<211> LENGTH: 342
<212> TYPE: PRT
<213> ORGANISM: Homo sapiens
<220> FEATURE:
<223> OTHER INFORMATION: ERK2

<400> SEQUENCE: 8

```
Ala Gly Pro Glu Met Val Arg Gly Gln Val Phe Asp Val Gly Pro Arg
  1               5                  10                  15

Tyr Thr Asn Leu Ser Tyr Ile Gly Glu Gly Ala Tyr Gly Met Val Cys
             20                  25                  30

Ser Ala Tyr Asp Asn Val Asn Lys Val Arg Val Ala Ile Lys Lys Ile
         35                  40                  45

Ser Pro Phe Glu His Gln Thr Tyr Cys Gln Arg Thr Leu Arg Glu Ile
     50                  55                  60

Lys Ile Leu Leu Arg Phe Arg His Glu Asn Ile Ile Gly Ile Asn Asp
 65                  70                  75                  80

Ile Ile Arg Ala Pro Thr Ile Glu Gln Met Lys Asp Val Tyr Ile Val
                 85                  90                  95

Gln Asp Leu Met Glu Thr Asp Leu Tyr Lys Leu Leu Lys Thr Gln His
            100                 105                 110

Leu Ser Asn Asp His Ile Cys Tyr Phe Leu Tyr Gln Ile Leu Arg Gly
        115                 120                 125

Leu Lys Tyr Ile His Ser Ala Asn Val Leu His Arg Asp Leu Lys Pro
    130                 135                 140

Ser Asn Leu Leu Leu Asn Thr Thr Cys Asp Leu Lys Ile Cys Asp Phe
145                 150                 155                 160

Gly Leu Ala Arg Val Ala Asp Pro Asp His Asp His Thr Gly Phe Leu
                165                 170                 175

Thr Glu Tyr Val Ala Thr Arg Trp Tyr Arg Ala Pro Glu Ile Met Leu
            180                 185                 190

Asn Ser Lys Gly Tyr Thr Lys Ser Ile Asp Ile Trp Ser Val Gly Cys
        195                 200                 205

Ile Leu Ala Glu Met Leu Ser Asn Arg Pro Ile Phe Pro Gly Lys His
    210                 215                 220

Tyr Leu Asp Gln Leu Asn His Ile Leu Gly Ile Leu Gly Ser Pro Ser
225                 230                 235                 240

Gln Glu Asp Leu Asn Cys Ile Ile Asn Leu Lys Ala Arg Asn Tyr Leu
                245                 250                 255

Leu Ser Leu Pro His Lys Asn Lys Val Pro Trp Asn Arg Leu Phe Pro
            260                 265                 270

Asn Ala Asp Ser Lys Ala Leu Asp Leu Leu Asp Lys Met Leu Thr Phe
        275                 280                 285

Asn Pro His Lys Arg Ile Glu Val Glu Gln Ala Leu Ala His Pro Tyr
    290                 295                 300

Leu Glu Gln Tyr Tyr Asp Pro Ser Asp Glu Pro Ile Ala Glu Ala Pro
305                 310                 315                 320

Phe Lys Phe Asp Met Glu Leu Asp Asp Leu Pro Lys Glu Lys Leu Lys
                325                 330                 335

Glu Leu Ile Phe Glu Glu
            340
```

<210> SEQ ID NO 9

-continued

```
<211> LENGTH: 256
<212> TYPE: PRT
<213> ORGANISM: Homo sapiens
<220> FEATURE:
<223> OTHER INFORMATION: cAPK

<400> SEQUENCE: 9

Asp Gln Phe Asp Arg Ile Lys Thr Leu Gly Thr Gly Ser Phe Gly Arg
1               5                   10                  15

Val Met Leu Val Lys His Lys Glu Ser Gly Asn His Tyr Ala Met Lys
                20                  25                  30

Ile Leu Asp Lys Gln Lys Val Val Lys Leu Lys Gln Ile Glu His Thr
            35                  40                  45

Leu Asn Glu Lys Arg Ile Leu Gln Ala Val Asn Phe Pro Phe Leu Val
        50                  55                  60

Lys Leu Glu Phe Ser Phe Lys Asp Asn Ser Asn Leu Tyr Met Val Met
65                  70                  75                  80

Glu Tyr Val Ala Gly Gly Glu Met Phe Ser His Leu Arg Arg Ile Gly
                85                  90                  95

Arg Phe Ser Glu Pro His Ala Arg Phe Tyr Ala Ala Gln Ile Val Leu
                100                 105                 110

Thr Phe Glu Tyr Leu His Ser Leu Asp Leu Ile Tyr Arg Asp Leu Lys
                115                 120                 125

Pro Glu Asn Leu Leu Ile Asp Gln Gln Gly Tyr Ile Gln Val Thr Asp
            130                 135                 140

Phe Gly Phe Ala Lys Arg Val Lys Gly Arg Thr Trp Thr Leu Cys Gly
145                 150                 155                 160

Thr Pro Glu Tyr Leu Ala Pro Glu Ile Ile Leu Ser Lys Gly Tyr Asn
                165                 170                 175

Lys Ala Val Asp Trp Trp Ala Leu Gly Val Leu Ile Tyr Glu Met Ala
                180                 185                 190

Ala Gly Tyr Pro Pro Phe Phe Ala Asp Gln Pro Ile Gln Ile Tyr Glu
            195                 200                 205

Lys Ile Val Ser Gly Lys Val Arg Phe Pro Ser His Phe Ser Ser Asp
        210                 215                 220

Leu Lys Asp Leu Leu Arg Asn Leu Leu Gln Val Asp Leu Thr Lys Arg
225                 230                 235                 240

Phe Gly Asn Leu Lys Asn Gly Val Asn Asp Ile Lys Asn His Lys Trp
                245                 250                 255
```

CRYSTALLIZATION OF C-JUN N-TERMINAL KINASE 3 (JNK3)

This application is a divisional of U.S. patent application Ser. No. 09/706,128, filed Nov. 3, 2000, now U.S. Pat. No. 7,383,135 which is a continuation of PCT Application No. PCT/US99/09824, filed May 4, 1999, which claims priority from Provisional Application 60/084,056, filed May 4, 1998, all of which are incorporated herein by reference.

TECHNICAL FIELD OF INVENTION

The present invention relates to crystallizable complexes of a JNK protein, particularly JNK3, and adenosine monophosphate. The present invention also relates to a data storage medium encoded with the structural coordinates of crystallized molecules and molecular complexes which comprise the active site binding pockets of JNK3. A computer comprising such data storage material is capable of displaying such molecules and molecular complexes, or their structural homologues, as a graphical three-dimensional representation on a computer screen. This invention also relates to methods of using the structure coordinates to solve the structure of homologous proteins or protein complexes. In addition, this invention relates to methods of using the structure coordinates to screen for and design compounds, including inhibitory compounds, that bind to JNK3 or homologues thereof.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases are serine/threonine kinases that are activated by dual phosphorylation of threonine and tyrosine at the Thr-X-Tyr segment in the activation loop. MAP kinases phosphorylate various substrates including transcription factors, which in turn regulate the expression of specific sets of genes and thus mediate a specific response to the stimulus.

Three distinct genes, Jnk1, Jnk2, Jnk3 have been identified and at least ten different splicing isoforms of JNK exist in mammalian cells [S. Gupta et al., *EMBO J.*, 15, pp. 2760-2770 (1996)]. Members of the JNK kinases are activated by proinflammatory cytokines tumor necrosis factor-alpha and interleukin-1 beta as well as environmental stress, such as anisomycin, UV irradiation, hypoxia, and osmotic shock [A. Minden et al., *Biochemica et Biophysica Acta*, 1333, F85-F104 (1997)]. Regulation & function of the JNK subgroup of MAP kinases. The down-stream substrates of JNKs include transcription factors c-Jun, ATF-2, Elk1, p53 and a cell death domain protein (DENN) [Y. Zhang et al. *Proc. Natl. Acad. Sci. USA*, 95, pp. 2586-2591 (1998)]. Each JNK isoform binds to these substrates with different affinities, suggesting a regulation of signaling pathways by substrate specificity of different JNKs in vivo (S. Gupta et al., 1996)

JNK1 and JNK2 are widely expressed in a variety of tissues. In contrast, JNK3 is selectively expressed in the brain and to a lesser extent in the heart and testis [S. Gupta et al., (1996); A. A. Mohit et al., *Neuron*, 14, pp. 67-78 (1995); J. H. Martin et al., *Brain Res. Mol. Brain. Res.*, 35, pp. 47-57 (1996)]. In the adult human brain, JNK3 expression is localized to a subpopulation of pyramidal neurons in the CA1, CA4 and subiculum regions of the hippocampus and layers 3 and 5 of the neocortex [A. A. Mohit et al. (1995)]. The CA1 neurons of patients with acute hypoxia showed strong nuclear JNK3-immunoreactivity compared to minimal, diffuse cytoplasmic staining of the hippocampal neurons from brain tissues of normal patients [Y. Zhang et al. (1998)]. In addition, JNK3 co-localizes immunochemically with neurons vulnerable in Alzheimer's disease [A. A. Mohit et al., (1995)]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (D. D. Yang et al., *Nature*, 389, pp. 865-870 (1997)]. Thus, selective modulation of JNK3 activity could potentially provide therapeutic intervention for neurodegenerative diseases such as stroke and epilepsy.

Despite the fact that the genes for various JNKs have been isolated and the amino acid sequences are known, no one has described X-ray crystal structural coordinate information of any of the JNKs. Such information would be extremely useful in identifying and designing potential inhibitors of various JNKs which, in turn, could have therapeutic utility.

SUMMARY OF THE INVENTION

Applicants have solved this problem by providing, for the first time, a crystallizable composition comprising unphosphorylated JNK3 in complex with MgAMP-PNP and the resulting crystal. The crystal was resolved at 2.3 Å resolution. Solving this crystal structure has allowed applicants to determine the key structural features of JNK3, particularly the shape of its substrate binding site.

The invention also provides a machine readable storage medium which comprises the structure coordinates of the JNK3 binding site. Such storage medium encoded with these data when read and utilized by a computer programmed with appropriate software displays, on a computer screen or similar viewing device, a three-dimensional graphical representation of a molecule or molecular complex comprising such binding sites or similarly shaped homologous binding pockets.

The invention also provides methods for designing, evaluating and identifying compounds which bind to the aforementioned binding sites, as well as compounds produced by such methods. Such compounds are potential inhibitors of JNK3 or its homologues.

The invention also provides a method for determining at least a portion of the three-dimensional structure of molecules or molecular complexes which contain at least some structurally similar features to JNK3, particularly JNK1, JNK2 and other JNK isoforms. This is achieved by using at least some of the structural coordinates obtained for the unphosphorylated JNK3 in complex with MgAMP-PNP.

The invention also provides a method for crystallizing unphosphorylated JNK3 in complex with MgAMP-PNP.

"Atom type" refers to the element whose coordinates are measured. The first letter in the column defines the element.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Figure 1B:
FIG. 1A (1A-1 to 1A-60; JNK3α amino acid residues 40-402 of SEQ ID NO:1) lists the atomic structure coordinates for unphosphorylated JNK3 in complex with MgAMP-PNP as derived by X-ray diffraction from a crystal of that complex. The following abbreviations are used in FIG. 1A.

FIG. 1B is a structure-based sequence alignment of JNK3, ERK2, p38 and cAPK (SEQ ID NOs 1, 7, 8 and 9, respectively).

Figure 2A:
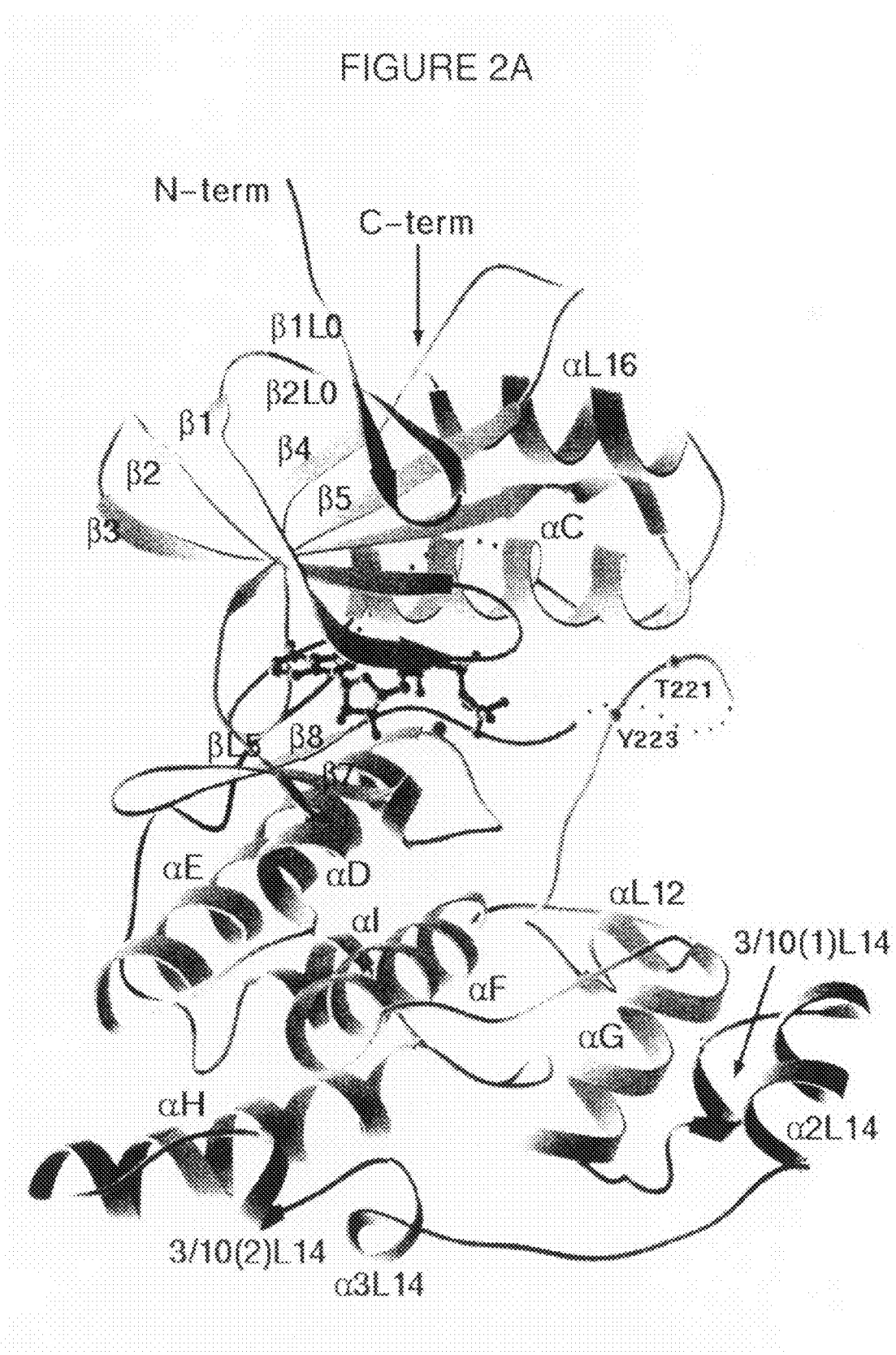

FIG. 2a is a ribbon representation of the overall fold of JNK3 complexed with MgAMP-PNP.

Figure 2B:
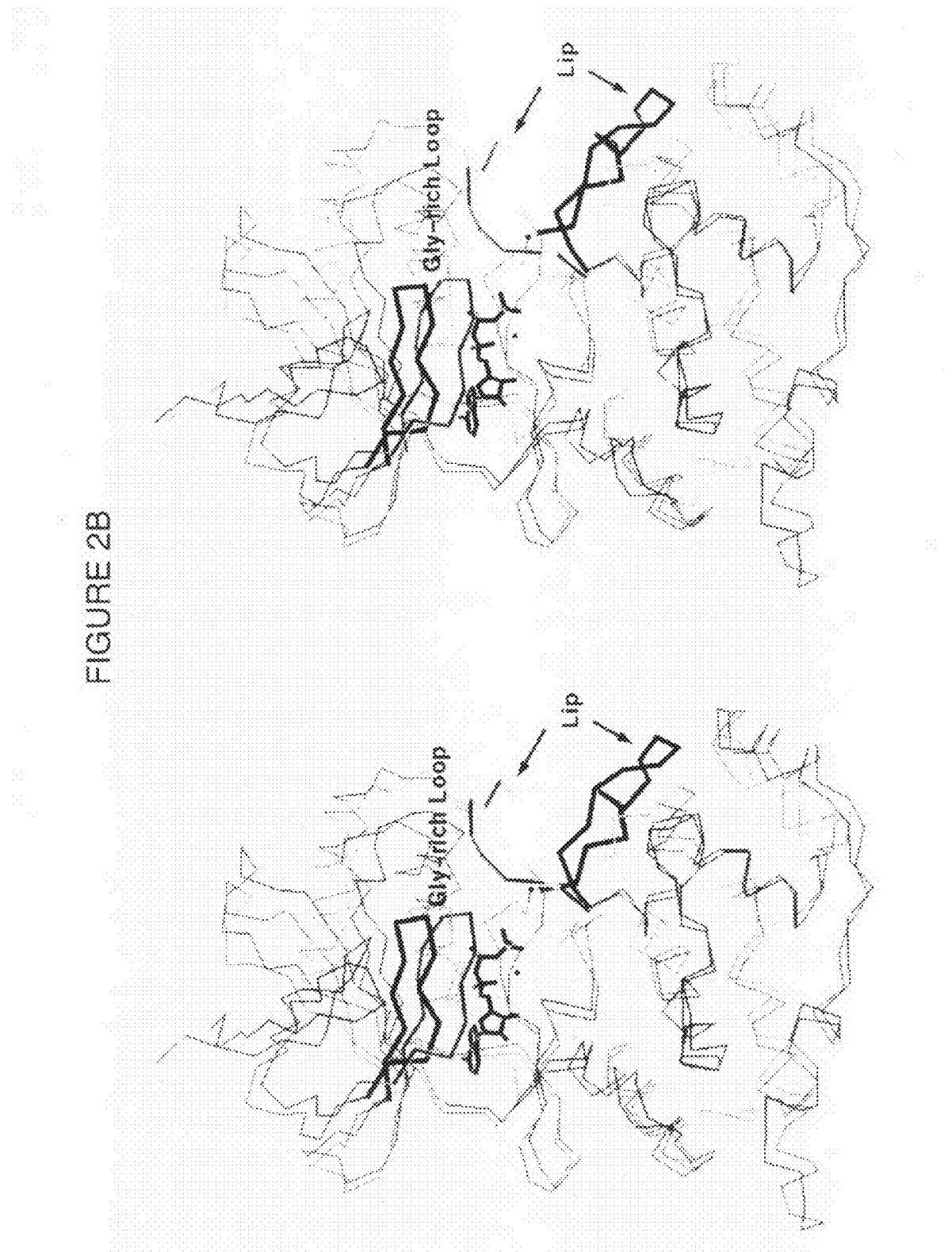

FIG. 2b is a stereoscopic view of the superimposed structures of JNK3/MgAMP-PNP and Erk2.

Figure 3:
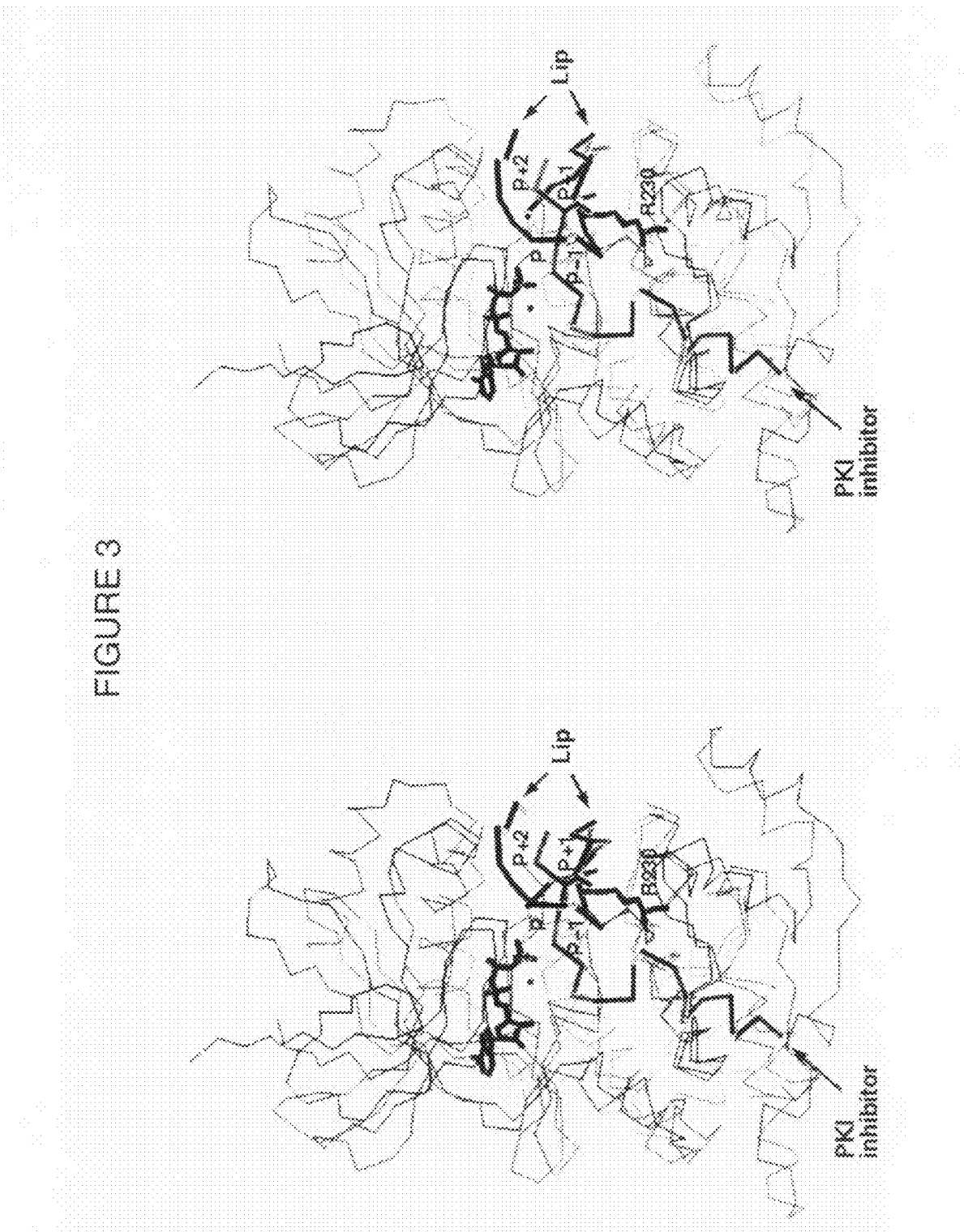

FIG. 3 is stereoscopic view of the superimposed structures of JNK3 and cAPK.

FIG. 4a is stereoscopic view of the active site of JNK3.

FIG. 4b is a detailed comparison of the active site of JNK3 with that of cAPK.

Figure 5:
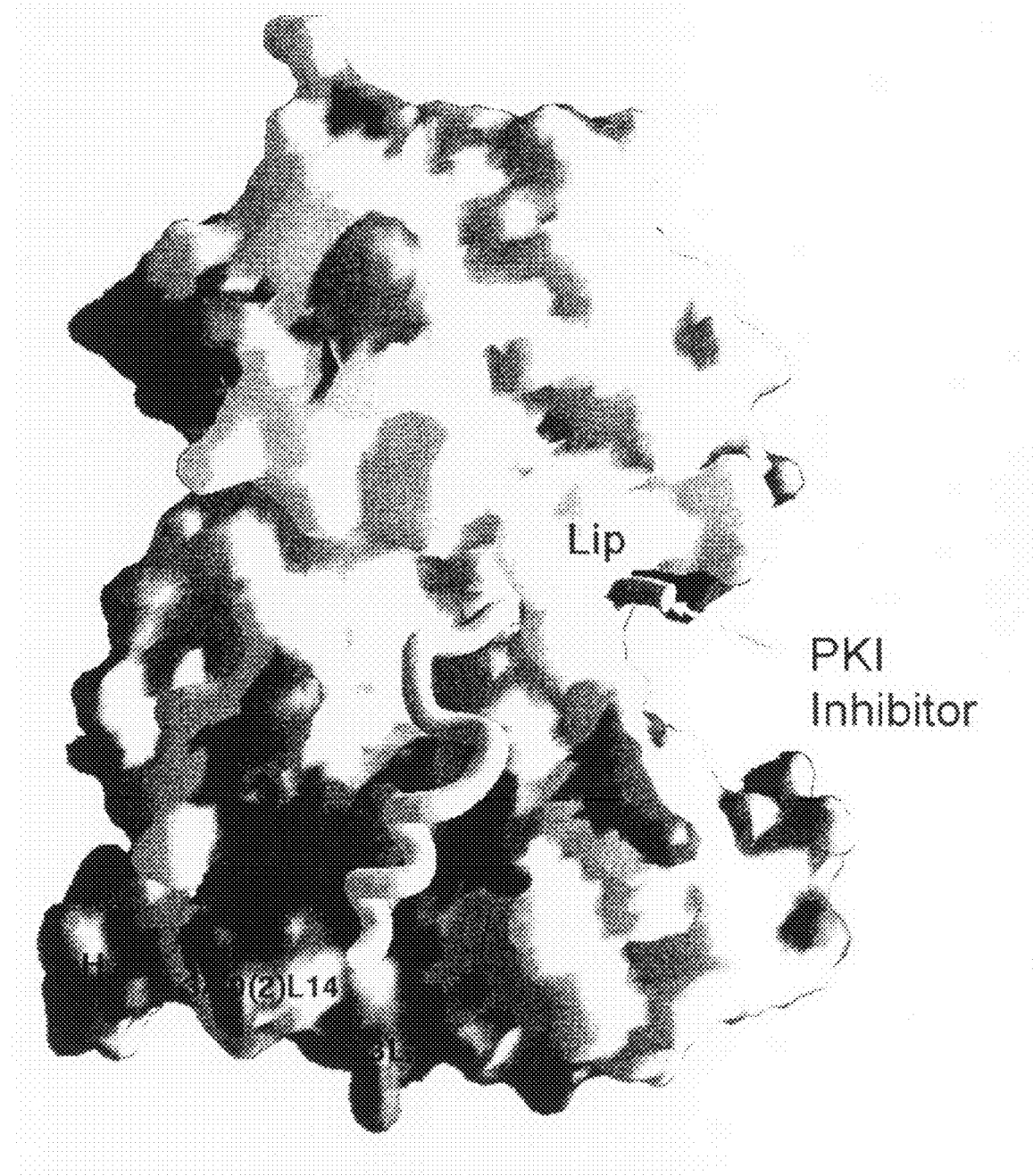

FIG. 5 is a substrate binding specificity of JNK isoforms.

Figure 6:
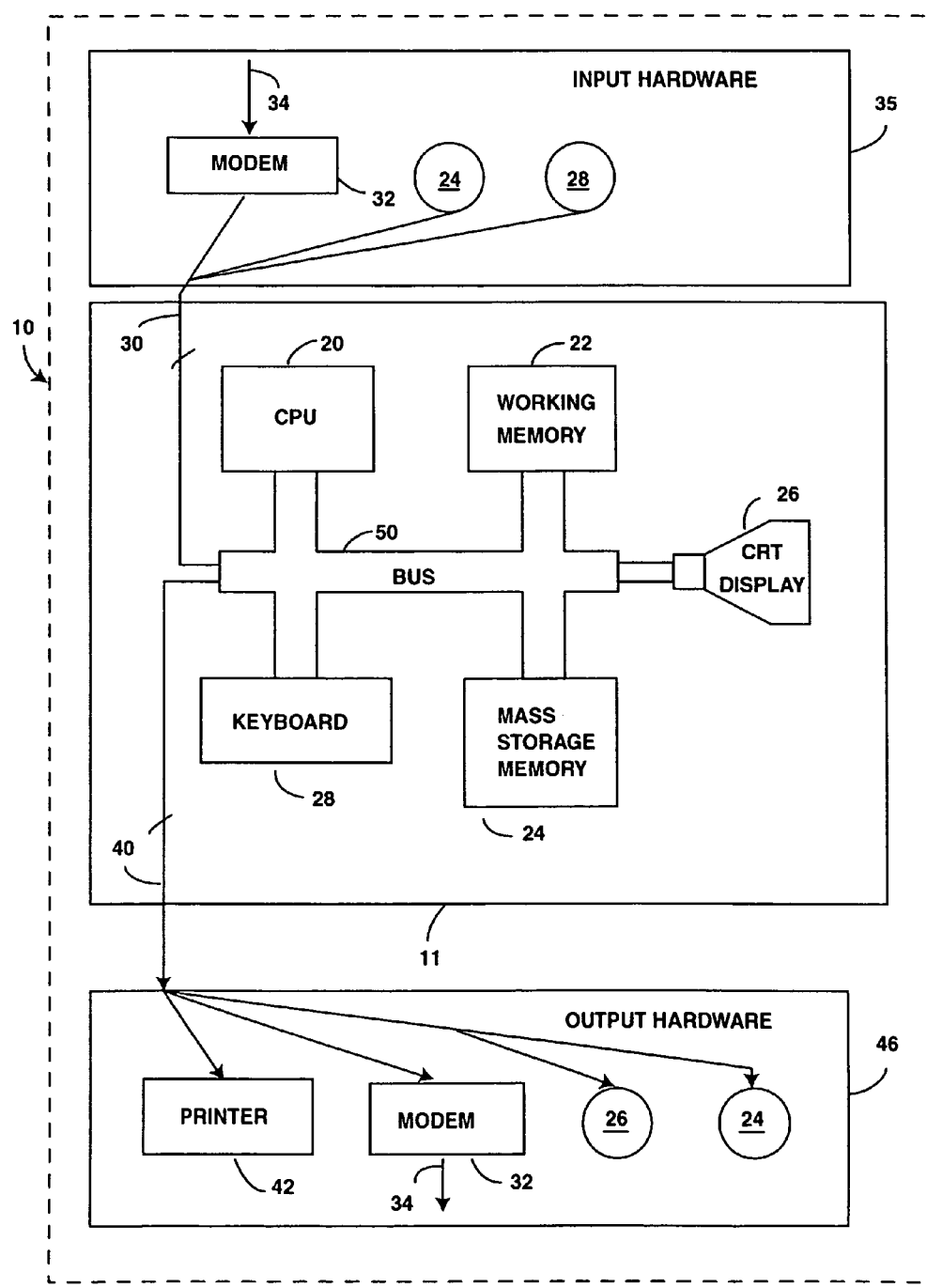
Figure 7:
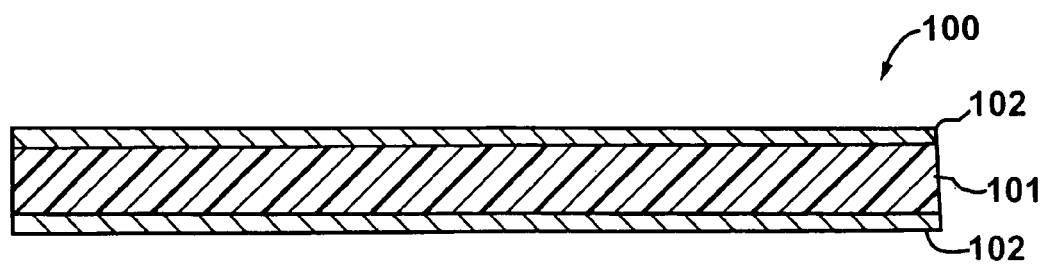
Figure 8:
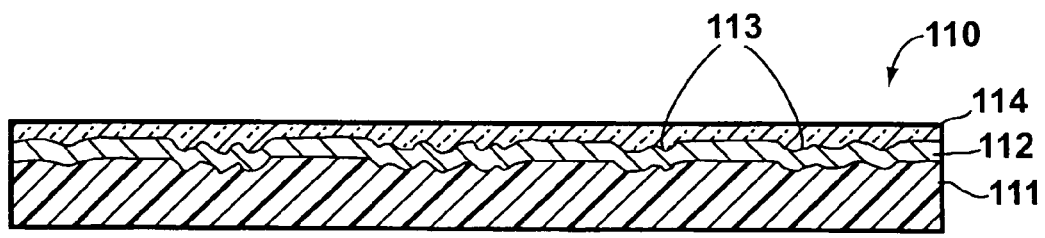

FIG. 6 shows a diagram of a system used to carry out the instructions encoded by the storage medium of FIGS. 7 and 8.

FIG. 7 shows a cross section of a magnetic storage medium.

FIG. 8 shows a cross section of a optically-readable data storage medium.

DETAILED DESCRIPTION OF THE INVENTION

The following abbreviations are used throughout the application:

A=Ala=Alanine T=Thr=Threonine
V=Val=Valine C=Cys=Cysteine
L=Leu=Leucine Y=Tyr=Tyrosine
I=Ile=Isoleucine N=Asn=Asparagine
P=Pro=Proline Q=Gln=Glutamine
F=Phe=Phenylalanine D=Asp=Aspartic Acid
W=Trp=Tryptophan E=Glu=Glutamic Acid
M=Met=Methionine K=Lys=Lysine
G=Gly=Glycine R=Arg=Arginine
S=Ser=Serine H=His=Histidine Additional definitions are set forth in the specification where necessary.

In order that the invention described herein may be more fully understood, the following detailed description is set forth.

According to one embodiment, the invention provides a crystallizable composition comprising an unphosphorylated JNK protein complexed with adenosine monophosphate. The JNK protein in the crystallizable complexes of this invention, if it is JNK3 or a JNK3 variant (as opposed to JNK1 or JNK2), must be truncated at the N-terminus. Specifically, the JNK3 proteins contain an N-terminal extension of about 40 amino acids as compared to JNK1 and JNK2 proteins (see GenBank entries for JNK1, JNK2 and JNK3 proteins and their isoforms). Those 40 amino acid must be removed from JNK3 proteins in the crystallizable compositions of this invention.

In addition, any JNK protein in these crystallizable compositions preferably have a C-terminal truncation of about 20 amino acids. We have found that the C-terminal truncation is necessary to obtain diffraction quality crystals.

The second component in these compositions is a non-hydrolyzable ATP analog or a suicidal substrate. Non-hydrolyzable ATP analogs useful in the crystallizable compositions of this invention include AMP-PCH$_2$P, AMP-PSP and AMP-PNP. An example of a suicidal substrate is FSBA. Preferably, the crystallizable compositions of this invention comprise AMP-PNP as the substrate. The third component is magnesium ions. Mg can be introduced by incubating the non-hydrolyzable ATP analog or suicide substrate with MgCl$_2$ prior to incubation with the JNK protein.

We have also determined that the buffer conditions of the composition are crucial for crystallization. Thus, the crystallizable compositions of this invention also comprise polyethylene glycol monomethyl ether at between about 10 to 30% v/v, ethylene glycol at between about 5 to 20% v/v, a reducing agent, such as 1-mercaptoethanol at between about 5 to 50 mM, and a buffer that maintains pH at between about 7.0 and 7.5. Preferably the buffer is 100 mM Hepes at pH 7.0.

The invention also relates to crystals of a JNK protein complexes with Mg and a non-hydrolyzable ATP analog or a suicidal substrate. These crystals are obtained from the above described compositions by standard crystallization protocols.

The invention also related to a method of making JNK-containing crystals. Such methods comprise the steps of:
a) obtaining a crystallizable composition comprising a JNK protein complexed with Mg and a non-hydrolyzable ATP analog or a suicidal substrate, as described above; and
b) subjecting said composition to conditions which promote crystallization.

In each of the above embodiments, it is preferred that the JNK protein be a JNK3, and in particular JNK3α1.

As mentioned above, applicants have solved the three-dimensional X-ray crystal structure of JNK3a1. The atomic coordinate data is presented in FIG. 1.

In order to use the structure coordinates generated for the JNK3/MgAMP-PNP complex or one of its binding pockets or homologues thereof, it is often times necessary to convert them into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations will help lead to the design of drugs having more favorable associations with their target receptor or enzyme, and thus, improved biological effects. Therefore, this information is valuable in designing potential inhibitors of the binding sites of biologically important targets.

The term "binding pocket", as used herein, refers to a region of a molecule or molecular complex, that, as a result of its shape, favorably associates with another chemical entity or compound.

The term "JNK3-like binding pocket" refers to a portion of a molecule or molecular complex whose shape is sufficiently similar to the JNK3 binding pockets as to bind common ligands. This commonality of shape is defined by a root mean square deviation from the structure coordinates of the backbone atoms of the amino acids that make up the binding pockets in JNK3 (as set forth in FIG. 1) of not more than 1.5 Å. The method of performing this calculation is described below.

The "active site binding pockets" or "active site" of JNK3 refers to the area on the JNK3 enzyme surface where the nucleotide substrate binds. In resolving the crystal structure of unphosphorylated JNK3 1 in complex with MgAMP-PNP, applicants have determined that JNK3 amino acids Ile70, Gly71, Ser72, Gly73, Ala74, Gln75, Gly76, Val78, Ala91, Lys93, Glu111, Ile124, Met146, Glu147, Leu148, Met149, Asp150, Ala151, Asn152, Gln155, Lys191, Ser193, Asn194, Val196 and Leu206 are within 5 Å of and therefore close enough to interact with MgAMP-PNP. Thus, a binding pocket defined by the structural coordinates of those amino acids, as set forth in FIG. 1; or a binding pocket whose root mean square deviation from the structure coordinates of the backbone atoms of those amino acids of not more than 1.5 Å is considered a JNK3-like binding pocket of this invention.

Applicants have also determined that in addition to the JNK3 amino acids set forth above, Ile77, Cys79, Ala80, Val90, Ile92, Lys94, Leu95, His104, Arg107, Ser125, Leu144, Val145, Leu153, Cys154, Asp189, Pro192, Ile195, Val197, Lys204 and Asp207 are within 8 Å of bound MgAMP-PNP and therefore are also close enough to interact with that substrate. Thus, in a preferred embodiment, a binding pocket defined by the structural coordinates of the amino acids within 8 Å bound MgAMP-PNP, as set forth in FIG. 1; or a binding pocket whose root mean square deviation from the structure coordinates of the backbone atoms of those amino acids of not more than 1.5 Å is considered a preferred JNK3-like binding pocket of this invention.

It will be readily apparent to those of skill in the art that the numbering of amino acids in other isoforms of JNK may be different than that set forth for JNK3 1. Corresponding amino acids in other isoforms of JNK are easily identified by visual inspection of the amino acid sequences or by using commercially available homology software programs.

Each of those amino acids of JNK3α1 is defined by a set of structure coordinates set forth in FIG. 1. The term "structure coordinates" refers to Cartesian coordinates derived from mathematical equations related to the patterns obtained on diffraction of a monochromatic beam of X-rays by the atoms (scattering centers) of a protein or protein-ligand complex in crystal form. The diffraction data are used to calculate an electron density map of the repeating unit of the crystal. The electron density maps are then used to establish the positions of the individual atoms of the enzyme or enzyme complex.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The variations in coordinates discussed above may be generated because of mathematical manipulations of the JNK3/MgAMP-PNP structure coordinates. For example, the structure coordinates set forth in FIG. 1 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same. Thus, for example, a ligand that bound to the active site binding pocket of JNK3 would also be expected to bind to another binding pocket whose structure coordinates defined a shape that fell within the acceptable error.

Various computational analyses are therefore necessary to determine whether a molecule or the binding pocket portion thereof is sufficiently similar to the JNK3 binding pockets described above. Such analyses may be carried out in well known software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof that has a root mean square deviation of conserved residue backbone atoms (N, Cα, C, O) of less than 1.5 Å when superimposed on the relevant backbone atoms described by structure coordinates listed in FIG. 1 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of JNK3 or a binding pocket portion thereof, as defined by the structure coordinates of JNK3 described herein.

Therefore, according to another embodiment of this invention is provided a machine-readable data storage medium, comprising a data storage material encoded with machine readable data which, when used by a machine programmed with instructions for using said data, displays a graphical three-dimensional representation of a molecule or molecular complex comprising a binding pocket defined by structure coordinates of JNK3 amino acids Ile70, Gly71, Ser72, Gly73, Ala74, Gln75, Gly76, Val78, Ala91, Lys93, Glu111, Ile24, Met146, Glu147, Leu148, Met149, Asp150, Ala151, Asn152, Gln155, Lys191, Ser193, Asn194, Val196 and Leu206 according to FIG. 1, or a homologue of said molecule or molecular complex, wherein said homologue comprises a binding pocket that has a root mean square deviation from the backbone atoms of said amino acids of not more than 1.5 Å.

Preferably, the machine readable data, when used by a machine programmed with instructions for using said data, displays a graphical three-dimensional representation of a molecule or molecular complex comprising a binding pocket defined by structure coordinates of JNK3 amino acids Ile70, Gly71, Ser72, Gly73, Ala74, Gln75, Gly76, Ile77, Val78, Cys79, Ala80, Val90, Ala91, Ile92, Lys93, Lys94, Leu95, His104, Arg107, Glu111, Ile124, Ser125, Leu144, Val145, Met146, Glu147, Leu148, Met149, Asp150, Ala151, Asn152, Leu153, Cys154, Gln155, Asp189, Lys191, Pro192, Ser193, Asn194, Ile195, Val196 Val197, Lys204, Leu206 and Asp207 according to FIG. 1, or a homologue of said molecule or molecular complex, wherein said homologue comprises a binding pocket that has a root mean square deviation from the backbone atoms of said amino acids of not more than 1.5 Å.

Even more preferred is a machine-readable data storage medium that is capable of displaying a graphical three-dimensional representation of a molecule or molecular complex that is defined by the structure coordinates of all of the amino acids in FIG. 1 or a homologue of said molecule or molecular complex, wherein said homologue has a root mean square deviation from the backbone atoms of all of the amino acids in FIG. 1 of not more than 1.5 Å.

According to an alternate embodiment, the machine-readable data storage medium comprises a data storage material encoded with a first set of machine readable data which comprises the Fourier transform of the structure coordinates set forth in FIG. 1, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

For example, the Fourier transform of the structure coordinates set forth in FIG. 1 may be used to determine at least a portion of the structure coordinates of other JNKs, such as JNK1, JNK2 and isoforms of JNK1, JNK2 or JNK3.

FIG. 6 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

According to an alternate embodiment, the present invention provides a computer for producing a three-dimensional representation of a molecule or molecular complex, wherein said molecule or molecular complex comprises a binding pocket defined by Ile70, Gly71, Ser72, Gly73, Ala74, Gln75, Gly76, Val78, Ala91, Lys93, Glu111, Ile124, Met146, Glu147, Leu148, Met149, Asp150, Ala151, Asn152, Gln155, Lys191, Ser193, Asn194, Val196 and Leu206 according to FIG. 1, or a homologue of said molecule or molecular complex, wherein said homologue comprises a binding pocket that has a root mean square deviation from the backbone atoms of said amino acids of not more than 1.5 Å, wherein said computer comprises:
  (a) a machine readable data storage medium comprising a data storage material encoded with machine-readable data, wherein said machine readable data comprises the structure coordinates of JNK3 or portions thereof;
  (b) a working memory for storing instructions for processing said machine-readable data;
  (c) a central-processing unit coupled to said working memory and to said machine-readable data storage medium, for processing said machine-readable data into said three-dimensional representation; and
  (d) an output hardware coupled to said central processing unit, for receiving said three Dimensional representation.

Preferably, the computer produces a three-dimensional representation of a molecule or molecular complex, wherein said molecule or molecular complex comprises a binding pocket defined by the binding pocket is defined by structure coordinates of JNK3 amino acids Ile70, Gly71, Ser72, Gly73, Ala74, Gln75, Gly76, Ile77, Val78, Cys79, Ala80, Val90, Ala91, Ile92, Lys93, Lys94, Leu95, His104, Arg107, Glu111, Ile124, Ser125, Leu144, Val145, Met146, Glu147, Leu148, Met149, Asp150, Ala151, Asn152, Leu153, Cys154, Gln155, Asp189, Lys191, Pro192, Ser193, Asn194, Ile195, Val196 Val197, Lys204, Leu206 and Asp207 according to FIG. 1, or a homologue of said molecule or molecular complex, wherein said homologue comprises a binding pocket that has a root mean square deviation from the backbone atoms of said amino acids of not more than 1.5 Å.

FIG. 7 shows a cross section of a magnetic data storage medium 100 which can be encoded with a machine-readable data that can be carried out by a system such as system 10 of FIG. 6. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 6.

FIG. 8 shows a cross section of an optically-readable data storage medium 110 which also can be encoded with such a machine-readable data, or set of instructions, which can be carried out by a system such as system 10 of FIG. 6. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Thus, in accordance with the present invention, data capable of displaying the three dimensional structure of JNK3 and portions thereof and their structurally similar homologues is stored in a machine-readable storage medium, which is capable of displaying a graphical three-dimensional representation of the structure.

The JNK3 X-ray coordinate data, when used in conjunction with a computer programmed with software to translate those coordinates into the 3-dimensional structure of JNK3 may be used for a variety of purposes, such as drug discovery.

For example, the structure encoded by the data may be computationally evaluated for its ability to associate with chemical entities. Chemical entities that associate with JNK3 may inhibit JNK3, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a molecule or molecular complex comprising a binding pocket defined by structure coordinates of JNK3 amino acids Ile70, Gly71, Ser72, Gly73, Ala74, Gln75, Gly76, Val78, Ala91, Lys93, Glu111, Ile124, Met146, Glu147, Leu148, Met149, Asp150, Ala151, Asn152, Gln155, Lys191, Ser193, Asn194, Val196 and Leu206 according to FIG. 1, or a homologue of said molecule or molecular complex, wherein said homologue comprises a binding pocket that has a root mean square deviation from the backbone atoms of said amino acids of not more than 1.5 Å.

This method comprises the steps of: a) employing computational means to perform a fitting operation between the chemical entity and a binding pocket of the molecule or molecular complex; b) analyzing the results of said fitting operation to quantify the association between the chemical entity and the binding pocket; and c) outputting said quantified association to a suitable output hardware, such as a CRT display terminal, a printer or a disk drive, as described previously. The term "chemical entity", as used herein, refers to chemical compounds, complexes of at least two chemical compounds, and fragments of such compounds or complexes.

Preferably, the method evaluates the potential of a chemical entity to associate with a molecule or molecular complex comprising a binding pocket defined by structure coordinates of JNK3 amino acids Ile70, Gly71, Ser72, Gly73, Ala74, Gln75, Gly76, Ile77, Val78, Cys79, Ala80, Val90, Ala91, Ile92, Lys93, Lys94, Leu95, His 104, Arg107, Glu111, Ile124, Ser125, Leu144, Val145, Met146, Glu147, Leu148, Met149, Asp150, Ala151, Asn152, Leu153, Cys154, Gln155, Asp189, Lys191, Pro192, Ser193, Asn194, Ile195, Val196 Val197, Lys204, Leu206 and Asp207 according to FIG. 1, or a homologue of said molecule or molecular complex, wherein said homologue comprises a binding pocket that has a root mean square deviation from the backbone atoms of said amino acids of not more than 1.5 Å.

Even more preferably, the method evaluates the potential of a chemical entity to associate with a molecule or molecular complex defined by structure coordinates of all of the JNK3 amino acids, as set forth in FIG. 1, or a homologue of said molecule or molecular complex having a root mean square deviation from the backbone atoms of said amino acids of not more than 1.5 Å.

Alternatively, the structural coordinates of the JNK3 binding pocket can be utilized in a method for identifying a potential agonist or antagonist of a molecule comprising a JNK3-like binding pocket. This method comprises the steps of:

a. using the atomic coordinates of Ile70, Gly71, Ser72, Gly73, Ala74, Gln75, Gly76, Val78, Ala91, Lys93, Glu111, Ile124, Met146, Glu147, Leu148, Met149, Asp150, Ala151, Asn152, Gln155, Lys191, Ser193, Asn194, Val196 and Leu206 according to FIG. 1±a root mean square deviation from the backbone atoms of said amino acids of not more than 1.5 Å, to generate a three-dimensional structure of molecule comprising a JNK3-like binding pocket;

b. employing said three-dimensional structure to design or select said potential agonist or antagonist;

c. synthesizing said agonist or antagonist; and d. contacting said agonist or antagonist with said molecule to determine the ability of said potential agonist or antagonist to interact with said molecule.

More preferred is when the atomic coordinates of Ile70, Gly71, Ser72, Gly73, Ala74, Gln75, Gly76, Ile77, Val78, Cys79, Ala80, Val90, Ala91, Ile92, Lys93, Lys94, Leu95, His104, Arg107, Glu111, Ile124, Ser125, Leu144, Val145, Met146, Glu147, Leu148, Met149, Asp150, Ala151, Asn152, Leu153, Cys154, Gln155, Asp189, Lys191, Pro192, Ser193, Asn194, Ile195, Val196 Val197, Lys204, Leu206 and Asp207 according to FIG. 1±a root mean square deviation from the backbone atoms of said amino acids of not more than 1.5 Å, are used to generate a three-dimensional structure of molecule comprising a JNK3-like binding pocket.

Most preferred is when the atomic coordinates of all the amino acids of JNK3 according to FIG. 1±a root mean square deviation from the backbone atoms of said amino acids of not more than 1.5 Å, are used to generate a three-dimensional structure of molecule comprising a JNK3-like binding pocket.

For the first time, the present invention permits the use of molecular design techniques to identify, select and design chemical entities, including inhibitory compounds, capable of binding to JNK3-like binding pockets.

Applicants' elucidation of binding sites on JNK3 provides the necessary information for designing new chemical entities and compounds that may interact with JNK3-like binding pockets, in whole or in part.

Throughout this section, discussions about the ability of an entity to bind to, associate with or inhibit a JNK3-like binding pocket refers to features of the entity alone. Assays to determine if a compound binds to JNK3 are well known in the art and are exemplified below.

The design of compounds that bind to or inhibit JNK3-like binding pockets according to this invention generally involves consideration of two factors. First, the entity must be capable of physically and structurally associating with parts or all of the JNK3-like binding pockets. Non-covalent molecular interactions important in this association include hydrogen bonding, van der Waals interactions, hydrophobic interactions and electrostatic interactions.

Second, the entity must be able to assume a conformation that allows it to associate with the JNK3-like binding pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the JNK3-like binding pocket or homologues thereof.

The potential inhibitory or binding effect of a chemical entity on a JNK3-like binding pocket may be analyzed prior to its actual synthesis and testing by the use of computer modeling techniques. If the theoretical structure of the given entity suggests insufficient interaction and association between it and the JNK3-like binding pocket, testing of the entity is obviated. However, if computer modeling indicates a strong interaction, the molecule may then be synthesized and tested for its ability to bind to a JNK3-like binding pocket. This may be achieved by testing the ability of the molecule to inhibit JNK3 using the assays described in Example 6. In this manner, synthesis of inoperative compounds may be avoided.

A potential inhibitor of a JNK3-like binding pocket may be computationally evaluated by means of a series of steps in which chemical entities or fragments are screened and selected for their ability to associate with the JNK3-like binding pockets.

One skilled in the art may use one of several methods to screen chemical entities or fragments for their ability to associate with a JNK3-like binding pocket. This process may begin by visual inspection of, for example, a JNK3-like binding pocket on the computer screen based on the JNK3 structure coordinates in FIG. 1 or other coordinates which define a similar shape generated from the machine-readable storage medium. Selected fragments or chemical entities may then be positioned in a variety of orientations, or docked, within that binding pocket as defined supra. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:
1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.
2. MCSS (A. Miranker et al., "Functionality Maps of Binding Sites: A Multiple Copy Simultaneous Search Method." *Proteins: Structure Function and Genetics,* 11, pp. 29-34 (1991)). MCSS is available from Molecular Simulations, San Diego, Calif.
3. AUTODOCK (D. S. Goodsell et al., "Automated Docking of Substrates to Proteins by Simulated Annealing", *Proteins: Structure Function and Genetics,* 8, pp. 195-202 (1990)). AUTODOCK is available from Scripps Research Institute, La Jolla, Calif.
4. DOCK (I. D. Kuntz et al., "A Geometric Approach to Macromolecule-Ligand Interactions", *J. Mol. Biol.,* 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of JNK3. This would be followed by manual model building using software such as Quanta or Sybyl [Tripos Associates, St. Louis, Mo.].

Useful programs to aid one of skill in the art in connecting the individual chemical entities or fragments include:
1. CAVEAT (P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.,* 8, pp. 51-66 (1994)). CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", *J. Med. Chem.,* 35, pp. 2145-2154 (1992).
3. HOOK (M. B. Eisen et al, "HOOK: A Program for Finding Novel Molecular Architectures that Satisfy the Chemical and Steric Requirements of a Macromolecule Binding Site", *Proteins: Struct., Funct., Genet.,* 19, pp. 199-221 (1994). HOOK is available from Molecular Simulations, San Diego, Calif.

Instead of proceeding to build an inhibitor of a JNK3-like binding pocket in a step-wise fashion one fragment or chemical entity at a time as described above, inhibitory or other JNK3 binding compounds may be designed as a whole or "de novo" using either an empty binding site or optionally including some portion(s) of a known inhibitor(s). There are many de novo ligand design methods including:
1. LUDI (H.-J. Bohm, "The Computer Program LUDI: A New Method for the De Novo Design of Enzyme Inhibitors", *J. Comp. Aid. Molec. Design,* 6, pp. 61-78 (1992)). LUDI is available from Molecular Simulations Incorporated, San Diego, Calif.
2. LEGEND (Y. Nishibata et al., *Tetrahedron,* 47, p. 8985 (1991)). LEGEND is available from Molecular Simulations Incorporated, San Diego, Calif.
3. LeapFrog (available from Tripos Associates, St. Louis, Mo.).
4. SPROUT (V. Gillet et al, "SPROUT: A Program for Structure Generation)", *J. Comput. Aided Mol. Design,* 7, pp. 127-153 (1993)). SPROUT is available from the University of Leeds, UK.

Other molecular modeling techniques may also be employed in accordance with this invention [see, e.g., N. C. Cohen et al., "Molecular Modeling Software and Methods for Medicinal Chemistry, *J. Med. Chem.*, 33, pp. 883-894 (1990); see also, M. A. Navia and M. A. Murcko, "The Use of Structural Information in Drug Design", *Current Opinions in Structural Biology*, 2, pp. 202-210 (1992); L. M. Balbes et al., "A Perspective of Modern Methods in Computer-Aided Drug Design", in *Reviews in Computational Chemistry*, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology*, 4, pp. 777-781 (1994)].

Once a compound has been designed or selected by the above methods, the efficiency with which that entity may bind to an JNK3 binding pocket may be tested and optimized by computational evaluation. For example, an effective JNK3 binding pocket inhibitor must preferably demonstrate a relatively small difference in energy between its bound and free states (i.e., a small deformation energy of binding). Thus, the most efficient JNK3 binding pocket inhibitors should preferably be designed with a deformation energy of binding of not greater than about 10 kcal/mole, more preferably, not greater than 7 kcal/mole. JNK3 binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to an JNK3 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1995); Insight II/Discover (Molecular Simulations, Inc., San Diego, Calif. ©1995); DelPhi (Molecular Simulations, Inc., San Diego, Calif. ©1995); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that can bind in whole, or in part, to a JNK3 binding pocket. In this screening, the quality of fit of such entities to the binding site may be judged either by shape complementarity or by estimated interaction energy [E. C. Meng et al., *J. Comp. Chem.*, 13, pp. 505-524 (1992)].

According to another embodiment, the invention provides compounds which associate with a JNK3-like binding pocket produced or identified by the method set forth above.

The structure coordinates set forth in FIG. 1 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex whose structure is unknown comprising the steps of:

a) crystallizing said molecule or molecular complex of unknown structure;

b) generating an X-ray diffraction pattern from said crystallized molecule or molecular complex; and c) applying at least a portion of the structure coordinates set forth in FIG. 1 to the X-ray diffraction pattern to generate a three-dimensional electron density map of the molecule or molecular complex whose structure is unknown.

By using molecular replacement, all or part of the structure coordinates of the JNK3/MgAMP-PNP complex as provided by this invention (and set forth in FIG. 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the JNK3/MgAMP-PNP complex according to FIG. 1 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55-77 (1985); M. G. Rossmann, ed., "The Molecular Replacement Method", *Int. Sci. Rev. Ser.*, No. 13, Gordon & Breach, New York (1972)].

The structure of any portion of any crystallized molecule or molecular complex that is sufficiently homologous to any portion of the JNK3/MgAMP-PNP complex can be resolved by this method.

In a preferred embodiment, the method of molecular replacement is utilized to obtain structural information about another JNK, such as JNK1, JNK2, or isoforms of JNK1, JNK2 or JNK3. The structure coordinates of JNK3 as provided by this invention are particularly useful in solving the structure of other isoforms of JNK3 or JNK3 complexes.

Furthermore, the structure coordinates of JNK3 as provided by this invention are useful in solving the structure of JNK3 proteins that have amino acid substitutions, additions and/or deletions (referred to collectively as "JNK3 mutants", as compared to naturally occurring JNK3 isoforms. These JNK3 mutants may optionally be crystallized in co-complex with a chemical entity, such as a non-hydrolyzable ATP analogue or a suicide substrate. The crystal structures of a series of such complexes may then be solved by molecular replacement and compared with that of wild-type JNK3. Potential sites for modification within the various binding sites of the enzyme may thus be identified. This information provides an additional tool for determining the most efficient binding interactions, for example, increased hydrophobic interactions, between JNK3 and a chemical entity or compound.

The structure coordinates are also particularly useful to solve the structure of crystals of JNK3 or JNK3 homologues co-complexed with a variety of chemical entities. This approach enables the determination of the optimal sites for interaction between chemical entities, including candidate JNK3 inhibitors and JNK3. For example, high resolution X-ray diffraction data collected from crystals exposed to different types of solvent allows the determination of where each type of solvent molecule resides. Small molecules that bind tightly to those sites can then be designed and synthesized and tested for their JNK3 inhibition activity.

All of the complexes referred to above may be studied using well-known X-ray diffraction techniques and may be refined versus 1.5-3 Å resolution X-ray data to an R value of about 0.20 or less using computer software, such as X-PLOR [Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)]. This information may thus be used to optimize known JNK3 inhibitors, and more importantly, to design new JNK3 inhibitors.

In order that this invention be more fully understood, the following examples are set forth. These examples are for the purpose of illustration only and are not to be construed as limiting the scope of the invention in any way.

Example 1

Expression and Purification of JNK3

A BLAST search of the EST database using the published JNK3α1 cDNA [S. Gupta et al. (1996)] as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites for expression of the protein in *E. coli*. Due to the poor solubility of the expressed full length protein (Met 1-Gln 422), an N-terminally truncated protein starting at Ser residue at position 40 (Ser 40), corresponding to Ser 2 of JNK1 and JNK2 proteins [S. Gupta et al. (1996)], preceded by Met (initiation) and Gly residues, was produced. The Gly residue was added in order to introduce an NcoI site for cloning into the expression vector. Further, systematic C-terminal truncations were performed by PCR to identify a construct that give rise to diffraction-quality crystals. This construct, which was prepared by PCR using deoxyoligonucleotides 5' GCTCTA-GAGCTCCATGGGCAGCAAAAGCAAAGTTGACAA 3' (SEQ ID NO:2; forward primer with initiation codon underlined) and 5' TAGCGGATCCTCATTCTGAA TTCAT-TACTTCCTTGTA 3' (SEQ ID NO:3; reverse primer with stop codon underlined) as primers and confirmed by DNA sequencing, encodes amino acid residues Ser40-Glu402 of JNK3α1, preceded by Met and Gly residues, was used for structural studies described in this paper. Control experiments indicated that the truncated JNK3 protein has an equivalent kinase activity towards myelin basic protein when activated with an upstream kinase MKK7 in vitro (unpublished results).

*E. coli* strain BL21 (DE3) (Novagen) transformed with the JNK3 expression construct was grown at 30° C. in shaker flasks into log phase (OD600~0.8) in LB supplemented with 100 μg/ml carbenicillin. IPTG was then added to a final concentration of 0.8 mM and the cells were harvested 2 hours later by centrifugation. *E. coli* cell paste containing the truncated JNK3 protein was resuspended in 10 volumes/g lysis buffer [50 mM HEPES, pH 7.2, 10% glycerol (v/v), 100 mM NaCl, 2 mM dithiothreitol (DTT), 0.1 mM PMSF, 2 μg/ml Pepstatin, 1 μg/ml each of E-64 and Leupeptin]. Cells were lysed on ice using a microfluidizer and centrifuged at 100,000×g for 30 min at 4° C. The 100,000×g supernatant was diluted 5 fold with Buffer A [20 mM HEPES, pH 7.0, 10% glycerol (v/v), 2 mM DTT) and applied to an SP-Sepharose (Pharmacia) cation-exchange column at 4° C. The column was washed with column volumes of Buffer A, followed by 5 column volumes of Buffer A containing 50 mM NaCl. Bound protein was eluted with a 7.5 column volume linear gradient of 50-300 mM NaCl, and the truncated JNK3 protein was eluted between 150-200 mM NaCl. Eluted JNK3 protein from the SP-Sepharose column was dialyzed at ~1 mg/ml against Buffer B [25 mM HEPES, pH 7.0, containing 5% glycerol (v/v), 50 mM NaCl, mM DTT] overnight at 4° C. and centrifuged at 3,000×g. The supernatant was concentrated by ultrafiltration (Centriprep-30, Amicon) to 10 mg/ml, centrifuged at 16,000×g and stored at −70° C.

Example 2

Crystallization of JNK3

Full length human JNK3 1 has an 39-residue extension in the N-terminus when compared to JNK1, JNK2 and other MAP kinases [FIG. 1 and S. Gupta et al. (1996)]. We expressed the conserved MAP kinase homologous region of JNK3 without the first 39 residues for crystallographic studies. Initial crystallization trials yielded only small crystals that diffracted to 8 Å. Since residues at the C-terminus of Erk2 and p38 are disordered [F. Zhang et al., *Nature*, 367, pp. 704-11 (1994); K. P. Wilson et al., *J. Biol. Chem.*, 271, pp. 27696-700 (1996)], we reasoned that C-terminal portions of JNK3 might also be flexible and interfere with the formation of a well-ordered crystal lattice. We therefore searched for an active truncated JNK3 by combining limited proteolysis and systematic truncation of the protein. This screening approach resulted in the growth of larger, well-ordered JNK3 crystals. These crystals are grown from the JNK3 protein lacking the N-terminal 39 and C-terminal 20 residues. The truncated enzyme (residues Ser40-Glu402) displays wild-type kinase activity when activated by MKK7 in vitro. All crystallographic studies were carried out using this form of the enzyme.

Crystallization trials were performed by combining the hanging-drop vapor diffusion technique and a sparse matrix search, in the presence and absence of MgAMP-PNP. No crystals were obtained in the absence of MgAMP-PNP, while crystallization trials carried out in the presence of MgAMP-PNP yielded an orthorhombic crystal form at 20° C. over a reservoir solution containing 18-20% (v/v) polyethylene glycol monomethyl ether (average $M_r$=550), 10% (v/v) ethylene glycol, 20 mM β-Mercaptoethanol and 10 mM Hepes (pH 7.0). The crystallization droplet contained a mixture of 1 μL of reservoir solution plus 1 mL of a protein solution that had been preincubated for one hour with 1 mM AMP-PNP and 2 mM $MgCl_2$ on ice. The crystals belong to the orthorhombic space group $P2_12_12_1$ (a=51.50 Å, b=71.24 Å and c=107.60 Å) with one enzyme molecule per asymmetric unit. The solvent content of the crystal is 44%. Before data collection, crystals were equilibrated in their reservoir solution for 2-5 minutes before flash-frozen in nitrogen gas for X-ray data collection at −170° C.

Example 3

X-Ray Data Collection and Structure Determination

X-ray data were measured on an Raxis IIC image plate, with mirror-focused CuKα X-rays generated by a rotating anode source. The diffraction images were processed with the program DENZO and data scaled using SCALPACK [Z. Otwinowski, In "Data Collection and Processing", L. Sawyer, N. Isaacs and S. W. Bailey, eds., Warrington, U.K.: Science and Engineering Council/Daresbury Laboratory. pp. 55-62 (1993)]. The data processing statistics are summarized in Table 1. The starting phases for JNK3 were obtained by molecular replacement using coordinates of phosphorylated ERK2 as search model in the program AMoRe [J. Nazaza, Acta Crystallogr., A50, pp. 157-63 (1994)]. The Erk2 atomic model was modified by truncating to Ala for those residues that are different from JNK3 and deleting those loops that have significant insertions or deletions between Erk2 and JNK3. This hybrid model successfully produced rotation and translation function solution for JNK3, which provided a starting model with an R-factor=50% for reflections between 10 and 4.0 Å resolution, and an R-free=51% based on 10% of X-ray data set aside at the start of the refinement. Refinement of the model using both conventional least-squares and simulated-annealing procedures was done with X-PLOR [A. T. Brunger, XPLOR, Version 3.1 Manual, Yale University Press, New Haven, Conn. (1992)] using 8-2.3 Å data. The electron density corresponding to AMP-PNP molecule was visible from the map calculated using the initial model phases, but AMP-PNP was not included in the model refinement until the R-factor dropped to 28% and R-free to 39%. The refined model, at 2.3 Å resolution (Table 1), includes 339 residues of JNK3, one AMP-PNP molecule, two $Mg^{2+}$ and 183 water molecules. The electron density maps revealed several discrete regions of disorder, leading the omission of some amino acid residues from the final model. N-terminal residues 40-44 and C-terminal residue 401 and 402 are disordered. In addition, two central regions of the enzyme are disordered, including residues 212-216 and 374-378. Finally, side chain atoms for Tyr223 was not modeled beyond C: due to poor electron density. The present R-factor is 22.1% (R-free=27.4%). Anisotropic scaling and bulk solvent correction were applied at the final stage of refinement (ref). The peptide torsion angles for 337 out of 339 well defined residues fall within most favored or generally allowed regions of the Ramachandran plot, as defined in the program PROCHECK [R. A. Laskowski et al., J. Appl. Crystallog., 26, pp. 283-91 (1993)].

Example 4

Overall Structure

The crystal structure includes unphosphorylated JNK3 (residues 45-211, 217-373, 379-400), adenylyl imidodiphosphate (AMP-PNP, an ATP analogue) and two $Mg^{2+}$ ions. Electron density for residues 40-44, 212-216 and 401-402 is not seen, and these amino acids are presumed disordered. The MAP kinase homologous region of JNK3 (Phe48-Glu397) is 45% identical in amino acid sequence to Erk2 and 51% to p38, whose structures have been reported (F. Zhang et al. (1994); K. P. Wilson et al. (1996); FIG. 1). As expected, the overall architecture of JNK3 is highly similar to that of Erk2 and p38. The N-terminal lobe (residues 45-149, and 379-400) of JNK3 contains mostly beta-strands, whereas the C-terminal lobe (residues 150-211, 217-374) is predominantly alpha-helical. A deep cleft between the two domains comprises the ATP binding site, where the glycine-rich sequence of the enzyme (GSGAQGIV) (SEQ ID NO: 5) forms a well defined β strand-turn-β strand structure over the nucleotide. The MAP kinase insertion in the C-terminal domain is 12 residues longer in JNK3 than in Erk2 and p38, resulting in the N-terminal extension of helix αH and an extra $3_{10}$ helix, denoted 3/10(2)L14 between αH and α3L14 (FIG. 2a). We refer to this 12-residue insertion as "the JNK insertion" since it is present in all c-Jun N-terminal kinases [S. Gupta et al., (1996)].

The relative orientation of the N- and C-terminal domains is different between the structure of JNK3 and Erk2 (FIG. 2b). Superposition of the C-terminal domain of JNK3 onto the corresponding lobe of Erk2 revealed a rotation of the N-terminal domain of JNK3 by about 2.5° towards the active site. Despite the rotation of the domains, the structure of the individual domains of JNK3 and Erk2 are similar. Independent superpositions of the N- and C-terminal domains of Erk2 onto JNK3, ignoring the phosphorylation lip region, the JNK insertion and the protein termini, yielded protein backbone root mean square (rms) deviation of 1.23 Å for the N-terminal domain (JNK3 residues 56-149 and 382-400) and 1.60 Å for the C-terminal domain (JNK3 residues 150-208, 226-315 and 329-369).

Electron density is not visible for two disordered regions within the core region of JNK3. One region is Arg212-Thr216 in the C-terminal domain (FIG. 2a). The corresponding residues in Erk2 form beta strand β9 that precedes the "phosphorylation lip" (see below). In the unphosphorylated JNK3 structure, the disordered β9 indicates the flexible structure of the phosphorylation lip. The second disordered region includes residues Gln374-Lys378. These amino acids may be coupled to the activation state of the enzyme, since the structure of phosphorylated Erk2 showed that this portion of L16 is rearranged to a $3_{10}$ helix upon phosphorylation [B. J. Canagarajah et al., Cell, 90, pp. 859-69 (1997)].

Phosphorylation Lip

We refer to the region spanning residues Thr217-Thr226, part of linker L12, as the "phosphorylation lip" or "activation loop", since it contains the regulatory phosphorylation sites Thr221 and Tyr223 (FIG. 2a). The conserved residue between two phosphorylation sites in the Thr-X-Tyr tripeptide sequence of JNKs is Pro, while it is Glu and Gly in Erk2 and p38 respectively. Most of the JNK3 residues in the phosphorylation lip are well ordered. The phosphorylation lip is four residues shorter in JNK3 than in Erk2 and two residues longer than in p38. The differences in length of the phosphorylation lip and the center residues in the tripeptide sequence Thr-X-Tyr result in variations in the position and conformation of the activation residues, Thr221 and Tyr223 and in the path of the activation loop. Superposition of the C-terminal domain of Erk2 onto JNK3 reveals a 2.5 Å shift in the C position of Thr226 relative to Thr188 in Erk2 (FIG. 2b). The conformation of Thr226 is also different when compared to Thr188 in Erk2. In JNK3, a pair of water molecules are hydrogen bonded to the main chain carbonyl and amide groups of Thr226, and mediate interactions with the side chain of Lys199. As a result, Thr226 adopts a different Φ, Ψ angle (Thr226 of JNK3: Φ=−88° and Ψ=114°; Thr188 of Erk2: Φ=−46° and Ψ=130°), which redirects the path of the phosphorylation lip. The N-terminal portion of the lip makes van der Waals contacts with the C helix, which in turn contacts the glycine-rich flap covering the nucleotide. Taken together, the protein backbone of the phosphosylation lip is well ordered, and takes up a conformation completely distinct from the corresponding residues in Erk2 and p38.

As a result of the conformation of the lip, the regulatory phosphorylation sites in JNK3 are differently positioned compared to that in Erk2 and p38. Thr221 and Tyr223 are 16 Å away from the location of the corresponding residues in Erk2 and 12 Å in p38. Despite the different locations, the regulatory threonine residues in all three enzymes are solvent exposed. In contrast, the local environments of the tyrosine residues are different. The side chain of Tyr221 is exposed to solvent in the JNK3 structure, and is disordered. The corresponding tyrosine residue in p38 is also exposed to the solvent, but its side chain is well-ordered and interacts with the hydroxyl group of Thr221 of p38 through a water molecule [K. P. Wilson et al, (1996)]. In contrast, the side chain of the corresponding tyrosine in Erk2 is buried. The Erk2 residue Tyr185 forms a hydrogen bond with the side chain of Arg146, and makes van der Waals contacts with nearby hydrophobic amino acid side chains [F. Zhang et al. (1994)]. The side chain conformation of Tyr185 in the unphosphorylated Erk2 structure suggests that the phosphorylation lip must be refolded before Tyr185 can become a substrate for the Erk2 upstream activating kinase. A similar movement may not be needed to phosphorylate JNK3 and p38, since both threonine and tyrosine are accessible to the solvent in the unphosphorylated forms of JNK3 and p38.

Peptide Substrate Binding Channel

The peptide substrate binding sites in JNK3 may be mapped by its homology to c-AMP-dependent protein kinase (cAPK, FIG. 1). The structure of the ternary complex formed by cAPK, PKI inhibitor and MnAMP-PNP [D. Bossemeyer et al., *EMBO J.*, 12, pp. 849-59 (1993); D. R. Knighton et al., *Science*, 253, pp. 414-20 (1991)] shows that the peptide binding channel lies mainly in the C-terminal domain, and the position of the P+1 binding site is formed by a loop (residues Leu198 to Leu205) contiguous with the phosphorylation lip and connecting to αL12 (FIG. 3). The C-terminal domain of JNK3 superimposes well with that of cAPK, and it allows one to identify the residues that may be important for JNK3 peptide substrate binding. In JNK3, the protein backbone of residues Arg227 to Arg230 follows a similar path to the corresponding residues in cAPK (residues Pro202 to Leu205), with the side chain of Arg230 filling the P+1 site in an unfavorable conformation for the binding of the substrate (FIG. 3). While a portion of the phosphorylation lip (corresponding to residues Leu198-Thr201 in cAPK) takes a path distinct from that of cAPK and occupies the positions of P+1 and P+2 sites of the peptide substrate (FIG. 3).

Structural comparison of JNK3 and the phosphorylated Erk2 suggest how phosphorylation at Thr221 and Tyr223 of JNK3 might play a role in the activation of JNK kinases. In the phosphorylated Erk2, phosphothreonine pThr183 interacts directly with three arginine residues, Arg68 in αC, Arg146 in the catalytic loop (C loop) and Arg170 from the phosphorylation lip, while phosphotyrosine pTyr185 is ligated by Arg189 and Arg192 [B. J. Canagarajah et al (1997)]. Assuming that Thr221 and Tyr223 are ligated similarly in the phosphorylated form of JNK3, they would have to move by approximately 15 Å upon phosphorylation to be in close proximity with their ligands, and a large conformational change of the phosphorylation lip would be required. As a consequence of phosphorylation at Thr221 and Tyr223, restructuring of the phosphorylation lip may help to unblock the peptide substrate binding channel. These phosphorylation-related conformational changes in the phosphorylation lip as well as the peptide substrate binding channel have been observed in the crystal structures of low activity and phosphorylated Erk2 [F. Zhang et al. (1994); B. J. Canagarajah et al. (1997)].

Active Site

Crystals of the binary complex of JNK3/MgAMP-PNP obtained from crystallizations of JNK3 in the presense of AMP-PNP and $Mg^{2+}$ have allowed us to obtain structural data for the nucleotide-bound form of JNK3. As revealed in the structure, AMP-PNP is bound in the deep cleft between the two lobes of JNK3 (FIG. 2a). The binding mode of the nucleotide analog is similar to that found in the ternary complex formed by cAPK, MnAMP-PNP and the inhibitor peptide PKI(5-24) [D. Bossemeyer et al. (1993)] (FIG. 4a), which is believed to represent the bioactive conformation for protein kinases. These findings differ from previous crystal soaking experiments with Erk2 [F. Zhang et al. (1994)], and permit a more detailed description of the interactions between the JNK3 and nucleotide.

The catalytic core of protein kinases contains a nucleotide binding sequence Gly-X-Gly-X-X-Gly-X-X (SEQ ID NO: 3) that is referred to as "the glycine-rich phosphate anchor loop" due to its structural feature and role in the nucleotide binding [D. R. Knighton et al., *Science*, 253, pp. 407-13 (1991)]. The glycine-rich loop is well defined in JNK3, and superimposes well with that of cAPK, with an rms deviation 0.54 Å for the protein main chain atoms from Ile70 to Ser79 (FIG. 4). The glycine-rich sequence Gly71-Ser-Gly73-Ala-Gln-Gly76-Ile-Val78 (SEQ ID NO: 4) forms a flap over the nucleotide, covering it almost completely. The adenine base of the nucleotide is deep in the back of the domain interface, with its amino group (N6) making a hydrogen bond to the backbone carbonyl of Glu147, and N1 to the backbone amide of Met149. Non-polar interactions are also found at both sides of the purine ring, including Ile70 and Val78 from the glycine-rich flap on one side and Val196 from 7 on the other. The ribose O2' and O3' hydroxyls form a hydrogen-bonding network to the side chain of Asn152 and the carbonyl group of Ser193. The triphosphate group is tightly connected via hydrogen bondings, involving directly or indirectly, most of the invariant amino acids of protein kinases. Hydrogen bonds to phosphate oxygen atoms are formed by main chain amides of Gln75 and side chains of Gln75 and Lys93. Two magnesium ions (M1 and M2) are observed in the JNK3-MgAMP-PNP complex. The side chain carbonyl group of Asn194 is in close contact with M1 metal ion, which in turn bridges the oxygens of the α and γ phosphoryl groups of AMP-PNP. Asp207 interacts through water molecules with M2, which is bound to the β and γ phosphoryl group oxygens, while in cAPK, the corresponding residue (Asp 184) directly coordinates both M1 and M2. This significant difference appears to be due to the inactive conformation of the JNK3 enzyme. An important role in metal chelation has been proposed for Asp 184 in cAPK which requires direct interaction of the aspartic residue with the metal ion [D. R. Knighton et al., *Science*, 253, pp. 407-13 (1991); D. Bossemeyer et al. (1993)]. Asp207 is located at a loop called the "DFG loop" preceding the disordered β9 in unphosphorylated JNK3. The structure of JNK3 suggests that upon phosphorylation, the refolding the phosphorylation lip and domain rotation should bring Asp207 closer to the nucleotide to allow its direct interaction with the metal ion.

Structural comparison of JNK3 and cAPK reveals that the two domains of JNK3 are rotated apart relative to their orientation in the structure of cAPK (FIG. 3). This twist results in the misalignment of the two halves of the catalytic site of JNK3. From the N-terminal domain, the putative catalytic Lys93 takes the similar position of its equivalent residues in cAPK and forms hydrogen bonds to the oxygen atoms of α and β phosphoryl groups. However, the catalytic loop (Arg188-Asn194) and the DFG loop (Asp207-Gly209) in the C-terminal domain are misaligned (FIG. 4b). The conserved Asp 189 and Asp207, both are thought to be essential for protein kinase activity [C. S. Gibbs et al., *J. Biol. Chem.*, 267, pp. 4806-10 (1992)], are located 3 Å further away from Lys93 in JNK3, compared to that of their corresponding residues in cAPK. These differences suggest that the "open" conformation of the domains in JNK3 may contribute to the low activity of the unphosphorylated enzyme.

Similarity of JNK3 to Other Enzymes

The overall fold of JNK3 reveals similarities to the known structures of cAMP-dependent protein kinase and other MAP kinases, Erk2 and p38. The unphosphorylated JNK3 assumes an "open" conformation, in which the N- and C-terminal domains are oriented so that some of the catalytic residues are misaligned. In addition, the phosphorylation lip partially blocks the substrate peptide binding site. The combination of these regulatory mechanisms suggests that both global (domain closure to bring the catalytic residues in close proximity) and local (refolding of the lip to relieve steric constraints to substrate binding) conformational changes are required for JNK3 activation.

Crystallographic studies of Erk2, p38 and JNK3 have shown that the region of β9 and the phosphorylation lip has the most diverse and labile conformation in unphosphorylated MAP kinases. This region of ERK2 adopts a conformation stabilized by interactions between the phosphates and residues near the activation loop in the phosphorylated enzyme [B. J. Canagarajah et al. (1997)]. Using the phosphorylated Erk2 structure as a model for the active conformation of JNK3 shows that the two phosphorylation sites, Thr221 and Tyr223, may play similar roles in activating JNK3 as they do in Erk2. In JNK3, phosphorylation of Thr221 may promote domain closure by interacting with Arg107 and Arg188, while phosphorylation of Tyr223 may promote new interaction of the phosphotyrosine with Arg227 and Arg230, which in turn constitute the proline-directed P+1 pocket.

The JNK3/MgAMP-PNP binary complex is the first kinase structure of the JNK subfamily of MAP kinases to be determined. In the region spanning residues Ser40 to Ala418, JNK3 shares 92% and 87% amino acid identity with JNK1 and JNK2, respectively. Thus, the JNK3 structure provides detailed structural information which provides insight into the mechanism of regulation for this class of MAP kinases. The variant residues among JNK isoforms are clustered in two regions (FIG. 1). One region is the C-terminal portion of αF and its following loop L13. Most of the variant residues in this region are solvent exposed in the JNK3 structure and appear to be involved in substrate binding when compared with cAPK (FIG. 5), suggesting their role in substrate binding specificity. This is consistent with results obtained from the study of JNK chimeras which shows that JNK specificity towards c-Jun is directed to this region [T. Kallunki et al., *Genes Dev.*, 8, pp. 2996-3007 (1994)]. Previous binding studies of JNK isoforms and various substrates further support this hypothesis and have shown that JNK isoforms with higher homology in this region display similar binding selectivity towards substrates [S. Gupta et al., 1996]. The other region is the α3L14 and JNK insertion, which lies on the protein surface next to the peptide substrate binding channel identified in cAPK (FIG. 5). The location of this region suggests that it might be an extended substrate binding site in JNK kinase, and the sequence in this region may be important for substrate binding specificity.

FIGS. 2A, 2B, 3, 4A, 4B and 5 further depict the structure of the JNK3/MgAMP-PNP complex. FIG. 1B depicts the structure-based sequence alignment of JNK3 [S. Gupta et al., (1996)], ERK2 [T. G. Boulton et al., *Cell*, 65, pp. 663-75 (1991)], p38 (J. C. Lee et al., *Nature*, 372, pp. 739-46 (1994)] and cAPK (M. D. Uhler, *Proc. Natl. Acad. Sci. USA*, 83, pp. 1300-04 (1986)]. The amino acid sequences of JNK3, human ERK2, human p38 kinase, and murine cAPK are aligned based on structural similarity. The divergent N- and C-terminal regions of Erk2, p38, cAPK are not shown in FIG. 1B. N- and C-terminal residues that are not included in the truncated JNK3 (JNK3: residues Ser40-Glu402) for crystallographic studies are denoted by lowercase letters in FIG. 1B. Residues in italics are not included in the model. Subdomains in FIG. 1B are labeled by Roman numerals according to S. K. Hanks et al., *Science*, 241, pp. 42-52 (1988). The secondary structural elements for JNK3 are indicated above the sequences (nomenclature as for FIG. 2A), with open boxes designating αα helices and 3/10 helices and open arrows for ββ strands. Disordered regions are indicated with dashed lines. Both JNK3 and cAPK sequence numbering are shown. Phosphorylation sites in the phosphorylation lip are denoted by an asterisk. JNK3 residues that differ from JNK1 and JNK2 are highlighted in bold.

FIG. 2a is a ribbon representation of the overall fold of JNK3 complexed with MgAMP-PNP. The structure indicates secondary structural elements and loops conserved among protein kinases as well as extensions and insertions characteristic of MAP kinases. The JNK insertion and the phosphorylation lip are shown. The disordered region (residues 212-216) is indicated with dotted lines. Bound AMP-PNP and two $Mg^{2+}$ ions are represented by space-filling models. The Cα positions of the regulatory phosphorylation sites Thr221 and Tyr223 are shown and labeled. Secondary structural elements are labeled according to ref. This diagram was constructed using RIBBONS [M. Carson, *J. Appl. Cryst.*, 24, pp. 958-61 (1987)].

FIG. 2b is a stereoscopic view of the superimposed structures of JNK3/MgAMP-PNP and Erk2 Cα representations of the structures of JNK3 and Erk2 are shown after superposition of their C-terminal domains. Segments with largest structural divergence are labeled and highlighted.

FIG. 3 is stereoscopic view of the superimposed structures of JNK3 and cAPK. Cα representation of JNK3 and cAPK ternary complex are shown after superposition of C-terminal domains. The phosphorylation lip in JNK3 and in cAPK, and the PKI inhibitor show the difference in the conformation of the lip between two enzymes, and the lip of JNK3 occupying part of the peptide binding channel. MnAMP-PNP in cAPK ternary complex is omitted from the drawing and only the kinase catalytic core portion of cAPK is shown.

FIG. 4a is stereoscopic view of the active site of JNK3. Molecules of AMP-PNP and Mg2+ are shown together with their surrounding JNK3 residues. The AMP-PNP molecule is shown as thick bonds, and the protein residues as thin bonds. Two $Mg^{2+}$ ions (labeled M1 and M2) and two water molecules (labeled W1 and W2) are shown as spheres. Hydrogen bonds are indicated by dashed lines.

FIG. 4b is a detailed comparison of the active site of JNK3 with that of cAPK. Cα representation of the ATP binding sites of JNK3 and cAPK with the side chains of selected residues included. The atoms of AMP-PNP in the JNK3 binary complex and cAPK ternary complex have been superimposed. The N-terminal domains of the two enzymes are well aligned, while the difference in domain orientation results in the misalignment of the catalytic residues clustered in C loop and DFG loop, such as Asp 189 and Asp207, with those in the N-terminal domain, such as Lys93.

FIG. 5 is a substrate binding specificity of JNK isoforms. The solvent accessible surface of JNK3 is shown with the PKI inhibitor (drawn as tube) after the same superposition of JNK3 and cAPK structures done in FIG. 3. Surface area corresponding to the JNK3 residues not conserved in JNK1 and JNK2 are shaded. Two clusters of divergent regions of JNK isoforms identified from the amino acid sequence alignment are located next to each other on the protein surface in the C-terminal lobe. The area containing αF and L13 has been shown to direct the substrate binding specificity toward cJun.

Example 5

The Use of JNK3/MgAMP-PNP Coordinates for Inhibitor Design

The coordinates of FIG. 1 are used to design compounds, including inhibitory compounds, that associate with JNK3 or homologues of JNK3. This process may be aided by using a computer comprising a machine-readable data storage medium encoded with a set of machine-executable instructions, wherein the recorded instructions are capable of displaying a three-dimensional representation of the JNK3/MGAMP-PNP complex or a portion thereof. The graphical representation is used according to the methods described herein to design compounds. Such compounds associate with the JNK3 at the active site.

Example 6

JNK3 Activity Inhibition Assay

A. JNK3 Activation

Five mg of JNK3 was diluted to 0.5 mg/ml in 50 mM HEPES buffer, pH 7.5, containing 100 mM NaCl, 5 mM DTT, 20 mM $MgCl_2$, 1 mM ATP. GST-MKK7(DD) kinase (the upstream mutant form of one of the activating kinases of JNK3) was added at a molar ratio of 1 GST-MKK7:2.5 JNK3. After 30 min at 25° C. the reaction mixture was concentrated 5-fold by ultrafiltration in a Centriprep-30 (Amicon, Beverly, Mass.), then diluted back up to 10 ml and an additional 1 mM ATP added. This procedure was repeated three times to remove ADP and replenish ATP. The final (third) addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interactions chromatography (at 25° C.) using a Rainin Hydropore column. GST-MKK7 and unactivated JNK3 do not bind under these conditions and when a 1.1 to 0.05M potassium phosphate gradient is developed over 60 min at a flow rate of 1 ml/min, doubly phosphorylated JNK3 is separated from singly phosphorylated JNK.

Activated JNK3 (i.e. doubly phosphorylated) was stored at −70° C. at 0.25-1 mg/ml.

B. JNK3 Inhibition Assay

To determine $IC_{50}$ of the compound binding to JNK3, the kinase activity of JNK3 was monitored by coupled enzyme assay. In this assay, for every molecule of ADP generated by the JNK3 kinase activity one molecule of NADH is converted to NAD which can be conveniently monitored as an absorbance decrease at 340 nm. The following are the final concentrations of various reagents used in the assay: 100 mM HEPES buffer, pH 7.6, 10 mM $MgCl_2$, 25 mM β-glycerophosphate, 30 μM ATP, 2 mM phosphoenolpyruvate, 2 μM pyruvate kinase, 2 μM lactate dehydrogenase, 200 μM NADH, 200 μM EGF receptor peptide KRELVEPLTPSGEAPNQALLR (SEQ ID NO: 6), and 10 mM activated JNK3. First, all of the above reagents with the exception of ATP were mixed and 175 μl aliquots were placed per well of 96-well plate. A 5 μl DMSO solution of the compound was added to each well, mixed, and allowed to stand at 30° C. for 10 minutes. Typically about 10 different concentrations of the compound were tested. The reactions were initiated with the addition of 20 μl of ATP solution. Absorbance change at 340 nm were monitored as a function of time. $IC_{50}$ is obtained by fitting the rates vs. compound concentration data to a simple competitive inhibition model.

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

TABLE 1

Summary of data collection and structure refinement

| Data Statistics | Resolution (Å) | Reflections (Measured/Unique) | Completeness (%) (Overall/Outer Shell) | $R_{merge}$[1] (%) (Overall/Outer Shell) | | |
|---|---|---|---|---|---|---|
| | 50-2.3 | 66063/16394 | 90.0/75.4 | 5.2/16.5 | | |
| Structure Refinement | Resolution (Å) | Number of Reflections | R-factor | Free R-factor | No. of water molecules | No. of AMP-PNP molecule | No. of $Mg^{2+}$ |
| Data with F > 2.0 σF | 30-2.3 | 14511 | 0.221 | 0.274[2] | 18.3 | 1 | 2 |
| Rms deviations | Bonds lengths 0.009Å | | Bond angles 1.5° | | | | |

[1]$R_{merge} = 100 \times \Sigma_h \Sigma_j I_{hi} - \langle I_h \rangle / \Sigma_h \Sigma_j I_{hi}$.
[2]Free R-factor (ref, Brunger) was calculated with 10% of the data.

We claim:

1. A crystallizable composition comprising:
   a) a purified unphosphorylated c-Jun N-terminal kinase 3 (JNK3) polypeptide consisting of amino acid residues 40-402 of SEQ ID NO:1 and an N-terminal Met-Gly;
   b) adenylyl imidodiphosphate (AMP-PNP);
   c) magnesium ions;
   d) 18-20% v/v polyethylene glycol monomethyl ether;
   e) 10% v/v ethylene glycol;
   f) 20 mM β-mercaptoethanol; and
   g) 100 mM HEPES buffer at pH 7.0,
   wherein said crystallizable composition forms crystals of X-ray diffraction quality.

2. A crystallized composition comprising a crystal, wherein said crystal comprises:
   a) an unphosphorylated JNK3 polypeptide consisting of amino acid residues 40-402 of SEQ ID NO:1 and an N-terminal Met-Gly;
   b) AMP-PNP; and
   c) magnesium ions,
   wherein said crystal is in space group $P2_12_12_1$ and has unit cell parameters of a=51.50 Å, b=71.24 Å, and c=107.60 Å.

3. A method of obtaining a crystal comprising a purified unphosphorylated JNK3 polypeptide, the method comprising subjecting the crystallizable composition according to claim 1 to conditions which promote crystallization, and obtaining a crystal in space group $P2_12_12_1$ having unit cell parameters of a=51.50 Å, b=71.24 Å, and c=107.60 Å.

4. A crystal comprising an unphosphorylated JNK3 polypeptide in complex with magnesium ions and AMP-PNP, wherein said unphosphorylated JNK3 polypeptide consists of amino acid residues 40-402 of SEQ ID NO:1 and an N-terminal Met-Gly, and wherein said crystal is in space group $P2_12_12_1$ and has unit cell parameters of a=51.50 Å, b=71.24 Å, and c=107.60 Å.

5. A hanging drop vapor diffusion method of obtaining a crystal comprising a purified unphosphorylated JNK3 polypeptide, the method comprising:
   a) preparing a crystallization droplet comprising the crystallizable composition according to claim 1;
   b) hanging said crystallization droplet over a reservoir solution comprising:
      i) 18-20% v/v polyethylene glycol monomethyl ether;
      ii) 10% v/v ethylene glycol;
      iii) 20 mM β-mercaptoethanol; and
      iv) 100 mM HEPES buffer at pH 7.0; and
   c) obtaining a crystal of X-ray diffraction quality.

* * * * *